United States Patent
Zhai et al.

(10) Patent No.: US 12,037,613 B2
(45) Date of Patent: Jul. 16, 2024

(54) PHYTASE VARIANTS AND POLYNUCLEOTIDES ENCODING SAME

(71) Applicant: Novozymes A/S, Bagsvaerd (DK)

(72) Inventors: Hengxiao Zhai, Bazhou Hebel (CN); Jesper Vind, Vaerlose (DK); Lars Kobberoe Skov, Ballerup (DK); Qian Zhang, Bazhou Hebel (CN); Ester Santigosa, Village-Neuf (FR); Jose-Otavio B. Sorbara, Basel (CH); Aurelia Anne Catherine Charlotte Seon, Kaiseraugst (CH); Carrie Louise Walk, Kaiseraugst (CH)

(73) Assignee: Novozymes A/S, Bagsvaerd (DK)

( * ) Notice: Subject to any disclaimer, the term of this patent is extended or adjusted under 35 U.S.C. 154(b) by 55 days.

(21) Appl. No.: 17/402,099

(22) Filed: Aug. 13, 2021

(65) Prior Publication Data

US 2022/0049230 A1 Feb. 17, 2022

(30) Foreign Application Priority Data

| Aug. 13, 2020 | (EP) | 20190917 |
| Oct. 12, 2020 | (EP) | 20201328 |
| Mar. 18, 2021 | (WO) | PCT/CN2021/081613 |
| May 7, 2021 | (EP) | 21172706 |

(51) Int. Cl.
| C12N 9/16 | (2006.01) |
| A23K 10/14 | (2016.01) |
| A23K 20/174 | (2016.01) |
| A23K 20/189 | (2016.01) |
| A23K 20/20 | (2016.01) |
| C12N 15/75 | (2006.01) |

(52) U.S. Cl.
CPC .............. *C12N 9/16* (2013.01); *A23K 10/14* (2016.05); *A23K 20/174* (2016.05); *A23K 20/189* (2016.05); *A23K 20/30* (2016.05); *C12N 15/75* (2013.01); *C12Y 301/03008* (2013.01)

(58) Field of Classification Search
CPC ........ C12N 9/16; C12N 15/8243; C12N 9/96; C12Y 301/03008; C12Y 301/03072; C12Y 301/03026; C12P 21/00; C12P 7/00

USPC ...................... 435/196, 183, 320.1
See application file for complete search history.

(56) References Cited

FOREIGN PATENT DOCUMENTS

| CN | 110724676 A | 1/2020 |
| EP | 3805381 A1 | 4/2021 |
| WO | 2004085638 A1 | 10/2004 |
| WO | 2006037328 A1 | 4/2006 |
| WO | 2006038062 A1 | 4/2006 |
| WO | 2006038128 A2 | 4/2006 |
| WO | 2007/112739 A1 | 10/2007 |
| WO | 2010/034835 A2 | 4/2010 |
| WO | 2011/117396 A2 | 9/2011 |
| WO | 2011/117397 A1 | 9/2011 |
| WO | 2011/117406 A1 | 9/2011 |
| WO | 2012/110776 A2 | 8/2012 |
| WO | 2019228441 A1 | 12/2019 |
| WO | 2020/190323 A1 | 9/2020 |

OTHER PUBLICATIONS

Davos et al., (Proteins: Structure, Function and Genetics, 2000, vol. 41: 98-107.*
Wristlock et al., (Quarterly Reviews of Biophysics 2003, vol. 36 (3): 307-340.*
Kwiatkowski et al., (Biochemistry 38:11643-11650, 1999.*
Kiselev L., (Structure, 2002, vol. 10: 8-9.*
Tan et al., J. Microbiol. Biotechnol., vol. 26, No. 10, pp. 1717-1722 (2016).
KR 2004045267—Accession No. ADU50737.
WO 2012110776A2—Genbank No. AY390262.
Zinin et al., 2004, Accession No. Q676V7—EBI No. AY390262.

* cited by examiner

*Primary Examiner* — Robert B Mondesi
*Assistant Examiner* — Mohammad Y Meah
(74) *Attorney, Agent, or Firm* — Adam Rucker

(57) ABSTRACT

The present invention relates to phytase variants. The present invention also relates to polynucleotides encoding the variants; nucleic acid constructs, vectors, and host cells comprising the polynucleotides; and methods of using the variants.

20 Claims, 61 Drawing Sheets

Specification includes a Sequence Listing.

```
SEQ2      1                           EEQNGMKLERVVIVSRHGVRAPTKFTPI        28
                                      ||.||||||||||||||||||||||||
SEQ9      1 MSTFIIRLLFFSLLCGSFSIHAEEPNGMKLERVVIVSRHGVRAPTKFTPI        50

SEQ2     29 MKNVTPDQWPQWDVPLGWLTPRGGELVSELGQYQRLWFTSKGLLNNQTCP        78
            ||:|||||||||||||||||||||||||||||||||||||||||||||||
SEQ9     51 MKDVTPDQWPQWDVPLGWLTPRGGELVSELGQYQRLWFTSKGLLNNQTCP       100

SEQ2     79 SPGQVAVIADTDQRTRKTGEAFLAGLAPKCQIQVHYQKDEEKNDPLFNPV       128
            ||||||||||||||||||||||||||||||||||||||||.||||||||
SEQ9    101 SPGQVAVIADTDQRTRKTGEAFLAGLAPKCQIQVHYQKDEEKTDPLFNPV       150

SEQ2    129 KMGKCSFNTLQVKNAILERAGGNIELYTQRYQSSFRTLENVLNFSQSETC       178
            |||.||||||:|||||||||||||||||||||||||||||||||||||||
SEQ9    151 KMGTCSFNTLKVKNAILERAGGNIELYTQRYQSSFRTLENVLNFSQSETC       200

SEQ2    179 KTTEKSTKCTLPEALPSELKVTPDNVSLPGAWSLSSTLTEIFLLQEAQGM       228
            |||||||||||||||||||||||||||||||||||||||||||||||||
SEQ9    201 KTTEKSTKCTLPEALPSELKVTPDNVSLPGAWSLSSTLTEIFLLQEAQGM       250

SEQ2    229 PQVAWGRITGEKEWRDLLSLHNAQFDLLQRTPEVARSRATPLLDMIDTAL       278
            |||||||||||||||||||||||||||||||||||||||||||||||||
SEQ9    251 PQVAWGRITGEKEWRDLLSLHNAQFDLLQRTPEVARSRATPLLDMIDTAL       300

SEQ2    279 LTNGTTENRYGIKLPVSLLFIAGHDTNLANLSGALDLNWSLPGQPDNTPP       328
            |||||||||||||||||||||||||||||||||||||||||||||||||
SEQ9    301 LTNGTTENRYGIKLPVSLLFIAGHDTNLANLSGALDLNWSLPGQPDNTPP       350

SEQ2    329 GGELVFEKWKRTSDNTDWVQVSFVYQTLRDMRDIQPLSLEKPAGKVDLKL       378
            |||||||||||||||||||||||||||||||||||||||||||||||||
SEQ9    351 GGELVFEKWKRTSDNTDWVQVSFVYQTLRDMRDIQPLSLEKPAGKVDLKL       400

SEQ2    379 IACEEKNSQGMCSLKSFSRLIKEIRVPECAVTE        411
            |||||||||||||||||||||||||||||||||
SEQ9    401 IACEEKNSQGMCSLKSFSRLIKEIRVPECAVTE        433
```

Fig. 1

```
ATOM      1  N   GLY A   5     -14.638  16.094  42.125  1.00 54.10           B  N
ATOM      2  CA  GLY A   5     -15.897  16.043  41.297  1.00 48.79           B  C
ATOM      3  C   GLY A   5     -15.811  15.052  40.146  1.00 39.17           B  C
ATOM      4  O   GLY A   5     -16.655  15.172  39.240  1.00 35.11           B  O
ATOM      5  N   MET A   6     -14.890  14.075  40.212  1.00 40.74           B  N
ATOM      6  CA  MET A   6     -14.412  13.242  39.062  1.00 37.72           B  C
ATOM      7  CB  MET A   6     -12.939  13.539  38.771  1.00 40.34           B  C
ATOM      8  CG  MET A   6     -12.684  14.989  38.575  1.00 46.28           B  C
ATOM      9  SD  MET A   6     -13.492  15.429  37.060  1.00 52.01           B  S
ATOM     10  CE  MET A   6     -12.054  15.422  36.022  1.00 33.09           B  C
ATOM     11  C   MET A   6     -14.503  11.748  39.358  1.00 31.32           B  C
ATOM     12  O   MET A   6     -13.995  11.326  40.373  1.00 37.72           B  O
ATOM     13  N   LYS A   7     -15.046  10.993  38.425  1.00 29.14           B  N
ATOM     14  CA  LYS A   7     -15.179   9.516  38.476  1.00 31.19           B  C
ATOM     15  CB  LYS A   7     -16.642   9.128  38.228  1.00 35.92           B  C
ATOM     16  CG  LYS A   7     -16.987   7.684  38.524  1.00 44.61           B  C
ATOM     17  CD  LYS A   7     -18.252   7.187  37.855  1.00 50.51           B  C
ATOM     18  CE  LYS A   7     -18.624   5.809  38.369  1.00 60.08           B  C
ATOM     19  NZ  LYS A   7     -18.809   4.845  37.258  1.00 65.98           B  N
ATOM     20  C   LYS A   7     -14.258   8.961  37.385  1.00 27.78           B  C
ATOM     21  O   LYS A   7     -14.446   9.297  36.192  1.00 24.28           B  O
ATOM     22  N   LEU A   8     -13.418   7.990  37.744  1.00 27.52           B  N
ATOM     23  CA  LEU A   8     -12.608   7.241  36.745  1.00 27.34           B  C
ATOM     24  CB  LEU A   8     -11.411   6.577  37.431  1.00 26.27           B  C
ATOM     25  CG  LEU A   8     -10.373   5.923  36.501  1.00 25.54           B  C
ATOM     26  CD1 LEU A   8      -9.827   6.902  35.452  1.00 23.52           B  C
ATOM     27  CD2 LEU A   8      -9.237   5.355  37.329  1.00 28.69           B  C
ATOM     28  C   LEU A   8     -13.480   6.207  36.034  1.00 26.90           B  C
ATOM     29  O   LEU A   8     -14.007   5.267  36.684  1.00 27.75           B  O
ATOM     30  N   GLU A   9     -13.636   6.329  34.723  1.00 24.05           B  N
ATOM     31  CA  GLU A   9     -14.540   5.500  33.907  1.00 25.74           B  C
ATOM     32  CB  GLU A   9     -15.313   6.378  32.931  1.00 30.35           B  C
ATOM     33  CG  GLU A   9     -16.156   7.426  33.621  1.00 36.12           B  C
ATOM     34  CD  GLU A   9     -17.584   6.954  33.799  1.00 43.98           B  C
ATOM     35  OE1 GLU A   9     -18.432   7.351  32.981  1.00 48.09           B  O
ATOM     36  OE2 GLU A   9     -17.818   6.180  34.736  1.00 50.69           B  O
ATOM     37  C   GLU A   9     -13.770   4.429  33.126  1.00 25.69           B  C
ATOM     38  O   GLU A   9     -14.266   3.326  33.045  1.00 25.23           B  O
ATOM     39  N   ARG A  10     -12.625   4.757  32.542  1.00 23.75           B  N
ATOM     40  CA  ARG A  10     -11.929   3.817  31.620  1.00 25.30           B  C
ATOM     41  CB  ARG A  10     -12.341   3.936  30.164  1.00 25.77           B  C
ATOM     42  CG  ARG A  10     -13.758   3.509  29.881  1.00 26.91           B  C
ATOM     43  CD  ARG A  10     -14.030   3.555  28.413  1.00 30.15           B  C
ATOM     44  NE  ARG A  10     -15.471   3.685  28.244  1.00 32.57           B  N
ATOM     45  CZ  ARG A  10     -16.091   3.865  27.107  1.00 33.88           B  C
ATOM     46  NH1 ARG A  10     -15.437   3.885  25.969  1.00 28.83           B  N
ATOM     47  NH2 ARG A  10     -17.407   3.980  27.090  1.00 40.76           B  N
ATOM     48  C   ARG A  10     -10.469   4.199  31.566  1.00 27.26           B  C
ATOM     49  O   ARG A  10     -10.167   5.366  31.750  1.00 23.20           B  O
ATOM     50  N   VAL A  11      -9.605   3.220  31.379  1.00 21.08           B  N
ATOM     51  CA  VAL A  11      -8.142   3.419  31.258  1.00 21.25           B  C
ATOM     52  CB  VAL A  11      -7.394   3.054  32.561  1.00 22.53           B  C
ATOM     53  CG1 VAL A  11      -5.895   3.144  32.405  1.00 24.39           B  C
ATOM     54  CG2 VAL A  11      -7.804   3.931  33.744  1.00 25.89           B  C
ATOM     55  C   VAL A  11      -7.637   2.616  30.083  1.00 21.58           B  C
ATOM     56  O   VAL A  11      -8.061   1.477  29.887  1.00 21.59           B  O
```

Fig. 5A

```
ATOM     57  N   VAL A  12      -6.757   3.215  29.270  1.00 18.76           B  N
ATOM     58  CA  VAL A  12      -5.894   2.521  28.293  1.00 18.33           B  C
ATOM     59  CB  VAL A  12      -6.111   2.926  26.824  1.00 20.13           B  C
ATOM     60  CG1 VAL A  12      -5.227   2.148  25.888  1.00 21.20           B  C
ATOM     61  CG2 VAL A  12      -7.567   2.794  26.414  1.00 22.29           B  C
ATOM     62  C   VAL A  12      -4.453   2.727  28.702  1.00 15.60           B  C
ATOM     63  O   VAL A  12      -4.036   3.890  28.865  1.00 17.78           B  O
ATOM     64  N   ILE A  13      -3.710   1.631  28.877  1.00 16.65           B  N
ATOM     65  CA  ILE A  13      -2.253   1.665  29.151  1.00 15.98           B  C
ATOM     66  CB  ILE A  13      -1.841   0.850  30.369  1.00 17.29           B  C
ATOM     67  CG1 ILE A  13      -2.512   1.400  31.625  1.00 18.59           B  C
ATOM     68  CG2 ILE A  13      -0.358   0.716  30.470  1.00 17.26           B  C
ATOM     69  CD1 ILE A  13      -2.327   0.552  32.892  1.00 20.41           B  C
ATOM     70  C   ILE A  13      -1.545   1.200  27.901  1.00 16.56           B  C
ATOM     71  O   ILE A  13      -1.842   0.059  27.452  1.00 17.50           B  O
ATOM     72  N   VAL A  14      -0.549   1.935  27.460  1.00 16.23           B  N
ATOM     73  CA  VAL A  14       0.422   1.423  26.463  1.00 15.88           B  C
ATOM     74  CB  VAL A  14       0.582   2.317  25.197  1.00 17.37           B  C
ATOM     75  CG1 VAL A  14       1.539   1.672  24.222  1.00 18.75           B  C
ATOM     76  CG2 VAL A  14      -0.785   2.563  24.559  1.00 19.91           B  C
ATOM     77  C   VAL A  14       1.737   1.263  27.191  1.00 15.81           B  C
ATOM     78  O   VAL A  14       2.276   2.251  27.702  1.00 16.08           B  O
ATOM     79  N   SER A  15       2.230   0.034  27.316  1.00 15.17           B  N
ATOM     80  CA  SER A  15       3.406  -0.307  28.113  1.00 15.61           B  C
ATOM     81  CB  SER A  15       3.066  -1.425  29.120  1.00 16.35           B  C
ATOM     82  OG  SER A  15       4.156  -1.741  29.939  1.00 15.99           B  O
ATOM     83  C   SER A  15       4.533  -0.736  27.220  1.00 15.08           B  C
ATOM     84  O   SER A  15       4.323  -1.561  26.311  1.00 17.28           B  O
ATOM     85  N   ARG A  16       5.731  -0.334  27.529  1.00 14.56           B  N
ATOM     86  CA  ARG A  16       6.911  -1.048  27.041  1.00 14.68           B  C
ATOM     87  CB  ARG A  16       8.203  -0.278  27.290  1.00 15.67           B  C
ATOM     88  CG  ARG A  16       9.442  -0.922  26.702  1.00 16.66           B  C
ATOM     89  CD  ARG A  16      10.664  -0.091  26.884  1.00 16.63           B  C
ATOM     90  NE  ARG A  16      11.803  -0.788  26.309  1.00 16.62           B  N
ATOM     91  CZ  ARG A  16      13.033  -0.629  26.665  1.00 15.92           B  C
ATOM     92  NH1 ARG A  16      13.388   0.330  27.493  1.00 16.70           B  N
ATOM     93  NH2 ARG A  16      13.980  -1.407  26.135  1.00 20.39           B  N
ATOM     94  C   ARG A  16       6.934  -2.426  27.748  1.00 14.45           B  C
ATOM     95  O   ARG A  16       6.635  -2.543  28.943  1.00 14.95           B  O
ATOM     96  N   HIS A  17       7.540  -3.393  27.071  1.00 14.74           B  N
ATOM     97  CA  HIS A  17       7.969  -4.639  27.745  1.00 14.90           B  C
ATOM     98  CB  HIS A  17       8.576  -5.599  26.718  1.00 15.61           B  C
ATOM     99  CG  HIS A  17       9.720  -4.978  26.046  1.00 15.93           B  C
ATOM    100  ND1 HIS A  17      10.930  -4.813  26.637  1.00 17.27           B  N
ATOM    101  CE1 HIS A  17      11.758  -4.206  25.769  1.00 18.76           B  C
ATOM    102  NE2 HIS A  17      11.128  -3.959  24.669  1.00 19.69           B  N
ATOM    103  CD2 HIS A  17       9.832  -4.449  24.810  1.00 16.08           B  C
ATOM    104  C   HIS A  17       8.906  -4.318  28.894  1.00 15.53           B  C
ATOM    105  O   HIS A  17       9.562  -3.277  28.974  1.00 14.28           B  O
ATOM    106  N   GLY A  18       9.019  -5.301  29.783  1.00 14.08           B  N
ATOM    107  CA  GLY A  18       9.873  -5.191  30.954  1.00 13.96           B  C
ATOM    108  C   GLY A  18      11.332  -5.453  30.665  1.00 13.89           B  C
ATOM    109  O   GLY A  18      11.784  -5.562  29.506  1.00 14.62           B  O
ATOM    110  N   VAL A  19      12.148  -5.511  31.720  1.00 14.53           B  N
ATOM    111  CA  VAL A  19      13.595  -5.714  31.643  1.00 15.25           B  C
ATOM    112  CB  VAL A  19      14.250  -5.731  33.023  1.00 15.83           B  C
ATOM    113  CG1 VAL A  19      15.707  -6.047  32.946  1.00 17.22           B  C
ATOM    114  CG2 VAL A  19      14.028  -4.392  33.772  1.00 15.90           B  C
```

Fig. 5B

```
ATOM    115  C    VAL A  19      13.916  -7.007  30.899  1.00 15.60           B  C
ATOM    116  O    VAL A  19      13.268  -8.049  31.160  1.00 17.21           B  O
ATOM    117  N    ARG A  20      14.741  -6.895  29.908  1.00 16.25           B  N
ATOM    118  CA   ARG A  20      15.075  -7.992  28.990  1.00 16.35           B  C
ATOM    119  CB   ARG A  20      14.507  -7.758  27.614  1.00 16.57           B  C
ATOM    120  CG   ARG A  20      14.819  -6.374  26.998  1.00 16.66           B  C
ATOM    121  CD   ARG A  20      14.617  -6.414  25.480  1.00 19.04           B  C
ATOM    122  NE   ARG A  20      14.860  -5.097  24.854  1.00 19.16           B  N
ATOM    123  CZ   ARG A  20      16.027  -4.615  24.641  1.00 18.99           B  C
ATOM    124  NH1  ARG A  20      17.148  -5.249  24.926  1.00 19.07           B  N
ATOM    125  NH2  ARG A  20      16.146  -3.372  24.105  1.00 21.69           B  N
ATOM    126  C    ARG A  20      16.583  -8.038  28.821  1.00 16.05           B  C
ATOM    127  O    ARG A  20      17.310  -7.034  29.024  1.00 16.77           B  O
ATOM    128  N    ALA A  21      17.092  -9.170  28.339  1.00 15.89           B  N
ATOM    129  CA   ALA A  21      18.458  -9.253  27.859  1.00 15.60           B  C
ATOM    130  CB   ALA A  21      18.759 -10.726  27.533  1.00 17.00           B  C
ATOM    131  C    ALA A  21      18.630  -8.375  26.595  1.00 17.00           B  C
ATOM    132  O    ALA A  21      17.649  -8.062  25.921  1.00 17.14           B  O
ATOM    133  N    PRO A  22      19.864  -8.026  26.247  1.00 17.23           B  N
ATOM    134  CA   PRO A  22      20.146  -7.295  25.023  1.00 18.58           B  C
ATOM    135  CB   PRO A  22      21.680  -7.185  24.971  1.00 18.95           B  C
ATOM    136  CG   PRO A  22      22.075  -7.281  26.419  1.00 18.80           B  C
ATOM    137  CD   PRO A  22      21.098  -8.331  26.954  1.00 18.02           B  C
ATOM    138  C    PRO A  22      19.569  -7.995  23.801  1.00 20.33           B  C
ATOM    139  O    PRO A  22      19.505  -9.213  23.776  1.00 18.82           B  O
ATOM    140  N    THR A  23      19.178  -7.250  22.768  1.00 20.99           B  N
ATOM    141  CA   THR A  23      18.518  -7.856  21.582  1.00 22.36           B  C
ATOM    142  CB   THR A  23      17.684  -6.859  20.769  1.00 22.97           B  C
ATOM    143  OG1  THR A  23      18.565  -5.833  20.322  1.00 25.18           B  O
ATOM    144  CG2  THR A  23      16.515  -6.286  21.551  1.00 24.95           B  C
ATOM    145  C    THR A  23      19.576  -8.494  20.702  1.00 22.21           B  C
ATOM    146  O    THR A  23      19.152  -9.283  19.860  1.00 26.58           B  O
ATOM    147  N    LYS A  24      20.826  -8.115  20.825  1.00 21.87           B  N
ATOM    148  CA   LYS A  24      21.876  -8.622  19.910  1.00 23.70           B  C
ATOM    149  CB   LYS A  24      21.882  -7.792  18.622  1.00 27.07           B  C
ATOM    150  CG   LYS A  24      22.186  -6.325  18.832  1.00 30.11           B  C
ATOM    151  CD   LYS A  24      21.989  -5.525  17.561  1.00 34.66           B  C
ATOM    152  CE   LYS A  24      22.162  -4.044  17.776  1.00 34.80           B  C
ATOM    153  NZ   LYS A  24      21.752  -3.303  16.556  1.00 39.07           B  N
ATOM    154  C    LYS A  24      23.241  -8.575  20.572  1.00 23.69           B  C
ATOM    155  O    LYS A  24      23.442  -7.871  21.598  1.00 22.64           B  O
ATOM    156  N    PHE A  25      24.188  -9.324  20.020  1.00 24.37           B  N
ATOM    157  CA   PHE A  25      25.603  -9.308  20.429  1.00 22.97           B  C
ATOM    158  CB   PHE A  25      25.931 -10.434  21.427  1.00 25.44           B  C
ATOM    159  CG   PHE A  25      27.337 -10.356  21.933  1.00 27.34           B  C
ATOM    160  CD1  PHE A  25      27.718  -9.316  22.762  1.00 29.83           B  C
ATOM    161  CE1  PHE A  25      29.013  -9.234  23.249  1.00 32.40           B  C
ATOM    162  CZ   PHE A  25      29.931 -10.171  22.887  1.00 35.48           B  C
ATOM    163  CD2  PHE A  25      28.278 -11.305  21.578  1.00 33.41           B  C
ATOM    164  CE2  PHE A  25      29.577 -11.206  22.049  1.00 35.46           B  C
ATOM    165  C    PHE A  25      26.434  -9.377  19.159  1.00 25.61           B  C
ATOM    166  O    PHE A  25      26.583 -10.467  18.566  1.00 26.75           B  O
ATOM    167  N    THR A  26      26.977  -8.242  18.740  1.00 23.17           B  N
ATOM    168  CA   THR A  26      27.574  -8.098  17.397  1.00 26.89           B  C
ATOM    169  CB   THR A  26      26.839  -7.038  16.587  1.00 29.04           B  C
ATOM    170  OG1  THR A  26      27.096  -5.849  17.332  1.00 28.58           B  O
ATOM    171  CG2  THR A  26      25.380  -7.325  16.407  1.00 28.03           B  C
ATOM    172  C    THR A  26      29.064  -7.816  17.504  1.00 25.69           B  C
```

Fig. 5C

```
ATOM    173  O    THR A  26      29.612  -7.437  18.539  1.00 25.41           B    O
ATOM    174  N    PRO A  27      29.797  -8.109  16.406  1.00 26.53           B    N
ATOM    175  CA   PRO A  27      31.226  -7.869  16.414  1.00 26.08           B    C
ATOM    176  CB   PRO A  27      31.661  -8.277  14.991  1.00 30.49           B    C
ATOM    177  CG   PRO A  27      30.599  -9.276  14.532  1.00 31.98           B    C
ATOM    178  CD   PRO A  27      29.313  -8.822  15.196  1.00 32.47           B    C
ATOM    179  C    PRO A  27      31.640  -6.420  16.738  1.00 25.60           B    C
ATOM    180  O    PRO A  27      32.561  -6.271  17.485  1.00 26.19           B    O
ATOM    181  N    ILE A  28      30.849  -5.464  16.276  1.00 26.52           B    N
ATOM    182  CA   ILE A  28      31.164  -4.032  16.546  1.00 26.94           B    C
ATOM    183  CB   ILE A  28      30.303  -3.111  15.704  1.00 27.80           B    C
ATOM    184  CG1  ILE A  28      30.893  -1.705  15.669  1.00 32.28           B    C
ATOM    185  CG2  ILE A  28      28.869  -3.094  16.210  1.00 30.45           B    C
ATOM    186  CD1  ILE A  28      30.091  -0.793  14.792  1.00 42.98           B    C
ATOM    187  C    ILE A  28      31.082  -3.761  18.053  1.00 28.88           B    C
ATOM    188  O    ILE A  28      31.929  -3.045  18.576  1.00 26.61           B    O
ATOM    189  N    MET A  29      30.208  -4.459  18.794  1.00 26.83           B    N
ATOM    190  CA   MET A  29      30.136  -4.286  20.259  1.00 25.03           B    C
ATOM    191  CB   MET A  29      28.940  -5.059  20.802  1.00 23.41           B    C
ATOM    192  CG   MET A  29      27.661  -4.579  20.269  1.00 23.89           B    C
ATOM    193  SD   MET A  29      26.244  -5.532  20.857  1.00 27.71           B    S
ATOM    194  CE   MET A  29      26.623  -5.693  22.569  1.00 30.96           B    C
ATOM    195  C    MET A  29      31.424  -4.707  20.955  1.00 25.76           B    C
ATOM    196  O    MET A  29      31.846  -4.123  21.980  1.00 26.76           B    O
ATOM    197  N    LYS A  30      32.074  -5.768  20.452  1.00 27.82           B    N
ATOM    198  CA   LYS A  30      33.391  -6.173  20.963  1.00 28.23           B    C
ATOM    199  CB   LYS A  30      33.675  -7.614  20.491  1.00 31.57           B    C
ATOM    200  CG   LYS A  30      32.707  -8.624  21.084  1.00 34.50           B    C
ATOM    201  CD   LYS A  30      33.123 -10.057  20.838  1.00 40.02           B    C
ATOM    202  CE   LYS A  30      32.654 -10.562  19.501  1.00 45.94           B    C
ATOM    203  NZ   LYS A  30      33.387 -11.802  19.146  1.00 49.41           B    N
ATOM    204  C    LYS A  30      34.508  -5.248  20.461  1.00 24.44           B    C
ATOM    205  O    LYS A  30      35.471  -5.097  21.158  1.00 27.36           B    O
ATOM    206  N    CYS A  31      34.370  -4.718  19.262  1.00 25.71           B    N
ATOM    207  CA   CYS A  31      35.395  -3.865  18.601  1.00 27.49           B    C
ATOM    208  CB   CYS A  31      35.014  -3.626  17.150  1.00 27.39           B    C
ATOM    209  SG   CYS A  31      36.380  -2.880  16.206  1.00 36.07           B    S
ATOM    210  C    CYS A  31      35.566  -2.541  19.385  1.00 25.80           B    C
ATOM    211  O    CYS A  31      36.656  -2.055  19.433  1.00 26.84           B    O
ATOM    212  N    VAL A  32      34.538  -2.053  20.103  1.00 24.70           B    N
ATOM    213  CA   VAL A  32      34.583  -0.643  20.638  1.00 23.41           B    C
ATOM    214  CB   VAL A  32      33.256   0.091  20.365  1.00 21.28           B    C
ATOM    215  CG1  VAL A  32      32.959   0.271  18.900  1.00 22.24           B    C
ATOM    216  CG2  VAL A  32      32.108  -0.621  21.091  1.00 22.78           B    C
ATOM    217  C    VAL A  32      34.962  -0.634  22.101  1.00 21.84           B    C
ATOM    218  O    VAL A  32      35.055   0.467  22.708  1.00 24.38           B    O
ATOM    219  N    THR A  33      35.295  -1.778  22.720  1.00 21.94           B    N
ATOM    220  CA   THR A  33      35.765  -1.885  24.105  1.00 20.84           B    C
ATOM    221  CB   THR A  33      34.609  -2.094  25.106  1.00 23.14           B    C
ATOM    222  OG1  THR A  33      35.161  -2.147  26.414  1.00 20.93           B    O
ATOM    223  CG2  THR A  33      33.735  -3.307  24.788  1.00 23.76           B    C
ATOM    224  C    THR A  33      36.781  -3.016  24.231  1.00 24.68           B    C
ATOM    225  O    THR A  33      36.575  -4.086  23.651  1.00 24.71           B    O
ATOM    226  N    PRO A  34      37.848  -2.811  25.003  1.00 24.49           B    N
ATOM    227  CA   PRO A  34      38.800  -3.891  25.300  1.00 26.16           B    C
ATOM    228  CB   PRO A  34      39.988  -3.189  25.925  1.00 28.59           B    C
ATOM    229  CG   PRO A  34      39.419  -1.904  26.503  1.00 25.40           B    C
ATOM    230  CD   PRO A  34      38.332  -1.517  25.520  1.00 25.83           B    C
```

Fig. 5D

```
ATOM    231  C   PRO A  34      38.225  -4.871  26.315  1.00 28.57           B  C
ATOM    232  O   PRO A  34      38.700  -5.994  26.374  1.00 28.67           B  O
ATOM    233  N   ASP A  35      37.155  -4.494  26.996  1.00 25.86           B  N
ATOM    234  CA  ASP A  35      36.575  -5.243  28.115  1.00 26.24           B  C
ATOM    235  CB  ASP A  35      36.077  -4.252  29.181  1.00 28.35           B  C
ATOM    236  CG  ASP A  35      37.219  -3.446  29.775  1.00 33.11           B  C
ATOM    237  OD1 ASP A  35      38.228  -4.086  30.163  1.00 37.82           B  O
ATOM    238  OD2 ASP A  35      37.179  -2.209  29.696  1.00 32.82           B  O
ATOM    239  C   ASP A  35      35.479  -6.204  27.618  1.00 20.75           B  C
ATOM    240  O   ASP A  35      35.085  -6.179  26.443  1.00 25.38           B  O
ATOM    241  N   GLN A  36      35.105  -7.098  28.533  1.00 23.58           B  N
ATOM    242  CA  GLN A  36      34.182  -8.213  28.236  1.00 22.81           B  C
ATOM    243  CB  GLN A  36      34.627  -9.493  28.954  1.00 26.53           B  C
ATOM    244  CG  GLN A  36      36.088  -9.876  28.720  1.00 28.33           B  C
ATOM    245  CD  GLN A  36      36.406 -10.038  27.255  1.00 26.87           B  C
ATOM    246  OE1 GLN A  36      35.655 -10.590  26.455  1.00 32.61           B  O
ATOM    247  NE2 GLN A  36      37.508  -9.396  26.865  1.00 31.19           B  N
ATOM    248  C   GLN A  36      32.743  -7.870  28.654  1.00 19.61           B  C
ATOM    249  O   GLN A  36      32.544  -7.464  29.842  1.00 23.42           B  O
ATOM    250  N   TRP A  37      31.823  -8.070  27.759  1.00 20.37           B  N
ATOM    251  CA  TRP A  37      30.409  -7.831  28.094  1.00 21.36           B  C
ATOM    252  CB  TRP A  37      29.601  -7.755  26.835  1.00 20.66           B  C
ATOM    253  CG  TRP A  37      29.923  -6.532  26.021  1.00 21.31           B  C
ATOM    254  CD1 TRP A  37      30.803  -6.429  24.992  1.00 23.78           B  C
ATOM    255  NE1 TRP A  37      30.820  -5.144  24.495  1.00 23.75           B  N
ATOM    256  CE2 TRP A  37      29.905  -4.400  25.202  1.00 21.99           B  C
ATOM    257  CD2 TRP A  37      29.316  -5.229  26.175  1.00 22.24           B  C
ATOM    258  CE3 TRP A  37      28.360  -4.710  27.052  1.00 20.49           B  C
ATOM    259  CZ3 TRP A  37      27.998  -3.375  26.918  1.00 21.26           B  C
ATOM    260  CH2 TRP A  37      28.570  -2.579  25.932  1.00 22.38           B  C
ATOM    261  CZ2 TRP A  37      29.553  -3.057  25.083  1.00 22.90           B  C
ATOM    262  C   TRP A  37      29.906  -8.930  29.028  1.00 22.60           B  C
ATOM    263  O   TRP A  37      30.127 -10.124  28.775  1.00 23.43           B  O
ATOM    264  N   PRO A  38      29.196  -8.627  30.095  1.00 20.66           B  N
ATOM    265  CA  PRO A  38      28.585  -9.648  30.957  1.00 21.26           B  C
ATOM    266  CB  PRO A  38      27.999  -8.921  32.142  1.00 25.92           B  C
ATOM    267  CG  PRO A  38      28.203  -7.457  31.862  1.00 24.54           B  C
ATOM    268  CD  PRO A  38      28.919  -7.255  30.558  1.00 20.67           B  C
ATOM    269  C   PRO A  38      27.460 -10.348  30.207  1.00 20.37           B  C
ATOM    270  O   PRO A  38      26.839  -9.828  29.321  1.00 20.30           B  O
ATOM    271  N   GLN A  39      27.300 -11.644  30.510  1.00 20.17           B  N
ATOM    272  CA  GLN A  39      26.372 -12.555  29.824  1.00 19.07           B  C
ATOM    273  CB  GLN A  39      27.073 -13.885  29.565  1.00 21.09           B  C
ATOM    274  CG  GLN A  39      28.274 -13.651  28.636  1.00 22.15           B  C
ATOM    275  CD  GLN A  39      29.181 -14.831  28.419  1.00 25.54           B  C
ATOM    276  OE1 GLN A  39      29.475 -15.596  29.340  1.00 23.06           B  O
ATOM    277  NE2 GLN A  39      29.648 -14.928  27.189  1.00 26.55           B  N
ATOM    278  C   GLN A  39      25.117 -12.754  30.651  1.00 15.99           B  C
ATOM    279  O   GLN A  39      25.179 -12.680  31.893  1.00 18.63           B  O
ATOM    280  N   TRP A  40      24.003 -12.978  29.977  1.00 19.06           B  N
ATOM    281  CA  TRP A  40      22.658 -13.084  30.573  1.00 17.57           B  C
ATOM    282  CB  TRP A  40      21.644 -12.213  29.812  1.00 18.88           B  C
ATOM    283  CG  TRP A  40      21.962 -10.734  29.850  1.00 16.98           B  C
ATOM    284  CD1 TRP A  40      23.067 -10.111  29.377  1.00 18.54           B  C
ATOM    285  NE1 TRP A  40      22.998  -8.751  29.662  1.00 18.15           B  N
ATOM    286  CE2 TRP A  40      21.829  -8.518  30.303  1.00 18.74           B  C
ATOM    287  CD2 TRP A  40      21.138  -9.744  30.487  1.00 17.90           B  C
ATOM    288  CE3 TRP A  40      19.873  -9.760  31.071  1.00 17.60           B  C
```

Fig. 5E

```
ATOM    289  CZ3 TRP A  40      19.360  -8.568  31.546  1.00 18.65      B    C
ATOM    290  CH2 TRP A  40      20.060  -7.365  31.366  1.00 18.29      B    C
ATOM    291  CZ2 TRP A  40      21.284  -7.308  30.758  1.00 18.10      B    C
ATOM    292  C   TRP A  40      22.259 -14.577  30.625  1.00 19.04      B    C
ATOM    293  O   TRP A  40      22.963 -15.436  30.006  1.00 21.88      B    O
ATOM    294  N  AASP A  41      21.205 -14.923  31.320  0.50 17.59      B    N
ATOM    295  N  BASP A  41      21.155 -14.849  31.296  0.50 18.21      B    N
ATOM    296  CA AASP A  41      20.829 -16.367  31.404  0.50 17.73      B    C
ATOM    297  CA BASP A  41      20.673 -16.216  31.654  0.50 19.92      B    C
ATOM    298  CB AASP A  41      20.989 -16.929  32.821  0.50 19.22      B    C
ATOM    299  CB BASP A  41      20.436 -16.277  33.169  0.50 20.61      B    C
ATOM    300  CG AASP A  41      20.033 -16.304  33.815  0.50 20.61      B    C
ATOM    301  CG BASP A  41      21.708 -16.081  33.984  0.50 23.80      B    C
ATOM    302  OD1AASP A  41      19.087 -15.599  33.384  0.50 19.46      B    O
ATOM    303  OD1BASP A  41      22.652 -16.895  33.835  0.50 27.27      B    O
ATOM    304  OD2AASP A  41      20.207 -16.594  35.035  0.50 24.45      B    O
ATOM    305  OD2BASP A  41      21.780 -15.065  34.712  0.50 27.66      B    O
ATOM    306  C  AASP A  41      19.424 -16.566  30.816  0.50 18.97      B    C
ATOM    307  C  BASP A  41      19.412 -16.550  30.837  0.50 19.77      B    C
ATOM    308  O  AASP A  41      18.738 -17.570  31.143  0.50 19.47      B    O
ATOM    309  O  BASP A  41      18.799 -17.615  31.055  0.50 20.48      B    O
ATOM    310  N   VAL A  42      18.998 -15.687  29.903  1.00 17.64      B    N
ATOM    311  CA  VAL A  42      17.844 -15.891  29.031  1.00 16.66      B    C
ATOM    312  CB  VAL A  42      16.620 -15.038  29.443  1.00 17.15      B    C
ATOM    313  CG1 VAL A  42      16.120 -15.331  30.816  1.00 18.26      B    C
ATOM    314  CG2 VAL A  42      16.933 -13.567  29.282  1.00 18.80      B    C
ATOM    315  C   VAL A  42      18.274 -15.611  27.609  1.00 16.53      B    C
ATOM    316  O   VAL A  42      19.296 -14.955  27.387  1.00 19.14      B    O
ATOM    317  N   PRO A  43      17.522 -16.024  26.583  1.00 17.55      B    N
ATOM    318  CA  PRO A  43      17.873 -15.691  25.226  1.00 17.88      B    C
ATOM    319  CB  PRO A  43      16.753 -16.336  24.386  1.00 19.72      B    C
ATOM    320  CG  PRO A  43      16.205 -17.446  25.272  1.00 19.88      B    C
ATOM    321  CD  PRO A  43      16.348 -16.876  26.676  1.00 18.61      B    C
ATOM    322  C   PRO A  43      17.903 -14.163  24.943  1.00 18.81      B    C
ATOM    323  O   PRO A  43      17.237 -13.397  25.622  1.00 18.70      B    O
ATOM    324  N   LEU A  44      18.718 -13.806  23.979  1.00 18.24      B    N
ATOM    325  CA  LEU A  44      18.801 -12.389  23.613  1.00 18.85      B    C
ATOM    326  CB  LEU A  44      19.754 -12.232  22.435  1.00 21.23      B    C
ATOM    327  CG  LEU A  44      21.230 -12.554  22.646  1.00 22.61      B    C
ATOM    328  CD1 LEU A  44      21.992 -12.304  21.380  1.00 27.29      B    C
ATOM    329  CD2 LEU A  44      21.872 -11.777  23.769  1.00 27.76      B    C
ATOM    330  C   LEU A  44      17.416 -11.873  23.299  1.00 19.06      B    C
ATOM    331  O   LEU A  44      16.596 -12.535  22.640  1.00 19.24      B    O
ATOM    332  N   GLY A  45      17.110 -10.688  23.844  1.00 18.13      B    N
ATOM    333  CA  GLY A  45      15.817 -10.059  23.573  1.00 18.68      B    C
ATOM    334  C   GLY A  45      14.687 -10.554  24.433  1.00 18.44      B    C
ATOM    335  O   GLY A  45      13.563 -10.058  24.227  1.00 19.91      B    O
ATOM    336  N   TRP A  46      14.919 -11.519  25.331  1.00 17.62      B    N
ATOM    337  CA  TRP A  46      13.831 -12.056  26.159  1.00 16.62      B    C
ATOM    338  CB  TRP A  46      14.025 -13.573  26.348  1.00 16.16      B    C
ATOM    339  CG  TRP A  46      13.627 -14.369  25.152  1.00 17.80      B    C
ATOM    340  CD1 TRP A  46      13.786 -14.064  23.833  1.00 20.29      B    C
ATOM    341  NE1 TRP A  46      13.251 -15.058  23.047  1.00 20.67      B    N
ATOM    342  CE2 TRP A  46      12.723 -16.029  23.857  1.00 18.66      B    C
ATOM    343  CD2 TRP A  46      12.981 -15.672  25.197  1.00 17.30      B    C
ATOM    344  CE3 TRP A  46      12.527 -16.462  26.250  1.00 17.10      B    C
ATOM    345  CZ3 TRP A  46      11.905 -17.655  25.941  1.00 20.68      B    C
ATOM    346  CH2 TRP A  46      11.679 -18.009  24.626  1.00 19.78      B    C
```

Fig. 5F

```
ATOM    347  CZ2  TRP A  46      12.073 -17.238  23.559  1.00 19.41           B    C
ATOM    348  C    TRP A  46      13.710 -11.337  27.497  1.00 15.65           B    C
ATOM    349  O    TRP A  46      14.695 -10.956  28.080  1.00 16.90           B    O
ATOM    350  N    LEU A  47      12.471 -11.222  27.947  1.00 15.26           B    N
ATOM    351  CA   LEU A  47      12.126 -10.759  29.269  1.00 15.54           B    C
ATOM    352  CB   LEU A  47      10.617 -10.746  29.493  1.00 17.70           B    C
ATOM    353  CG   LEU A  47      10.096 -10.088  30.739  1.00 15.87           B    C
ATOM    354  CD1  LEU A  47      10.141  -8.559  30.616  1.00 18.79           B    C
ATOM    355  CD2  LEU A  47       8.703 -10.472  31.005  1.00 18.46           B    C
ATOM    356  C    LEU A  47      12.805 -11.641  30.278  1.00 16.65           B    C
ATOM    357  O    LEU A  47      12.748 -12.893  30.105  1.00 17.97           B    O
ATOM    358  N    THR A  48      13.434 -11.118  31.304  1.00 16.61           B    N
ATOM    359  CA   THR A  48      13.995 -11.924  32.401  1.00 15.66           B    C
ATOM    360  CB   THR A  48      15.213 -11.277  33.044  1.00 17.09           B    C
ATOM    361  OG1  THR A  48      14.761 -10.095  33.724  1.00 16.93           B    O
ATOM    362  CG2  THR A  48      16.296 -10.976  32.064  1.00 17.68           B    C
ATOM    363  C    THR A  48      12.949 -12.160  33.466  1.00 16.56           B    C
ATOM    364  O    THR A  48      11.942 -11.478  33.594  1.00 16.09           B    O
ATOM    365  N    PRO A  49      13.113 -13.208  34.325  1.00 17.34           B    N
ATOM    366  CA   PRO A  49      12.226 -13.319  35.475  1.00 16.97           B    C
ATOM    367  CB   PRO A  49      12.788 -14.563  36.203  1.00 18.35           B    C
ATOM    368  CG   PRO A  49      13.364 -15.359  35.078  1.00 19.48           B    C
ATOM    369  CD   PRO A  49      14.010 -14.375  34.112  1.00 18.77           B    C
ATOM    370  C    PRO A  49      12.084 -12.089  36.377  1.00 16.86           B    C
ATOM    371  O    PRO A  49      11.000 -11.808  36.763  1.00 17.49           B    O
ATOM    372  N    ARG A  50      13.216 -11.449  36.629  1.00 17.63           B    N
ATOM    373  CA   ARG A  50      13.156 -10.200  37.402  1.00 17.95           B    C
ATOM    374  CB   ARG A  50      14.563  -9.697  37.626  1.00 20.13           B    C
ATOM    375  CG   ARG A  50      14.635  -8.287  38.151  1.00 30.72           B    C
ATOM    376  CD   ARG A  50      16.034  -8.328  38.694  1.00 41.58           B    C
ATOM    377  NE   ARG A  50      16.498  -7.060  39.146  1.00 48.22           B    N
ATOM    378  CZ   ARG A  50      17.231  -6.924  40.221  1.00 43.88           B    C
ATOM    379  NH1  ARG A  50      17.559  -7.967  40.999  1.00 40.29           B    N
ATOM    380  NH2  ARG A  50      17.620  -5.717  40.493  1.00 42.38           B    N
ATOM    381  C    ARG A  50      12.325  -9.161  36.636  1.00 16.26           B    C
ATOM    382  O    ARG A  50      11.512  -8.494  37.271  1.00 19.14           B    O
ATOM    383  N    GLY A  51      12.505  -9.104  35.321  1.00 16.05           B    N
ATOM    384  CA   GLY A  51      11.681  -8.207  34.472  1.00 16.34           B    C
ATOM    385  C    GLY A  51      10.212  -8.505  34.635  1.00 15.03           B    C
ATOM    386  O    GLY A  51       9.380  -7.612  34.786  1.00 16.76           B    O
ATOM    387  N    CYS A  52       9.871  -9.805  34.667  1.00 15.20           B    N
ATOM    388  CA   CYS A  52       8.498 -10.217  34.877  1.00 16.41           B    C
ATOM    389  CB   CYS A  52       8.428 -11.752  34.765  1.00 16.79           B    C
ATOM    390  SG   CYS A  52       6.804 -12.503  35.066  1.00 18.95           B    S
ATOM    391  C    CYS A  52       7.990  -9.757  36.262  1.00 16.30           B    C
ATOM    392  O    CYS A  52       6.858  -9.236  36.378  1.00 17.45           B    O
ATOM    393  N    GLU A  53       8.762 -10.013  37.324  1.00 16.82           B    N
ATOM    394  CA   GLU A  53       8.339  -9.612  38.666  1.00 17.81           B    C
ATOM    395  CB   GLU A  53       9.396 -10.088  39.642  1.00 20.10           B    C
ATOM    396  CG   GLU A  53       9.032  -9.775  41.066  1.00 21.92           B    C
ATOM    397  CD   GLU A  53       9.972 -10.366  42.099  1.00 24.07           B    C
ATOM    398  OE1  GLU A  53      10.915 -11.018  41.718  1.00 26.05           B    O
ATOM    399  OE2  GLU A  53       9.670 -10.172  43.314  1.00 25.80           B    O
ATOM    400  C    GLU A  53       8.143  -8.072  38.693  1.00 16.18           B    C
ATOM    401  O    GLU A  53       7.173  -7.659  39.293  1.00 17.52           B    O
ATOM    402  N    LEU A  54       9.088  -7.308  38.120  1.00 16.78           B    N
ATOM    403  CA   LEU A  54       8.945  -5.829  38.146  1.00 16.79           B    C
ATOM    404  CB   LEU A  54      10.184  -5.225  37.510  1.00 16.62           B    C
```

Fig. 5G

```
ATOM    405  CG  LEU A  54      11.445  -5.266  38.358  1.00 17.80      B    C
ATOM    406  CD1 LEU A  54      12.632  -4.863  37.535  1.00 18.18      B    C
ATOM    407  CD2 LEU A  54      11.255  -4.338  39.590  1.00 18.09      B    C
ATOM    408  C   LEU A  54       7.657  -5.389  37.461  1.00 17.06      B    C
ATOM    409  O   LEU A  54       6.956  -4.500  37.928  1.00 18.24      B    O
ATOM    410  N   VAL A  55       7.339  -6.039  36.334  1.00 15.71      B    N
ATOM    411  CA  VAL A  55       6.057  -5.721  35.673  1.00 16.60      B    C
ATOM    412  CB  VAL A  55       5.942  -6.342  34.261  1.00 17.49      B    C
ATOM    413  CG1 VAL A  55       4.554  -6.257  33.710  1.00 17.74      B    C
ATOM    414  CG2 VAL A  55       7.001  -5.736  33.331  1.00 17.97      B    C
ATOM    415  C   VAL A  55       4.888  -6.100  36.574  1.00 16.61      B    C
ATOM    416  O   VAL A  55       3.827  -5.435  36.661  1.00 16.79      B    O
ATOM    417  N   SER A  56       4.961  -7.294  37.190  1.00 17.39      B    N
ATOM    418  CA  SER A  56       3.884  -7.707  38.111  1.00 18.81      B    C
ATOM    419  CB  SER A  56       4.158  -9.128  38.606  1.00 19.13      B    C
ATOM    420  OG  SER A  56       5.058  -9.136  39.699  1.00 23.71      B    O
ATOM    421  C   SER A  56       3.691  -6.707  39.272  1.00 17.17      B    C
ATOM    422  O   SER A  56       2.560  -6.507  39.669  1.00 18.06      B    O
ATOM    423  N   TYR A  57       4.755  -6.072  39.730  1.00 18.44      B    N
ATOM    424  CA  TYR A  57       4.630  -5.015  40.756  1.00 18.13      B    C
ATOM    425  CB  TYR A  57       5.967  -4.535  41.255  1.00 20.27      B    C
ATOM    426  CG  TYR A  57       6.715  -5.500  42.143  1.00 22.90      B    C
ATOM    427  CD1 TYR A  57       6.235  -6.748  42.450  1.00 24.55      B    C
ATOM    428  CE1 TYR A  57       6.938  -7.602  43.291  1.00 30.29      B    C
ATOM    429  CZ  TYR A  57       8.139  -7.201  43.804  1.00 31.54      B    C
ATOM    430  OH  TYR A  57       8.794  -8.089  44.623  1.00 36.51      B    O
ATOM    431  CE2 TYR A  57       8.651  -5.953  43.497  1.00 36.25      B    C
ATOM    432  CD2 TYR A  57       7.951  -5.136  42.624  1.00 31.24      B    C
ATOM    433  C   TYR A  57       3.845  -3.816  40.223  1.00 19.16      B    C
ATOM    434  O   TYR A  57       3.036  -3.271  40.960  1.00 20.24      B    O
ATOM    435  N   LEU A  58       4.027  -3.464  38.945  1.00 18.49      B    N
ATOM    436  CA  LEU A  58       3.172  -2.392  38.337  1.00 17.29      B    C
ATOM    437  CB  LEU A  58       3.699  -1.990  36.948  1.00 18.17      B    C
ATOM    438  CG  LEU A  58       5.021  -1.266  37.046  1.00 19.32      B    C
ATOM    439  CD1 LEU A  58       5.622  -1.089  35.651  1.00 19.59      B    C
ATOM    440  CD2 LEU A  58       4.828   0.087  37.692  1.00 21.94      B    C
ATOM    441  C   LEU A  58       1.754  -2.857  38.242  1.00 16.92      B    C
ATOM    442  O   LEU A  58       0.817  -2.101  38.462  1.00 18.27      B    O
ATOM    443  N   GLY A  59       1.523  -4.147  37.937  1.00 17.46      B    N
ATOM    444  CA  GLY A  59       0.168  -4.664  37.943  1.00 17.46      B    C
ATOM    445  C   GLY A  59      -0.472  -4.612  39.339  1.00 17.89      B    C
ATOM    446  O   GLY A  59      -1.670  -4.258  39.424  1.00 18.79      B    O
ATOM    447  N   GLN A  60       0.284  -4.956  40.365  1.00 19.51      B    N
ATOM    448  CA  GLN A  60      -0.236  -4.871  41.769  1.00 20.97      B    C
ATOM    449  CB  GLN A  60       0.800  -5.426  42.750  1.00 23.82      B    C
ATOM    450  CG  GLN A  60       0.973  -6.932  42.636  1.00 23.63      B    C
ATOM    451  CD  GLN A  60       1.900  -7.508  43.686  1.00 33.66      B    C
ATOM    452  OE1 GLN A  60       3.066  -7.164  43.788  1.00 34.90      B    O
ATOM    453  NE2 GLN A  60       1.379  -8.456  44.431  1.00 40.19      B    N
ATOM    454  C   GLN A  60      -0.524  -3.406  42.121  1.00 21.60      B    C
ATOM    455  O   GLN A  60      -1.627  -3.115  42.662  1.00 23.62      B    O
ATOM    456  N   TYR A  61       0.350  -2.478  41.765  1.00 20.93      B    N
ATOM    457  CA  TYR A  61       0.162  -1.033  42.014  1.00 22.73      B    C
ATOM    458  CB  TYR A  61       1.402  -0.251  41.584  1.00 22.35      B    C
ATOM    459  CG  TYR A  61       1.154   1.234  41.533  1.00 24.65      B    C
ATOM    460  CD1 TYR A  61       1.121   1.946  42.730  1.00 27.76      B    C
ATOM    461  CE1 TYR A  61       0.780   3.294  42.749  1.00 31.75      B    C
ATOM    462  CZ  TYR A  61       0.484   3.930  41.558  1.00 30.83      B    C
```

Fig. 5H

```
ATOM    463  OH   TYR A  61       0.187   5.268  41.588  1.00 41.60      B   O
ATOM    464  CE2  TYR A  61       0.503   3.246  40.361  1.00 30.22      B   C
ATOM    465  CD2  TYR A  61       0.793   1.888  40.359  1.00 27.07      B   C
ATOM    466  C    TYR A  61      -1.067  -0.520  41.280  1.00 22.70      B   C
ATOM    467  O    TYR A  61      -1.944   0.134  41.875  1.00 21.30      B   O
ATOM    468  N    GLN A  62      -1.250  -0.881  39.992  1.00 20.71      B   N
ATOM    469  CA   GLN A  62      -2.413  -0.431  39.207  1.00 21.72      B   C
ATOM    470  CB   GLN A  62      -2.220  -0.690  37.704  1.00 21.11      B   C
ATOM    471  CG   GLN A  62      -1.048   0.105  37.112  1.00 20.68      B   C
ATOM    472  CD   GLN A  62      -1.351   1.574  36.947  1.00 21.08      B   C
ATOM    473  OE1  GLN A  62      -2.182   2.159  37.660  1.00 23.84      B   O
ATOM    474  NE2  GLN A  62      -0.643   2.192  36.023  1.00 20.65      B   N
ATOM    475  C    GLN A  62      -3.714  -1.031  39.754  1.00 20.59      B   C
ATOM    476  O    GLN A  62      -4.736  -0.360  39.755  1.00 21.95      B   O
ATOM    477  N   AARG A  63      -3.695  -2.291  40.195  0.50 21.81      B   N
ATOM    478  N   BARG A  63      -3.677  -2.285  40.199  0.50 22.47      B   N
ATOM    479  CA  AARG A  63      -4.909  -2.901  40.795  0.50 21.02      B   C
ATOM    480  CA  BARG A  63      -4.882  -2.896  40.800  0.50 22.28      B   C
ATOM    481  CB  AARG A  63      -4.712  -4.392  41.113  0.50 21.51      B   C
ATOM    482  CB  BARG A  63      -4.659  -4.360  41.186  0.50 24.05      B   C
ATOM    483  CG  AARG A  63      -5.944  -5.083  41.706  0.50 22.20      B   C
ATOM    484  CG  BARG A  63      -5.882  -4.996  41.843  0.50 26.19      B   C
ATOM    485  CD  AARG A  63      -5.636  -6.456  42.313  0.50 26.21      B   C
ATOM    486  CD  BARG A  63      -7.134  -4.936  40.977  0.50 30.47      B   C
ATOM    487  NE  AARG A  63      -6.785  -7.169  42.855  0.50 32.01      B   N
ATOM    488  NE  BARG A  63      -8.036  -6.077  41.163  0.50 35.42      B   N
ATOM    489  CZ  AARG A  63      -7.682  -7.892  42.171  0.50 35.51      B   C
ATOM    490  CZ  BARG A  63      -9.231  -6.069  41.744  0.50 39.28      B   C
ATOM    491  NH1 AARG A  63      -7.705  -7.957  40.840  0.50 30.88      B   N
ATOM    492  NH1 BARG A  63      -9.902  -7.207  41.812  0.50 35.41      B   N
ATOM    493  NH2 AARG A  63      -8.625  -8.508  42.864  0.50 33.49      B   N
ATOM    494  NH2 BARG A  63      -9.746  -4.962  42.262  0.50 39.30      B   N
ATOM    495  C   AARG A  63      -5.278  -2.083  42.036  0.50 20.52      B   C
ATOM    496  C   BARG A  63      -5.273  -2.072  42.026  0.50 21.05      B   C
ATOM    497  O   AARG A  63      -6.461  -1.763  42.175  0.50 22.27      B   O
ATOM    498  O   BARG A  63      -6.463  -1.759  42.148  0.50 22.44      B   O
ATOM    499  N    LEU A  64      -4.330  -1.747  42.884  1.00 21.84      B   N
ATOM    500  CA   LEU A  64      -4.658  -0.947  44.098  1.00 23.30      B   C
ATOM    501  CB   LEU A  64      -3.434  -0.783  44.962  1.00 23.80      B   C
ATOM    502  CG   LEU A  64      -2.969  -2.075  45.620  1.00 28.58      B   C
ATOM    503  CD1  LEU A  64      -1.579  -1.882  46.166  1.00 30.76      B   C
ATOM    504  CD2  LEU A  64      -3.918  -2.487  46.753  1.00 30.73      B   C
ATOM    505  C    LEU A  64      -5.232   0.402  43.672  1.00 24.94      B   C
ATOM    506  O    LEU A  64      -6.281   0.833  44.208  1.00 26.72      B   O
ATOM    507  N    TRP A  65      -4.562   1.086  42.747  1.00 22.92      B   N
ATOM    508  CA   TRP A  65      -4.985   2.436  42.333  1.00 25.39      B   C
ATOM    509  CB   TRP A  65      -3.892   3.001  41.410  1.00 29.33      B   C
ATOM    510  CG   TRP A  65      -3.986   4.478  41.393  1.00 38.65      B   C
ATOM    511  CD1  TRP A  65      -3.687   5.351  42.402  1.00 43.02      B   C
ATOM    512  NE1  TRP A  65      -4.033   6.619  42.034  1.00 42.92      B   N
ATOM    513  CE2  TRP A  65      -4.544   6.583  40.769  1.00 43.76      B   C
ATOM    514  CD2  TRP A  65      -4.594   5.236  40.359  1.00 38.69      B   C
ATOM    515  CE3  TRP A  65      -5.052   4.908  39.092  1.00 37.01      B   C
ATOM    516  CZ3  TRP A  65      -5.530   5.922  38.313  1.00 40.01      B   C
ATOM    517  CH2  TRP A  65      -5.502   7.254  38.740  1.00 45.81      B   C
ATOM    518  CZ2  TRP A  65      -4.996   7.620  39.964  1.00 41.83      B   C
ATOM    519  C    TRP A  65      -6.367   2.363  41.688  1.00 24.46      B   C
ATOM    520  O    TRP A  65      -7.296   3.143  42.102  1.00 26.04      B   O
```

Fig. 5I

```
ATOM    521  N    PHE A  66      -6.577   1.511  40.685  1.00 22.90           B  N
ATOM    522  CA   PHE A  66      -7.840   1.405  39.946  1.00 25.27           B  C
ATOM    523  CB   PHE A  66      -7.736   0.472  38.731  1.00 27.18           B  C
ATOM    524  CG   PHE A  66      -6.792   0.958  37.658  1.00 29.82           B  C
ATOM    525  CD1  PHE A  66      -6.595   2.311  37.438  1.00 32.75           B  C
ATOM    526  CE1  PHE A  66      -5.700   2.755  36.470  1.00 36.97           B  C
ATOM    527  CZ   PHE A  66      -5.016   1.837  35.711  1.00 34.02           B  C
ATOM    528  CD2  PHE A  66      -6.091   0.042  36.890  1.00 32.84           B  C
ATOM    529  CE2  PHE A  66      -5.253   0.486  35.876  1.00 30.85           B  C
ATOM    530  C    PHE A  66      -8.953   1.005  40.916  1.00 27.84           B  C
ATOM    531  O    PHE A  66     -10.078   1.490  40.730  1.00 28.32           B  O
ATOM    532  N    THR A  67      -8.686   0.100  41.854  1.00 26.52           B  N
ATOM    533  CA   THR A  67      -9.711  -0.339  42.856  1.00 26.80           B  C
ATOM    534  CB   THR A  67      -9.244  -1.597  43.596  1.00 29.15           B  C
ATOM    535  OG1  THR A  67      -9.139  -2.638  42.618  1.00 33.08           B  O
ATOM    536  CG2  THR A  67     -10.242  -1.956  44.676  1.00 31.71           B  C
ATOM    537  C    THR A  67     -10.047   0.853  43.763  1.00 28.30           B  C
ATOM    538  O    THR A  67     -11.274   1.092  43.965  1.00 29.58           B  O
ATOM    539  N    SER A  68      -9.052   1.617  44.205  1.00 26.40           B  N
ATOM    540  CA   SER A  68      -9.257   2.805  45.089  1.00 28.27           B  C
ATOM    541  CB   SER A  68      -7.961   3.382  45.551  1.00 28.96           B  C
ATOM    542  OG   SER A  68      -7.396   4.223  44.547  1.00 34.58           B  O
ATOM    543  C    SER A  68     -10.133   3.840  44.366  1.00 33.89           B  C
ATOM    544  O    SER A  68     -10.940   4.528  45.021  1.00 32.70           B  O
ATOM    545  N    LYS A  69     -10.045   3.955  43.045  1.00 31.80           B  N
ATOM    546  CA   LYS A  69     -10.888   4.891  42.255  1.00 30.45           B  C
ATOM    547  CB   LYS A  69     -10.087   5.374  41.037  1.00 31.62           B  C
ATOM    548  CG   LYS A  69      -8.743   5.966  41.382  1.00 33.45           B  C
ATOM    549  CD   LYS A  69      -8.842   7.212  42.239  1.00 37.70           B  C
ATOM    550  CE   LYS A  69      -7.486   7.748  42.631  1.00 44.56           B  C
ATOM    551  NZ   LYS A  69      -7.591   8.795  43.674  1.00 50.99           B  N
ATOM    552  C    LYS A  69     -12.198   4.250  41.789  1.00 30.94           B  C
ATOM    553  O    LYS A  69     -12.916   4.908  41.056  1.00 34.24           B  O
ATOM    554  N    GLY A  70     -12.519   3.009  42.135  1.00 32.18           B  N
ATOM    555  CA   GLY A  70     -13.791   2.364  41.770  1.00 35.49           B  C
ATOM    556  C    GLY A  70     -13.838   1.861  40.340  1.00 39.62           B  C
ATOM    557  O    GLY A  70     -14.910   1.431  39.919  1.00 37.95           B  O
ATOM    558  N    LEU A  71     -12.726   1.892  39.596  1.00 36.98           B  N
ATOM    559  CA   LEU A  71     -12.704   1.363  38.211  1.00 35.32           B  C
ATOM    560  CB   LEU A  71     -11.411   1.807  37.529  1.00 32.31           B  C
ATOM    561  CG   LEU A  71     -11.294   1.305  36.094  1.00 33.79           B  C
ATOM    562  CD1  LEU A  71     -12.302   1.990  35.197  1.00 35.20           B  C
ATOM    563  CD2  LEU A  71      -9.888   1.491  35.574  1.00 34.48           B  C
ATOM    564  C    LEU A  71     -12.818  -0.169  38.219  1.00 34.59           B  C
ATOM    565  O    LEU A  71     -13.417  -0.743  37.281  1.00 38.90           B  O
ATOM    566  N    LEU A  72     -12.138  -0.836  39.144  1.00 34.02           B  N
ATOM    567  CA   LEU A  72     -12.130  -2.312  39.208  1.00 34.64           B  C
ATOM    568  CB   LEU A  72     -10.721  -2.885  39.069  1.00 35.20           B  C
ATOM    569  CG   LEU A  72     -10.098  -2.747  37.678  1.00 32.11           B  C
ATOM    570  CD1  LEU A  72      -8.707  -3.362  37.637  1.00 34.13           B  C
ATOM    571  CD2  LEU A  72     -10.969  -3.333  36.606  1.00 35.51           B  C
ATOM    572  C    LEU A  72     -12.750  -2.671  40.537  1.00 43.65           B  C
ATOM    573  O    LEU A  72     -12.522  -1.974  41.521  1.00 36.78           B  O
ATOM    574  N    PRO A  73     -13.593  -3.719  40.591  1.00 53.78           B  N
ATOM    575  CA   PRO A  73     -14.381  -3.950  41.793  1.00 54.48           B  C
ATOM    576  CB   PRO A  73     -15.494  -4.905  41.319  1.00 60.52           B  C
ATOM    577  CG   PRO A  73     -15.266  -5.071  39.813  1.00 61.04           B  C
ATOM    578  CD   PRO A  73     -13.797  -4.770  39.584  1.00 59.41           B  C
```

Fig. 5J

```
ATOM    579  C   PRO A  73     -13.354  -4.507  42.789  1.00 49.83           B  C
ATOM    580  O   PRO A  73     -12.324  -4.985  42.353  1.00 43.78           B  O
ATOM    581  N   ASN A  74     -13.610  -4.376  44.090  1.00 48.00           B  N
ATOM    582  CA  ASN A  74     -12.783  -5.043  45.125  1.00 51.16           B  C
ATOM    583  CB  ASN A  74     -12.711  -4.256  46.444  1.00 56.12           B  C
ATOM    584  CG  ASN A  74     -11.485  -4.599  47.266  1.00 56.97           B  C
ATOM    585  OD1 ASN A  74     -10.777  -5.555  46.961  1.00 73.14           B  O
ATOM    586  ND2 ASN A  74     -11.208  -3.821  48.298  1.00 60.71           B  N
ATOM    587  C   ASN A  74     -13.372  -6.448  45.274  1.00 60.82           B  C
ATOM    588  O   ASN A  74     -13.962  -6.750  46.322  1.00 71.20           B  O
ATOM    589  N   GLN A  75     -13.298  -7.233  44.203  1.00 57.96           B  N
ATOM    590  CA  GLN A  75     -13.574  -8.691  44.218  1.00 55.06           B  C
ATOM    591  CB  GLN A  75     -14.798  -9.056  43.376  1.00 58.18           B  C
ATOM    592  CG  GLN A  75     -14.594  -8.891  41.872  1.00 61.86           B  C
ATOM    593  CD  GLN A  75     -15.860  -8.631  41.080  1.00 62.12           B  C
ATOM    594  OE1 GLN A  75     -16.938  -8.376  41.627  1.00 64.51           B  O
ATOM    595  NE2 GLN A  75     -15.733  -8.668  39.760  1.00 50.92           B  N
ATOM    596  C   GLN A  75     -12.316  -9.372  43.697  1.00 47.08           B  C
ATOM    597  O   GLN A  75     -11.410  -8.689  43.146  1.00 45.37           B  O
ATOM    598  N   THR A  76     -12.286 -10.683  43.772  1.00 40.61           B  N
ATOM    599  CA  THR A  76     -11.033 -11.435  43.517  1.00 38.98           B  C
ATOM    600  CB  THR A  76     -11.242 -12.910  43.873  1.00 43.03           B  C
ATOM    601  OG1 THR A  76     -11.621 -12.896  45.257  1.00 40.48           B  O
ATOM    602  CG2 THR A  76     -10.001 -13.736  43.611  1.00 40.50           B  C
ATOM    603  C   THR A  76     -10.614 -11.228  42.057  1.00 38.15           B  C
ATOM    604  O   THR A  76      -9.384 -11.002  41.767  1.00 39.10           B  O
ATOM    605  N   CYS A  77     -11.583 -11.317  41.156  1.00 28.81           B  N
ATOM    606  CA  CYS A  77     -11.300 -11.244  39.714  1.00 25.59           B  C
ATOM    607  CB  CYS A  77     -11.453 -12.576  39.005  1.00 25.32           B  C
ATOM    608  SG  CYS A  77     -10.223 -13.807  39.472  1.00 27.52           B  S
ATOM    609  C   CYS A  77     -12.191 -10.241  39.007  1.00 30.31           B  C
ATOM    610  O   CYS A  77     -13.391 -10.163  39.259  1.00 29.85           B  O
ATOM    611  N   PRO A  78     -11.645  -9.534  38.000  1.00 26.33           B  N
ATOM    612  CA  PRO A  78     -12.464  -8.715  37.112  1.00 28.93           B  C
ATOM    613  CB  PRO A  78     -11.447  -8.139  36.108  1.00 28.49           B  C
ATOM    614  CG  PRO A  78     -10.178  -8.095  36.918  1.00 28.02           B  C
ATOM    615  CD  PRO A  78     -10.203  -9.389  37.726  1.00 28.19           B  C
ATOM    616  C   PRO A  78     -13.519  -9.571  36.412  1.00 25.95           B  C
ATOM    617  O   PRO A  78     -13.242 -10.762  36.121  1.00 29.20           B  O
ATOM    618  N   SER A  79     -14.678  -8.975  36.118  1.00 30.72           B  N
ATOM    619  CA  SER A  79     -15.745  -9.548  35.267  1.00 31.73           B  C
ATOM    620  CB  SER A  79     -16.942  -8.648  35.242  1.00 36.68           B  C
ATOM    621  OG  SER A  79     -17.478  -8.563  36.541  1.00 41.93           B  O
ATOM    622  C   SER A  79     -15.269  -9.760  33.839  1.00 35.62           B  C
ATOM    623  O   SER A  79     -14.378  -9.058  33.370  1.00 31.32           B  O
ATOM    624  N   PRO A  80     -15.906 -10.646  33.053  1.00 34.02           B  N
ATOM    625  CA  PRO A  80     -15.713 -10.654  31.596  1.00 36.17           B  C
ATOM    626  CB  PRO A  80     -16.711 -11.702  31.072  1.00 35.82           B  C
ATOM    627  CG  PRO A  80     -17.009 -12.554  32.295  1.00 35.63           B  C
ATOM    628  CD  PRO A  80     -16.905 -11.638  33.497  1.00 34.87           B  C
ATOM    629  C   PRO A  80     -16.003  -9.285  30.966  1.00 34.78           B  C
ATOM    630  O   PRO A  80     -16.894  -8.564  31.434  1.00 36.03           B  O
ATOM    631  N   GLY A  81     -15.136  -8.893  30.025  1.00 46.72           B  N
ATOM    632  CA  GLY A  81     -15.193  -7.595  29.323  1.00 50.35           B  C
ATOM    633  C   GLY A  81     -14.834  -6.429  30.228  1.00 48.08           B  C
ATOM    634  O   GLY A  81     -15.187  -5.292  29.858  1.00 53.45           B  O
ATOM    635  N   GLN A  82     -14.184  -6.661  31.379  1.00 38.39           B  N
ATOM    636  CA  GLN A  82     -13.700  -5.538  32.201  1.00 31.64           B  C
```

Fig. 5K

```
ATOM    637  CB   GLN A  82     -13.744  -5.745  33.708  1.00 33.94       B  C
ATOM    638  CG   GLN A  82     -15.046  -5.315  34.333  1.00 40.78       B  C
ATOM    639  CD   GLN A  82     -14.808  -5.045  35.784  1.00 42.48       B  C
ATOM    640  OE1  GLN A  82     -14.699  -5.960  36.602  1.00 39.15       B  O
ATOM    641  NE2  GLN A  82     -14.699  -3.762  36.084  1.00 41.80       B  N
ATOM    642  C    GLN A  82     -12.228  -5.267  31.857  1.00 28.77       B  C
ATOM    643  O    GLN A  82     -11.858  -4.072  31.843  1.00 29.47       B  O
ATOM    644  N    VAL A  83     -11.427  -6.313  31.690  1.00 25.81       B  N
ATOM    645  CA   VAL A  83      -9.957  -6.161  31.415  1.00 23.86       B  C
ATOM    646  CB   VAL A  83      -9.095  -6.669  32.564  1.00 22.19       B  C
ATOM    647  CG1  VAL A  83      -7.597  -6.653  32.194  1.00 23.39       B  C
ATOM    648  CG2  VAL A  83      -9.370  -5.929  33.833  1.00 23.71       B  C
ATOM    649  C    VAL A  83      -9.610  -6.872  30.147  1.00 26.32       B  C
ATOM    650  O    VAL A  83     -10.042  -8.022  29.963  1.00 29.75       B  O
ATOM    651  N    ALA A  84      -8.805  -6.265  29.312  1.00 22.80       B  N
ATOM    652  CA   ALA A  84      -8.317  -6.872  28.061  1.00 22.10       B  C
ATOM    653  CB   ALA A  84      -9.092  -6.482  26.822  1.00 25.27       B  C
ATOM    654  C    ALA A  84      -6.847  -6.496  27.949  1.00 21.02       B  C
ATOM    655  O    ALA A  84      -6.436  -5.349  28.264  1.00 19.99       B  O
ATOM    656  N    VAL A  85      -6.094  -7.448  27.497  1.00 19.70       B  N
ATOM    657  CA   VAL A  85      -4.643  -7.324  27.221  1.00 17.64       B  C
ATOM    658  CB   VAL A  85      -3.833  -8.157  28.213  1.00 18.93       B  C
ATOM    659  CG1  VAL A  85      -2.363  -8.046  27.920  1.00 18.72       B  C
ATOM    660  CG2  VAL A  85      -4.125  -7.744  29.599  1.00 20.83       B  C
ATOM    661  C    VAL A  85      -4.344  -7.683  25.792  1.00 19.15       B  C
ATOM    662  O    VAL A  85      -4.753  -8.779  25.363  1.00 20.80       B  O
ATOM    663  N    ILE A  86      -3.602  -6.838  25.092  1.00 18.41       B  N
ATOM    664  CA   ILE A  86      -3.030  -7.098  23.772  1.00 19.16       B  C
ATOM    665  CB   ILE A  86      -3.511  -6.052  22.755  1.00 19.66       B  C
ATOM    666  CG1  ILE A  86      -5.030  -6.142  22.572  1.00 21.88       B  C
ATOM    667  CG2  ILE A  86      -2.782  -6.189  21.458  1.00 22.14       B  C
ATOM    668  CD1  ILE A  86      -5.600  -4.855  21.973  1.00 23.62       B  C
ATOM    669  C    ILE A  86      -1.522  -7.063  23.923  1.00 19.53       B  C
ATOM    670  O    ILE A  86      -0.978  -6.096  24.543  1.00 21.23       B  O
ATOM    671  N    ALA A  87      -0.809  -7.955  23.296  1.00 18.96       B  N
ATOM    672  CA   ALA A  87       0.661  -7.937  23.227  1.00 17.23       B  C
ATOM    673  CB   ALA A  87       1.222  -9.052  24.097  1.00 18.49       B  C
ATOM    674  C    ALA A  87       1.143  -8.139  21.812  1.00 19.52       B  C
ATOM    675  O    ALA A  87       0.484  -8.901  21.077  1.00 19.49       B  O
ATOM    676  N    ASP A  88       2.283  -7.605  21.473  1.00 17.46       B  N
ATOM    677  CA   ASP A  88       2.984  -7.967  20.236  1.00 18.23       B  C
ATOM    678  CB   ASP A  88       4.129  -6.989  19.999  1.00 17.83       B  C
ATOM    679  CG   ASP A  88       4.590  -6.911  18.562  1.00 20.70       B  C
ATOM    680  OD1  ASP A  88       3.978  -7.647  17.706  1.00 21.28       B  O
ATOM    681  OD2  ASP A  88       5.548  -6.202  18.304  1.00 21.62       B  O
ATOM    682  C    ASP A  88       3.430  -9.442  20.352  1.00 17.51       B  C
ATOM    683  O    ASP A  88       3.412  -9.992  21.468  1.00 19.11       B  O
ATOM    684  N    THR A  89       3.902  -9.977  19.257  1.00 20.25       B  N
ATOM    685  CA   THR A  89       4.119 -11.442  19.126  1.00 21.52       B  C
ATOM    686  CB   THR A  89       4.062 -11.837  17.648  1.00 23.32       B  C
ATOM    687  OG1  THR A  89       5.138 -11.170  17.021  1.00 25.36       B  O
ATOM    688  CG2  THR A  89       2.700 -11.584  17.045  1.00 28.07       B  C
ATOM    689  C    THR A  89       5.430 -11.856  19.769  1.00 21.54       B  C
ATOM    690  O    THR A  89       5.639 -13.090  19.958  1.00 22.09       B  O
ATOM    691  N    ASP A  90       6.325 -10.961  20.143  1.00 19.06       B  N
ATOM    692  CA   ASP A  90       7.603 -11.285  20.808  1.00 17.58       B  C
ATOM    693  CB   ASP A  90       8.454 -10.028  21.005  1.00 20.81       B  C
ATOM    694  CG   ASP A  90       8.911  -9.358  19.730  1.00 28.78       B  C
```

Fig. 5L

```
ATOM    695  OD1 ASP A  90       9.041 -10.050  18.713  1.00 29.63           B  O
ATOM    696  OD2 ASP A  90       9.211  -8.170  19.789  1.00 31.52           B  O
ATOM    697  C   ASP A  90       7.377 -11.928  22.203  1.00 16.36           B  C
ATOM    698  O   ASP A  90       6.385 -11.648  22.905  1.00 17.08           B  O
ATOM    699  N   GLN A  91       8.304 -12.786  22.631  1.00 16.47           B  N
ATOM    700  CA  GLN A  91       8.255 -13.299  24.014  1.00 17.23           B  C
ATOM    701  CB  GLN A  91       9.456 -14.208  24.320  1.00 16.45           B  C
ATOM    702  CG  GLN A  91       9.461 -14.731  25.752  1.00 17.01           B  C
ATOM    703  CD  GLN A  91      10.196 -13.863  26.729  1.00 19.77           B  C
ATOM    704  OE1 GLN A  91      10.688 -12.787  26.412  1.00 18.34           B  O
ATOM    705  NE2 GLN A  91      10.419 -14.325  27.955  1.00 22.05           B  N
ATOM    706  C   GLN A  91       8.187 -12.093  24.977  1.00 16.76           B  C
ATOM    707  O   GLN A  91       7.472 -12.133  25.980  1.00 16.61           B  O
ATOM    708  N   ARG A  92       8.949 -11.037  24.682  1.00 16.89           B  N
ATOM    709  CA  ARG A  92       9.138 -10.003  25.731  1.00 15.92           B  C
ATOM    710  CB  ARG A  92      10.288  -9.094  25.394  1.00 17.40           B  C
ATOM    711  CG  ARG A  92      10.097  -8.278  24.140  1.00 17.91           B  C
ATOM    712  CD  ARG A  92      11.410  -7.544  24.041  1.00 21.15           B  C
ATOM    713  NE  ARG A  92      11.565  -6.867  22.790  1.00 24.74           B  N
ATOM    714  CZ  ARG A  92      12.276  -7.300  21.761  1.00 27.81           B  C
ATOM    715  NH1 ARG A  92      12.871  -8.483  21.755  1.00 28.64           B  N
ATOM    716  NH2 ARG A  92      12.328  -6.560  20.678  1.00 28.27           B  N
ATOM    717  C   ARG A  92       7.828  -9.254  25.964  1.00 15.26           B  C
ATOM    718  O   ARG A  92       7.498  -8.929  27.116  1.00 15.36           B  O
ATOM    719  N   THR A  93       7.038  -9.076  24.914  1.00 15.07           B  N
ATOM    720  CA  THR A  93       5.738  -8.457  25.026  1.00 14.75           B  C
ATOM    721  CB  THR A  93       5.374  -7.779  23.700  1.00 15.43           B  C
ATOM    722  OG1 THR A  93       5.586  -8.661  22.605  1.00 17.22           B  O
ATOM    723  CG2 THR A  93       6.188  -6.535  23.446  1.00 16.55           B  C
ATOM    724  C   THR A  93       4.647  -9.389  25.561  1.00 16.33           B  C
ATOM    725  O   THR A  93       3.851  -9.026  26.414  1.00 16.15           B  O
ATOM    726  N   ARG A  94       4.593 -10.625  25.021  1.00 15.95           B  N
ATOM    727  CA  ARG A  94       3.598 -11.596  25.522  1.00 17.09           B  C
ATOM    728  CB  ARG A  94       3.700 -12.944  24.795  1.00 18.99           B  C
ATOM    729  CG  ARG A  94       3.234 -12.888  23.339  1.00 21.91           B  C
ATOM    730  CD  ARG A  94       3.399 -14.197  22.592  1.00 23.86           B  C
ATOM    731  NE  ARG A  94       2.793 -15.301  23.321  1.00 26.12           B  N
ATOM    732  CZ  ARG A  94       2.867 -16.569  22.982  1.00 30.06           B  C
ATOM    733  NH1 ARG A  94       3.600 -16.913  21.943  1.00 28.54           B  N
ATOM    734  NH2 ARG A  94       2.279 -17.467  23.754  1.00 31.51           B  N
ATOM    735  C   ARG A  94       3.754 -11.833  27.028  1.00 14.41           B  C
ATOM    736  O   ARG A  94       2.805 -11.747  27.775  1.00 16.28           B  O
ATOM    737  N   LYS A  95       5.008 -11.999  27.438  1.00 14.99           B  N
ATOM    738  CA  LYS A  95       5.271 -12.240  28.867  1.00 16.88           B  C
ATOM    739  CB  LYS A  95       6.634 -12.877  29.115  1.00 18.49           B  C
ATOM    740  CG  LYS A  95       6.592 -14.393  28.801  1.00 22.72           B  C
ATOM    741  CD  LYS A  95       5.676 -15.181  29.722  1.00 24.76           B  C
ATOM    742  CE  LYS A  95       5.491 -16.657  29.401  1.00 26.59           B  C
ATOM    743  NZ  LYS A  95       4.629 -17.281  30.452  1.00 27.69           B  N
ATOM    744  C   LYS A  95       5.037 -10.989  29.703  1.00 16.08           B  C
ATOM    745  O   LYS A  95       4.600 -11.064  30.855  1.00 16.49           B  O
ATOM    746  N   THR A  96       5.345  -9.807  29.155  1.00 15.68           B  N
ATOM    747  CA  THR A  96       4.952  -8.576  29.863  1.00 15.64           B  C
ATOM    748  CB  THR A  96       5.435  -7.303  29.135  1.00 14.15           B  C
ATOM    749  OG1 THR A  96       6.845  -7.301  29.185  1.00 14.33           B  O
ATOM    750  CG2 THR A  96       4.887  -6.027  29.745  1.00 15.72           B  C
ATOM    751  C   THR A  96       3.461  -8.574  30.155  1.00 14.61           B  C
ATOM    752  O   THR A  96       3.010  -8.226  31.258  1.00 16.89           B  O
```

Fig. 5M

| | | | | | | | | | | | |
|---|---|---|---|---|---|---|---|---|---|---|---|
| ATOM | 753 | N | GLY | A | 97 | 2.650 | -8.897 | 29.153 | 1.00 15.68 | B | N |
| ATOM | 754 | CA | GLY | A | 97 | 1.201 | -8.963 | 29.357 | 1.00 16.27 | B | C |
| ATOM | 755 | C | GLY | A | 97 | 0.826 | -9.967 | 30.454 | 1.00 17.07 | B | C |
| ATOM | 756 | O | GLY | A | 97 | 0.019 | -9.675 | 31.333 | 1.00 17.08 | B | O |
| ATOM | 757 | N | GLU | A | 98 | 1.401 | -11.167 | 30.407 | 1.00 15.92 | B | N |
| ATOM | 758 | CA | GLU | A | 98 | 1.060 | -12.219 | 31.372 | 1.00 18.27 | B | C |
| ATOM | 759 | CB | GLU | A | 98 | 1.731 | -13.545 | 30.991 | 1.00 18.88 | B | C |
| ATOM | 760 | CG | GLU | A | 98 | 1.217 | -14.116 | 29.683 | 1.00 19.11 | B | C |
| ATOM | 761 | CD | GLU | A | 98 | 1.754 | -15.501 | 29.294 | 1.00 28.24 | B | C |
| ATOM | 762 | OE1 | GLU | A | 98 | 1.712 | -15.889 | 28.113 | 1.00 30.80 | B | O |
| ATOM | 763 | OE2 | GLU | A | 98 | 2.079 | -16.219 | 30.192 | 1.00 31.25 | B | O |
| ATOM | 764 | C | GLU | A | 98 | 1.541 | -11.788 | 32.743 | 1.00 16.35 | B | C |
| ATOM | 765 | O | GLU | A | 98 | 0.835 | -12.021 | 33.735 | 1.00 18.13 | B | O |
| ATOM | 766 | N | CYS | A | 99 | 2.726 | -11.202 | 32.829 | 1.00 16.31 | B | N |
| ATOM | 767 | CA | CYS | A | 99 | 3.291 | -10.784 | 34.112 | 1.00 16.35 | B | C |
| ATOM | 768 | CB | CYS | A | 99 | 4.750 | -10.470 | 33.972 | 1.00 18.14 | B | C |
| ATOM | 769 | SG | CYS | A | 99 | 5.726 | -11.918 | 33.425 | 1.00 19.09 | B | S |
| ATOM | 770 | C | CYS | A | 99 | 2.477 | -9.644 | 34.703 | 1.00 16.99 | B | C |
| ATOM | 771 | O | CYS | A | 99 | 2.352 | -9.533 | 35.947 | 1.00 19.62 | B | O |
| ATOM | 772 | N | PHE | A | 100 | 1.994 | -8.720 | 33.872 | 1.00 16.84 | B | N |
| ATOM | 773 | CA | PHE | A | 100 | 1.160 | -7.619 | 34.372 | 1.00 17.94 | B | C |
| ATOM | 774 | CB | PHE | A | 100 | 0.850 | -6.625 | 33.244 | 1.00 17.80 | B | C |
| ATOM | 775 | CG | PHE | A | 100 | 0.008 | -5.453 | 33.691 | 1.00 17.53 | B | C |
| ATOM | 776 | CD1 | PHE | A | 100 | 0.594 | -4.378 | 34.375 | 1.00 17.21 | B | C |
| ATOM | 777 | CE1 | PHE | A | 100 | -0.176 | -3.272 | 34.731 | 1.00 18.39 | B | C |
| ATOM | 778 | CZ | PHE | A | 100 | -1.518 | -3.300 | 34.541 | 1.00 19.44 | B | C |
| ATOM | 779 | CD2 | PHE | A | 100 | -1.361 | -5.438 | 33.495 | 1.00 17.44 | B | C |
| ATOM | 780 | CE2 | PHE | A | 100 | -2.119 | -4.351 | 33.905 | 1.00 18.77 | B | C |
| ATOM | 781 | C | PHE | A | 100 | -0.110 | -8.227 | 35.003 | 1.00 17.42 | B | C |
| ATOM | 782 | O | PHE | A | 100 | -0.505 | -7.785 | 36.061 | 1.00 18.31 | B | O |
| ATOM | 783 | N | LEU | A | 101 | -0.730 | -9.157 | 34.289 | 1.00 19.81 | B | N |
| ATOM | 784 | CA | LEU | A | 101 | -1.943 | -9.829 | 34.800 | 1.00 20.53 | B | C |
| ATOM | 785 | CB | LEU | A | 101 | -2.522 | -10.740 | 33.735 | 1.00 20.79 | B | C |
| ATOM | 786 | CG | LEU | A | 101 | -3.221 | -10.007 | 32.592 | 1.00 21.04 | B | C |
| ATOM | 787 | CD1 | LEU | A | 101 | -3.642 | -10.961 | 31.494 | 1.00 20.77 | B | C |
| ATOM | 788 | CD2 | LEU | A | 101 | -4.434 | -9.235 | 33.064 | 1.00 22.07 | B | C |
| ATOM | 789 | C | LEU | A | 101 | -1.636 | -10.622 | 36.067 | 1.00 20.76 | B | C |
| ATOM | 790 | O | LEU | A | 101 | -2.524 | -10.646 | 36.915 | 1.00 20.62 | B | O |
| ATOM | 791 | N | ALA | A | 102 | -0.444 | -11.173 | 36.220 | 1.00 19.34 | B | N |
| ATOM | 792 | CA | ALA | A | 102 | -0.086 | -11.913 | 37.466 | 1.00 21.77 | B | C |
| ATOM | 793 | CB | ALA | A | 102 | 1.298 | -12.475 | 37.388 | 1.00 21.65 | B | C |
| ATOM | 794 | C | ALA | A | 102 | -0.168 | -10.956 | 38.642 | 1.00 21.28 | B | C |
| ATOM | 795 | O | ALA | A | 102 | -0.480 | -11.403 | 39.732 | 1.00 23.63 | B | O |
| ATOM | 796 | N | GLY | A | 103 | 0.097 | -9.650 | 38.452 | 1.00 20.65 | B | N |
| ATOM | 797 | CA | GLY | A | 103 | 0.002 | -8.636 | 39.510 | 1.00 19.89 | B | C |
| ATOM | 798 | C | GLY | A | 103 | -1.386 | -8.030 | 39.611 | 1.00 20.31 | B | C |
| ATOM | 799 | O | GLY | A | 103 | -1.916 | -7.798 | 40.729 | 1.00 21.90 | B | O |
| ATOM | 800 | N | LEU | A | 104 | -2.011 | -7.770 | 38.478 | 1.00 19.26 | B | N |
| ATOM | 801 | CA | LEU | A | 104 | -3.324 | -7.113 | 38.472 | 1.00 20.43 | B | C |
| ATOM | 802 | CB | LEU | A | 104 | -3.652 | -6.638 | 37.062 | 1.00 19.97 | B | C |
| ATOM | 803 | CG | LEU | A | 104 | -4.917 | -5.767 | 36.965 | 1.00 21.43 | B | C |
| ATOM | 804 | CD1 | LEU | A | 104 | -4.586 | -4.298 | 37.161 | 1.00 23.05 | B | C |
| ATOM | 805 | CD2 | LEU | A | 104 | -5.610 | -5.987 | 35.645 | 1.00 20.39 | B | C |
| ATOM | 806 | C | LEU | A | 104 | -4.426 | -8.063 | 38.962 | 1.00 22.24 | B | C |
| ATOM | 807 | O | LEU | A | 104 | -5.323 | -7.572 | 39.666 | 1.00 24.02 | B | O |
| ATOM | 808 | N | ALA | A | 105 | -4.393 | -9.337 | 38.539 | 1.00 23.14 | B | N |
| ATOM | 809 | CA | ALA | A | 105 | -5.555 | -10.259 | 38.606 | 1.00 23.22 | B | C |
| ATOM | 810 | CB | ALA | A | 105 | -6.436 | -10.148 | 37.388 | 1.00 23.01 | B | C |

Fig. 5N

```
ATOM   811  C   ALA A 105      -5.025 -11.679  38.745  1.00 21.20           B  C
ATOM   812  O   ALA A 105      -5.233 -12.493  37.881  1.00 24.24           B  O
ATOM   813  N   PRO A 106      -4.216 -11.938  39.769  1.00 25.23           B  N
ATOM   814  CA  PRO A 106      -3.560 -13.245  39.840  1.00 28.49           B  C
ATOM   815  CB  PRO A 106      -2.768 -13.163  41.139  1.00 26.20           B  C
ATOM   816  CG  PRO A 106      -3.309 -12.023  41.922  1.00 30.15           B  C
ATOM   817  CD  PRO A 106      -3.917 -11.081  40.902  1.00 25.10           B  C
ATOM   818  C   PRO A 106      -4.572 -14.409  39.848  1.00 27.80           B  C
ATOM   819  O   PRO A 106      -5.587 -14.314  40.546  1.00 28.73           B  O
ATOM   820  N   LYS A 107      -4.315 -15.412  39.009  1.00 30.64           B  N
ATOM   821  CA  LYS A 107      -5.076 -16.694  38.942  1.00 31.30           B  C
ATOM   822  CB  LYS A 107      -5.270 -17.267  40.348  1.00 33.39           B  C
ATOM   823  CG  LYS A 107      -3.979 -17.523  41.104  1.00 39.37           B  C
ATOM   824  CD  LYS A 107      -4.188 -18.322  42.367  1.00 46.82           B  C
ATOM   825  CE  LYS A 107      -3.004 -18.274  43.304  1.00 54.50           B  C
ATOM   826  NZ  LYS A 107      -3.341 -17.554  44.552  1.00 62.92           B  N
ATOM   827  C   LYS A 107      -6.427 -16.535  38.243  1.00 32.90           B  C
ATOM   828  O   LYS A 107      -7.209 -17.543  38.194  1.00 31.26           B  O
ATOM   829  N   CYS A 108      -6.716 -15.363  37.659  1.00 25.89           B  N
ATOM   830  CA  CYS A 108      -8.029 -15.063  37.029  1.00 25.19           B  C
ATOM   831  CB  CYS A 108      -8.332 -13.561  37.115  1.00 25.56           B  C
ATOM   832  SG  CYS A 108      -8.467 -12.964  38.820  1.00 25.90           B  S
ATOM   833  C   CYS A 108      -8.081 -15.611  35.599  1.00 25.31           B  C
ATOM   834  O   CYS A 108      -9.155 -15.538  34.995  1.00 28.93           B  O
ATOM   835  N   GLN A 109      -6.956 -16.062  35.028  1.00 29.52           B  N
ATOM   836  CA  GLN A 109      -6.882 -16.625  33.659  1.00 29.24           B  C
ATOM   837  CB  GLN A 109      -7.663 -17.944  33.528  1.00 38.25           B  C
ATOM   838  CG  GLN A 109      -7.397 -18.967  34.624  1.00 45.02           B  C
ATOM   839  CD  GLN A 109      -8.430 -20.071  34.531  1.00 55.94           B  C
ATOM   840  OE1 GLN A 109      -8.318 -20.982  33.709  1.00 63.17           B  O
ATOM   841  NE2 GLN A 109      -9.482 -19.967  35.332  1.00 62.89           B  N
ATOM   842  C   GLN A 109      -7.433 -15.629  32.647  1.00 29.04           B  C
ATOM   843  O   GLN A 109      -7.993 -16.046  31.675  1.00 30.01           B  O
ATOM   844  N   ILE A 110      -7.185 -14.323  32.809  1.00 25.11           B  N
ATOM   845  CA  ILE A 110      -7.478 -13.390  31.712  1.00 24.22           B  C
ATOM   846  CB  ILE A 110      -7.363 -11.963  32.254  1.00 22.85           B  C
ATOM   847  CG1 ILE A 110      -8.451 -11.722  33.305  1.00 26.60           B  C
ATOM   848  CG2 ILE A 110      -7.461 -10.928  31.167  1.00 22.60           B  C
ATOM   849  CD1 ILE A 110      -8.215 -10.500  34.157  1.00 28.12           B  C
ATOM   850  C   ILE A 110      -6.527 -13.684  30.554  1.00 23.31           B  C
ATOM   851  O   ILE A 110      -5.297 -13.922  30.835  1.00 26.34           B  O
ATOM   852  N   GLN A 111      -7.045 -13.617  29.328  1.00 25.86           B  N
ATOM   853  CA  GLN A 111      -6.336 -13.915  28.069  1.00 31.45           B  C
ATOM   854  CB  GLN A 111      -7.381 -13.938  26.939  1.00 34.82           B  C
ATOM   855  CG  GLN A 111      -6.861 -14.374  25.578  1.00 38.42           B  C
ATOM   856  CD  GLN A 111      -6.208 -15.738  25.686  1.00 47.49           B  C
ATOM   857  OE1 GLN A 111      -5.068 -15.870  26.132  1.00 52.02           B  O
ATOM   858  NE2 GLN A 111      -6.935 -16.777  25.309  1.00 49.44           B  N
ATOM   859  C   GLN A 111      -5.361 -12.807  27.742  1.00 25.92           B  C
ATOM   860  O   GLN A 111      -5.631 -11.618  27.971  1.00 31.52           B  O
ATOM   861  N   VAL A 112      -4.182 -13.145  27.262  1.00 20.94           B  N
ATOM   862  CA  VAL A 112      -3.383 -12.155  26.519  1.00 20.99           B  C
ATOM   863  CB  VAL A 112      -1.909 -12.267  26.879  1.00 20.06           B  C
ATOM   864  CG1 VAL A 112      -0.962 -11.485  25.929  1.00 22.09           B  C
ATOM   865  CG2 VAL A 112      -1.702 -11.942  28.312  1.00 19.73           B  C
ATOM   866  C   VAL A 112      -3.611 -12.423  25.050  1.00 25.82           B  C
ATOM   867  O   VAL A 112      -3.252 -13.558  24.540  1.00 26.67           B  O
ATOM   868  N   HIS A 113      -4.215 -11.447  24.394  1.00 22.98           B  N
```

Fig. 50

```
ATOM    869  CA  HIS A 113     -4.444 -11.538  22.943  1.00 23.02      B    C
ATOM    870  CB  HIS A 113     -5.508 -10.581  22.520  1.00 24.40      B    C
ATOM    871  CG  HIS A 113     -6.836 -10.872  23.101  1.00 25.05      B    C
ATOM    872  ND1 HIS A 113     -7.825 -11.540  22.401  1.00 32.90      B    N
ATOM    873  CE1 HIS A 113     -8.888 -11.623  23.167  1.00 29.18      B    C
ATOM    874  NE2 HIS A 113     -8.650 -11.077  24.320  1.00 32.43      B    N
ATOM    875  CD2 HIS A 113     -7.357 -10.591  24.298  1.00 23.86      B    C
ATOM    876  C   HIS A 113     -3.159 -11.215  22.210  1.00 24.46      B    C
ATOM    877  O   HIS A 113     -2.513 -10.205  22.565  1.00 24.88      B    O
ATOM    878  N   TYR A 114     -2.846 -11.917  21.137  1.00 25.01      B    N
ATOM    879  CA  TYR A 114     -1.685 -11.632  20.273  1.00 24.37      B    C
ATOM    880  CB  TYR A 114     -0.401 -12.112  20.970  1.00 24.09      B    C
ATOM    881  CG  TYR A 114     -0.281 -13.612  21.092  1.00 24.54      B    C
ATOM    882  CD1 TYR A 114     -0.818 -14.286  22.178  1.00 28.95      B    C
ATOM    883  CE1 TYR A 114     -0.666 -15.666  22.298  1.00 28.78      B    C
ATOM    884  CZ  TYR A 114     -0.053 -16.385  21.288  1.00 34.79      B    C
ATOM    885  OH  TYR A 114      0.071 -17.766  21.371  1.00 35.25      B    O
ATOM    886  CE2 TYR A 114      0.493 -15.721  20.202  1.00 32.41      B    C
ATOM    887  CD2 TYR A 114      0.385 -14.338  20.109  1.00 31.01      B    C
ATOM    888  C   TYR A 114     -1.966 -12.251  18.899  1.00 28.39      B    C
ATOM    889  O   TYR A 114     -2.773 -13.200  18.810  1.00 28.46      B    O
ATOM    890  N   GLN A 115     -1.309 -11.752  17.872  1.00 27.51      B    N
ATOM    891  CA  GLN A 115     -1.501 -12.285  16.498  1.00 31.96      B    C
ATOM    892  CB  GLN A 115     -0.968 -11.245  15.513  1.00 32.82      B    C
ATOM    893  CG  GLN A 115     -0.714 -11.783  14.114  1.00 39.76      B    C
ATOM    894  CD  GLN A 115     -0.239 -10.663  13.223  1.00 35.50      B    C
ATOM    895  OE1 GLN A 115     -0.921  -9.653  13.042  1.00 40.99      B    O
ATOM    896  NE2 GLN A 115      0.969 -10.805  12.724  1.00 36.59      B    N
ATOM    897  C   GLN A 115     -0.843 -13.685  16.449  1.00 31.81      B    C
ATOM    898  O   GLN A 115      0.327 -13.830  16.832  1.00 33.77      B    O
ATOM    899  N   LYS A 116     -1.580 -14.722  16.047  1.00 40.01      B    N
ATOM    900  CA  LYS A 116     -1.097 -16.133  16.129  1.00 40.60      B    C
ATOM    901  CB  LYS A 116     -2.298 -17.080  16.067  1.00 46.42      B    C
ATOM    902  CG  LYS A 116     -3.168 -17.061  17.321  1.00 50.32      B    C
ATOM    903  CD  LYS A 116     -2.388 -17.337  18.611  1.00 50.83      B    C
ATOM    904  CE  LYS A 116     -3.247 -17.200  19.851  1.00 51.85      B    C
ATOM    905  NZ  LYS A 116     -3.761 -15.816  19.985  1.00 51.73      B    N
ATOM    906  C   LYS A 116     -0.033 -16.426  15.059  1.00 47.86      B    C
ATOM    907  O   LYS A 116      0.730 -17.397  15.255  1.00 51.36      B    O
ATOM    908  N   ASP A 117      0.062 -15.603  14.013  1.00 50.28      B    N
ATOM    909  CA  ASP A 117      1.083 -15.743  12.941  1.00 53.29      B    C
ATOM    910  CB  ASP A 117      0.468 -15.331  11.603  1.00 54.74      B    C
ATOM    911  CG  ASP A 117      1.338 -15.663  10.402  1.00 63.20      B    C
ATOM    912  OD1 ASP A 117      2.551 -15.961  10.594  1.00 63.75      B    O
ATOM    913  OD2 ASP A 117      0.799 -15.613   9.292  1.00 59.18      B    O
ATOM    914  C   ASP A 117      2.342 -14.942  13.324  1.00 55.32      B    C
ATOM    915  O   ASP A 117      2.488 -13.794  12.854  1.00 55.05      B    O
ATOM    916  N   GLU A 118      3.233 -15.539  14.129  1.00 53.62      B    N
ATOM    917  CA  GLU A 118      4.508 -14.931  14.603  1.00 58.20      B    C
ATOM    918  CB  GLU A 118      5.213 -15.916  15.533  1.00 67.60      B    C
ATOM    919  CG  GLU A 118      6.333 -15.308  16.346  1.00 71.45      B    C
ATOM    920  CD  GLU A 118      7.111 -16.354  17.128  1.00 77.55      B    C
ATOM    921  OE1 GLU A 118      8.307 -16.550  16.809  1.00 77.85      B    O
ATOM    922  OE2 GLU A 118      6.516 -16.984  18.051  1.00 71.17      B    O
ATOM    923  C   GLU A 118      5.425 -14.597  13.418  1.00 60.04      B    C
ATOM    924  O   GLU A 118      6.321 -13.737  13.579  1.00 52.86      B    O
ATOM    925  N   GLU A 119      5.236 -15.281  12.284  1.00 65.12      B    N
ATOM    926  CA  GLU A 119      6.045 -15.110  11.044  1.00 68.74      B    C
```

Fig. 5P

```
ATOM    927  CB  GLU A 119       5.828 -16.291  10.089  1.00 76.99           B  C
ATOM    928  CG  GLU A 119       5.954 -17.652  10.765  1.00 83.81           B  C
ATOM    929  CD  GLU A 119       6.452 -18.794   9.891  1.00 87.81           B  C
ATOM    930  OE1 GLU A 119       7.461 -18.602   9.179  1.00 93.36           B  O
ATOM    931  OE2 GLU A 119       5.840 -19.881   9.939  1.00 91.28           B  O
ATOM    932  C   GLU A 119       5.682 -13.771  10.380  1.00 61.96           B  C
ATOM    933  O   GLU A 119       6.576 -13.136   9.796  1.00 57.10           B  O
ATOM    934  N   LYS A 120       4.418 -13.354  10.468  1.00 58.87           B  N
ATOM    935  CA  LYS A 120       3.930 -12.067   9.897  1.00 53.86           B  C
ATOM    936  CB  LYS A 120       2.498 -12.213   9.373  1.00 56.87           B  C
ATOM    937  CG  LYS A 120       2.220 -11.419   8.105  1.00 69.89           B  C
ATOM    938  CD  LYS A 120       1.100 -10.404   8.220  1.00 76.26           B  C
ATOM    939  CE  LYS A 120       1.434  -9.092   7.537  1.00 77.53           B  C
ATOM    940  NZ  LYS A 120       2.009  -9.295   6.182  1.00 74.84           B  N
ATOM    941  C   LYS A 120       3.973 -11.006  10.996  1.00 47.19           B  C
ATOM    942  O   LYS A 120       3.575 -11.300  12.116  1.00 43.74           B  O
ATOM    943  N   PRO A 121       4.432  -9.759  10.724  1.00 38.48           B  N
ATOM    944  CA  PRO A 121       4.423  -8.710  11.748  1.00 38.01           B  C
ATOM    945  CB  PRO A 121       5.120  -7.497  11.123  1.00 39.37           B  C
ATOM    946  CG  PRO A 121       5.702  -7.980   9.797  1.00 41.84           B  C
ATOM    947  CD  PRO A 121       5.024  -9.293   9.456  1.00 42.37           B  C
ATOM    948  C   PRO A 121       2.971  -8.373  12.103  1.00 32.26           B  C
ATOM    949  O   PRO A 121       2.147  -8.397  11.204  1.00 34.34           B  O
ATOM    950  N   ASP A 122       2.706  -8.042  13.371  1.00 27.88           B  N
ATOM    951  CA  ASP A 122       1.461  -7.385  13.883  1.00 25.56           B  C
ATOM    952  CB  ASP A 122       1.148  -7.617  15.366  1.00 25.61           B  C
ATOM    953  CG  ASP A 122      -0.208  -7.104  15.819  1.00 28.14           B  C
ATOM    954  OD1 ASP A 122      -0.778  -6.225  15.126  1.00 25.54           B  O
ATOM    955  OD2 ASP A 122      -0.671  -7.448  16.887  1.00 27.01           B  O
ATOM    956  C   ASP A 122       1.553  -5.872  13.674  1.00 24.93           B  C
ATOM    957  O   ASP A 122       2.272  -5.140  14.356  1.00 24.67           B  O
ATOM    958  N   PRO A 123       0.782  -5.385  12.708  1.00 26.73           B  N
ATOM    959  CA  PRO A 123       0.920  -3.990  12.312  1.00 24.42           B  C
ATOM    960  CB  PRO A 123       0.075  -3.935  11.021  1.00 27.95           B  C
ATOM    961  CG  PRO A 123      -0.950  -5.007  11.221  1.00 28.33           B  C
ATOM    962  CD  PRO A 123      -0.187  -6.129  11.877  1.00 26.88           B  C
ATOM    963  C   PRO A 123       0.428  -2.981  13.362  1.00 23.81           B  C
ATOM    964  O   PRO A 123       0.755  -1.840  13.185  1.00 22.57           B  O
ATOM    965  N   LEU A 124      -0.316  -3.381  14.405  1.00 22.20           B  N
ATOM    966  CA  LEU A 124      -0.630  -2.446  15.518  1.00 21.38           B  C
ATOM    967  CB  LEU A 124      -1.361  -3.184  16.639  1.00 22.17           B  C
ATOM    968  CG  LEU A 124      -1.771  -2.333  17.837  1.00 23.42           B  C
ATOM    969  CD1 LEU A 124      -2.817  -1.313  17.467  1.00 23.55           B  C
ATOM    970  CD2 LEU A 124      -2.273  -3.173  18.987  1.00 24.57           B  C
ATOM    971  C   LEU A 124       0.655  -1.796  16.019  1.00 20.50           B  C
ATOM    972  O   LEU A 124       0.610  -0.630  16.402  1.00 20.56           B  O
ATOM    973  N   PHE A 125       1.736  -2.547  16.074  1.00 19.96           B  N
ATOM    974  CA  PHE A 125       3.014  -2.116  16.704  1.00 20.74           B  C
ATOM    975  CB  PHE A 125       3.649  -3.282  17.475  1.00 21.35           B  C
ATOM    976  CG  PHE A 125       2.747  -3.794  18.569  1.00 20.89           B  C
ATOM    977  CD1 PHE A 125       2.754  -3.178  19.812  1.00 20.09           B  C
ATOM    978  CE1 PHE A 125       1.848  -3.557  20.775  1.00 20.00           B  C
ATOM    979  CZ  PHE A 125       0.985  -4.597  20.552  1.00 18.98           B  C
ATOM    980  CD2 PHE A 125       1.847  -4.834  18.352  1.00 20.91           B  C
ATOM    981  CE2 PHE A 125       0.949  -5.208  19.333  1.00 19.89           B  C
ATOM    982  C   PHE A 125       3.956  -1.490  15.715  1.00 21.43           B  C
ATOM    983  O   PHE A 125       4.989  -0.943  16.103  1.00 21.02           B  O
ATOM    984  N   ASN A 126       3.597  -1.566  14.424  1.00 20.84           B  N
```

Fig. 5Q

```
ATOM    985  CA  ASN A 126       4.415  -0.911  13.384  1.00 21.60      B    C
ATOM    986  CB  ASN A 126       5.817  -1.466  13.231  1.00 22.41      B    C
ATOM    987  CG  ASN A 126       6.585  -0.749  12.135  1.00 23.29      B    C
ATOM    988  OD1 ASN A 126       6.073   0.216  11.566  1.00 25.38      B    O
ATOM    989  ND2 ASN A 126       7.781  -1.229  11.872  1.00 27.93      B    N
ATOM    990  C   ASN A 126       3.675  -1.073  12.059  1.00 23.60      B    C
ATOM    991  O   ASN A 126       3.782  -2.099  11.391  1.00 22.76      B    O
ATOM    992  N   PRO A 127       2.827  -0.099  11.707  1.00 21.96      B    N
ATOM    993  CA  PRO A 127       1.975  -0.230  10.522  1.00 22.05      B    C
ATOM    994  CB  PRO A 127       0.985   0.915  10.649  1.00 22.85      B    C
ATOM    995  CG  PRO A 127       1.776   1.954  11.405  1.00 23.09      B    C
ATOM    996  CD  PRO A 127       2.549   1.152  12.438  1.00 23.16      B    C
ATOM    997  C   PRO A 127       2.758  -0.119   9.212  1.00 22.95      B    C
ATOM    998  O   PRO A 127       2.174  -0.540   8.195  1.00 23.81      B    O
ATOM    999  N   VAL A 128       4.001   0.315   9.237  1.00 21.89      B    N
ATOM   1000  CA  VAL A 128       4.813   0.465   8.005  1.00 25.86      B    C
ATOM   1001  CB  VAL A 128       6.017   1.378   8.265  1.00 29.56      B    C
ATOM   1002  CG1 VAL A 128       6.742   1.720   6.990  1.00 37.89      B    C
ATOM   1003  CG2 VAL A 128       5.604   2.668   8.961  1.00 32.13      B    C
ATOM   1004  C   VAL A 128       5.166  -0.924   7.487  1.00 28.64      B    C
ATOM   1005  O   VAL A 128       5.478  -1.018   6.283  1.00 26.95      B    O
ATOM   1006  N   LYS A 129       4.886  -1.988   8.234  1.00 25.78      B    N
ATOM   1007  CA  LYS A 129       4.990  -3.360   7.674  1.00 30.18      B    C
ATOM   1008  CB  LYS A 129       4.957  -4.418   8.775  1.00 30.16      B    C
ATOM   1009  CG  LYS A 129       6.104  -4.323   9.768  1.00 35.31      B    C
ATOM   1010  CD  LYS A 129       7.452  -4.412   9.121  1.00 39.21      B    C
ATOM   1011  CE  LYS A 129       8.541  -4.816  10.094  1.00 43.07      B    C
ATOM   1012  NZ  LYS A 129       9.869  -4.738   9.449  1.00 51.32      B    N
ATOM   1013  C   LYS A 129       3.852  -3.643   6.686  1.00 30.67      B    C
ATOM   1014  O   LYS A 129       3.954  -4.660   5.983  1.00 31.85      B    O
ATOM   1015  N   MET A 130       2.780  -2.865   6.644  1.00 26.60      B    N
ATOM   1016  CA  MET A 130       1.673  -3.048   5.665  1.00 26.90      B    C
ATOM   1017  CB  MET A 130       0.362  -2.445   6.158  1.00 26.75      B    C
ATOM   1018  CG  MET A 130      -0.173  -3.079   7.432  1.00 25.88      B    C
ATOM   1019  SD  MET A 130      -1.745  -2.401   7.840  1.00 30.21      B    S
ATOM   1020  CE  MET A 130      -1.283  -0.693   8.045  1.00 28.01      B    C
ATOM   1021  C   MET A 130       2.078  -2.363   4.364  1.00 28.56      B    C
ATOM   1022  O   MET A 130       2.709  -1.295   4.417  1.00 27.48      B    O
ATOM   1023  N   GLY A 131       1.774  -3.001   3.221  1.00 31.19      B    N
ATOM   1024  CA  GLY A 131       2.136  -2.440   1.907  1.00 34.41      B    C
ATOM   1025  C   GLY A 131       1.602  -1.029   1.750  1.00 29.65      B    C
ATOM   1026  O   GLY A 131       2.366  -0.112   1.316  1.00 31.52      B    O
ATOM   1027  N   LYS A 132       0.368  -0.793   2.179  1.00 27.70      B    N
ATOM   1028  CA  LYS A 132      -0.282   0.524   1.883  1.00 29.17      B    C
ATOM   1029  CB  LYS A 132      -1.809   0.498   1.831  1.00 33.37      B    C
ATOM   1030  CG  LYS A 132      -2.459  -0.639   2.559  1.00 45.28      B    C
ATOM   1031  CD  LYS A 132      -2.622  -0.272   3.949  1.00 40.74      B    C
ATOM   1032  CE  LYS A 132      -4.080  -0.093   4.273  1.00 40.50      B    C
ATOM   1033  NZ  LYS A 132      -4.246   0.481   5.629  1.00 36.00      B    N
ATOM   1034  C   LYS A 132       0.181   1.625   2.838  1.00 26.79      B    C
ATOM   1035  O   LYS A 132      -0.157   2.788   2.629  1.00 25.95      B    O
ATOM   1036  N   CYS A 133       0.966   1.290   3.873  1.00 25.47      B    N
ATOM   1037  CA  CYS A 133       1.467   2.308   4.805  1.00 25.90      B    C
ATOM   1038  CB  CYS A 133       1.138   1.885   6.235  1.00 24.20      B    C
ATOM   1039  SG  CYS A 133       1.844   2.915   7.564  1.00 24.10      B    S
ATOM   1040  C   CYS A 133       2.958   2.459   4.602  1.00 22.36      B    C
ATOM   1041  O   CYS A 133       3.732   1.532   4.829  1.00 24.01      B    O
ATOM   1042  N   GLN A 134       3.372   3.636   4.209  1.00 22.75      B    N
```

Fig. 5R

```
ATOM   1043  CA   GLN A 134       4.775   3.868   3.853  1.00 23.41           B  C
ATOM   1044  CB   GLN A 134       5.006   3.769   2.320  1.00 24.46           B  C
ATOM   1045  CG   GLN A 134       4.668   2.412   1.728  1.00 27.23           B  C
ATOM   1046  CD   GLN A 134       5.066   2.330   0.261  1.00 26.16           B  C
ATOM   1047  OE1  GLN A 134       6.048   2.941  -0.140  1.00 31.30           B  O
ATOM   1048  NE2  GLN A 134       4.260   1.595  -0.481  1.00 28.10           B  N
ATOM   1049  C    GLN A 134       5.146   5.254   4.319  1.00 23.15           B  C
ATOM   1050  O    GLN A 134       4.332   6.159   4.317  1.00 24.65           B  O
ATOM   1051  N    PHE A 135       6.385   5.410   4.696  1.00 23.19           B  N
ATOM   1052  CA   PHE A 135       6.905   6.746   4.988  1.00 23.96           B  C
ATOM   1053  CB   PHE A 135       8.287   6.712   5.638  1.00 24.24           B  C
ATOM   1054  CG   PHE A 135       8.309   6.179   7.061  1.00 24.50           B  C
ATOM   1055  CD1  PHE A 135       7.453   6.719   8.018  1.00 24.68           B  C
ATOM   1056  CE1  PHE A 135       7.468   6.223   9.326  1.00 25.67           B  C
ATOM   1057  CZ   PHE A 135       8.291   5.172   9.656  1.00 24.75           B  C
ATOM   1058  CD2  PHE A 135       9.105   5.091   7.400  1.00 24.40           B  C
ATOM   1059  CE2  PHE A 135       9.116   4.604   8.711  1.00 26.49           B  C
ATOM   1060  C    PHE A 135       7.002   7.554   3.712  1.00 25.07           B  C
ATOM   1061  O    PHE A 135       7.377   6.947   2.684  1.00 26.18           B  O
ATOM   1062  N    ASN A 136       6.671   8.823   3.826  1.00 24.28           B  N
ATOM   1063  CA   ASN A 136       6.935   9.840   2.786  1.00 23.54           B  C
ATOM   1064  CB   ASN A 136       5.954  11.001   2.891  1.00 23.25           B  C
ATOM   1065  CG   ASN A 136       6.210  12.087   1.867  1.00 23.11           B  C
ATOM   1066  OD1  ASN A 136       7.362  12.296   1.478  1.00 26.79           B  O
ATOM   1067  ND2  ASN A 136       5.159  12.818   1.523  1.00 26.56           B  N
ATOM   1068  C    ASN A 136       8.383  10.226   3.000  1.00 22.45           B  C
ATOM   1069  O    ASN A 136       8.684  11.020   3.926  1.00 24.63           B  O
ATOM   1070  N    THR A 137       9.304   9.613   2.271  1.00 23.27           B  N
ATOM   1071  CA   THR A 137      10.727   9.643   2.628  1.00 21.88           B  C
ATOM   1072  CB   THR A 137      11.527   8.621   1.830  1.00 23.13           B  C
ATOM   1073  OG1  THR A 137      11.198   8.866   0.436  1.00 23.16           B  O
ATOM   1074  CG2  THR A 137      11.138   7.197   2.137  1.00 22.64           B  C
ATOM   1075  C    THR A 137      11.272  11.058   2.548  1.00 24.34           B  C
ATOM   1076  O    THR A 137      12.154  11.399   3.372  1.00 24.55           B  O
ATOM   1077  N    LEU A 138      10.808  11.875   1.595  1.00 23.46           B  N
ATOM   1078  CA   LEU A 138      11.279  13.274   1.467  1.00 23.81           B  C
ATOM   1079  CB   LEU A 138      10.676  13.903   0.200  1.00 25.95           B  C
ATOM   1080  CG   LEU A 138      11.128  15.327  -0.070  1.00 28.35           B  C
ATOM   1081  CD1  LEU A 138      12.651  15.420  -0.200  1.00 29.29           B  C
ATOM   1082  CD2  LEU A 138      10.462  15.860  -1.336  1.00 28.01           B  C
ATOM   1083  C    LEU A 138      10.854  14.014   2.733  1.00 23.22           B  C
ATOM   1084  O    LEU A 138      11.710  14.713   3.291  1.00 23.73           B  O
ATOM   1085  N    GLN A 139       9.573  13.917   3.066  1.00 24.50           B  N
ATOM   1086  CA   GLN A 139       9.012  14.710   4.197  1.00 24.76           B  C
ATOM   1087  CB   GLN A 139       7.522  14.477   4.321  1.00 29.68           B  C
ATOM   1088  CG   GLN A 139       6.723  15.613   4.906  1.00 42.90           B  C
ATOM   1089  CD   GLN A 139       5.270  15.451   4.511  1.00 52.44           B  C
ATOM   1090  OE1  GLN A 139       4.837  15.926   3.461  1.00 57.93           B  O
ATOM   1091  NE2  GLN A 139       4.501  14.757   5.341  1.00 50.67           B  N
ATOM   1092  C    GLN A 139       9.700  14.271   5.497  1.00 23.98           B  C
ATOM   1093  O    GLN A 139      10.083  15.129   6.276  1.00 24.49           B  O
ATOM   1094  N    VAL A 140       9.900  12.981   5.670  1.00 23.84           B  N
ATOM   1095  CA   VAL A 140      10.524  12.469   6.916  1.00 22.44           B  C
ATOM   1096  CB   VAL A 140      10.405  10.945   7.016  1.00 23.75           B  C
ATOM   1097  CG1  VAL A 140      11.430  10.344   7.967  1.00 26.19           B  C
ATOM   1098  CG2  VAL A 140       8.987  10.584   7.329  1.00 24.41           B  C
ATOM   1099  C    VAL A 140      11.976  12.889   6.959  1.00 23.54           B  C
ATOM   1100  O    VAL A 140      12.415  13.418   7.996  1.00 22.04           B  O
```

Fig. 5S

```
ATOM   1101  N    CYS A 141      12.756  12.707   5.909  1.00 22.30           B  N
ATOM   1102  CA   CYS A 141      14.188  13.052   5.944  1.00 21.54           B  C
ATOM   1103  CB   CYS A 141      14.955  12.545   4.721  1.00 24.14           B  C
ATOM   1104  SG   CYS A 141      16.140  11.246   5.163  1.00 28.31           B  S
ATOM   1105  C    CYS A 141      14.341  14.563   6.111  1.00 24.95           B  C
ATOM   1106  O    CYS A 141      15.193  14.981   6.892  1.00 25.19           B  O
ATOM   1107  N    ASN A 142      13.576  15.373   5.395  1.00 25.41           B  N
ATOM   1108  CA   ASN A 142      13.620  16.853   5.563  1.00 26.14           B  C
ATOM   1109  CB   ASN A 142      12.654  17.574   4.617  1.00 26.59           B  C
ATOM   1110  CG   ASN A 142      13.147  17.623   3.173  1.00 27.99           B  C
ATOM   1111  OD1  ASN A 142      14.289  17.334   2.894  1.00 29.48           B  O
ATOM   1112  ND2  ASN A 142      12.270  17.987   2.263  1.00 28.30           B  N
ATOM   1113  C    ASN A 142      13.312  17.212   7.034  1.00 25.03           B  C
ATOM   1114  O    ASN A 142      14.024  18.048   7.567  1.00 25.08           B  O
ATOM   1115  N    ALA A 143      12.277  16.615   7.626  1.00 23.46           B  N
ATOM   1116  CA   ALA A 143      11.839  16.950   9.002  1.00 22.52           B  C
ATOM   1117  CB   ALA A 143      10.519  16.357   9.338  1.00 24.15           B  C
ATOM   1118  C    ALA A 143      12.931  16.550   9.985  1.00 24.91           B  C
ATOM   1119  O    ALA A 143      13.231  17.350  10.924  1.00 25.25           B  O
ATOM   1120  N    ILE A 144      13.500  15.356   9.840  1.00 22.68           B  N
ATOM   1121  CA   ILE A 144      14.521  14.892  10.802  1.00 22.52           B  C
ATOM   1122  CB   ILE A 144      14.837  13.409  10.612  1.00 23.52           B  C
ATOM   1123  CG1  ILE A 144      13.647  12.539  10.990  1.00 23.57           B  C
ATOM   1124  CG2  ILE A 144      16.109  13.041  11.374  1.00 24.77           B  C
ATOM   1125  CD1  ILE A 144      13.837  11.078  10.671  1.00 25.72           B  C
ATOM   1126  C    ILE A 144      15.764  15.763  10.707  1.00 27.84           B  C
ATOM   1127  O    ILE A 144      16.340  16.124  11.768  1.00 27.22           B  O
ATOM   1128  N    LEU A 145      16.225  16.080   9.500  1.00 25.12           B  N
ATOM   1129  CA   LEU A 145      17.438  16.898   9.313  1.00 28.20           B  C
ATOM   1130  CB   LEU A 145      17.801  16.982   7.827  1.00 28.64           B  C
ATOM   1131  CG   LEU A 145      18.381  15.675   7.291  1.00 29.26           B  C
ATOM   1132  CD1  LEU A 145      18.455  15.707   5.771  1.00 30.79           B  C
ATOM   1133  CD2  LEU A 145      19.743  15.361   7.876  1.00 33.14           B  C
ATOM   1134  C    LEU A 145      17.218  18.262   9.963  1.00 27.85           B  C
ATOM   1135  O    LEU A 145      18.183  18.685  10.620  1.00 34.04           B  O
ATOM   1136  N    GLU A 146      16.034  18.870   9.823  1.00 29.05           B  N
ATOM   1137  CA   GLU A 146      15.684  20.168  10.490  1.00 30.76           B  C
ATOM   1138  CB   GLU A 146      14.269  20.623  10.105  1.00 40.12           B  C
ATOM   1139  CG   GLU A 146      14.220  21.570   8.932  1.00 54.79           B  C
ATOM   1140  CD   GLU A 146      15.050  22.830   9.149  1.00 64.72           B  C
ATOM   1141  OE1  GLU A 146      14.628  23.672   9.959  1.00 69.22           B  O
ATOM   1142  OE2  GLU A 146      16.143  22.940   8.538  1.00 79.12           B  O
ATOM   1143  C    GLU A 146      15.875  19.989  12.013  1.00 34.12           B  C
ATOM   1144  O    GLU A 146      16.625  20.787  12.633  1.00 37.92           B  O
ATOM   1145  N   AARG A 147      15.293  18.943  12.602  0.50 29.75           B  N
ATOM   1146  N   BARG A 147      15.266  18.952  12.605  0.50 32.38           B  N
ATOM   1147  CA  AARG A 147      15.280  18.739  14.081  0.50 28.39           B  C
ATOM   1148  CA  BARG A 147      15.222  18.714  14.083  0.50 32.66           B  C
ATOM   1149  CB  AARG A 147      14.376  17.570  14.445  0.50 24.37           B  C
ATOM   1150  CB  BARG A 147      14.225  17.592  14.393  0.50 31.41           B  C
ATOM   1151  CG  AARG A 147      12.909  17.883  14.226  0.50 23.44           B  C
ATOM   1152  CG  BARG A 147      13.809  17.429  15.853  0.50 31.70           B  C
ATOM   1153  CD  AARG A 147      11.994  16.938  14.953  0.50 23.64           B  C
ATOM   1154  CD  BARG A 147      13.122  16.099  15.980  0.50 35.13           B  C
ATOM   1155  NE  AARG A 147      12.086  17.180  16.397  0.50 22.81           B  N
ATOM   1156  NE  BARG A 147      12.561  15.855  17.291  0.50 32.83           B  N
ATOM   1157  CZ  AARG A 147      12.176  16.235  17.327  0.50 22.96           B  C
ATOM   1158  CZ  BARG A 147      11.323  16.198  17.625  0.50 34.60           B  C
```

Fig. 5T

```
ATOM   1159  NH1AARG A 147      12.152  14.957  16.984  0.50 19.86      B    N
ATOM   1160  NH1BARG A 147      10.545  16.828  16.758  0.50 36.15      B    N
ATOM   1161  NH2AARG A 147      12.253  16.595  18.600  0.50 22.66      B    N
ATOM   1162  NH2BARG A 147      10.880  15.933  18.836  0.50 36.73      B    N
ATOM   1163  C  AARG A 147      16.659  18.399  14.640  0.50 34.01      B    C
ATOM   1164  C  BARG A 147      16.614  18.370  14.639  0.50 36.59      B    C
ATOM   1165  O  AARG A 147      16.932  18.666  15.845  0.50 34.67      B    O
ATOM   1166  O  BARG A 147      16.877  18.664  15.834  0.50 38.80      B    O
ATOM   1167  N   ALA A 148      17.474  17.745  13.830  1.00 31.68      B    N
ATOM   1168  CA  ALA A 148      18.826  17.303  14.202  1.00 30.49      B    C
ATOM   1169  CB  ALA A 148      19.325  16.326  13.152  1.00 31.81      B    C
ATOM   1170  C   ALA A 148      19.759  18.499  14.249  1.00 32.14      B    C
ATOM   1171  O   ALA A 148      20.878  18.339  14.736  1.00 35.82      B    O
ATOM   1172  N   GLY A 149      19.338  19.606  13.660  1.00 34.49      B    N
ATOM   1173  CA  GLY A 149      20.164  20.821  13.647  1.00 41.38      B    C
ATOM   1174  C   GLY A 149      20.436  21.278  12.235  1.00 45.06      B    C
ATOM   1175  O   GLY A 149      21.054  22.330  12.109  1.00 48.33      B    O
ATOM   1176  N   GLY A 150      20.084  20.477  11.226  1.00 42.51      B    N
ATOM   1177  CA  GLY A 150      20.249  20.820   9.792  1.00 33.31      B    C
ATOM   1178  C   GLY A 150      21.013  19.745   9.029  1.00 40.22      B    C
ATOM   1179  O   GLY A 150      20.781  19.587   7.840  1.00 41.60      B    O
ATOM   1180  N   ASN A 151      21.921  19.037   9.688  1.00 34.60      B    N
ATOM   1181  CA  ASN A 151      22.511  17.774   9.194  1.00 36.34      B    C
ATOM   1182  CB  ASN A 151      23.624  18.000   8.177  1.00 36.22      B    C
ATOM   1183  CG  ASN A 151      24.777  18.792   8.745  1.00 38.92      B    C
ATOM   1184  OD1 ASN A 151      25.383  18.413   9.738  1.00 40.68      B    O
ATOM   1185  ND2 ASN A 151      25.039  19.942   8.164  1.00 42.53      B    N
ATOM   1186  C   ASN A 151      23.004  16.958  10.385  1.00 34.24      B    C
ATOM   1187  O   ASN A 151      22.978  17.428  11.544  1.00 30.32      B    O
ATOM   1188  N   ILE A 152      23.411  15.739  10.128  1.00 28.97      B    N
ATOM   1189  CA  ILE A 152      23.819  14.797  11.194  1.00 30.90      B    C
ATOM   1190  CB  ILE A 152      23.826  13.357  10.662  1.00 31.58      B    C
ATOM   1191  CG1 ILE A 152      22.397  12.910  10.337  1.00 32.56      B    C
ATOM   1192  CG2 ILE A 152      24.534  12.409  11.615  1.00 33.14      B    C
ATOM   1193  CD1 ILE A 152      21.390  13.216  11.436  1.00 31.99      B    C
ATOM   1194  C   ILE A 152      25.148  15.239  11.800  1.00 31.68      B    C
ATOM   1195  O   ILE A 152      25.342  15.014  12.992  1.00 30.06      B    O
ATOM   1196  N   GLU A 153      25.993  15.965  11.066  1.00 31.80      B    N
ATOM   1197  CA  GLU A 153      27.260  16.462  11.658  1.00 33.51      B    C
ATOM   1198  CB  GLU A 153      28.160  17.134  10.612  1.00 41.08      B    C
ATOM   1199  CG  GLU A 153      28.987  16.166   9.785  1.00 53.35      B    C
ATOM   1200  CD  GLU A 153      30.243  16.795   9.180  1.00 61.48      B    C
ATOM   1201  OE1 GLU A 153      30.168  17.964   8.712  1.00 63.63      B    O
ATOM   1202  OE2 GLU A 153      31.308  16.135   9.214  1.00 71.91      B    O
ATOM   1203  C   GLU A 153      26.928  17.437  12.802  1.00 28.89      B    C
ATOM   1204  O   GLU A 153      27.617  17.351  13.827  1.00 28.06      B    O
ATOM   1205  N   LEU A 154      25.924  18.297  12.653  1.00 26.06      B    N
ATOM   1206  CA  LEU A 154      25.581  19.300  13.663  1.00 27.70      B    C
ATOM   1207  CB  LEU A 154      24.612  20.356  13.110  1.00 30.60      B    C
ATOM   1208  CG  LEU A 154      25.236  21.351  12.113  1.00 33.82      B    C
ATOM   1209  CD1 LEU A 154      24.177  22.241  11.491  1.00 35.01      B    C
ATOM   1210  CD2 LEU A 154      26.285  22.205  12.811  1.00 33.46      B    C
ATOM   1211  C   LEU A 154      24.972  18.555  14.863  1.00 24.43      B    C
ATOM   1212  O   LEU A 154      25.167  18.947  16.014  1.00 24.68      B    O
ATOM   1213  N   PHE A 155      24.171  17.512  14.582  1.00 23.50      B    N
ATOM   1214  CA  PHE A 155      23.509  16.728  15.652  1.00 23.86      B    C
ATOM   1215  CB  PHE A 155      22.552  15.722  15.013  1.00 25.25      B    C
ATOM   1216  CG  PHE A 155      21.755  14.891  15.975  1.00 26.29      B    C
```

Fig. 5U

```
ATOM   1217  CD1 PHE A 155      20.818  15.461  16.799  1.00 28.89      B   C
ATOM   1218  CE1 PHE A 155      20.057  14.622  17.625  1.00 26.23      B   C
ATOM   1219  CZ  PHE A 155      20.261  13.279  17.609  1.00 25.42      B   C
ATOM   1220  CD2 PHE A 155      21.951  13.519  15.983  1.00 28.58      B   C
ATOM   1221  CE2 PHE A 155      21.195  12.703  16.803  1.00 29.24      B   C
ATOM   1222  C   PHE A 155      24.589  16.034  16.466  1.00 20.47      B   C
ATOM   1223  O   PHE A 155      24.557  16.027  17.719  1.00 19.95      B   O
ATOM   1224  N   THR A 156      25.593  15.468  15.823  1.00 22.67      B   N
ATOM   1225  CA  THR A 156      26.753  14.886  16.493  1.00 21.16      B   C
ATOM   1226  CB  THR A 156      27.690  14.229  15.483  1.00 24.43      B   C
ATOM   1227  OG1 THR A 156      26.937  13.219  14.781  1.00 25.33      B   O
ATOM   1228  CG2 THR A 156      28.904  13.666  16.154  1.00 23.15      B   C
ATOM   1229  C   THR A 156      27.464  15.939  17.337  1.00 22.66      B   C
ATOM   1230  O   THR A 156      27.825  15.719  18.527  1.00 22.20      B   O
ATOM   1231  N   GLN A 157      27.695  17.130  16.764  1.00 22.55      B   N
ATOM   1232  CA  GLN A 157      28.379  18.209  17.535  1.00 25.38      B   C
ATOM   1233  CB  GLN A 157      28.550  19.490  16.700  1.00 28.57      B   C
ATOM   1234  CG  GLN A 157      29.043  20.698  17.566  1.00 33.59      B   C
ATOM   1235  CD  GLN A 157      29.150  22.066  16.907  1.00 43.97      B   C
ATOM   1236  OE1 GLN A 157      29.279  23.132  17.563  1.00 40.30      B   O
ATOM   1237  NE2 GLN A 157      29.090  22.067  15.583  1.00 37.07      B   N
ATOM   1238  C   GLN A 157      27.595  18.547  18.809  1.00 21.56      B   C
ATOM   1239  O   GLN A 157      28.160  18.751  19.900  1.00 23.48      B   O
ATOM   1240  N   ARG A 158      26.280  18.582  18.717  1.00 20.55      B   N
ATOM   1241  CA  ARG A 158      25.399  18.881  19.843  1.00 18.95      B   C
ATOM   1242  CB  ARG A 158      23.956  18.822  19.350  1.00 19.54      B   C
ATOM   1243  CG  ARG A 158      22.891  18.903  20.413  1.00 20.85      B   C
ATOM   1244  CD  ARG A 158      21.462  18.756  19.944  1.00 24.19      B   C
ATOM   1245  NE  ARG A 158      20.983  19.962  19.246  1.00 27.75      B   N
ATOM   1246  CZ  ARG A 158      19.734  20.429  19.312  1.00 41.39      B   C
ATOM   1247  NH1 ARG A 158      18.793  19.785  19.994  1.00 43.30      B   N
ATOM   1248  NH2 ARG A 158      19.429  21.565  18.701  1.00 43.85      B   N
ATOM   1249  C   ARG A 158      25.599  17.920  21.024  1.00 20.98      B   C
ATOM   1250  O   ARG A 158      25.404  18.264  22.191  1.00 20.99      B   O
ATOM   1251  N   TYR A 159      25.957  16.668  20.727  1.00 20.39      B   N
ATOM   1252  CA  TYR A 159      26.147  15.596  21.730  1.00 20.09      B   C
ATOM   1253  CB  TYR A 159      25.256  14.401  21.363  1.00 18.47      B   C
ATOM   1254  CG  TYR A 159      23.796  14.648  21.597  1.00 17.43      B   C
ATOM   1255  CD1 TYR A 159      23.252  14.468  22.852  1.00 18.82      B   C
ATOM   1256  CE1 TYR A 159      21.928  14.760  23.102  1.00 17.46      B   C
ATOM   1257  CZ  TYR A 159      21.053  15.169  22.130  1.00 17.49      B   C
ATOM   1258  OH  TYR A 159      19.753  15.381  22.393  1.00 18.67      B   O
ATOM   1259  CE2 TYR A 159      21.585  15.355  20.870  1.00 16.71      B   C
ATOM   1260  CD2 TYR A 159      22.927  15.104  20.619  1.00 17.66      B   C
ATOM   1261  C   TYR A 159      27.609  15.189  21.875  1.00 20.15      B   C
ATOM   1262  O   TYR A 159      27.905  14.130  22.482  1.00 19.59      B   O
ATOM   1263  N   GLN A 160      28.561  15.953  21.406  1.00 20.72      B   N
ATOM   1264  CA  GLN A 160      29.987  15.567  21.486  1.00 23.02      B   C
ATOM   1265  CB  GLN A 160      30.943  16.691  21.014  1.00 30.71      B   C
ATOM   1266  CG  GLN A 160      30.938  16.886  19.517  1.00 40.95      B   C
ATOM   1267  CD  GLN A 160      31.869  15.967  18.763  1.00 51.19      B   C
ATOM   1268  OE1 GLN A 160      31.496  15.345  17.768  1.00 65.06      B   O
ATOM   1269  NE2 GLN A 160      33.126  15.941  19.165  1.00 60.93      B   N
ATOM   1270  C   GLN A 160      30.376  15.226  22.906  1.00 20.21      B   C
ATOM   1271  O   GLN A 160      31.064  14.187  23.120  1.00 20.22      B   O
ATOM   1272  N   SER A 161      29.972  15.968  23.931  1.00 20.43      B   N
ATOM   1273  CA  SER A 161      30.367  15.738  25.328  1.00 19.76      B   C
ATOM   1274  CB  SER A 161      29.981  16.933  26.246  1.00 23.35      B   C
```

Fig. 5V

```
ATOM   1275  OG  SER A 161      28.655  16.858  26.711  1.00 27.62      B    O
ATOM   1276  C   SER A 161      29.832  14.379  25.830  1.00 20.55      B    C
ATOM   1277  O   SER A 161      30.492  13.776  26.724  1.00 21.28      B    O
ATOM   1278  N   SER A 162      28.664  14.010  25.364  1.00 18.65      B    N
ATOM   1279  CA  SER A 162      28.084  12.689  25.742  1.00 18.30      B    C
ATOM   1280  CB  SER A 162      26.635  12.662  25.423  1.00 18.48      B    C
ATOM   1281  OG  SER A 162      25.905  13.731  26.067  1.00 19.36      B    O
ATOM   1282  C   SER A 162      28.855  11.564  25.059  1.00 17.92      B    C
ATOM   1283  O   SER A 162      29.048  10.540  25.749  1.00 19.68      B    O
ATOM   1284  N   PHE A 163      29.188  11.669  23.783  1.00 18.48      B    N
ATOM   1285  CA  PHE A 163      30.079  10.653  23.168  1.00 19.06      B    C
ATOM   1286  CB  PHE A 163      30.324  10.961  21.712  1.00 19.54      B    C
ATOM   1287  CG  PHE A 163      29.175  10.650  20.814  1.00 18.67      B    C
ATOM   1288  CD1 PHE A 163      28.863   9.316  20.531  1.00 18.42      B    C
ATOM   1289  CE1 PHE A 163      27.827   9.029  19.689  1.00 21.00      B    C
ATOM   1290  CZ  PHE A 163      27.120  10.014  19.062  1.00 20.91      B    C
ATOM   1291  CD2 PHE A 163      28.436  11.625  20.184  1.00 19.40      B    C
ATOM   1292  CE2 PHE A 163      27.390  11.323  19.339  1.00 19.12      B    C
ATOM   1293  C   PHE A 163      31.342  10.541  23.991  1.00 21.12      B    C
ATOM   1294  O   PHE A 163      31.843   9.451  24.262  1.00 21.42      B    O
ATOM   1295  N   ARG A 164      31.938  11.638  24.453  1.00 20.72      B    N
ATOM   1296  CA  ARG A 164      33.178  11.530  25.251  1.00 20.35      B    C
ATOM   1297  CB  ARG A 164      33.734  12.913  25.687  1.00 21.66      B    C
ATOM   1298  CG  ARG A 164      34.234  13.832  24.565  1.00 23.27      B    C
ATOM   1299  CD  ARG A 164      35.251  13.202  23.628  1.00 25.35      B    C
ATOM   1300  NE  ARG A 164      34.692  12.437  22.534  1.00 26.69      B    N
ATOM   1301  CZ  ARG A 164      34.121  12.920  21.454  1.00 24.54      B    C
ATOM   1302  NH1 ARG A 164      34.093  14.241  21.243  1.00 27.57      B    N
ATOM   1303  NH2 ARG A 164      33.558  12.104  20.582  1.00 25.05      B    N
ATOM   1304  C   ARG A 164      32.896  10.750  26.515  1.00 20.22      B    C
ATOM   1305  O   ARG A 164      33.715   9.854  26.859  1.00 21.13      B    O
ATOM   1306  N   THR A 165      31.791  10.927  27.197  1.00 19.61      B    N
ATOM   1307  CA  THR A 165      31.456  10.155  28.392  1.00 20.40      B    C
ATOM   1308  CB  THR A 165      30.166  10.678  29.023  1.00 19.99      B    C
ATOM   1309  OG1 THR A 165      30.395  12.061  29.405  1.00 22.01      B    O
ATOM   1310  CG2 THR A 165      29.772   9.918  30.241  1.00 21.95      B    C
ATOM   1311  C   THR A 165      31.299   8.657  28.018  1.00 19.90      B    C
ATOM   1312  O   THR A 165      31.812   7.828  28.785  1.00 21.41      B    O
ATOM   1313  N   LEU A 166      30.620   8.346  26.927  1.00 19.12      B    N
ATOM   1314  CA  LEU A 166      30.460   6.908  26.507  1.00 18.11      B    C
ATOM   1315  CB  LEU A 166      29.529   6.828  25.306  1.00 18.06      B    C
ATOM   1316  CG  LEU A 166      29.336   5.422  24.680  1.00 18.84      B    C
ATOM   1317  CD1 LEU A 166      28.876   4.435  25.750  1.00 19.51      B    C
ATOM   1318  CD2 LEU A 166      28.387   5.537  23.537  1.00 19.82      B    C
ATOM   1319  C   LEU A 166      31.828   6.343  26.202  1.00 22.15      B    C
ATOM   1320  O   LEU A 166      32.100   5.168  26.608  1.00 20.34      B    O
ATOM   1321  N   GLU A 167      32.666   7.047  25.473  1.00 19.09      B    N
ATOM   1322  CA  GLU A 167      34.004   6.571  25.143  1.00 21.06      B    C
ATOM   1323  CB  GLU A 167      34.735   7.494  24.164  1.00 19.18      B    C
ATOM   1324  CG  GLU A 167      34.125   7.683  22.827  1.00 22.10      B    C
ATOM   1325  CD  GLU A 167      34.374   8.991  22.102  1.00 20.50      B    C
ATOM   1326  OE1 GLU A 167      35.256   9.762  22.604  1.00 25.17      B    O
ATOM   1327  OE2 GLU A 167      33.675   9.217  21.093  1.00 22.86      B    O
ATOM   1328  C   GLU A 167      34.775   6.303  26.425  1.00 22.01      B    C
ATOM   1329  O   GLU A 167      35.474   5.236  26.500  1.00 21.99      B    O
ATOM   1330  N   ASN A 168      34.659   7.117  27.466  1.00 21.50      B    N
ATOM   1331  CA  ASN A 168      35.327   6.864  28.751  1.00 22.37      B    C
ATOM   1332  CB  ASN A 168      35.197   8.099  29.632  1.00 23.68      B    C
```

Fig. 5W

```
ATOM   1333  CG   ASN A 168      35.969   7.936  30.903  1.00 30.17           B   C
ATOM   1334  OD1  ASN A 168      37.159   7.609  30.868  1.00 36.02           B   O
ATOM   1335  ND2  ASN A 168      35.306   8.131  32.021  1.00 39.58           B   N
ATOM   1336  C    ASN A 168      34.788   5.609  29.422  1.00 22.05           B   C
ATOM   1337  O    ASN A 168      35.591   4.825  30.002  1.00 25.05           B   O
ATOM   1338  N    VAL A 169      33.488   5.361  29.368  1.00 20.57           B   N
ATOM   1339  CA   VAL A 169      32.906   4.120  29.956  1.00 21.32           B   C
ATOM   1340  CB   VAL A 169      31.378   4.220  30.040  1.00 22.28           B   C
ATOM   1341  CG1  VAL A 169      30.742   2.920  30.494  1.00 22.96           B   C
ATOM   1342  CG2  VAL A 169      30.999   5.286  31.027  1.00 22.33           B   C
ATOM   1343  C    VAL A 169      33.393   2.870  29.201  1.00 20.02           B   C
ATOM   1344  O    VAL A 169      33.648   1.874  29.887  1.00 21.47           B   O
ATOM   1345  N    LEU A 170      33.455   2.910  27.886  1.00 19.05           B   N
ATOM   1346  CA   LEU A 170      33.912   1.779  27.038  1.00 19.52           B   C
ATOM   1347  CB   LEU A 170      33.569   2.083  25.592  1.00 20.88           B   C
ATOM   1348  CG   LEU A 170      32.089   2.094  25.242  1.00 19.53           B   C
ATOM   1349  CD1  LEU A 170      31.871   2.549  23.825  1.00 22.22           B   C
ATOM   1350  CD2  LEU A 170      31.518   0.693  25.459  1.00 22.08           B   C
ATOM   1351  C    LEU A 170      35.424   1.577  27.175  1.00 24.43           B   C
ATOM   1352  O    LEU A 170      35.910   0.494  26.738  1.00 24.64           B   O
ATOM   1353  N    ASN A 171      36.189   2.559  27.640  1.00 21.64           B   N
ATOM   1354  CA   ASN A 171      37.655   2.647  27.371  1.00 23.16           B   C
ATOM   1355  CB   ASN A 171      38.409   1.585  28.179  1.00 29.97           B   C
ATOM   1356  CG   ASN A 171      39.839   2.014  28.479  1.00 47.49           B   C
ATOM   1357  OD1  ASN A 171      40.272   3.107  28.076  1.00 54.70           B   O
ATOM   1358  ND2  ASN A 171      40.586   1.164  29.174  1.00 53.75           B   N
ATOM   1359  C    ASN A 171      37.907   2.537  25.883  1.00 22.59           B   C
ATOM   1360  O    ASN A 171      38.810   1.715  25.442  1.00 24.69           B   O
ATOM   1361  N    PHE A 172      37.131   3.245  25.064  1.00 22.09           B   N
ATOM   1362  CA   PHE A 172      37.159   3.200  23.599  1.00 23.06           B   C
ATOM   1363  CB   PHE A 172      36.208   4.240  22.991  1.00 22.64           B   C
ATOM   1364  CG   PHE A 172      36.234   4.289  21.501  1.00 22.96           B   C
ATOM   1365  CD1  PHE A 172      35.722   3.252  20.742  1.00 24.38           B   C
ATOM   1366  CE1  PHE A 172      35.818   3.248  19.365  1.00 26.63           B   C
ATOM   1367  CZ   PHE A 172      36.453   4.276  18.724  1.00 27.56           B   C
ATOM   1368  CD2  PHE A 172      36.891   5.327  20.836  1.00 24.95           B   C
ATOM   1369  CE2  PHE A 172      36.963   5.318  19.455  1.00 24.88           B   C
ATOM   1370  C    PHE A 172      38.593   3.369  23.054  1.00 25.67           B   C
ATOM   1371  O    PHE A 172      38.928   2.742  21.999  1.00 26.73           B   O
ATOM   1372  N    SER A 173      39.399   4.220  23.669  1.00 24.73           B   N
ATOM   1373  CA   SER A 173      40.734   4.574  23.081  1.00 26.79           B   C
ATOM   1374  CB   SER A 173      41.348   5.778  23.741  1.00 28.53           B   C
ATOM   1375  OG   SER A 173      41.732   5.515  25.064  1.00 29.83           B   O
ATOM   1376  C    SER A 173      41.668   3.366  23.158  1.00 31.39           B   C
ATOM   1377  O    SER A 173      42.678   3.412  22.444  1.00 33.26           B   O
ATOM   1378  N    GLN A 174      41.354   2.365  23.995  1.00 29.42           B   N
ATOM   1379  CA   GLN A 174      42.130   1.089  24.144  1.00 30.26           B   C
ATOM   1380  CB   GLN A 174      42.181   0.667  25.608  1.00 33.46           B   C
ATOM   1381  CG   GLN A 174      42.424   1.801  26.584  1.00 42.94           B   C
ATOM   1382  CD   GLN A 174      43.798   1.885  27.187  1.00 58.52           B   C
ATOM   1383  OE1  GLN A 174      44.528   2.855  26.979  1.00 77.75           B   O
ATOM   1384  NE2  GLN A 174      44.146   0.884  27.977  1.00 69.31           B   N
ATOM   1385  C    GLN A 174      41.493  -0.034  23.329  1.00 31.35           B   C
ATOM   1386  O    GLN A 174      41.977  -1.190  23.385  1.00 32.74           B   O
ATOM   1387  N    SER A 175      40.482   0.253  22.536  1.00 28.74           B   N
ATOM   1388  CA   SER A 175      39.759  -0.763  21.757  1.00 29.51           B   C
ATOM   1389  CB   SER A 175      38.297  -0.374  21.683  1.00 26.82           B   C
ATOM   1390  OG   SER A 175      38.040   0.545  20.613  1.00 27.82           B   O
```

Fig. 5X

| | | | | | | | | | | | |
|---|---|---|---|---|---|---|---|---|---|---|---|
| ATOM | 1391 | C | | SER | A | 175 | 40.386 | -0.950 | 20.376 | 1.00 30.84 | B C |
| ATOM | 1392 | O | | SER | A | 175 | 41.168 | -0.067 | 19.926 | 1.00 29.59 | B O |
| ATOM | 1393 | N | | GLU | A | 176 | 40.013 | -2.040 | 19.691 | 1.00 32.52 | B N |
| ATOM | 1394 | CA | | GLU | A | 176 | 40.443 | -2.296 | 18.292 | 1.00 33.10 | B C |
| ATOM | 1395 | CB | | GLU | A | 176 | 39.993 | -3.675 | 17.800 | 1.00 42.72 | B C |
| ATOM | 1396 | CG | | GLU | A | 176 | 40.651 | -4.785 | 18.583 | 1.00 50.67 | B C |
| ATOM | 1397 | CD | | GLU | A | 176 | 40.527 | -6.171 | 17.970 | 1.00 57.67 | B C |
| ATOM | 1398 | OE1 | | GLU | A | 176 | 39.571 | -6.388 | 17.180 | 1.00 61.64 | B O |
| ATOM | 1399 | OE2 | | GLU | A | 176 | 41.393 | -7.026 | 18.279 | 1.00 67.87 | B O |
| ATOM | 1400 | C | | GLU | A | 176 | 39.898 | -1.258 | 17.330 | 1.00 38.52 | B C |
| ATOM | 1401 | O | | GLU | A | 176 | 40.557 | -1.030 | 16.326 | 1.00 35.18 | B O |
| ATOM | 1402 | N | | CYS | A | 177 | 38.712 | -0.704 | 17.594 | 1.00 31.76 | B N |
| ATOM | 1403 | CA | | CYS | A | 177 | 37.993 | 0.201 | 16.675 | 1.00 32.12 | B C |
| ATOM | 1404 | CB | | CYS | A | 177 | 36.495 | 0.136 | 16.903 | 1.00 32.25 | B C |
| ATOM | 1405 | SG | | CYS | A | 177 | 35.705 | -1.014 | 15.753 | 1.00 40.30 | B S |
| ATOM | 1406 | C | | CYS | A | 177 | 38.531 | 1.632 | 16.814 | 1.00 28.03 | B C |
| ATOM | 1407 | O | | CYS | A | 177 | 38.144 | 2.471 | 15.988 | 1.00 36.57 | B O |
| ATOM | 1408 | N | | CYS | A | 178 | 39.316 | 1.889 | 17.839 | 1.00 29.35 | B N |
| ATOM | 1409 | CA | | CYS | A | 178 | 40.094 | 3.144 | 17.975 | 1.00 31.43 | B C |
| ATOM | 1410 | CB | | CYS | A | 178 | 40.773 | 3.264 | 19.315 | 1.00 29.54 | B C |
| ATOM | 1411 | SG | | CYS | A | 178 | 41.811 | 4.741 | 19.364 | 1.00 30.51 | B S |
| ATOM | 1412 | C | | CYS | A | 178 | 41.148 | 3.216 | 16.866 | 1.00 36.00 | B C |
| ATOM | 1413 | O | | CYS | A | 178 | 42.161 | 2.505 | 16.956 | 1.00 39.50 | B O |
| ATOM | 1414 | N | | LYS | A | 179 | 40.964 | 4.177 | 15.973 | 1.00 45.28 | B N |
| ATOM | 1415 | CA | | LYS | A | 179 | 41.715 | 4.287 | 14.696 | 1.00 56.14 | B C |
| ATOM | 1416 | CB | | LYS | A | 179 | 40.692 | 4.348 | 13.559 | 1.00 59.19 | B C |
| ATOM | 1417 | CG | | LYS | A | 179 | 39.850 | 3.086 | 13.409 | 1.00 62.57 | B C |
| ATOM | 1418 | CD | | LYS | A | 179 | 38.668 | 3.210 | 12.461 | 1.00 63.16 | B C |
| ATOM | 1419 | CE | | LYS | A | 179 | 37.986 | 1.877 | 12.210 | 1.00 59.94 | B C |
| ATOM | 1420 | NZ | | LYS | A | 179 | 37.255 | 1.402 | 13.407 | 1.00 51.91 | B N |
| ATOM | 1421 | C | | LYS | A | 179 | 42.638 | 5.511 | 14.743 | 1.00 56.16 | B C |
| ATOM | 1422 | O | | LYS | A | 179 | 43.845 | 5.317 | 14.420 | 1.00 67.81 | B O |
| ATOM | 1423 | N | | SER | A | 184 | 46.494 | 13.975 | 15.961 | 1.00 61.85 | B N |
| ATOM | 1424 | CA | | SER | A | 184 | 46.661 | 14.769 | 17.211 | 1.00 64.98 | B C |
| ATOM | 1425 | CB | | SER | A | 184 | 46.351 | 16.235 | 16.979 | 1.00 69.99 | B C |
| ATOM | 1426 | OG | | SER | A | 184 | 47.144 | 16.783 | 15.941 | 1.00 78.25 | B O |
| ATOM | 1427 | C | | SER | A | 184 | 45.730 | 14.233 | 18.305 | 1.00 58.56 | B C |
| ATOM | 1428 | O | | SER | A | 184 | 46.216 | 13.780 | 19.356 | 1.00 57.57 | B O |
| ATOM | 1429 | N | | THR | A | 185 | 44.429 | 14.315 | 18.019 | 1.00 49.46 | B N |
| ATOM | 1430 | CA | | THR | A | 185 | 43.280 | 14.180 | 18.947 | 1.00 39.98 | B C |
| ATOM | 1431 | CB | | THR | A | 185 | 42.077 | 14.939 | 18.378 | 1.00 35.44 | B C |
| ATOM | 1432 | OG1 | | THR | A | 185 | 41.870 | 14.557 | 17.019 | 1.00 33.55 | B O |
| ATOM | 1433 | CG2 | | THR | A | 185 | 42.264 | 16.440 | 18.411 | 1.00 38.19 | B C |
| ATOM | 1434 | C | | THR | A | 185 | 42.952 | 12.694 | 19.145 | 1.00 33.05 | B C |
| ATOM | 1435 | O | | THR | A | 185 | 43.168 | 11.897 | 18.202 | 1.00 34.90 | B O |
| ATOM | 1436 | N | | LYS | A | 186 | 42.411 | 12.362 | 20.317 | 1.00 34.92 | B N |
| ATOM | 1437 | CA | | LYS | A | 186 | 42.048 | 10.970 | 20.692 | 1.00 33.50 | B C |
| ATOM | 1438 | CB | | LYS | A | 186 | 41.508 | 10.895 | 22.128 | 1.00 34.17 | B C |
| ATOM | 1439 | CG | | LYS | A | 186 | 41.053 | 9.519 | 22.619 | 1.00 37.89 | B C |
| ATOM | 1440 | CD | | LYS | A | 186 | 40.151 | 9.555 | 23.876 | 1.00 37.28 | B C |
| ATOM | 1441 | CE | | LYS | A | 186 | 38.749 | 10.116 | 23.671 | 1.00 37.82 | B C |
| ATOM | 1442 | NZ | | LYS | A | 186 | 37.825 | 9.118 | 23.077 | 1.00 32.60 | B N |
| ATOM | 1443 | C | | LYS | A | 186 | 40.994 | 10.514 | 19.690 | 1.00 31.56 | B C |
| ATOM | 1444 | O | | LYS | A | 186 | 40.143 | 11.320 | 19.284 | 1.00 28.17 | B O |
| ATOM | 1445 | N | | CYS | A | 187 | 41.083 | 9.267 | 19.255 | 1.00 28.78 | B N |
| ATOM | 1446 | CA | | CYS | A | 187 | 40.047 | 8.622 | 18.442 | 1.00 27.45 | B C |
| ATOM | 1447 | CB | | CYS | A | 187 | 40.349 | 7.136 | 18.276 | 1.00 28.89 | B C |
| ATOM | 1448 | SG | | CYS | A | 187 | 40.587 | 6.297 | 19.866 | 1.00 29.54 | B S |

Fig. 5Y

```
ATOM   1449  C   CYS A 187      38.688   8.766  19.129  1.00 23.42           B  C
ATOM   1450  O   CYS A 187      38.613   8.681  20.364  1.00 27.92           B  O
ATOM   1451  N   THR A 188      37.667   8.903  18.319  1.00 26.18           B  N
ATOM   1452  CA  THR A 188      36.277   9.063  18.819  1.00 27.50           B  C
ATOM   1453  CB  THR A 188      35.762  10.485  18.573  1.00 25.89           B  C
ATOM   1454  OG1 THR A 188      35.540  10.643  17.168  1.00 26.36           B  O
ATOM   1455  CG2 THR A 188      36.676  11.483  19.232  1.00 28.91           B  C
ATOM   1456  C   THR A 188      35.386   8.031  18.160  1.00 27.26           B  C
ATOM   1457  O   THR A 188      35.661   7.547  17.050  1.00 27.16           B  O
ATOM   1458  N   LEU A 189      34.249   7.767  18.794  1.00 25.94           B  N
ATOM   1459  CA  LEU A 189      33.277   6.848  18.176  1.00 24.57           B  C
ATOM   1460  CB  LEU A 189      32.178   6.609  19.217  1.00 27.43           B  C
ATOM   1461  CG  LEU A 189      32.330   5.363  20.057  1.00 29.88           B  C
ATOM   1462  CD1 LEU A 189      31.258   5.375  21.160  1.00 30.49           B  C
ATOM   1463  CD2 LEU A 189      32.245   4.091  19.217  1.00 30.56           B  C
ATOM   1464  C   LEU A 189      32.711   7.405  16.868  1.00 27.50           B  C
ATOM   1465  O   LEU A 189      32.542   6.669  15.873  1.00 25.57           B  O
ATOM   1466  N   PRO A 190      32.277   8.683  16.785  1.00 25.66           B  N
ATOM   1467  CA  PRO A 190      31.732   9.151  15.519  1.00 27.72           B  C
ATOM   1468  CB  PRO A 190      31.229  10.554  15.851  1.00 26.09           B  C
ATOM   1469  CG  PRO A 190      30.917  10.445  17.343  1.00 26.03           B  C
ATOM   1470  CD  PRO A 190      32.076   9.654  17.883  1.00 25.27           B  C
ATOM   1471  C   PRO A 190      32.731   9.115  14.356  1.00 28.36           B  C
ATOM   1472  O   PRO A 190      32.267   8.993  13.216  1.00 29.61           B  O
ATOM   1473  N   GLU A 191      34.011   9.238  14.647  1.00 30.11           B  N
ATOM   1474  CA  GLU A 191      35.046   9.230  13.572  1.00 35.39           B  C
ATOM   1475  CB  GLU A 191      36.381   9.856  14.002  1.00 39.83           B  C
ATOM   1476  CG  GLU A 191      37.331   8.887  14.681  1.00 52.60           B  C
ATOM   1477  CD  GLU A 191      38.700   9.423  15.090  1.00 56.07           B  C
ATOM   1478  OE1 GLU A 191      39.697   8.696  14.893  1.00 68.71           B  O
ATOM   1479  OE2 GLU A 191      38.766  10.538  15.633  1.00 68.86           B  O
ATOM   1480  C   GLU A 191      35.233   7.787  13.104  1.00 31.49           B  C
ATOM   1481  O   GLU A 191      35.343   7.603  11.895  1.00 32.55           B  O
ATOM   1482  N   ALA A 192      35.202   6.808  14.014  1.00 30.18           B  N
ATOM   1483  CA  ALA A 192      35.395   5.372  13.724  1.00 31.81           B  C
ATOM   1484  CB  ALA A 192      35.632   4.607  14.989  1.00 32.98           B  C
ATOM   1485  C   ALA A 192      34.179   4.850  12.975  1.00 31.02           B  C
ATOM   1486  O   ALA A 192      34.319   3.996  12.090  1.00 31.00           B  O
ATOM   1487  N   LEU A 193      32.989   5.300  13.371  1.00 27.13           B  N
ATOM   1488  CA  LEU A 193      31.706   4.829  12.839  1.00 26.67           B  C
ATOM   1489  CB  LEU A 193      30.981   4.081  13.960  1.00 27.25           B  C
ATOM   1490  CG  LEU A 193      31.695   2.829  14.421  1.00 29.24           B  C
ATOM   1491  CD1 LEU A 193      31.013   2.270  15.666  1.00 30.28           B  C
ATOM   1492  CD2 LEU A 193      31.756   1.784  13.299  1.00 32.25           B  C
ATOM   1493  C   LEU A 193      30.896   6.016  12.375  1.00 29.53           B  C
ATOM   1494  O   LEU A 193      29.962   6.472  13.037  1.00 25.45           B  O
ATOM   1495  N   PRO A 194      31.202   6.542  11.176  1.00 28.79           B  N
ATOM   1496  CA  PRO A 194      30.424   7.644  10.651  1.00 27.83           B  C
ATOM   1497  CB  PRO A 194      31.006   7.868   9.241  1.00 30.81           B  C
ATOM   1498  CG  PRO A 194      32.363   7.238   9.285  1.00 30.16           B  C
ATOM   1499  CD  PRO A 194      32.290   6.100  10.280  1.00 32.70           B  C
ATOM   1500  C   PRO A 194      28.946   7.270  10.544  1.00 26.43           B  C
ATOM   1501  O   PRO A 194      28.628   6.156  10.182  1.00 26.70           B  O
ATOM   1502  N   SER A 195      28.061   8.198  10.890  1.00 26.31           B  N
ATOM   1503  CA  SER A 195      26.599   7.990  10.957  1.00 24.88           B  C
ATOM   1504  CB  SER A 195      26.038   8.504  12.265  1.00 26.46           B  C
ATOM   1505  OG  SER A 195      26.759   8.032  13.372  1.00 27.68           B  O
ATOM   1506  C   SER A 195      25.913   8.643   9.777  1.00 27.34           B  C
```

Fig. 5Z

```
ATOM   1507  O    SER A 195      26.257   9.768   9.430  1.00 33.29           B  O
ATOM   1508  N    GLU A 196      24.954   7.959   9.200  1.00 29.98           B  N
ATOM   1509  CA   GLU A 196      24.177   8.441   8.050  1.00 32.65           B  C
ATOM   1510  CB   GLU A 196      24.622   7.623   6.837  1.00 42.35           B  C
ATOM   1511  CG   GLU A 196      23.699   7.728   5.647  1.00 51.68           B  C
ATOM   1512  CD   GLU A 196      24.198   7.004   4.405  1.00 57.08           B  C
ATOM   1513  OE1  GLU A 196      23.931   7.504   3.297  1.00 64.01           B  O
ATOM   1514  OE2  GLU A 196      24.830   5.930   4.555  1.00 60.00           B  O
ATOM   1515  C    GLU A 196      22.697   8.308   8.408  1.00 28.17           B  C
ATOM   1516  O    GLU A 196      22.297   7.242   8.949  1.00 30.78           B  O
ATOM   1517  N    LEU A 197      21.912   9.308   8.074  1.00 26.08           B  N
ATOM   1518  CA   LEU A 197      20.457   9.221   8.160  1.00 25.97           B  C
ATOM   1519  CB   LEU A 197      19.862  10.620   8.272  1.00 26.19           B  C
ATOM   1520  CG   LEU A 197      18.346  10.650   8.333  1.00 28.20           B  C
ATOM   1521  CD1  LEU A 197      17.809   9.984   9.593  1.00 27.14           B  C
ATOM   1522  CD2  LEU A 197      17.851  12.086   8.231  1.00 32.14           B  C
ATOM   1523  C    LEU A 197      19.955   8.524   6.899  1.00 27.88           B  C
ATOM   1524  O    LEU A 197      20.297   8.981   5.772  1.00 29.25           B  O
ATOM   1525  N    LYS A 198      19.171   7.462   7.064  1.00 26.22           B  N
ATOM   1526  CA   LYS A 198      18.553   6.722   5.939  1.00 28.73           B  C
ATOM   1527  CB   LYS A 198      19.063   5.282   5.863  1.00 29.89           B  C
ATOM   1528  CG   LYS A 198      20.561   5.151   5.671  1.00 35.97           B  C
ATOM   1529  CD   LYS A 198      21.059   3.728   5.475  1.00 44.78           B  C
ATOM   1530  CE   LYS A 198      22.298   3.669   4.604  1.00 53.88           B  C
ATOM   1531  NZ   LYS A 198      23.314   2.746   5.164  1.00 60.59           B  N
ATOM   1532  C    LYS A 198      17.057   6.759   6.155  1.00 27.13           B  C
ATOM   1533  O    LYS A 198      16.574   6.334   7.227  1.00 28.64           B  O
ATOM   1534  N    CYS A 199      16.331   7.273   5.194  1.00 24.86           B  N
ATOM   1535  CA   CYS A 199      14.877   7.332   5.153  1.00 24.44           B  C
ATOM   1536  CB   CYS A 199      14.387   8.762   4.973  1.00 26.78           B  C
ATOM   1537  SG   CYS A 199      15.025   9.867   6.267  1.00 25.75           B  S
ATOM   1538  C    CYS A 199      14.426   6.462   4.004  1.00 25.80           B  C
ATOM   1539  O    CYS A 199      14.506   6.914   2.861  1.00 26.30           B  O
ATOM   1540  N    THR A 200      13.877   5.324   4.297  1.00 24.03           B  N
ATOM   1541  CA   THR A 200      13.292   4.385   3.314  1.00 24.34           B  C
ATOM   1542  CB   THR A 200      13.988   3.033   3.317  1.00 25.22           B  C
ATOM   1543  OG1  THR A 200      13.446   2.242   4.376  1.00 27.42           B  O
ATOM   1544  CG2  THR A 200      15.488   3.176   3.379  1.00 26.41           B  C
ATOM   1545  C    THR A 200      11.809   4.279   3.580  1.00 25.28           B  C
ATOM   1546  O    THR A 200      11.299   4.700   4.628  1.00 24.25           B  O
ATOM   1547  N    PRO A 201      11.031   3.748   2.624  1.00 24.41           B  N
ATOM   1548  CA   PRO A 201       9.592   3.671   2.810  1.00 25.27           B  C
ATOM   1549  CB   PRO A 201       9.115   3.005   1.493  1.00 27.70           B  C
ATOM   1550  CG   PRO A 201      10.136   3.543   0.498  1.00 29.32           B  C
ATOM   1551  CD   PRO A 201      11.454   3.432   1.233  1.00 26.87           B  C
ATOM   1552  C    PRO A 201       9.198   2.835   4.031  1.00 26.80           B  C
ATOM   1553  O    PRO A 201       8.080   3.019   4.510  1.00 25.51           B  O
ATOM   1554  N    ASP A 202      10.038   1.899   4.467  1.00 28.58           B  N
ATOM   1555  CA   ASP A 202       9.590   1.116   5.649  1.00 32.58           B  C
ATOM   1556  CB   ASP A 202       9.328  -0.359   5.350  1.00 42.40           B  C
ATOM   1557  CG   ASP A 202      10.561  -1.071   4.853  1.00 48.70           B  C
ATOM   1558  OD1  ASP A 202      11.660  -0.520   5.027  1.00 51.41           B  O
ATOM   1559  OD2  ASP A 202      10.403  -2.166   4.284  1.00 61.96           B  O
ATOM   1560  C    ASP A 202      10.528   1.301   6.832  1.00 26.88           B  C
ATOM   1561  O    ASP A 202      10.236   0.677   7.860  1.00 29.80           B  O
ATOM   1562  N    LEU A 203      11.517   2.187   6.791  1.00 26.29           B  N
ATOM   1563  CA   LEU A 203      12.436   2.288   7.951  1.00 25.17           B  C
ATOM   1564  CB   LEU A 203      13.422   1.107   7.956  1.00 25.87           B  C
```

Fig. 5AA

| | | | | | | | | | | | |
|---|---|---|---|---|---|---|---|---|---|---|---|
| ATOM | 1565 | CG | LEU | A | 203 | 14.372 | 1.055 | 9.141 | 1.00 | 27.09 | B | C |
| ATOM | 1566 | CD1 | LEU | A | 203 | 13.567 | 0.715 | 10.389 | 1.00 | 28.35 | B | C |
| ATOM | 1567 | CD2 | LEU | A | 203 | 15.493 | 0.039 | 8.924 | 1.00 | 29.49 | B | C |
| ATOM | 1568 | C | LEU | A | 203 | 13.185 | 3.609 | 7.929 | 1.00 | 24.57 | B | C |
| ATOM | 1569 | O | LEU | A | 203 | 13.744 | 3.991 | 6.886 | 1.00 | 25.59 | B | O |
| ATOM | 1570 | N | AVAL | A | 204 | 13.254 | 4.302 | 9.076 | 0.50 | 22.84 | B | N |
| ATOM | 1571 | N | BVAL | A | 204 | 13.272 | 4.263 | 9.082 | 0.50 | 23.53 | B | N |
| ATOM | 1572 | CA | AVAL | A | 204 | 14.185 | 5.444 | 9.283 | 0.50 | 23.23 | B | C |
| ATOM | 1573 | CA | BVAL | A | 204 | 14.207 | 5.391 | 9.260 | 0.50 | 24.09 | B | C |
| ATOM | 1574 | CB | AVAL | A | 204 | 13.496 | 6.747 | 9.735 | 0.50 | 25.80 | B | C |
| ATOM | 1575 | CB | BVAL | A | 204 | 13.497 | 6.678 | 9.687 | 0.50 | 27.26 | B | C |
| ATOM | 1576 | CG1AVAL | | A | 204 | 12.515 | 7.234 | 8.693 | 0.50 | 28.74 | B | C |
| ATOM | 1577 | CG1BVAL | | A | 204 | 14.477 | 7.817 | 9.730 | 0.50 | 25.49 | B | C |
| ATOM | 1578 | CG2AVAL | | A | 204 | 12.807 | 6.645 | 11.090 | 0.50 | 22.70 | B | C |
| ATOM | 1579 | CG2BVAL | | A | 204 | 12.347 | 7.020 | 8.762 | 0.50 | 30.61 | B | C |
| ATOM | 1580 | C | AVAL | A | 204 | 15.273 | 5.006 | 10.256 | 0.50 | 22.96 | B | C |
| ATOM | 1581 | C | BVAL | A | 204 | 15.286 | 4.967 | 10.244 | 0.50 | 23.47 | B | C |
| ATOM | 1582 | O | AVAL | A | 204 | 14.934 | 4.408 | 11.313 | 0.50 | 24.16 | B | O |
| ATOM | 1583 | O | BVAL | A | 204 | 14.963 | 4.330 | 11.282 | 0.50 | 24.44 | B | O |
| ATOM | 1584 | N | SER | A | 205 | 16.533 | 5.274 | 9.939 | 1.00 | 23.46 | B | N |
| ATOM | 1585 | CA | SER | A | 205 | 17.658 | 4.779 | 10.734 | 1.00 | 23.46 | B | C |
| ATOM | 1586 | CB | SER | A | 205 | 18.121 | 3.406 | 10.268 | 1.00 | 30.10 | B | C |
| ATOM | 1587 | OG | SER | A | 205 | 18.692 | 3.534 | 8.999 | 1.00 | 35.64 | B | O |
| ATOM | 1588 | C | SER | A | 205 | 18.761 | 5.803 | 10.713 | 1.00 | 23.88 | B | C |
| ATOM | 1589 | O | SER | A | 205 | 18.793 | 6.666 | 9.805 | 1.00 | 23.56 | B | O |
| ATOM | 1590 | N | LEU | A | 206 | 19.528 | 5.802 | 11.779 | 1.00 | 22.45 | B | N |
| ATOM | 1591 | CA | LEU | A | 206 | 20.679 | 6.714 | 11.916 | 1.00 | 24.29 | B | C |
| ATOM | 1592 | CB | LEU | A | 206 | 20.381 | 7.896 | 12.867 | 1.00 | 24.63 | B | C |
| ATOM | 1593 | CG | LEU | A | 206 | 21.507 | 8.910 | 13.043 | 1.00 | 27.42 | B | C |
| ATOM | 1594 | CD1 | LEU | A | 206 | 21.950 | 9.543 | 11.719 | 1.00 | 31.65 | B | C |
| ATOM | 1595 | CD2 | LEU | A | 206 | 21.034 | 10.011 | 13.987 | 1.00 | 27.41 | B | C |
| ATOM | 1596 | C | LEU | A | 206 | 21.831 | 5.834 | 12.326 | 1.00 | 26.79 | B | C |
| ATOM | 1597 | O | LEU | A | 206 | 21.954 | 5.477 | 13.480 | 1.00 | 26.33 | B | O |
| ATOM | 1598 | N | THR | A | 207 | 22.659 | 5.438 | 11.366 | 1.00 | 27.31 | B | N |
| ATOM | 1599 | CA | THR | A | 207 | 23.624 | 4.333 | 11.441 | 1.00 | 26.25 | B | C |
| ATOM | 1600 | CB | THR | A | 207 | 24.032 | 3.981 | 9.991 | 1.00 | 26.99 | B | C |
| ATOM | 1601 | OG1 | THR | A | 207 | 24.780 | 5.078 | 9.464 | 1.00 | 31.80 | B | O |
| ATOM | 1602 | CG2 | THR | A | 207 | 22.858 | 3.696 | 9.088 | 1.00 | 34.38 | B | C |
| ATOM | 1603 | C | THR | A | 207 | 24.854 | 4.699 | 12.272 | 1.00 | 27.66 | B | C |
| ATOM | 1604 | O | THR | A | 207 | 24.942 | 5.771 | 12.917 | 1.00 | 25.57 | B | O |
| ATOM | 1605 | N | GLY | A | 208 | 25.823 | 3.836 | 12.334 | 1.00 | 23.76 | B | N |
| ATOM | 1606 | CA | GLY | A | 208 | 27.157 | 4.091 | 12.874 | 1.00 | 22.11 | B | C |
| ATOM | 1607 | C | GLY | A | 208 | 27.191 | 4.370 | 14.370 | 1.00 | 21.44 | B | C |
| ATOM | 1608 | O | GLY | A | 208 | 26.482 | 3.682 | 15.151 | 1.00 | 21.58 | B | O |
| ATOM | 1609 | N | ALA | A | 209 | 27.956 | 5.372 | 14.796 | 1.00 | 21.94 | B | N |
| ATOM | 1610 | CA | ALA | A | 209 | 28.147 | 5.705 | 16.229 | 1.00 | 21.64 | B | C |
| ATOM | 1611 | CB | ALA | A | 209 | 29.082 | 6.883 | 16.402 | 1.00 | 21.34 | B | C |
| ATOM | 1612 | C | ALA | A | 209 | 26.768 | 6.040 | 16.834 | 1.00 | 19.73 | B | C |
| ATOM | 1613 | O | ALA | A | 209 | 26.565 | 5.728 | 18.033 | 1.00 | 20.14 | B | O |
| ATOM | 1614 | N | TRP | A | 210 | 25.849 | 6.639 | 16.102 | 1.00 | 19.70 | B | N |
| ATOM | 1615 | CA | TRP | A | 210 | 24.525 | 6.993 | 16.691 | 1.00 | 19.62 | B | C |
| ATOM | 1616 | CB | TRP | A | 210 | 23.747 | 7.919 | 15.787 | 1.00 | 19.98 | B | C |
| ATOM | 1617 | CG | TRP | A | 210 | 24.086 | 9.352 | 16.089 | 1.00 | 19.60 | B | C |
| ATOM | 1618 | CD1 | TRP | A | 210 | 24.880 | 10.222 | 15.412 | 1.00 | 20.83 | B | C |
| ATOM | 1619 | NE1 | TRP | A | 210 | 24.893 | 11.432 | 16.060 | 1.00 | 21.66 | B | N |
| ATOM | 1620 | CE2 | TRP | A | 210 | 24.203 | 11.323 | 17.242 | 1.00 | 20.04 | B | C |
| ATOM | 1621 | CD2 | TRP | A | 210 | 23.687 | 10.019 | 17.289 | 1.00 | 18.48 | B | C |
| ATOM | 1622 | CE3 | TRP | A | 210 | 22.907 | 9.642 | 18.392 | 1.00 | 20.59 | B | C |

Fig. 5AB

```
ATOM   1623  CZ3 TRP A 210      22.739  10.543  19.421  1.00 20.17           B    C
ATOM   1624  CH2 TRP A 210      23.237  11.856  19.333  1.00 20.28           B    C
ATOM   1625  CZ2 TRP A 210      23.995  12.252  18.262  1.00 19.31           B    C
ATOM   1626  C   TRP A 210      23.761   5.727  17.073  1.00 20.58           B    C
ATOM   1627  O   TRP A 210      23.409   5.556  18.233  1.00 19.33           B    O
ATOM   1628  N  ASER A 211      23.551   4.837  16.100  0.50 20.28           B    N
ATOM   1629  N  BSER A 211      23.517   4.824  16.132  0.50 20.57           B    N
ATOM   1630  CA ASER A 211      22.803   3.570  16.315  0.50 19.85           B    C
ATOM   1631  CA BSER A 211      22.738   3.595  16.437  0.50 19.89           B    C
ATOM   1632  CB ASER A 211      22.675   2.743  15.027  0.50 21.63           B    C
ATOM   1633  CB BSER A 211      22.499   2.805  15.170  0.50 22.82           B    C
ATOM   1634  OG ASER A 211      22.127   1.458  15.317  0.50 23.15           B    O
ATOM   1635  OG BSER A 211      23.756   2.529  14.593  0.50 23.92           B    O
ATOM   1636  C  ASER A 211      23.493   2.799  17.432  0.50 19.18           B    C
ATOM   1637  C  BSER A 211      23.508   2.796  17.493  0.50 19.40           B    C
ATOM   1638  O  ASER A 211      22.783   2.301  18.319  0.50 18.91           B    O
ATOM   1639  O  BSER A 211      22.911   2.264  18.428  0.50 18.54           B    O
ATOM   1640  N   LEU A 212      24.816   2.704  17.394  1.00 19.13           B    N
ATOM   1641  CA  LEU A 212      25.581   1.905  18.349  1.00 18.09           B    C
ATOM   1642  CB  LEU A 212      27.037   1.720  17.982  1.00 20.30           B    C
ATOM   1643  CG  LEU A 212      27.853   0.822  18.906  1.00 22.01           B    C
ATOM   1644  CD1 LEU A 212      27.310  -0.590  18.929  1.00 23.03           B    C
ATOM   1645  CD2 LEU A 212      29.313   0.783  18.449  1.00 25.09           B    C
ATOM   1646  C   LEU A 212      25.437   2.461  19.753  1.00 19.68           B    C
ATOM   1647  O   LEU A 212      25.241   1.746  20.704  1.00 19.13           B    O
ATOM   1648  N  ASER A 213      25.595   3.770  19.910  0.50 19.42           B    N
ATOM   1649  N  BSER A 213      25.623   3.776  19.876  0.50 19.29           B    N
ATOM   1650  CA ASER A 213      25.542   4.395  21.255  0.50 18.95           B    C
ATOM   1651  CA BSER A 213      25.568   4.459  21.190  0.50 19.18           B    C
ATOM   1652  CB ASER A 213      25.955   5.867  21.170  0.50 19.27           B    C
ATOM   1653  CB BSER A 213      25.902   5.974  21.092  0.50 18.17           B    C
ATOM   1654  OG ASER A 213      27.290   5.924  20.708  0.50 21.44           B    O
ATOM   1655  OG BSER A 213      24.850   6.725  20.516  0.50 21.57           B    O
ATOM   1656  C  ASER A 213      24.147   4.249  21.870  0.50 15.96           B    C
ATOM   1657  C  BSER A 213      24.200   4.257  21.842  0.50 16.19           B    C
ATOM   1658  O  ASER A 213      24.019   4.069  23.092  0.50 17.05           B    O
ATOM   1659  O  BSER A 213      24.193   4.057  23.085  0.50 17.85           B    O
ATOM   1660  N   SER A 214      23.127   4.330  21.058  1.00 17.74           B    N
ATOM   1661  CA  SER A 214      21.756   4.154  21.522  1.00 17.28           B    C
ATOM   1662  CB  SER A 214      20.793   4.411  20.442  1.00 18.24           B    C
ATOM   1663  OG  SER A 214      19.468   4.260  20.882  1.00 20.04           B    O
ATOM   1664  C   SER A 214      21.629   2.736  22.107  1.00 19.43           B    C
ATOM   1665  O   SER A 214      21.056   2.556  23.222  1.00 18.28           B    O
ATOM   1666  N   THR A 215      22.176   1.745  21.406  1.00 19.15           B    N
ATOM   1667  CA  THR A 215      22.111   0.333  21.857  1.00 18.53           B    C
ATOM   1668  CB  THR A 215      22.628  -0.556  20.729  1.00 18.00           B    C
ATOM   1669  OG1 THR A 215      21.783  -0.436  19.613  1.00 20.67           B    O
ATOM   1670  CG2 THR A 215      22.712  -1.999  21.183  1.00 19.86           B    C
ATOM   1671  C   THR A 215      22.909   0.179  23.135  1.00 15.36           B    C
ATOM   1672  O   THR A 215      22.429  -0.400  24.137  1.00 17.35           B    O
ATOM   1673  N   LEU A 216      24.161   0.612  23.166  1.00 16.47           B    N
ATOM   1674  CA  LEU A 216      25.024   0.305  24.285  1.00 16.18           B    C
ATOM   1675  CB  LEU A 216      26.487   0.651  23.994  1.00 18.99           B    C
ATOM   1676  CG  LEU A 216      27.089  -0.036  22.759  1.00 19.54           B    C
ATOM   1677  CD1 LEU A 216      28.569   0.200  22.720  1.00 21.68           B    C
ATOM   1678  CD2 LEU A 216      26.837  -1.575  22.796  1.00 20.82           B    C
ATOM   1679  C   LEU A 216      24.559   0.958  25.572  1.00 17.51           B    C
ATOM   1680  O   LEU A 216      24.694   0.391  26.675  1.00 16.86           B    O
```

Fig. 5AC

```
ATOM   1681  N   THR A 217      24.163   2.255  25.478  1.00 16.76           B   N
ATOM   1682  CA  THR A 217      23.686   2.933  26.694  1.00 16.61           B   C
ATOM   1683  CB  THR A 217      23.489   4.435  26.390  1.00 15.80           B   C
ATOM   1684  OG1 THR A 217      22.556   4.683  25.368  1.00 16.79           B   O
ATOM   1685  CG2 THR A 217      24.828   5.083  26.114  1.00 15.84           B   C
ATOM   1686  C   THR A 217      22.446   2.228  27.264  1.00 16.67           B   C
ATOM   1687  O   THR A 217      22.301   2.175  28.481  1.00 16.66           B   O
ATOM   1688  N   GLU A 218      21.529   1.779  26.415  1.00 15.78           B   N
ATOM   1689  CA  GLU A 218      20.371   0.971  26.885  1.00 16.42           B   C
ATOM   1690  CB  GLU A 218      19.428   0.711  25.739  1.00 17.14           B   C
ATOM   1691  CG  GLU A 218      18.230  -0.131  26.106  1.00 17.23           B   C
ATOM   1692  CD  GLU A 218      17.221   0.546  27.014  1.00 19.18           B   C
ATOM   1693  OE1 GLU A 218      17.353   1.849  27.222  1.00 18.60           B   O
ATOM   1694  OE2 GLU A 218      16.243  -0.044  27.439  1.00 18.14           B   O
ATOM   1695  C   GLU A 218      20.835  -0.350  27.513  1.00 16.20           B   C
ATOM   1696  O   GLU A 218      20.308  -0.725  28.568  1.00 16.69           B   O
ATOM   1697  N   ILE A 219      21.898  -0.953  26.996  1.00 16.07           B   N
ATOM   1698  CA  ILE A 219      22.376  -2.229  27.620  1.00 16.43           B   C
ATOM   1699  CB  ILE A 219      23.464  -2.885  26.773  1.00 18.53           B   C
ATOM   1700  CG1 ILE A 219      22.832  -3.404  25.472  1.00 18.89           B   C
ATOM   1701  CG2 ILE A 219      24.173  -3.974  27.590  1.00 19.41           B   C
ATOM   1702  CD1 ILE A 219      23.802  -4.034  24.470  1.00 19.67           B   C
ATOM   1703  C   ILE A 219      22.877  -1.920  29.031  1.00 16.57           B   C
ATOM   1704  O   ILE A 219      22.598  -2.659  29.989  1.00 16.52           B   O
ATOM   1705  N   PHE A 220      23.626  -0.808  29.218  1.00 15.61           B   N
ATOM   1706  CA  PHE A 220      24.054  -0.525  30.599  1.00 16.09           B   C
ATOM   1707  CB  PHE A 220      24.906   0.768  30.626  1.00 16.69           B   C
ATOM   1708  CG  PHE A 220      26.153   0.756  29.780  1.00 17.95           B   C
ATOM   1709  CD1 PHE A 220      26.932  -0.389  29.621  1.00 19.91           B   C
ATOM   1710  CE1 PHE A 220      28.089  -0.381  28.832  1.00 19.87           B   C
ATOM   1711  CZ  PHE A 220      28.511   0.760  28.212  1.00 21.86           B   C
ATOM   1712  CD2 PHE A 220      26.589   1.901  29.137  1.00 20.03           B   C
ATOM   1713  CE2 PHE A 220      27.748   1.902  28.360  1.00 21.19           B   C
ATOM   1714  C   PHE A 220      22.862  -0.359  31.550  1.00 15.65           B   C
ATOM   1715  O   PHE A 220      22.848  -0.814  32.702  1.00 16.22           B   O
ATOM   1716  N   LEU A 221      21.846   0.395  31.069  1.00 16.14           B   N
ATOM   1717  CA  LEU A 221      20.625   0.571  31.853  1.00 15.89           B   C
ATOM   1718  CB  LEU A 221      19.638   1.464  31.105  1.00 17.82           B   C
ATOM   1719  CG  LEU A 221      18.463   1.855  31.960  1.00 18.65           B   C
ATOM   1720  CD1 LEU A 221      18.420   3.354  32.223  1.00 19.20           B   C
ATOM   1721  CD2 LEU A 221      17.186   1.380  31.389  1.00 20.95           B   C
ATOM   1722  C   LEU A 221      19.974  -0.781  32.233  1.00 15.49           B   C
ATOM   1723  O   LEU A 221      19.525  -0.964  33.365  1.00 16.34           B   O
ATOM   1724  N   LEU A 222      19.909  -1.680  31.263  1.00 15.63           B   N
ATOM   1725  CA  LEU A 222      19.301  -3.003  31.513  1.00 16.07           B   C
ATOM   1726  CB  LEU A 222      19.193  -3.724  30.172  1.00 16.04           B   C
ATOM   1727  CG  LEU A 222      18.155  -3.175  29.209  1.00 16.90           B   C
ATOM   1728  CD1 LEU A 222      18.298  -3.745  27.796  1.00 18.66           B   C
ATOM   1729  CD2 LEU A 222      16.781  -3.407  29.724  1.00 17.32           B   C
ATOM   1730  C   LEU A 222      20.143  -3.793  32.535  1.00 15.48           B   C
ATOM   1731  O   LEU A 222      19.563  -4.442  33.382  1.00 16.65           B   O
ATOM   1732  N   GLN A 223      21.466  -3.742  32.390  1.00 15.08           B   N
ATOM   1733  CA  GLN A 223      22.365  -4.389  33.388  1.00 16.87           B   C
ATOM   1734  CB  GLN A 223      23.842  -4.162  33.096  1.00 17.64           B   C
ATOM   1735  CG  GLN A 223      24.335  -4.729  31.785  1.00 17.53           B   C
ATOM   1736  CD  GLN A 223      25.739  -4.250  31.490  1.00 18.81           B   C
ATOM   1737  OE1 GLN A 223      26.236  -3.329  32.170  1.00 19.73           B   O
ATOM   1738  NE2 GLN A 223      26.373  -4.791  30.476  1.00 20.14           B   N
```

Fig. 5AD

```
ATOM   1739  C    GLN A 223      22.051  -3.915  34.802  1.00 16.96       B  C
ATOM   1740  O    GLN A 223      21.902  -4.679  35.743  1.00 18.21       B  O
ATOM   1741  N    GLU A 224      21.950  -2.598  34.958  1.00 16.73       B  N
ATOM   1742  CA   GLU A 224      21.629  -1.998  36.262  1.00 17.71       B  C
ATOM   1743  CB   GLU A 224      21.701  -0.455  36.147  1.00 17.69       B  C
ATOM   1744  CG   GLU A 224      21.459   0.274  37.460  1.00 18.40       B  C
ATOM   1745  CD   GLU A 224      22.658   0.357  38.384  1.00 24.12       B  C
ATOM   1746  OE1  GLU A 224      23.703  -0.191  38.052  1.00 25.22       B  O
ATOM   1747  OE2  GLU A 224      22.530   0.976  39.475  1.00 25.92       B  O
ATOM   1748  C    GLU A 224      20.264  -2.439  36.753  1.00 17.17       B  C
ATOM   1749  O    GLU A 224      20.093  -2.831  37.899  1.00 19.46       B  O
ATOM   1750  N    ALA A 225      19.234  -2.323  35.925  1.00 16.43       B  N
ATOM   1751  CA   ALA A 225      17.852  -2.664  36.253  1.00 17.49       B  C
ATOM   1752  CB   ALA A 225      16.915  -2.384  35.084  1.00 19.01       B  C
ATOM   1753  C    ALA A 225      17.758  -4.138  36.678  1.00 17.35       B  C
ATOM   1754  O    ALA A 225      16.879  -4.461  37.483  1.00 18.67       B  O
ATOM   1755  N    GLN A 226      18.531  -4.978  35.999  1.00 17.01       B  N
ATOM   1756  CA   GLN A 226      18.490  -6.441  36.192  1.00 16.61       B  C
ATOM   1757  CB   GLN A 226      19.082  -7.097  34.956  1.00 16.15       B  C
ATOM   1758  CG   GLN A 226      19.217  -8.626  35.078  1.00 17.65       B  C
ATOM   1759  CD   GLN A 226      17.884  -9.264  35.198  1.00 18.20       B  C
ATOM   1760  OE1  GLN A 226      16.858  -8.755  34.759  1.00 17.50       B  O
ATOM   1761  NE2  GLN A 226      17.895 -10.508  35.728  1.00 19.66       B  N
ATOM   1762  C    GLN A 226      19.198  -6.789  37.496  1.00 21.49       B  C
ATOM   1763  O    GLN A 226      19.081  -7.930  37.916  1.00 21.98       B  O
ATOM   1764  N    GLY A 227      19.916  -5.885  38.131  1.00 20.15       B  N
ATOM   1765  CA   GLY A 227      20.643  -6.256  39.360  1.00 20.45       B  C
ATOM   1766  C    GLY A 227      21.929  -6.985  39.090  1.00 23.14       B  C
ATOM   1767  O    GLY A 227      22.464  -7.646  40.027  1.00 24.10       B  O
ATOM   1768  N   AMET A 228      22.494  -6.848  37.906  0.50 20.85       B  N
ATOM   1769  N   BMET A 228      22.505  -6.835  37.906  0.50 21.37       B  N
ATOM   1770  CA  AMET A 228      23.773  -7.527  37.609  0.50 21.29       B  C
ATOM   1771  CA  BMET A 228      23.794  -7.496  37.598  0.50 22.21       B  C
ATOM   1772  CB  AMET A 228      24.043  -7.514  36.108  0.50 20.90       B  C
ATOM   1773  CB  BMET A 228      24.160  -7.398  36.121  0.50 23.06       B  C
ATOM   1774  CG  AMET A 228      22.945  -8.300  35.404  0.50 22.08       B  C
ATOM   1775  CG  BMET A 228      23.253  -8.219  35.236  0.50 25.52       B  C
ATOM   1776  SD  AMET A 228      22.950  -8.325  33.604  0.50 21.36       B  S
ATOM   1777  SD  BMET A 228      23.896  -8.219  33.554  0.50 27.92       B  S
ATOM   1778  CE  AMET A 228      24.200  -9.555  33.221  0.50 24.06       B  C
ATOM   1779  CE  BMET A 228      24.959  -9.659  33.613  0.50 32.90       B  C
ATOM   1780  C   AMET A 228      24.900  -6.916  38.437  0.50 22.85       B  C
ATOM   1781  C   BMET A 228      24.922  -6.902  38.433  0.50 23.39       B  C
ATOM   1782  O   AMET A 228      24.877  -5.732  38.795  0.50 24.61       B  O
ATOM   1783  O   BMET A 228      24.992  -5.699  38.706  0.50 24.02       B  O
ATOM   1784  N    PRO A 229      25.880  -7.738  38.858  1.00 25.95       B  N
ATOM   1785  CA   PRO A 229      26.892  -7.283  39.806  1.00 28.89       B  C
ATOM   1786  CB   PRO A 229      27.524  -8.633  40.211  1.00 31.52       B  C
ATOM   1787  CG   PRO A 229      27.392  -9.456  38.967  1.00 31.36       B  C
ATOM   1788  CD   PRO A 229      25.965  -9.166  38.536  1.00 26.57       B  C
ATOM   1789  C    PRO A 229      27.921  -6.326  39.185  1.00 29.06       B  C
ATOM   1790  O    PRO A 229      28.439  -5.473  39.894  1.00 35.52       B  O
ATOM   1791  N    GLN A 230      28.213  -6.458  37.909  1.00 26.61       B  N
ATOM   1792  CA   GLN A 230      29.136  -5.529  37.215  1.00 29.92       B  C
ATOM   1793  CB   GLN A 230      30.339  -6.314  36.685  1.00 34.19       B  C
ATOM   1794  CG   GLN A 230      31.500  -5.434  36.226  1.00 41.40       B  C
ATOM   1795  CD   GLN A 230      32.438  -6.166  35.291  1.00 49.83       B  C
ATOM   1796  OE1  GLN A 230      33.620  -6.313  35.578  1.00 55.56       B  O
```

Fig. 5AE

| | | | | | | | | | | | |
|---|---|---|---|---|---|---|---|---|---|---|---|
| ATOM | 1797 | NE2 | GLN | A | 230 | 31.924 | -6.628 | 34.154 | 1.00 | 50.66 | B | N |
| ATOM | 1798 | C | GLN | A | 230 | 28.374 | -4.829 | 36.092 | 1.00 | 25.20 | B | C |
| ATOM | 1799 | O | GLN | A | 230 | 28.237 | -5.425 | 35.039 | 1.00 | 24.41 | B | O |
| ATOM | 1800 | N | VAL | A | 231 | 28.075 | -3.542 | 36.287 | 1.00 | 23.25 | B | N |
| ATOM | 1801 | CA | VAL | A | 231 | 27.370 | -2.726 | 35.250 | 1.00 | 20.72 | B | C |
| ATOM | 1802 | CB | VAL | A | 231 | 26.291 | -1.907 | 35.975 | 1.00 | 20.45 | B | C |
| ATOM | 1803 | CG1 | VAL | A | 231 | 25.627 | -0.882 | 35.084 | 1.00 | 19.90 | B | C |
| ATOM | 1804 | CG2 | VAL | A | 231 | 25.244 | -2.809 | 36.614 | 1.00 | 21.07 | B | C |
| ATOM | 1805 | C | VAL | A | 231 | 28.387 | -1.830 | 34.567 | 1.00 | 19.95 | B | C |
| ATOM | 1806 | O | VAL | A | 231 | 29.041 | -1.027 | 35.294 | 1.00 | 22.51 | B | O |
| ATOM | 1807 | N | ALA | A | 232 | 28.542 | -1.916 | 33.272 | 1.00 | 20.37 | B | N |
| ATOM | 1808 | CA | ALA | A | 232 | 29.463 | -1.036 | 32.527 | 1.00 | 21.53 | B | C |
| ATOM | 1809 | CB | ALA | A | 232 | 28.890 | 0.378 | 32.469 | 1.00 | 23.10 | B | C |
| ATOM | 1810 | C | ALA | A | 232 | 30.827 | -1.030 | 33.224 | 1.00 | 23.21 | B | C |
| ATOM | 1811 | O | ALA | A | 232 | 31.477 | 0.047 | 33.365 | 1.00 | 22.01 | B | O |
| ATOM | 1812 | N | TRP | A | 233 | 31.277 | -2.216 | 33.657 | 1.00 | 21.86 | B | N |
| ATOM | 1813 | CA | TRP | A | 233 | 32.608 | -2.406 | 34.291 | 1.00 | 23.02 | B | C |
| ATOM | 1814 | CB | TRP | A | 233 | 33.663 | -2.202 | 33.213 | 1.00 | 24.27 | B | C |
| ATOM | 1815 | CG | TRP | A | 233 | 33.345 | -3.025 | 32.012 | 1.00 | 22.63 | B | C |
| ATOM | 1816 | CD1 | TRP | A | 233 | 33.506 | -4.386 | 31.905 | 1.00 | 26.61 | B | C |
| ATOM | 1817 | NE1 | TRP | A | 233 | 33.067 | -4.807 | 30.688 | 1.00 | 24.80 | B | N |
| ATOM | 1818 | CE2 | TRP | A | 233 | 32.583 | -3.750 | 29.953 | 1.00 | 22.05 | B | C |
| ATOM | 1819 | CD2 | TRP | A | 233 | 32.728 | -2.616 | 30.789 | 1.00 | 22.97 | B | C |
| ATOM | 1820 | CE3 | TRP | A | 233 | 32.313 | -1.388 | 30.269 | 1.00 | 21.61 | B | C |
| ATOM | 1821 | CZ3 | TRP | A | 233 | 31.727 | -1.357 | 29.030 | 1.00 | 21.99 | B | C |
| ATOM | 1822 | CH2 | TRP | A | 233 | 31.568 | -2.486 | 28.237 | 1.00 | 23.31 | B | C |
| ATOM | 1823 | CZ2 | TRP | A | 233 | 32.007 | -3.702 | 28.685 | 1.00 | 23.11 | B | C |
| ATOM | 1824 | C | TRP | A | 233 | 32.783 | -1.498 | 35.502 | 1.00 | 23.36 | B | C |
| ATOM | 1825 | O | TRP | A | 233 | 33.958 | -1.235 | 35.855 | 1.00 | 25.68 | B | O |
| ATOM | 1826 | N | GLY | A | 234 | 31.715 | -1.094 | 36.197 | 1.00 | 23.96 | B | N |
| ATOM | 1827 | CA | GLY | A | 234 | 31.817 | -0.272 | 37.420 | 1.00 | 23.94 | B | C |
| ATOM | 1828 | C | GLY | A | 234 | 32.097 | 1.186 | 37.099 | 1.00 | 23.72 | B | C |
| ATOM | 1829 | O | GLY | A | 234 | 32.337 | 1.951 | 38.056 | 1.00 | 28.31 | B | O |
| ATOM | 1830 | N | ARG | A | 235 | 31.987 | 1.603 | 35.835 | 1.00 | 24.32 | B | N |
| ATOM | 1831 | CA | ARG | A | 235 | 32.457 | 2.957 | 35.432 | 1.00 | 24.67 | B | C |
| ATOM | 1832 | CB | ARG | A | 235 | 33.191 | 2.862 | 34.123 | 1.00 | 24.88 | B | C |
| ATOM | 1833 | CG | ARG | A | 235 | 34.451 | 2.016 | 34.244 | 1.00 | 26.13 | B | C |
| ATOM | 1834 | CD | ARG | A | 235 | 34.972 | 1.816 | 32.842 | 1.00 | 29.02 | B | C |
| ATOM | 1835 | NE | ARG | A | 235 | 36.012 | 0.814 | 32.874 | 1.00 | 30.55 | B | N |
| ATOM | 1836 | CZ | ARG | A | 235 | 36.289 | -0.017 | 31.875 | 1.00 | 27.86 | B | C |
| ATOM | 1837 | NH1 | ARG | A | 235 | 35.710 | -0.005 | 30.689 | 1.00 | 25.29 | B | N |
| ATOM | 1838 | NH2 | ARG | A | 235 | 37.212 | -0.922 | 32.107 | 1.00 | 28.73 | B | N |
| ATOM | 1839 | C | ARG | A | 235 | 31.346 | 3.998 | 35.329 | 1.00 | 24.42 | B | C |
| ATOM | 1840 | O | ARG | A | 235 | 31.679 | 5.121 | 34.864 | 1.00 | 28.80 | B | O |
| ATOM | 1841 | N | ILE | A | 236 | 30.127 | 3.727 | 35.785 | 1.00 | 23.03 | B | N |
| ATOM | 1842 | CA | ILE | A | 236 | 29.053 | 4.753 | 35.845 | 1.00 | 22.90 | B | C |
| ATOM | 1843 | CB | ILE | A | 236 | 27.797 | 4.302 | 35.085 | 1.00 | 21.99 | B | C |
| ATOM | 1844 | CG1 | ILE | A | 236 | 28.109 | 3.868 | 33.664 | 1.00 | 22.33 | B | C |
| ATOM | 1845 | CG2 | ILE | A | 236 | 26.808 | 5.464 | 35.122 | 1.00 | 22.96 | B | C |
| ATOM | 1846 | CD1 | ILE | A | 236 | 26.942 | 3.193 | 32.928 | 1.00 | 22.57 | B | C |
| ATOM | 1847 | C | ILE | A | 236 | 28.784 | 5.053 | 37.325 | 1.00 | 26.43 | B | C |
| ATOM | 1848 | O | ILE | A | 236 | 28.430 | 4.149 | 38.082 | 1.00 | 29.91 | B | O |
| ATOM | 1849 | N | THR | A | 237 | 28.911 | 6.308 | 37.729 | 1.00 | 29.49 | B | N |
| ATOM | 1850 | CA | THR | A | 237 | 28.585 | 6.782 | 39.099 | 1.00 | 32.10 | B | C |
| ATOM | 1851 | CB | THR | A | 237 | 29.880 | 7.089 | 39.863 | 1.00 | 35.34 | B | C |
| ATOM | 1852 | OG1 | THR | A | 237 | 30.688 | 5.913 | 39.812 | 1.00 | 39.75 | B | O |
| ATOM | 1853 | CG2 | THR | A | 237 | 29.654 | 7.435 | 41.319 | 1.00 | 38.48 | B | C |
| ATOM | 1854 | C | THR | A | 237 | 27.649 | 8.011 | 39.033 | 1.00 | 25.09 | B | C |

Fig. 5AF

```
ATOM   1855  O    THR A 237      28.048   8.983  38.430  1.00 26.06           B    O
ATOM   1856  N    GLY A 238      26.447   7.891  39.579  1.00 28.36           B    N
ATOM   1857  CA   GLY A 238      25.574   9.048  39.841  1.00 28.74           B    C
ATOM   1858  C    GLY A 238      24.649   9.396  38.698  1.00 24.94           B    C
ATOM   1859  O    GLY A 238      24.878   8.991  37.540  1.00 24.44           B    O
ATOM   1860  N    GLU A 239      23.684  10.240  39.012  1.00 25.00           B    N
ATOM   1861  CA   GLU A 239      22.651  10.684  38.068  1.00 23.47           B    C
ATOM   1862  CB   GLU A 239      21.658  11.576  38.802  1.00 26.30           B    C
ATOM   1863  CG   GLU A 239      20.544  12.070  37.927  1.00 24.89           B    C
ATOM   1864  CD   GLU A 239      19.493  12.970  38.549  1.00 29.69           B    C
ATOM   1865  OE1  GLU A 239      19.835  13.615  39.555  1.00 33.58           B    O
ATOM   1866  OE2  GLU A 239      18.353  13.065  38.001  1.00 31.35           B    O
ATOM   1867  C    GLU A 239      23.251  11.406  36.867  1.00 22.15           B    C
ATOM   1868  O    GLU A 239      22.808  11.222  35.699  1.00 20.33           B    O
ATOM   1869  N    LYS A 240      24.209  12.326  37.077  1.00 20.15           B    N
ATOM   1870  CA   LYS A 240      24.686  13.097  35.937  1.00 19.85           B    C
ATOM   1871  CB   LYS A 240      25.668  14.198  36.372  1.00 22.64           B    C
ATOM   1872  CG   LYS A 240      24.964  15.235  37.227  1.00 26.74           B    C
ATOM   1873  CD   LYS A 240      25.923  16.241  37.810  1.00 27.79           B    C
ATOM   1874  CE   LYS A 240      25.201  17.285  38.611  1.00 29.12           B    C
ATOM   1875  NZ   LYS A 240      24.705  16.763  39.898  1.00 32.39           B    N
ATOM   1876  C    LYS A 240      25.287  12.199  34.861  1.00 19.45           B    C
ATOM   1877  O    LYS A 240      24.997  12.398  33.686  1.00 20.03           B    O
ATOM   1878  N    GLU A 241      26.078  11.206  35.265  1.00 20.42           B    N
ATOM   1879  CA   GLU A 241      26.737  10.342  34.258  1.00 20.66           B    C
ATOM   1880  CB   GLU A 241      27.856   9.532  34.921  1.00 22.62           B    C
ATOM   1881  CG   GLU A 241      29.121  10.262  35.313  1.00 31.40           B    C
ATOM   1882  CD   GLU A 241      30.117   9.401  36.093  1.00 35.76           B    C
ATOM   1883  OE1  GLU A 241      30.116   8.110  35.881  1.00 29.90           B    O
ATOM   1884  OE2  GLU A 241      30.910   9.993  36.926  1.00 38.89           B    O
ATOM   1885  C    GLU A 241      25.706   9.394  33.587  1.00 16.19           B    C
ATOM   1886  O    GLU A 241      25.675   9.300  32.347  1.00 18.84           B    O
ATOM   1887  N    TRP A 242      24.792   8.898  34.382  1.00 17.99           B    N
ATOM   1888  CA   TRP A 242      23.711   8.032  33.856  1.00 18.05           B    C
ATOM   1889  CB   TRP A 242      22.785   7.560  34.961  1.00 18.89           B    C
ATOM   1890  CG   TRP A 242      23.143   6.239  35.562  1.00 18.50           B    C
ATOM   1891  CD1  TRP A 242      23.667   6.007  36.798  1.00 19.37           B    C
ATOM   1892  NE1  TRP A 242      23.917   4.675  36.985  1.00 21.20           B    N
ATOM   1893  CE2  TRP A 242      23.623   4.032  35.817  1.00 19.79           B    C
ATOM   1894  CD2  TRP A 242      23.122   4.963  34.895  1.00 18.97           B    C
ATOM   1895  CE3  TRP A 242      22.775   4.540  33.607  1.00 19.08           B    C
ATOM   1896  CZ3  TRP A 242      22.876   3.198  33.296  1.00 19.81           B    C
ATOM   1897  CH2  TRP A 242      23.371   2.300  34.238  1.00 19.38           B    C
ATOM   1898  CZ2  TRP A 242      23.729   2.685  35.508  1.00 19.97           B    C
ATOM   1899  C    TRP A 242      22.933   8.801  32.793  1.00 19.29           B    C
ATOM   1900  O    TRP A 242      22.632   8.286  31.714  1.00 18.13           B    O
ATOM   1901  N   AARG A 243      22.555  10.053  33.067  0.50 18.46           B    N
ATOM   1902  N   BARG A 243      22.506  10.016  33.147  0.50 18.42           B    N
ATOM   1903  CA  AARG A 243      21.694  10.816  32.117  0.50 17.82           B    C
ATOM   1904  CA  BARG A 243      21.644  10.798  32.234  0.50 18.39           B    C
ATOM   1905  CB  AARG A 243      21.026  11.988  32.833  0.50 18.29           B    C
ATOM   1906  CB  BARG A 243      20.906  11.909  32.987  0.50 18.36           B    C
ATOM   1907  CG  AARG A 243      19.924  11.552  33.768  0.50 18.73           B    C
ATOM   1908  CG  BARG A 243      19.896  11.423  34.004  0.50 20.98           B    C
ATOM   1909  CD  AARG A 243      18.998  12.643  34.329  0.50 19.53           B    C
ATOM   1910  CD  BARG A 243      18.822  12.453  34.351  0.50 20.40           B    C
ATOM   1911  NE  AARG A 243      17.787  12.155  34.959  0.50 16.83           B    N
ATOM   1912  NE  BARG A 243      17.609  12.305  33.579  0.50 20.14           B    N
```

Fig. 5AG

| | | | | | | | | | | |
|---|---|---|---|---|---|---|---|---|---|---|
| ATOM | 1913 | CZ | AARG | A | 243 | 16.693 | 11.757 | 34.275 | 0.50 18.03 | B | C |
| ATOM | 1914 | CZ | BARG | A | 243 | 16.509 | 11.748 | 34.069 | 0.50 21.77 | B | C |
| ATOM | 1915 | NH1 | AARG | A | 243 | 16.519 | 11.973 | 32.988 | 0.50 15.14 | B | N |
| ATOM | 1916 | NH1 | BARG | A | 243 | 16.446 | 11.447 | 35.355 | 0.50 27.16 | B | N |
| ATOM | 1917 | NH2 | AARG | A | 243 | 15.701 | 11.240 | 34.944 | 0.50 25.36 | B | N |
| ATOM | 1918 | NH2 | BARG | A | 243 | 15.439 | 11.616 | 33.329 | 0.50 32.24 | B | N |
| ATOM | 1919 | C | AARG | A | 243 | 22.498 | 11.299 | 30.919 | 0.50 16.72 | B | C |
| ATOM | 1920 | C | BARG | A | 243 | 22.441 | 11.277 | 31.016 | 0.50 16.57 | B | C |
| ATOM | 1921 | O | AARG | A | 243 | 22.031 | 11.421 | 29.772 | 0.50 18.51 | B | O |
| ATOM | 1922 | O | BARG | A | 243 | 21.836 | 11.339 | 29.936 | 0.50 20.04 | B | O |
| ATOM | 1923 | N | ASP | A | 244 | 23.738 | 11.630 | 31.159 | 1.00 17.61 | B | N |
| ATOM | 1924 | CA | ASP | A | 244 | 24.627 | 11.983 | 30.058 | 1.00 18.94 | B | C |
| ATOM | 1925 | CB | ASP | A | 244 | 25.997 | 12.340 | 30.637 | 1.00 19.73 | B | C |
| ATOM | 1926 | CG | ASP | A | 244 | 26.864 | 13.162 | 29.709 | 1.00 19.91 | B | C |
| ATOM | 1927 | OD1 | ASP | A | 244 | 26.327 | 13.743 | 28.713 | 1.00 23.91 | B | O |
| ATOM | 1928 | OD2 | ASP | A | 244 | 28.084 | 13.163 | 29.943 | 1.00 21.63 | B | O |
| ATOM | 1929 | C | ASP | A | 244 | 24.677 | 10.834 | 29.025 | 1.00 17.54 | B | C |
| ATOM | 1930 | O | ASP | A | 244 | 24.585 | 11.043 | 27.834 | 1.00 19.07 | B | O |
| ATOM | 1931 | N | LEU | A | 245 | 24.862 | 9.625 | 29.520 | 1.00 19.10 | B | N |
| ATOM | 1932 | CA | LEU | A | 245 | 24.907 | 8.422 | 28.642 | 1.00 19.39 | B | C |
| ATOM | 1933 | CB | LEU | A | 245 | 25.276 | 7.210 | 29.523 | 1.00 18.27 | B | C |
| ATOM | 1934 | CG | LEU | A | 245 | 26.728 | 7.219 | 29.971 | 1.00 19.92 | B | C |
| ATOM | 1935 | CD1 | LEU | A | 245 | 26.955 | 6.231 | 31.088 | 1.00 20.25 | B | C |
| ATOM | 1936 | CD2 | LEU | A | 245 | 27.725 | 6.974 | 28.821 | 1.00 20.71 | B | C |
| ATOM | 1937 | C | LEU | A | 245 | 23.573 | 8.191 | 27.948 | 1.00 15.50 | B | C |
| ATOM | 1938 | O | LEU | A | 245 | 23.511 | 8.076 | 26.706 | 1.00 17.22 | B | O |
| ATOM | 1939 | N | LEU | A | 246 | 22.502 | 8.155 | 28.738 | 1.00 15.50 | B | N |
| ATOM | 1940 | CA | LEU | A | 246 | 21.159 | 7.875 | 28.239 | 1.00 17.11 | B | C |
| ATOM | 1941 | CB | LEU | A | 246 | 20.124 | 7.477 | 29.275 | 1.00 15.14 | B | C |
| ATOM | 1942 | CG | LEU | A | 246 | 20.058 | 5.950 | 29.588 | 1.00 16.98 | B | C |
| ATOM | 1943 | CD1 | LEU | A | 246 | 19.622 | 5.106 | 28.364 | 1.00 20.29 | B | C |
| ATOM | 1944 | CD2 | LEU | A | 246 | 21.329 | 5.414 | 30.130 | 1.00 18.01 | B | C |
| ATOM | 1945 | C | LEU | A | 246 | 20.654 | 8.955 | 27.293 | 1.00 15.70 | B | C |
| ATOM | 1946 | O | LEU | A | 246 | 19.757 | 8.745 | 26.495 | 1.00 17.24 | B | O |
| ATOM | 1947 | N | SER | A | 247 | 21.239 | 10.169 | 27.388 | 1.00 17.62 | B | N |
| ATOM | 1948 | CA | SER | A | 247 | 20.860 | 11.242 | 26.449 | 1.00 17.42 | B | C |
| ATOM | 1949 | CB | SER | A | 247 | 21.534 | 12.573 | 26.792 | 1.00 17.91 | B | C |
| ATOM | 1950 | OG | SER | A | 247 | 22.853 | 12.641 | 26.379 | 1.00 18.70 | B | O |
| ATOM | 1951 | C | SER | A | 247 | 21.133 | 10.880 | 24.985 | 1.00 15.00 | B | C |
| ATOM | 1952 | O | SER | A | 247 | 20.383 | 11.298 | 24.116 | 1.00 16.67 | B | O |
| ATOM | 1953 | N | LEU | A | 248 | 22.095 | 9.981 | 24.763 | 1.00 17.30 | B | N |
| ATOM | 1954 | CA | LEU | A | 248 | 22.399 | 9.526 | 23.380 | 1.00 17.41 | B | C |
| ATOM | 1955 | CB | LEU | A | 248 | 23.722 | 8.788 | 23.343 | 1.00 17.92 | B | C |
| ATOM | 1956 | CG | LEU | A | 248 | 24.943 | 9.656 | 23.631 | 1.00 19.16 | B | C |
| ATOM | 1957 | CD1 | LEU | A | 248 | 26.191 | 8.826 | 23.840 | 1.00 19.70 | B | C |
| ATOM | 1958 | CD2 | LEU | A | 248 | 25.158 | 10.683 | 22.500 | 1.00 20.14 | B | C |
| ATOM | 1959 | C | LEU | A | 248 | 21.255 | 8.648 | 22.884 | 1.00 16.12 | B | C |
| ATOM | 1960 | O | LEU | A | 248 | 20.736 | 8.804 | 21.773 | 1.00 16.68 | B | O |
| ATOM | 1961 | N | HIS | A | 249 | 20.820 | 7.752 | 23.766 | 1.00 16.97 | B | N |
| ATOM | 1962 | CA | HIS | A | 249 | 19.681 | 6.861 | 23.476 | 1.00 15.90 | B | C |
| ATOM | 1963 | CB | HIS | A | 249 | 19.526 | 5.898 | 24.666 | 1.00 16.28 | B | C |
| ATOM | 1964 | CG | HIS | A | 249 | 18.368 | 4.985 | 24.539 | 1.00 16.58 | B | C |
| ATOM | 1965 | ND1 | HIS | A | 249 | 18.447 | 3.769 | 23.842 | 1.00 18.28 | B | N |
| ATOM | 1966 | CE1 | HIS | A | 249 | 17.254 | 3.206 | 23.888 | 1.00 18.17 | B | C |
| ATOM | 1967 | NE2 | HIS | A | 249 | 16.408 | 3.902 | 24.631 | 1.00 18.14 | B | N |
| ATOM | 1968 | CD2 | HIS | A | 249 | 17.109 | 5.031 | 25.037 | 1.00 16.74 | B | C |
| ATOM | 1969 | C | HIS | A | 249 | 18.424 | 7.697 | 23.258 | 1.00 15.20 | B | C |
| ATOM | 1970 | O | HIS | A | 249 | 17.652 | 7.532 | 22.292 | 1.00 16.62 | B | O |

Fig. 5AH

```
ATOM   1971  N   ASN A 250      18.152   8.631  24.197  1.00 16.76      B   N
ATOM   1972  CA  ASN A 250      16.949   9.462  24.103  1.00 16.57      B   C
ATOM   1973  CB  ASN A 250      16.747  10.265  25.408  1.00 15.53      B   C
ATOM   1974  CG  ASN A 250      16.469   9.392  26.612  1.00 17.86      B   C
ATOM   1975  OD1 ASN A 250      15.761   8.351  26.493  1.00 16.26      B   O
ATOM   1976  ND2 ASN A 250      16.917   9.825  27.773  1.00 18.19      B   N
ATOM   1977  C   ASN A 250      16.974  10.371  22.831  1.00 13.61      B   C
ATOM   1978  O   ASN A 250      15.924  10.565  22.270  1.00 15.53      B   O
ATOM   1979  N   ALA A 251      18.155  10.813  22.454  1.00 16.31      B   N
ATOM   1980  CA  ALA A 251      18.334  11.656  21.242  1.00 17.91      B   C
ATOM   1981  CB  ALA A 251      19.702  12.203  21.155  1.00 17.27      B   C
ATOM   1982  C   ALA A 251      17.995  10.869  19.980  1.00 16.88      B   C
ATOM   1983  O   ALA A 251      17.251  11.356  19.096  1.00 18.16      B   O
ATOM   1984  N   AGLN A 252     18.467   9.612  19.930  0.50 16.42      B   N
ATOM   1985  N   BGLN A 252     18.465   9.609  19.926  0.50 17.50      B   N
ATOM   1986  CA  AGLN A 252     18.229   8.720  18.758  0.50 16.43      B   C
ATOM   1987  CA  BGLN A 252     18.196   8.757  18.732  0.50 18.84      B   C
ATOM   1988  CB  AGLN A 252     19.012   7.440  19.002  0.50 15.77      B   C
ATOM   1989  CB  BGLN A 252     18.895   7.409  18.806  0.50 21.05      B   C
ATOM   1990  CG  AGLN A 252     18.914   6.428  17.875  0.50 14.39      B   C
ATOM   1991  CG  BGLN A 252     18.513   6.563  17.606  0.50 22.94      B   C
ATOM   1992  CD  AGLN A 252     19.838   6.687  16.711  0.50 14.60      B   C
ATOM   1993  CD  BGLN A 252     19.466   5.436  17.315  0.50 29.30      B   C
ATOM   1994  OE1AGLN A 252      20.428   7.764  16.568  0.50 15.34      B   O
ATOM   1995  OE1BGLN A 252      19.196   4.295  17.671  0.50 32.77      B   O
ATOM   1996  NE2AGLN A 252      19.994   5.649  15.886  0.50 14.78      B   N
ATOM   1997  NE2BGLN A 252      20.561   5.742  16.627  0.50 27.53      B   N
ATOM   1998  C   AGLN A 252     16.719   8.482  18.650  0.50 15.59      B   C
ATOM   1999  C   BGLN A 252     16.691   8.509  18.650  0.50 16.61      B   C
ATOM   2000  O   AGLN A 252     16.135   8.560  17.542  0.50 17.29      B   O
ATOM   2001  O   BGLN A 252     16.089   8.589  17.556  0.50 17.55      B   O
ATOM   2002  N   PHE A 253      16.061   8.174  19.793  1.00 17.27      B   N
ATOM   2003  CA  PHE A 253      14.611   7.933  19.817  1.00 17.41      B   C
ATOM   2004  CB  PHE A 253      14.139   7.354  21.158  1.00 18.17      B   C
ATOM   2005  CG  PHE A 253      14.236   5.845  21.176  1.00 17.86      B   C
ATOM   2006  CD1 PHE A 253      15.456   5.212  21.122  1.00 18.64      B   C
ATOM   2007  CE1 PHE A 253      15.551   3.810  21.111  1.00 19.35      B   C
ATOM   2008  CZ  PHE A 253      14.392   3.098  21.044  1.00 19.37      B   C
ATOM   2009  CD2 PHE A 253      13.087   5.087  21.074  1.00 19.56      B   C
ATOM   2010  CE2 PHE A 253      13.185   3.702  21.065  1.00 19.37      B   C
ATOM   2011  C   PHE A 253      13.836   9.206  19.431  1.00 17.04      B   C
ATOM   2012  O   PHE A 253      12.816   9.153  18.805  1.00 17.42      B   O
ATOM   2013  N   ASP A 254      14.281  10.356  19.942  1.00 19.09      B   N
ATOM   2014  CA  ASP A 254      13.662  11.650  19.570  1.00 17.70      B   C
ATOM   2015  CB  ASP A 254      14.380  12.764  20.323  1.00 19.43      B   C
ATOM   2016  CG  ASP A 254      13.650  14.086  20.310  1.00 22.44      B   C
ATOM   2017  OD1 ASP A 254      12.482  14.151  20.072  1.00 20.97      B   O
ATOM   2018  OD2 ASP A 254      14.317  15.046  20.711  1.00 35.48      B   O
ATOM   2019  C   ASP A 254      13.640  11.840  18.027  1.00 16.15      B   C
ATOM   2020  O   ASP A 254      12.568  12.048  17.495  1.00 18.97      B   O
ATOM   2021  N   LEU A 255      14.799  11.705  17.407  1.00 18.84      B   N
ATOM   2022  CA  LEU A 255      14.845  11.915  15.930  1.00 18.98      B   C
ATOM   2023  CB  LEU A 255      16.256  11.850  15.392  1.00 22.41      B   C
ATOM   2024  CG  LEU A 255      17.129  13.045  15.678  1.00 23.76      B   C
ATOM   2025  CD1 LEU A 255      18.351  13.002  14.754  1.00 22.29      B   C
ATOM   2026  CD2 LEU A 255      16.411  14.380  15.509  1.00 23.34      B   C
ATOM   2027  C   LEU A 255      14.062  10.846  15.203  1.00 20.79      B   C
ATOM   2028  O   LEU A 255      13.237  11.135  14.301  1.00 21.04      B   O
```

Fig. 5AI

```
ATOM   2029  N    LEU A 256      14.346   9.566  15.525  1.00 18.91           B  N
ATOM   2030  CA   LEU A 256      13.808   8.464  14.686  1.00 19.84           B  C
ATOM   2031  CB   LEU A 256      14.697   7.239  14.805  1.00 19.68           B  C
ATOM   2032  CG   LEU A 256      16.133   7.416  14.374  1.00 20.16           B  C
ATOM   2033  CD1  LEU A 256      16.843   6.109  14.440  1.00 21.80           B  C
ATOM   2034  CD2  LEU A 256      16.201   7.971  12.923  1.00 23.42           B  C
ATOM   2035  C    LEU A 256      12.365   8.124  14.999  1.00 20.30           B  C
ATOM   2036  O    LEU A 256      11.696   7.507  14.150  1.00 21.96           B  O
ATOM   2037  N    GLN A 257      11.875   8.393  16.224  1.00 18.30           B  N
ATOM   2038  CA   GLN A 257      10.554   7.926  16.636  1.00 18.89           B  C
ATOM   2039  CB   GLN A 257      10.704   6.894  17.760  1.00 18.24           B  C
ATOM   2040  CG   GLN A 257      11.551   5.714  17.389  1.00 18.76           B  C
ATOM   2041  CD   GLN A 257      11.077   4.864  16.242  1.00 17.76           B  C
ATOM   2042  OE1  GLN A 257       9.913   4.847  15.854  1.00 20.53           B  O
ATOM   2043  NE2  GLN A 257      12.041   4.095  15.766  1.00 23.48           B  N
ATOM   2044  C    GLN A 257       9.624   9.037  17.145  1.00 16.01           B  C
ATOM   2045  O    GLN A 257       8.432   8.865  17.037  1.00 18.29           B  O
ATOM   2046  N    ARG A 258      10.166  10.189  17.556  1.00 17.43           B  N
ATOM   2047  CA   ARG A 258       9.269  11.287  18.025  1.00 18.77           B  C
ATOM   2048  CB   ARG A 258       9.767  11.997  19.280  1.00 17.27           B  C
ATOM   2049  CG   ARG A 258       9.912  11.089  20.523  1.00 17.82           B  C
ATOM   2050  CD   ARG A 258      10.373  11.850  21.736  1.00 21.31           B  C
ATOM   2051  NE   ARG A 258       9.302  12.670  22.256  1.00 22.41           B  N
ATOM   2052  CZ   ARG A 258       9.211  13.989  22.249  1.00 30.90           B  C
ATOM   2053  NH1  ARG A 258      10.161  14.729  21.690  1.00 34.50           B  N
ATOM   2054  NH2  ARG A 258       8.144  14.565  22.808  1.00 29.79           B  N
ATOM   2055  C    ARG A 258       8.976  12.327  16.928  1.00 20.35           B  C
ATOM   2056  O    ARG A 258       7.896  12.913  16.960  1.00 23.08           B  O
ATOM   2057  N    THR A 259       9.870  12.494  15.976  1.00 20.50           B  N
ATOM   2058  CA   THR A 259       9.578  13.453  14.855  1.00 19.67           B  C
ATOM   2059  CB   THR A 259      10.648  13.265  13.804  1.00 20.10           B  C
ATOM   2060  OG1  THR A 259      11.938  13.462  14.354  1.00 18.95           B  O
ATOM   2061  CG2  THR A 259      10.436  14.236  12.645  1.00 20.33           B  C
ATOM   2062  C    THR A 259       8.175  13.203  14.333  1.00 18.95           B  C
ATOM   2063  O    THR A 259       7.877  12.091  13.892  1.00 19.14           B  O
ATOM   2064  N    PRO A 260       7.265  14.214  14.296  1.00 20.62           B  N
ATOM   2065  CA   PRO A 260       5.885  13.947  13.950  1.00 21.54           B  C
ATOM   2066  CB   PRO A 260       5.186  15.285  14.051  1.00 25.33           B  C
ATOM   2067  CG   PRO A 260       6.021  16.033  15.005  1.00 26.77           B  C
ATOM   2068  CD   PRO A 260       7.457  15.577  14.811  1.00 24.19           B  C
ATOM   2069  C    PRO A 260       5.659  13.308  12.581  1.00 22.30           B  C
ATOM   2070  O    PRO A 260       4.741  12.554  12.403  1.00 22.15           B  O
ATOM   2071  N    GLU A 261       6.518  13.668  11.621  1.00 24.08           B  N
ATOM   2072  CA   GLU A 261       6.392  13.152  10.239  1.00 23.95           B  C
ATOM   2073  CB   GLU A 261       7.377  13.853   9.309  1.00 26.23           B  C
ATOM   2074  CG   GLU A 261       6.961  15.292   8.973  1.00 26.80           B  C
ATOM   2075  CD   GLU A 261       7.271  16.365   9.999  1.00 31.63           B  C
ATOM   2076  OE1  GLU A 261       7.868  16.074  11.103  1.00 27.77           B  O
ATOM   2077  OE2  GLU A 261       6.900  17.535   9.730  1.00 32.40           B  O
ATOM   2078  C    GLU A 261       6.605  11.641  10.210  1.00 24.27           B  C
ATOM   2079  O    GLU A 261       6.091  11.000   9.297  1.00 26.68           B  O
ATOM   2080  N    VAL A 262       7.316  11.077  11.196  1.00 22.07           B  N
ATOM   2081  CA   VAL A 262       7.417   9.609  11.402  1.00 22.48           B  C
ATOM   2082  CB   VAL A 262       8.773   9.250  12.016  1.00 22.35           B  C
ATOM   2083  CG1  VAL A 262       8.783   7.831  12.506  1.00 23.49           B  C
ATOM   2084  CG2  VAL A 262       9.949   9.538  11.089  1.00 26.08           B  C
ATOM   2085  C    VAL A 262       6.294   9.137  12.338  1.00 18.58           B  C
ATOM   2086  O    VAL A 262       5.619   8.162  12.033  1.00 20.63           B  O
```

Fig. 5AJ

```
ATOM   2087  N    ALA A 263       6.187   9.845  13.465  1.00 19.67           B  N
ATOM   2088  CA   ALA A 263       5.378   9.384  14.617  1.00 20.22           B  C
ATOM   2089  CB   ALA A 263       5.597  10.270  15.807  1.00 20.10           B  C
ATOM   2090  C    ALA A 263       3.907   9.261  14.305  1.00 20.44           B  C
ATOM   2091  O    ALA A 263       3.243   8.306  14.732  1.00 20.59           B  O
ATOM   2092  N   AARG A 264       3.342  10.233  13.560  0.50 20.01           B  N
ATOM   2093  N   BARG A 264       3.336  10.229  13.561  0.50 20.01           B  N
ATOM   2094  CA  AARG A 264       1.892  10.222  13.292  0.50 20.34           B  C
ATOM   2095  CA  BARG A 264       1.889  10.186  13.289  0.50 20.16           B  C
ATOM   2096  CB  AARG A 264       1.486  11.530  12.594  0.50 21.74           B  C
ATOM   2097  CB  BARG A 264       1.460  11.424  12.502  0.50 21.45           B  C
ATOM   2098  CG  AARG A 264       1.430  12.745  13.516  0.50 23.58           B  C
ATOM   2099  CG  BARG A 264       1.647  12.712  13.281  0.50 22.70           B  C
ATOM   2100  CD  AARG A 264       1.039  14.043  12.794  0.50 26.17           B  C
ATOM   2101  CD  BARG A 264       1.113  13.884  12.463  0.50 24.84           B  C
ATOM   2102  NE  AARG A 264       2.123  14.437  11.898  0.50 30.21           B  N
ATOM   2103  NE  BARG A 264       0.966  15.064  13.290  0.50 25.42           B  N
ATOM   2104  CZ  AARG A 264       2.227  15.590  11.254  0.50 32.40           B  C
ATOM   2105  CZ  BARG A 264       0.289  16.148  12.940  0.50 28.01           B  C
ATOM   2106  NH1AARG A 264       1.280  16.506  11.365  0.50 34.78           B  N
ATOM   2107  NH1BARG A 264      -0.347  16.171  11.774  0.50 30.79           B  N
ATOM   2108  NH2AARG A 264       3.277  15.823  10.489  0.50 30.20           B  N
ATOM   2109  NH2BARG A 264       0.219  17.172  13.772  0.50 28.23           B  N
ATOM   2110  C   AARG A 264       1.541   8.942  12.516  0.50 20.69           B  C
ATOM   2111  C   BARG A 264       1.550   8.907  12.527  0.50 20.62           B  C
ATOM   2112  O   AARG A 264       0.554   8.289  12.874  0.50 21.52           B  O
ATOM   2113  O   BARG A 264       0.570   8.248  12.883  0.50 21.58           B  O
ATOM   2114  N    SER A 265       2.308   8.589  11.467  1.00 21.33           B  N
ATOM   2115  CA   SER A 265       2.098   7.338  10.706  1.00 19.93           B  C
ATOM   2116  CB   SER A 265       3.045   7.233   9.538  1.00 22.49           B  C
ATOM   2117  OG   SER A 265       2.652   8.159   8.487  1.00 23.93           B  O
ATOM   2118  C    SER A 265       2.257   6.099  11.614  1.00 18.31           B  C
ATOM   2119  O    SER A 265       1.345   5.293  11.687  1.00 20.66           B  O
ATOM   2120  N    ARG A 266       3.391   6.047  12.261  1.00 19.99           B  N
ATOM   2121  CA   ARG A 266       3.761   4.814  13.015  1.00 19.67           B  C
ATOM   2122  CB   ARG A 266       5.221   4.856  13.393  1.00 19.96           B  C
ATOM   2123  CG   ARG A 266       5.874   3.478  13.493  1.00 21.28           B  C
ATOM   2124  CD   ARG A 266       7.355   3.571  13.707  1.00 21.54           B  C
ATOM   2125  NE   ARG A 266       8.033   2.263  13.813  1.00 21.66           B  N
ATOM   2126  CZ   ARG A 266       8.103   1.530  14.924  1.00 22.36           B  C
ATOM   2127  NH1  ARG A 266       7.484   1.899  16.036  1.00 22.08           B  N
ATOM   2128  NH2  ARG A 266       8.773   0.384  14.892  1.00 23.39           B  N
ATOM   2129  C    ARG A 266       2.869   4.606  14.245  1.00 18.76           B  C
ATOM   2130  O    ARG A 266       2.638   3.422  14.573  1.00 19.76           B  O
ATOM   2131  N    ALA A 267       2.301   5.656  14.813  1.00 19.61           B  N
ATOM   2132  CA   ALA A 267       1.380   5.573  15.973  1.00 18.62           B  C
ATOM   2133  CB   ALA A 267       1.523   6.812  16.817  1.00 19.50           B  C
ATOM   2134  C    ALA A 267      -0.070   5.414  15.567  1.00 19.64           B  C
ATOM   2135  O    ALA A 267      -0.911   5.287  16.409  1.00 18.93           B  O
ATOM   2136  N    THR A 268      -0.435   5.474  14.264  1.00 19.97           B  N
ATOM   2137  CA   THR A 268      -1.867   5.563  13.879  1.00 20.27           B  C
ATOM   2138  CB   THR A 268      -2.046   5.817  12.364  1.00 21.25           B  C
ATOM   2139  OG1  THR A 268      -1.775   7.193  12.079  1.00 21.68           B  O
ATOM   2140  CG2  THR A 268      -3.451   5.471  11.967  1.00 21.85           B  C
ATOM   2141  C    THR A 268      -2.644   4.389  14.442  1.00 19.38           B  C
ATOM   2142  O    THR A 268      -3.724   4.600  14.995  1.00 20.18           B  O
ATOM   2143  N    PRO A 269      -2.182   3.119  14.338  1.00 19.67           B  N
ATOM   2144  CA   PRO A 269      -3.022   2.052  14.871  1.00 20.13           B  C
```

Fig. 5AK

```
ATOM   2145  CB  PRO A 269      -2.245   0.789  14.523  1.00 20.77           B    C
ATOM   2146  CG  PRO A 269      -1.462   1.184  13.312  1.00 22.10           B    C
ATOM   2147  CD  PRO A 269      -1.078   2.633  13.523  1.00 20.65           B    C
ATOM   2148  C   PRO A 269      -3.285   2.198  16.372  1.00 17.46           B    C
ATOM   2149  O   PRO A 269      -4.391   1.934  16.778  1.00 19.45           B    O
ATOM   2150  N   LEU A 270      -2.245   2.562  17.113  1.00 19.90           B    N
ATOM   2151  CA  LEU A 270      -2.396   2.715  18.578  1.00 18.65           B    C
ATOM   2152  CB  LEU A 270      -1.023   2.820  19.235  1.00 19.95           B    C
ATOM   2153  CG  LEU A 270      -0.280   1.483  19.371  1.00 19.37           B    C
ATOM   2154  CD1 LEU A 270       1.169   1.674  19.701  1.00 18.28           B    C
ATOM   2155  CD2 LEU A 270      -0.942   0.579  20.387  1.00 19.81           B    C
ATOM   2156  C   LEU A 270      -3.273   3.913  18.901  1.00 19.62           B    C
ATOM   2157  O   LEU A 270      -4.117   3.824  19.785  1.00 19.62           B    O
ATOM   2158  N   LEU A 271      -3.139   5.002  18.138  1.00 19.58           B    N
ATOM   2159  CA  LEU A 271      -4.056   6.149  18.340  1.00 19.52           B    C
ATOM   2160  CB  LEU A 271      -3.658   7.318  17.433  1.00 21.24           B    C
ATOM   2161  CG  LEU A 271      -2.314   7.980  17.714  1.00 21.33           B    C
ATOM   2162  CD1 LEU A 271      -1.877   8.929  16.600  1.00 23.84           B    C
ATOM   2163  CD2 LEU A 271      -2.329   8.740  19.021  1.00 22.34           B    C
ATOM   2164  C   LEU A 271      -5.507   5.756  18.072  1.00 21.01           B    C
ATOM   2165  O   LEU A 271      -6.400   6.148  18.867  1.00 20.98           B    O
ATOM   2166  N   ASP A 272      -5.741   5.019  16.991  1.00 20.61           B    N
ATOM   2167  CA  ASP A 272      -7.111   4.596  16.635  1.00 22.38           B    C
ATOM   2168  CB  ASP A 272      -7.106   3.831  15.314  1.00 22.54           B    C
ATOM   2169  CG  ASP A 272      -6.964   4.688  14.080  1.00 25.59           B    C
ATOM   2170  OD1 ASP A 272      -6.937   5.953  14.201  1.00 25.15           B    O
ATOM   2171  OD2 ASP A 272      -6.866   4.044  13.021  1.00 25.09           B    O
ATOM   2172  C   ASP A 272      -7.661   3.720  17.759  1.00 20.61           B    C
ATOM   2173  O   ASP A 272      -8.818   3.780  18.072  1.00 21.99           B    O
ATOM   2174  N   LEU A 273      -6.827   2.812  18.272  1.00 21.30           B    N
ATOM   2175  CA  LEU A 273      -7.273   1.883  19.319  1.00 21.82           B    C
ATOM   2176  CB  LEU A 273      -6.182   0.823  19.486  1.00 21.19           B    C
ATOM   2177  CG  LEU A 273      -6.520  -0.231  20.524  1.00 22.10           B    C
ATOM   2178  CD1 LEU A 273      -7.868  -0.907  20.284  1.00 23.56           B    C
ATOM   2179  CD2 LEU A 273      -5.388  -1.270  20.584  1.00 22.08           B    C
ATOM   2180  C   LEU A 273      -7.584   2.626  20.631  1.00 18.98           B    C
ATOM   2181  O   LEU A 273      -8.626   2.356  21.253  1.00 20.60           B    O
ATOM   2182  N   ILE A 274      -6.709   3.580  21.003  1.00 20.58           B    N
ATOM   2183  CA  ILE A 274      -6.942   4.440  22.200  1.00 20.02           B    C
ATOM   2184  CB  ILE A 274      -5.742   5.348  22.454  1.00 20.53           B    C
ATOM   2185  CG1 ILE A 274      -4.470   4.591  22.847  1.00 19.66           B    C
ATOM   2186  CG2 ILE A 274      -6.135   6.357  23.512  1.00 22.86           B    C
ATOM   2187  CD1 ILE A 274      -3.183   5.345  22.587  1.00 20.42           B    C
ATOM   2188  C   ILE A 274      -8.255   5.225  22.017  1.00 21.38           B    C
ATOM   2189  O   ILE A 274      -9.084   5.271  22.921  1.00 22.64           B    O
ATOM   2190  N   ASP A 275      -8.415   5.836  20.858  1.00 22.89           B    N
ATOM   2191  CA  ASP A 275      -9.616   6.629  20.494  1.00 24.18           B    C
ATOM   2192  CB  ASP A 275      -9.468   7.197  19.081  1.00 25.90           B    C
ATOM   2193  CG  ASP A 275     -10.601   8.091  18.589  1.00 29.70           B    C
ATOM   2194  OD1 ASP A 275     -11.145   8.813  19.392  1.00 31.97           B    O
ATOM   2195  OD2 ASP A 275     -10.735   8.171  17.366  1.00 35.28           B    O
ATOM   2196  C   ASP A 275     -10.853   5.745  20.630  1.00 24.42           B    C
ATOM   2197  O   ASP A 275     -11.783   6.116  21.354  1.00 26.02           B    O
ATOM   2198  N   THR A 276     -10.889   4.600  19.968  1.00 22.50           B    N
ATOM   2199  CA  THR A 276     -12.033   3.674  20.032  1.00 23.00           B    C
ATOM   2200  CB  THR A 276     -11.845   2.456  19.144  1.00 25.66           B    C
ATOM   2201  OG1 THR A 276     -11.645   2.886  17.800  1.00 28.19           B    O
ATOM   2202  CG2 THR A 276     -13.028   1.521  19.190  1.00 28.22           B    C
```

Fig. 5AL

```
ATOM   2203  C   THR A 276     -12.272   3.272  21.479  1.00 25.27           B    C
ATOM   2204  O   THR A 276     -13.433   3.230  21.900  1.00 26.66           B    O
ATOM   2205  N   ALA A 277     -11.216   2.899  22.210  1.00 22.06           B    N
ATOM   2206  CA  ALA A 277     -11.408   2.343  23.557  1.00 22.76           B    C
ATOM   2207  CB  ALA A 277     -10.093   1.849  24.074  1.00 22.87           B    C
ATOM   2208  C   ALA A 277     -12.009   3.380  24.489  1.00 23.03           B    C
ATOM   2209  O   ALA A 277     -12.857   3.023  25.312  1.00 23.84           B    O
ATOM   2210  N   LEU A 278     -11.608   4.653  24.353  1.00 23.13           B    N
ATOM   2211  CA  LEU A 278     -12.110   5.739  25.237  1.00 23.62           B    C
ATOM   2212  CB  LEU A 278     -11.027   6.811  25.386  1.00 22.61           B    C
ATOM   2213  CG  LEU A 278      -9.752   6.353  26.081  1.00 24.23           B    C
ATOM   2214  CD1 LEU A 278      -8.819   7.520  26.297  1.00 26.00           B    C
ATOM   2215  CD2 LEU A 278     -10.043   5.658  27.413  1.00 26.11           B    C
ATOM   2216  C   LEU A 278     -13.417   6.371  24.733  1.00 24.63           B    C
ATOM   2217  O   LEU A 278     -14.131   6.897  25.566  1.00 26.83           B    O
ATOM   2218  N   LEU A 279     -13.713   6.283  23.440  1.00 26.15           B    N
ATOM   2219  CA  LEU A 279     -14.903   7.006  22.905  1.00 29.30           B    C
ATOM   2220  CB  LEU A 279     -14.536   7.835  21.693  1.00 33.29           B    C
ATOM   2221  CG  LEU A 279     -14.182   9.223  22.178  1.00 38.76           B    C
ATOM   2222  CD1 LEU A 279     -12.663   9.328  22.342  1.00 34.33           B    C
ATOM   2223  CD2 LEU A 279     -14.858  10.285  21.324  1.00 40.98           B    C
ATOM   2224  C   LEU A 279     -16.063   6.091  22.633  1.00 35.40           B    C
ATOM   2225  O   LEU A 279     -17.180   6.495  22.993  1.00 38.96           B    O
ATOM   2226  N   THR A 280     -15.818   4.873  22.200  1.00 35.14           B    N
ATOM   2227  CA  THR A 280     -16.897   3.893  21.923  1.00 35.70           B    C
ATOM   2228  CB  THR A 280     -16.360   2.555  21.414  1.00 40.72           B    C
ATOM   2229  OG1 THR A 280     -17.501   1.928  20.830  1.00 44.97           B    O
ATOM   2230  CG2 THR A 280     -15.789   1.661  22.503  1.00 39.31           B    C
ATOM   2231  C   THR A 280     -17.731   3.594  23.168  1.00 36.91           B    C
ATOM   2232  O   THR A 280     -17.236   3.630  24.309  1.00 37.29           B    O
ATOM   2233  N   ASN A 281     -19.021   3.338  22.950  1.00 38.97           B    N
ATOM   2234  CA  ASN A 281     -19.964   2.959  24.035  1.00 42.25           B    C
ATOM   2235  CB  ASN A 281     -21.130   3.957  24.051  1.00 52.15           B    C
ATOM   2236  CG  ASN A 281     -20.751   5.315  24.612  1.00 57.79           B    C
ATOM   2237  OD1 ASN A 281     -20.886   6.344  23.940  1.00 66.28           B    O
ATOM   2238  ND2 ASN A 281     -20.261   5.324  25.841  1.00 55.13           B    N
ATOM   2239  C   ASN A 281     -20.321   1.466  23.863  1.00 39.96           B    C
ATOM   2240  O   ASN A 281     -20.901   0.859  24.811  1.00 39.94           B    O
ATOM   2241  N   GLY A 282     -19.897   0.870  22.748  1.00 33.44           B    N
ATOM   2242  CA  GLY A 282     -19.999  -0.582  22.495  1.00 41.01           B    C
ATOM   2243  C   GLY A 282     -19.606  -0.909  21.068  1.00 41.89           B    C
ATOM   2244  O   GLY A 282     -20.274  -0.358  20.180  1.00 44.85           B    O
ATOM   2245  N   THR A 283     -18.548  -1.722  20.858  1.00 48.25           B    N
ATOM   2246  CA  THR A 283     -18.070  -2.291  19.554  1.00 51.73           B    C
ATOM   2247  CB  THR A 283     -17.114  -1.410  18.723  1.00 63.90           B    C
ATOM   2248  OG1 THR A 283     -16.371  -0.535  19.580  1.00 67.63           B    O
ATOM   2249  CG2 THR A 283     -17.802  -0.620  17.629  1.00 68.10           B    C
ATOM   2250  C   THR A 283     -17.176  -3.506  19.778  1.00 57.25           B    C
ATOM   2251  O   THR A 283     -16.540  -3.591  20.843  1.00 57.85           B    O
ATOM   2252  N   THR A 284     -17.024  -4.325  18.743  1.00 56.95           B    N
ATOM   2253  CA  THR A 284     -16.084  -5.469  18.717  1.00 64.26           B    C
ATOM   2254  CB  THR A 284     -16.757  -6.778  18.292  1.00 71.46           B    C
ATOM   2255  OG1 THR A 284     -15.676  -7.694  18.130  1.00 65.07           B    O
ATOM   2256  CG2 THR A 284     -17.581  -6.677  17.022  1.00 78.61           B    C
ATOM   2257  C   THR A 284     -14.929  -5.134  17.781  1.00 68.91           B    C
ATOM   2258  O   THR A 284     -15.146  -5.133  16.561  1.00 72.94           B    O
ATOM   2259  N   GLU A 285     -13.751  -4.844  18.339  1.00 67.98           B    N
ATOM   2260  CA  GLU A 285     -12.527  -4.642  17.526  1.00 67.77           B    C
```

Fig. 5AM

```
ATOM   2261  CB  GLU A 285     -11.406  -3.997  18.348  1.00 69.16           B  C
ATOM   2262  CG  GLU A 285     -10.660  -4.948  19.253  1.00 67.10           B  C
ATOM   2263  CD  GLU A 285      -9.773  -5.920  18.508  1.00 62.69           B  C
ATOM   2264  OE1 GLU A 285      -9.447  -6.958  19.094  1.00 67.72           B  O
ATOM   2265  OE2 GLU A 285      -9.447  -5.656  17.327  1.00 60.27           B  O
ATOM   2266  C   GLU A 285     -12.243  -6.003  16.888  1.00 62.89           B  C
ATOM   2267  O   GLU A 285     -12.024  -6.986  17.612  1.00 64.01           B  O
ATOM   2268  N   ASN A 286     -12.367  -6.067  15.567  1.00 72.00           B  N
ATOM   2269  CA  ASN A 286     -12.453  -7.345  14.813  1.00 69.68           B  C
ATOM   2270  CB  ASN A 286     -12.958  -7.131  13.379  1.00 74.10           B  C
ATOM   2271  CG  ASN A 286     -14.452  -6.873  13.289  1.00 79.08           B  C
ATOM   2272  OD1 ASN A 286     -14.973  -5.927  13.882  1.00 78.54           B  O
ATOM   2273  ND2 ASN A 286     -15.159  -7.696  12.529  1.00 83.32           B  N
ATOM   2274  C   ASN A 286     -11.101  -8.069  14.865  1.00 63.79           B  C
ATOM   2275  O   ASN A 286     -11.108  -9.288  14.589  1.00 69.69           B  O
ATOM   2276  N   ARG A 287      -9.993  -7.398  15.233  1.00 49.41           B  N
ATOM   2277  CA  ARG A 287      -8.652  -7.994  14.973  1.00 42.61           B  C
ATOM   2278  CB  ARG A 287      -7.579  -6.940  14.692  1.00 38.90           B  C
ATOM   2279  CG  ARG A 287      -7.562  -6.526  13.220  1.00 45.53           B  C
ATOM   2280  CD  ARG A 287      -6.163  -6.299  12.640  1.00 45.19           B  C
ATOM   2281  NE  ARG A 287      -5.581  -5.475  13.650  1.00 39.63           B  N
ATOM   2282  CZ  ARG A 287      -4.455  -5.682  14.323  1.00 37.83           B  C
ATOM   2283  NH1 ARG A 287      -3.578  -6.625  14.034  1.00 34.62           B  N
ATOM   2284  NH2 ARG A 287      -4.237  -4.882  15.327  1.00 36.07           B  N
ATOM   2285  C   ARG A 287      -8.286  -8.991  16.078  1.00 42.30           B  C
ATOM   2286  O   ARG A 287      -7.762 -10.042  15.717  1.00 50.69           B  O
ATOM   2287  N   TYR A 288      -8.570  -8.746  17.361  1.00 32.79           B  N
ATOM   2288  CA  TYR A 288      -8.226  -9.769  18.388  1.00 35.49           B  C
ATOM   2289  CB  TYR A 288      -7.329  -9.189  19.485  1.00 34.54           B  C
ATOM   2290  CG  TYR A 288      -6.130  -8.416  18.990  1.00 30.69           B  C
ATOM   2291  CD1 TYR A 288      -4.949  -9.049  18.654  1.00 31.93           B  C
ATOM   2292  CE1 TYR A 288      -3.869  -8.324  18.171  1.00 30.34           B  C
ATOM   2293  CZ  TYR A 288      -3.977  -6.951  18.048  1.00 29.73           B  C
ATOM   2294  OH  TYR A 288      -2.924  -6.257  17.551  1.00 29.59           B  O
ATOM   2295  CE2 TYR A 288      -5.158  -6.304  18.349  1.00 30.01           B  C
ATOM   2296  CD2 TYR A 288      -6.223  -7.042  18.831  1.00 31.96           B  C
ATOM   2297  C   TYR A 288      -9.509 -10.374  18.965  1.00 36.54           B  C
ATOM   2298  O   TYR A 288      -9.417 -11.346  19.734  1.00 41.47           B  O
ATOM   2299  N   GLY A 289     -10.664  -9.828  18.599  1.00 35.64           B  N
ATOM   2300  CA  GLY A 289     -11.968 -10.330  19.057  1.00 39.33           B  C
ATOM   2301  C   GLY A 289     -12.324  -9.723  20.386  1.00 36.29           B  C
ATOM   2302  O   GLY A 289     -13.214 -10.237  21.061  1.00 39.88           B  O
ATOM   2303  N   ILE A 290     -11.700  -8.603  20.758  1.00 35.99           B  N
ATOM   2304  CA  ILE A 290     -12.047  -7.971  22.049  1.00 30.73           B  C
ATOM   2305  CB  ILE A 290     -10.893  -7.094  22.582  1.00 32.22           B  C
ATOM   2306  CG1 ILE A 290      -9.635  -7.955  22.749  1.00 30.37           B  C
ATOM   2307  CG2 ILE A 290     -11.321  -6.383  23.856  1.00 32.28           B  C
ATOM   2308  CD1 ILE A 290      -8.354  -7.177  23.063  1.00 31.00           B  C
ATOM   2309  C   ILE A 290     -13.347  -7.180  21.886  1.00 34.83           B  C
ATOM   2310  O   ILE A 290     -13.437  -6.380  20.923  1.00 35.15           B  O
ATOM   2311  N   LYS A 291     -14.264  -7.348  22.837  1.00 33.83           B  N
ATOM   2312  CA  LYS A 291     -15.516  -6.558  22.961  1.00 39.88           B  C
ATOM   2313  CB  LYS A 291     -16.623  -7.315  23.710  1.00 45.71           B  C
ATOM   2314  CG  LYS A 291     -17.067  -8.630  23.083  1.00 56.45           B  C
ATOM   2315  CD  LYS A 291     -18.045  -8.446  21.928  1.00 65.71           B  C
ATOM   2316  CE  LYS A 291     -18.665  -9.743  21.439  1.00 65.18           B  C
ATOM   2317  NZ  LYS A 291     -18.011 -10.239  20.207  1.00 66.36           B  N
ATOM   2318  C   LYS A 291     -15.150  -5.288  23.725  1.00 36.02           B  C
```

Fig. 5AN

```
ATOM   2319  O    LYS A 291     -14.804  -5.394  24.919  1.00 39.38      B  O
ATOM   2320  N    LEU A 292     -15.137  -4.157  23.023  1.00 36.06      B  N
ATOM   2321  CA   LEU A 292     -14.915  -2.826  23.639  1.00 35.67      B  C
ATOM   2322  CB   LEU A 292     -14.044  -1.960  22.727  1.00 33.11      B  C
ATOM   2323  CG   LEU A 292     -12.604  -2.429  22.476  1.00 31.74      B  C
ATOM   2324  CD1  LEU A 292     -11.936  -1.526  21.476  1.00 32.92      B  C
ATOM   2325  CD2  LEU A 292     -11.800  -2.496  23.763  1.00 29.00      B  C
ATOM   2326  C    LEU A 292     -16.280  -2.188  23.851  1.00 36.16      B  C
ATOM   2327  O    LEU A 292     -17.226  -2.472  23.108  1.00 39.69      B  O
ATOM   2328  N    PRO A 293     -16.415  -1.285  24.823  1.00 31.27      B  N
ATOM   2329  CA   PRO A 293     -15.309  -0.846  25.664  1.00 32.17      B  C
ATOM   2330  CB   PRO A 293     -15.806   0.483  26.236  1.00 33.48      B  C
ATOM   2331  CG   PRO A 293     -17.312   0.234  26.356  1.00 34.09      B  C
ATOM   2332  CD   PRO A 293     -17.650  -0.536  25.110  1.00 36.56      B  C
ATOM   2333  C    PRO A 293     -15.039  -1.848  26.791  1.00 33.78      B  C
ATOM   2334  O    PRO A 293     -15.884  -2.718  27.047  1.00 30.56      B  O
ATOM   2335  N    VAL A 294     -13.876  -1.700  27.417  1.00 27.28      B  N
ATOM   2336  CA   VAL A 294     -13.486  -2.366  28.686  1.00 25.20      B  C
ATOM   2337  CB   VAL A 294     -12.307  -3.342  28.449  1.00 25.17      B  C
ATOM   2338  CG1  VAL A 294     -12.711  -4.511  27.599  1.00 27.15      B  C
ATOM   2339  CG2  VAL A 294     -11.109  -2.656  27.806  1.00 25.11      B  C
ATOM   2340  C    VAL A 294     -13.111  -1.332  29.724  1.00 23.75      B  C
ATOM   2341  O    VAL A 294     -12.829  -0.178  29.391  1.00 27.58      B  O
ATOM   2342  N    SER A 295     -13.061  -1.696  30.982  1.00 22.39      B  N
ATOM   2343  CA   SER A 295     -12.635  -0.810  32.064  1.00 22.62      B  C
ATOM   2344  CB   SER A 295     -12.911  -1.389  33.404  1.00 27.72      B  C
ATOM   2345  OG   SER A 295     -14.323  -1.538  33.562  1.00 30.37      B  O
ATOM   2346  C    SER A 295     -11.135  -0.512  31.917  1.00 21.89      B  C
ATOM   2347  O    SER A 295     -10.685   0.643  32.079  1.00 23.28      B  O
ATOM   2348  N    LEU A 296     -10.342  -1.545  31.610  1.00 22.03      B  N
ATOM   2349  CA   LEU A 296      -8.872  -1.432  31.467  1.00 20.37      B  C
ATOM   2350  CB   LEU A 296      -8.132  -1.949  32.701  1.00 23.56      B  C
ATOM   2351  CG   LEU A 296      -6.610  -2.012  32.536  1.00 25.61      B  C
ATOM   2352  CD1  LEU A 296      -6.004  -0.614  32.327  1.00 26.52      B  C
ATOM   2353  CD2  LEU A 296      -5.992  -2.736  33.714  1.00 27.62      B  C
ATOM   2354  C    LEU A 296      -8.428  -2.200  30.249  1.00 21.73      B  C
ATOM   2355  O    LEU A 296      -8.667  -3.424  30.182  1.00 21.74      B  O
ATOM   2356  N    LEU A 297      -7.758  -1.525  29.337  1.00 20.47      B  N
ATOM   2357  CA   LEU A 297      -7.109  -2.098  28.170  1.00 18.39      B  C
ATOM   2358  CB   LEU A 297      -7.573  -1.460  26.867  1.00 19.43      B  C
ATOM   2359  CG   LEU A 297      -6.873  -1.925  25.585  1.00 21.95      B  C
ATOM   2360  CD1  LEU A 297      -7.062  -3.417  25.324  1.00 24.31      B  C
ATOM   2361  CD2  LEU A 297      -7.334  -1.157  24.350  1.00 21.57      B  C
ATOM   2362  C    LEU A 297      -5.628  -1.863  28.389  1.00 18.27      B  C
ATOM   2363  O    LEU A 297      -5.190  -0.722  28.539  1.00 18.82      B  O
ATOM   2364  N    PHE A 298      -4.840  -2.932  28.379  1.00 18.28      B  N
ATOM   2365  CA   PHE A 298      -3.385  -2.909  28.557  1.00 16.84      B  C
ATOM   2366  CB   PHE A 298      -2.957  -3.675  29.818  1.00 16.63      B  C
ATOM   2367  CG   PHE A 298      -1.478  -3.746  30.075  1.00 15.76      B  C
ATOM   2368  CD1  PHE A 298      -0.652  -4.681  29.496  1.00 17.11      B  C
ATOM   2369  CE1  PHE A 298       0.696  -4.725  29.790  1.00 17.18      B  C
ATOM   2370  CZ   PHE A 298       1.253  -3.870  30.697  1.00 15.91      B  C
ATOM   2371  CD2  PHE A 298      -0.901  -2.884  31.014  1.00 15.77      B  C
ATOM   2372  CE2  PHE A 298       0.444  -2.941  31.285  1.00 15.46      B  C
ATOM   2373  C    PHE A 298      -2.779  -3.414  27.280  1.00 18.10      B  C
ATOM   2374  O    PHE A 298      -3.031  -4.551  26.908  1.00 17.86      B  O
ATOM   2375  N    ILE A 299      -1.839  -2.678  26.688  1.00 16.86      B  N
ATOM   2376  CA   ILE A 299      -1.181  -3.019  25.429  1.00 16.91      B  C
```

Fig. 5AO

```
ATOM   2377  CB   ILE A 299      -1.507  -1.966  24.340  1.00 18.01           B   C
ATOM   2378  CG1  ILE A 299      -3.012  -1.842  24.132  1.00 18.37           B   C
ATOM   2379  CG2  ILE A 299      -0.770  -2.235  23.054  1.00 19.72           B   C
ATOM   2380  CD1  ILE A 299      -3.460  -0.503  23.602  1.00 20.39           B   C
ATOM   2381  C    ILE A 299       0.310  -3.112  25.687  1.00 17.49           B   C
ATOM   2382  O    ILE A 299       0.924  -2.108  26.038  1.00 17.60           B   O
ATOM   2383  N    ALA A 300       0.903  -4.289  25.449  1.00 16.14           B   N
ATOM   2384  CA   ALA A 300       2.335  -4.536  25.651  1.00 14.95           B   C
ATOM   2385  CB   ALA A 300       2.518  -5.909  26.303  1.00 15.95           B   C
ATOM   2386  C    ALA A 300       3.095  -4.420  24.342  1.00 16.31           B   C
ATOM   2387  O    ALA A 300       2.986  -5.312  23.473  1.00 16.07           B   O
ATOM   2388  N    GLY A 301       3.824  -3.314  24.216  1.00 16.06           B   N
ATOM   2389  CA   GLY A 301       4.644  -2.982  23.052  1.00 15.19           B   C
ATOM   2390  C    GLY A 301       6.061  -2.657  23.375  1.00 15.90           B   C
ATOM   2391  O    GLY A 301       6.683  -3.243  24.287  1.00 15.52           B   O
ATOM   2392  N    HIS A 302       6.578  -1.599  22.728  1.00 16.09           B   N
ATOM   2393  CA   HIS A 302       8.007  -1.324  22.658  1.00 15.26           B   C
ATOM   2394  CB   HIS A 302       8.540  -1.664  21.263  1.00 16.83           B   C
ATOM   2395  CG   HIS A 302       8.185  -3.046  20.812  1.00 18.38           B   C
ATOM   2396  ND1  HIS A 302       8.899  -4.145  21.175  1.00 21.45           B   N
ATOM   2397  CE1  HIS A 302       8.275  -5.192  20.596  1.00 20.28           B   C
ATOM   2398  NE2  HIS A 302       7.207  -4.813  19.959  1.00 19.50           B   N
ATOM   2399  CD2  HIS A 302       7.133  -3.447  20.088  1.00 19.47           B   C
ATOM   2400  C    HIS A 302       8.268   0.143  23.040  1.00 15.85           B   C
ATOM   2401  O    HIS A 302       7.324   0.964  22.985  1.00 17.20           B   O
ATOM   2402  N    ASP A 303       9.490   0.415  23.308  1.00 14.97           B   N
ATOM   2403  CA   ASP A 303       9.915   1.831  23.487  1.00 16.28           B   C
ATOM   2404  CB   ASP A 303      11.368   1.919  23.834  1.00 16.35           B   C
ATOM   2405  CG   ASP A 303      12.353   0.987  23.112  1.00 19.57           B   C
ATOM   2406  OD1  ASP A 303      12.024   0.539  21.958  1.00 21.32           B   O
ATOM   2407  OD2  ASP A 303      13.486   0.855  23.636  1.00 18.98           B   O
ATOM   2408  C    ASP A 303       9.567   2.647  22.253  1.00 16.93           B   C
ATOM   2409  O    ASP A 303       9.208   3.837  22.432  1.00 17.86           B   O
ATOM   2410  N    THR A 304       9.703   2.103  21.048  1.00 16.23           B   N
ATOM   2411  CA   THR A 304       9.408   2.876  19.827  1.00 16.50           B   C
ATOM   2412  CB   THR A 304       9.682   2.119  18.522  1.00 18.35           B   C
ATOM   2413  OG1  THR A 304       8.868   0.956  18.488  1.00 20.59           B   O
ATOM   2414  CG2  THR A 304      11.127   1.748  18.449  1.00 18.90           B   C
ATOM   2415  C    THR A 304       7.973   3.305  19.856  1.00 17.36           B   C
ATOM   2416  O    THR A 304       7.673   4.439  19.410  1.00 17.49           B   O
ATOM   2417  N    ASN A 305       7.068   2.496  20.350  1.00 16.06           B   N
ATOM   2418  CA   ASN A 305       5.651   2.833  20.405  1.00 16.54           B   C
ATOM   2419  CB   ASN A 305       4.803   1.617  20.788  1.00 17.34           B   C
ATOM   2420  CG   ASN A 305       4.989   0.439  19.873  1.00 18.40           B   C
ATOM   2421  OD1  ASN A 305       5.317  -0.666  20.329  1.00 19.42           B   O
ATOM   2422  ND2  ASN A 305       4.771   0.610  18.576  1.00 18.32           B   N
ATOM   2423  C    ASN A 305       5.396   4.005  21.350  1.00 18.23           B   C
ATOM   2424  O    ASN A 305       4.569   4.880  21.044  1.00 18.55           B   O
ATOM   2425  N    LEU A 306       6.007   3.961  22.512  1.00 17.16           B   N
ATOM   2426  CA   LEU A 306       5.848   5.042  23.503  1.00 17.63           B   C
ATOM   2427  CB   LEU A 306       6.660   4.745  24.750  1.00 17.16           B   C
ATOM   2428  CG   LEU A 306       6.264   3.522  25.576  1.00 16.52           B   C
ATOM   2429  CD1  LEU A 306       7.167   3.411  26.768  1.00 18.41           B   C
ATOM   2430  CD2  LEU A 306       4.842   3.577  25.996  1.00 18.01           B   C
ATOM   2431  C    LEU A 306       6.355   6.328  22.861  1.00 16.48           B   C
ATOM   2432  O    LEU A 306       5.717   7.396  23.019  1.00 16.64           B   O
ATOM   2433  N    ALA A 307       7.508   6.280  22.227  1.00 16.33           B   N
ATOM   2434  CA   ALA A 307       8.087   7.476  21.557  1.00 16.42           B   C
```

Fig. 5AP

```
ATOM   2435  CB   ALA A 307       9.484   7.226  21.124  1.00 16.43           B  C
ATOM   2436  C    ALA A 307       7.183   7.948  20.418  1.00 17.82           B  C
ATOM   2437  O    ALA A 307       6.986   9.182  20.287  1.00 17.54           B  O
ATOM   2438  N    ASN A 308       6.615   7.080  19.622  1.00 17.76           B  N
ATOM   2439  CA   ASN A 308       5.749   7.518  18.486  1.00 17.57           B  C
ATOM   2440  CB   ASN A 308       5.264   6.332  17.652  1.00 19.21           B  C
ATOM   2441  CG   ASN A 308       6.332   5.574  16.894  1.00 18.70           B  C
ATOM   2442  OD1  ASN A 308       6.156   4.377  16.650  1.00 18.85           B  O
ATOM   2443  ND2  ASN A 308       7.462   6.156  16.629  1.00 17.70           B  N
ATOM   2444  C    ASN A 308       4.528   8.191  19.087  1.00 18.65           B  C
ATOM   2445  O    ASN A 308       4.048   9.220  18.575  1.00 18.81           B  O
ATOM   2446  N    LEU A 309       3.911   7.651  20.155  1.00 17.64           B  N
ATOM   2447  CA   LEU A 309       2.721   8.281  20.753  1.00 17.53           B  C
ATOM   2448  CB   LEU A 309       2.142   7.377  21.857  1.00 18.45           B  C
ATOM   2449  CG   LEU A 309       1.398   6.174  21.289  1.00 18.61           B  C
ATOM   2450  CD1  LEU A 309       1.169   5.114  22.397  1.00 19.77           B  C
ATOM   2451  CD2  LEU A 309       0.063   6.555  20.684  1.00 19.13           B  C
ATOM   2452  C    LEU A 309       3.148   9.626  21.328  1.00 17.47           B  C
ATOM   2453  O    LEU A 309       2.376  10.640  21.158  1.00 18.85           B  O
ATOM   2454  N    SER A 310       4.302   9.705  21.977  1.00 16.96           B  N
ATOM   2455  CA   SER A 310       4.827  10.973  22.522  1.00 17.84           B  C
ATOM   2456  CB   SER A 310       6.138  10.760  23.184  1.00 17.56           B  C
ATOM   2457  OG   SER A 310       6.750  11.964  23.511  1.00 20.95           B  O
ATOM   2458  C    SER A 310       4.920  12.017  21.398  1.00 18.41           B  C
ATOM   2459  O    SER A 310       4.486  13.187  21.563  1.00 18.76           B  O
ATOM   2460  N    GLY A 311       5.545  11.661  20.310  1.00 18.59           B  N
ATOM   2461  CA   GLY A 311       5.789  12.616  19.191  1.00 17.59           B  C
ATOM   2462  C    GLY A 311       4.503  13.000  18.525  1.00 20.52           B  C
ATOM   2463  O    GLY A 311       4.323  14.221  18.197  1.00 21.93           B  O
ATOM   2464  N    ALA A 312       3.587  12.101  18.278  1.00 18.55           B  N
ATOM   2465  CA   ALA A 312       2.307  12.401  17.601  1.00 19.28           B  C
ATOM   2466  CB   ALA A 312       1.559  11.147  17.270  1.00 19.10           B  C
ATOM   2467  C    ALA A 312       1.477  13.346  18.469  1.00 21.73           B  C
ATOM   2468  O    ALA A 312       0.779  14.228  17.950  1.00 21.76           B  O
ATOM   2469  N    LEU A 313       1.411  13.143  19.784  1.00 19.75           B  N
ATOM   2470  CA   LEU A 313       0.557  13.905  20.725  1.00 19.42           B  C
ATOM   2471  CB   LEU A 313       0.030  12.918  21.779  1.00 20.51           B  C
ATOM   2472  CG   LEU A 313      -0.968  11.908  21.230  1.00 19.98           B  C
ATOM   2473  CD1  LEU A 313      -1.234  10.803  22.251  1.00 23.20           B  C
ATOM   2474  CD2  LEU A 313      -2.258  12.565  20.798  1.00 21.43           B  C
ATOM   2475  C    LEU A 313       1.276  15.086  21.349  1.00 20.26           B  C
ATOM   2476  O    LEU A 313       0.674  15.674  22.295  1.00 23.30           B  O
ATOM   2477  N    ASP A 314       2.526  15.300  21.016  1.00 19.32           B  N
ATOM   2478  CA   ASP A 314       3.359  16.382  21.604  1.00 21.54           B  C
ATOM   2479  CB   ASP A 314       2.787  17.783  21.304  1.00 24.91           B  C
ATOM   2480  CG   ASP A 314       2.650  18.074  19.828  1.00 33.43           B  C
ATOM   2481  OD1  ASP A 314       3.672  17.993  19.162  1.00 38.37           B  O
ATOM   2482  OD2  ASP A 314       1.511  18.364  19.364  1.00 37.43           B  O
ATOM   2483  C    ASP A 314       3.459  16.270  23.133  1.00 24.12           B  C
ATOM   2484  O    ASP A 314       3.444  17.280  23.851  1.00 25.74           B  O
ATOM   2485  N    LEU A 315       3.685  15.057  23.624  1.00 20.93           B  N
ATOM   2486  CA   LEU A 315       3.881  14.757  25.052  1.00 21.19           B  C
ATOM   2487  CB   LEU A 315       3.335  13.393  25.420  1.00 21.79           B  C
ATOM   2488  CG   LEU A 315       1.866  13.141  25.162  1.00 23.97           B  C
ATOM   2489  CD1  LEU A 315       1.570  11.680  25.384  1.00 22.25           B  C
ATOM   2490  CD2  LEU A 315       0.978  14.042  26.010  1.00 27.60           B  C
ATOM   2491  C    LEU A 315       5.361  14.789  25.341  1.00 22.56           B  C
ATOM   2492  O    LEU A 315       6.157  13.944  24.866  1.00 24.88           B  O
```

Fig. 5AQ

```
ATOM   2493  N   AASN A 316       5.744  15.720  26.182  0.50 18.91           B    N
ATOM   2494  N   BASN A 316       5.756  15.730  26.173  0.50 19.59           B    N
ATOM   2495  CA  AASN A 316       7.151  15.938  26.550  0.50 18.35           B    C
ATOM   2496  CA  BASN A 316       7.173  15.900  26.540  0.50 20.05           B    C
ATOM   2497  CB  AASN A 316       7.480  17.418  26.373  0.50 18.63           B    C
ATOM   2498  CB  BASN A 316       7.654  17.318  26.239  0.50 23.43           B    C
ATOM   2499  CG  AASN A 316       7.198  17.841  24.947  0.50 21.02           B    C
ATOM   2500  CG  BASN A 316       8.108  17.359  24.802  0.50 30.31           B    C
ATOM   2501  OD1AASN A 316       7.769  17.259  23.998  0.50 27.35           B    O
ATOM   2502  OD1BASN A 316       7.309  17.627  23.900  0.50 35.76           B    O
ATOM   2503  ND2AASN A 316       6.364  18.861  24.776  0.50 21.36           B    N
ATOM   2504  ND2BASN A 316       9.319  16.899  24.569  0.50 31.04           B    N
ATOM   2505  C   AASN A 316       7.375  15.542  28.001  0.50 18.50           B    C
ATOM   2506  C   BASN A 316       7.383  15.549  28.002  0.50 19.16           B    C
ATOM   2507  O   AASN A 316       6.547  15.920  28.846  0.50 20.54           B    O
ATOM   2508  O   BASN A 316       6.559  15.944  28.842  0.50 20.69           B    O
ATOM   2509  N   TRP A 317       8.476  14.829  28.310  1.00 18.19           B    N
ATOM   2510  CA  TRP A 317       8.762  14.456  29.700  1.00 17.20           B    C
ATOM   2511  CB  TRP A 317       7.847  13.284  30.164  1.00 17.17           B    C
ATOM   2512  CG  TRP A 317       8.139  11.937  29.531  1.00 18.05           B    C
ATOM   2513  CD1 TRP A 317       9.199  11.126  29.827  1.00 16.98           B    C
ATOM   2514  NE1 TRP A 317       9.068   9.960  29.087  1.00 16.86           B    N
ATOM   2515  CE2 TRP A 317       7.967  10.008  28.302  1.00 16.06           B    C
ATOM   2516  CD2 TRP A 317       7.387  11.303  28.497  1.00 16.87           B    C
ATOM   2517  CE3 TRP A 317       6.194  11.580  27.831  1.00 17.67           B    C
ATOM   2518  CZ3 TRP A 317       5.688  10.699  26.919  1.00 16.99           B    C
ATOM   2519  CH2 TRP A 317       6.291   9.457  26.720  1.00 16.50           B    C
ATOM   2520  CZ2 TRP A 317       7.448   9.124  27.357  1.00 17.32           B    C
ATOM   2521  C   TRP A 317      10.213  14.137  29.938  1.00 16.82           B    C
ATOM   2522  O   TRP A 317      10.939  13.721  29.019  1.00 18.14           B    O
ATOM   2523  N   SER A 318      10.519  14.227  31.219  1.00 16.54           B    N
ATOM   2524  CA  SER A 318      11.715  13.656  31.812  1.00 17.40           B    C
ATOM   2525  CB  SER A 318      12.709  14.750  32.164  1.00 18.48           B    C
ATOM   2526  OG  SER A 318      13.842  14.218  32.740  1.00 20.74           B    O
ATOM   2527  C   SER A 318      11.231  12.931  33.059  1.00 18.32           B    C
ATOM   2528  O   SER A 318      10.244  13.374  33.704  1.00 18.00           B    O
ATOM   2529  N   LEU A 319      11.782  11.748  33.340  1.00 17.18           B    N
ATOM   2530  CA  LEU A 319      11.308  10.906  34.457  1.00 16.50           B    C
ATOM   2531  CB  LEU A 319      11.199   9.448  33.975  1.00 16.33           B    C
ATOM   2532  CG  LEU A 319      10.339   9.217  32.769  1.00 15.86           B    C
ATOM   2533  CD1 LEU A 319      10.329   7.709  32.411  1.00 16.54           B    C
ATOM   2534  CD2 LEU A 319       8.900   9.673  33.007  1.00 17.09           B    C
ATOM   2535  C   LEU A 319      12.285  10.930  35.601  1.00 17.73           B    C
ATOM   2536  O   LEU A 319      13.415  10.469  35.509  1.00 17.15           B    O
ATOM   2537  N   PRO A 320      11.901  11.525  36.746  1.00 17.65           B    N
ATOM   2538  CA  PRO A 320      12.830  11.577  37.870  1.00 18.21           B    C
ATOM   2539  CB  PRO A 320      12.037  12.308  38.969  1.00 22.07           B    C
ATOM   2540  CG  PRO A 320      11.053  13.145  38.187  1.00 20.81           B    C
ATOM   2541  CD  PRO A 320      10.676  12.319  36.957  1.00 19.61           B    C
ATOM   2542  C   PRO A 320      13.323  10.160  38.266  1.00 16.92           B    C
ATOM   2543  O   PRO A 320      12.509   9.263  38.403  1.00 18.72           B    O
ATOM   2544  N   GLY A 321      14.622  10.029  38.405  1.00 18.79           B    N
ATOM   2545  CA  GLY A 321      15.190   8.751  38.859  1.00 17.76           B    C
ATOM   2546  C   GLY A 321      15.243   7.723  37.755  1.00 18.68           B    C
ATOM   2547  O   GLY A 321      15.750   6.611  38.024  1.00 18.82           B    O
ATOM   2548  N   GLN A 322      14.883   8.070  36.529  1.00 17.69           B    N
ATOM   2549  CA  GLN A 322      14.866   7.048  35.441  1.00 16.75           B    C
ATOM   2550  CB  GLN A 322      13.468   6.559  35.238  1.00 16.13           B    C
```

Fig. 5AR

```
ATOM   2551  CG   GLN A 322      13.316    5.561   34.084  1.00 15.99      B    C
ATOM   2552  CD   GLN A 322      14.360    4.468   34.105  1.00 16.40      B    C
ATOM   2553  OE1  GLN A 322      15.352    4.495   33.402  1.00 16.25      B    O
ATOM   2554  NE2  GLN A 322      14.097    3.481   34.988  1.00 16.00      B    N
ATOM   2555  C    GLN A 322      15.497    7.670   34.211  1.00 16.71      B    C
ATOM   2556  O    GLN A 322      14.812    8.374   33.445  1.00 17.78      B    O
ATOM   2557  N    PRO A 323      16.780    7.414   33.918  1.00 16.53      B    N
ATOM   2558  CA   PRO A 323      17.426    8.077   32.796  1.00 16.67      B    C
ATOM   2559  CB   PRO A 323      18.910    7.714   32.882  1.00 18.92      B    C
ATOM   2560  CG   PRO A 323      19.067    6.889   34.112  1.00 24.65      B    C
ATOM   2561  CD   PRO A 323      17.704    6.601   34.702  1.00 18.91      B    C
ATOM   2562  C    PRO A 323      16.890    7.783   31.407  1.00 17.03      B    C
ATOM   2563  O    PRO A 323      17.090    8.541   30.493  1.00 17.70      B    O
ATOM   2564  N    ASP A 324      16.272    6.596   31.192  1.00 15.38      B    N
ATOM   2565  CA   ASP A 324      15.683    6.249   29.898  1.00 15.15      B    C
ATOM   2566  CB   ASP A 324      15.691    4.719   29.696  1.00 15.48      B    C
ATOM   2567  CG   ASP A 324      15.177    4.263   28.363  1.00 17.33      B    C
ATOM   2568  OD1  ASP A 324      14.645    5.017   27.543  1.00 16.21      B    O
ATOM   2569  OD2  ASP A 324      15.195    2.978   28.186  1.00 17.25      B    O
ATOM   2570  C    ASP A 324      14.280    6.852   29.862  1.00 15.56      B    C
ATOM   2571  O    ASP A 324      13.450    6.577   30.703  1.00 16.03      B    O
ATOM   2572  N    ASN A 325      14.012    7.693   28.860  1.00 15.39      B    N
ATOM   2573  CA   ASN A 325      12.673    8.284   28.734  1.00 15.97      B    C
ATOM   2574  CB   ASN A 325      12.624    9.341   27.634  1.00 17.79      B    C
ATOM   2575  CG   ASN A 325      13.401   10.597   27.949  1.00 18.55      B    C
ATOM   2576  OD1  ASN A 325      13.664   10.912   29.092  1.00 18.07      B    O
ATOM   2577  ND2  ASN A 325      13.742   11.289   26.895  1.00 20.10      B    N
ATOM   2578  C    ASN A 325      11.584    7.265   28.411  1.00 15.27      B    C
ATOM   2579  O    ASN A 325      10.422    7.509   28.624  1.00 16.48      B    O
ATOM   2580  N    THR A 326      11.992    6.102   27.893  1.00 15.47      B    N
ATOM   2581  CA   THR A 326      11.043    5.045   27.480  1.00 15.18      B    C
ATOM   2582  CB   THR A 326      10.960    4.919   25.930  1.00 15.22      B    C
ATOM   2583  OG1  THR A 326      12.258    4.855   25.394  1.00 16.58      B    O
ATOM   2584  CG2  THR A 326      10.240    6.105   25.357  1.00 17.29      B    C
ATOM   2585  C    THR A 326      11.507    3.756   28.184  1.00 15.44      B    C
ATOM   2586  O    THR A 326      11.948    2.800   27.516  1.00 15.65      B    O
ATOM   2587  N    PRO A 327      11.478    3.700   29.532  1.00 15.28      B    N
ATOM   2588  CA   PRO A 327      12.140    2.657   30.290  1.00 15.10      B    C
ATOM   2589  CB   PRO A 327      12.135    3.188   31.733  1.00 15.72      B    C
ATOM   2590  CG   PRO A 327      10.880    4.037   31.799  1.00 15.45      B    C
ATOM   2591  CD   PRO A 327      10.823    4.678   30.401  1.00 15.09      B    C
ATOM   2592  C    PRO A 327      11.377    1.328   30.267  1.00 13.72      B    C
ATOM   2593  O    PRO A 327      10.197    1.297   29.990  1.00 14.62      B    O
ATOM   2594  N    PRO A 328      12.106    0.242   30.674  1.00 15.03      B    N
ATOM   2595  CA   PRO A 328      11.458   -1.080   30.732  1.00 15.00      B    C
ATOM   2596  CB   PRO A 328      12.545   -1.977   31.275  1.00 16.22      B    C
ATOM   2597  CG   PRO A 328      13.828   -1.315   30.927  1.00 17.57      B    C
ATOM   2598  CD   PRO A 328      13.539    0.195   30.948  1.00 14.87      B    C
ATOM   2599  C    PRO A 328      10.211   -1.024   31.599  1.00 15.29      B    C
ATOM   2600  O    PRO A 328      10.320   -0.506   32.737  1.00 15.52      B    O
ATOM   2601  N    GLY A 329       9.101   -1.550   31.138  1.00 13.96      B    N
ATOM   2602  CA   GLY A 329       7.844   -1.526   31.874  1.00 15.67      B    C
ATOM   2603  C    GLY A 329       7.164   -0.174   31.989  1.00 15.47      B    C
ATOM   2604  O    GLY A 329       6.089   -0.079   32.576  1.00 15.93      B    O
ATOM   2605  N    GLY A 330       7.761    0.859   31.392  1.00 14.83      B    N
ATOM   2606  CA   GLY A 330       7.107    2.172   31.465  1.00 15.33      B    C
ATOM   2607  C    GLY A 330       5.772    2.199   30.754  1.00 15.74      B    C
ATOM   2608  O    GLY A 330       5.609    1.599   29.667  1.00 14.95      B    O
```

Fig. 5AS

| | | | | | | | | | | |
|---|---|---|---|---|---|---|---|---|---|---|
| ATOM | 2609 | N | GLU A 331 | 4.812 | 2.952 | 31.304 | 1.00 | 14.66 | B | N |
| ATOM | 2610 | CA | GLU A 331 | 3.428 | 2.958 | 30.896 | 1.00 | 15.06 | B | C |
| ATOM | 2611 | CB | GLU A 331 | 2.571 | 2.428 | 32.040 | 1.00 | 16.93 | B | C |
| ATOM | 2612 | CG | GLU A 331 | 2.824 | 0.990 | 32.391 | 1.00 | 16.75 | B | C |
| ATOM | 2613 | CD | GLU A 331 | 1.973 | 0.445 | 33.515 | 1.00 | 17.95 | B | C |
| ATOM | 2614 | OE1 | GLU A 331 | 1.102 | 1.149 | 34.015 | 1.00 | 18.92 | B | O |
| ATOM | 2615 | OE2 | GLU A 331 | 2.139 | -0.809 | 33.859 | 1.00 | 17.27 | B | O |
| ATOM | 2616 | C | GLU A 331 | 2.970 | 4.383 | 30.547 | 1.00 | 16.37 | B | C |
| ATOM | 2617 | O | GLU A 331 | 3.010 | 5.282 | 31.413 | 1.00 | 17.94 | B | O |
| ATOM | 2618 | N | ALEU A 332 | 2.471 | 4.539 | 29.314 | 0.50 | 15.69 | B | N |
| ATOM | 2619 | N | BLEU A 332 | 2.521 | 4.553 | 29.332 | 0.50 | 16.37 | B | N |
| ATOM | 2620 | CA | ALEU A 332 | 1.605 | 5.700 | 28.964 | 0.50 | 15.36 | B | C |
| ATOM | 2621 | CA | BLEU A 332 | 1.767 | 5.782 | 29.058 | 0.50 | 16.43 | B | C |
| ATOM | 2622 | CB | ALEU A 332 | 1.599 | 5.974 | 27.460 | 0.50 | 15.38 | B | C |
| ATOM | 2623 | CB | BLEU A 332 | 2.107 | 6.129 | 27.613 | 0.50 | 17.26 | B | C |
| ATOM | 2624 | CG | ALEU A 332 | 2.660 | 6.972 | 26.997 | 0.50 | 17.39 | B | C |
| ATOM | 2625 | CG | BLEU A 332 | 1.419 | 7.389 | 27.135 | 0.50 | 18.39 | B | C |
| ATOM | 2626 | CD1 | ALEU A 332 | 2.556 | 7.190 | 25.506 | 0.50 | 17.14 | B | C |
| ATOM | 2627 | CD1 | BLEU A 332 | -0.046 | 7.250 | 27.393 | 0.50 | 25.45 | B | C |
| ATOM | 2628 | CD2 | ALEU A 332 | 2.551 | 8.321 | 27.705 | 0.50 | 17.06 | B | C |
| ATOM | 2629 | CD2 | BLEU A 332 | 1.917 | 8.633 | 27.850 | 0.50 | 19.91 | B | C |
| ATOM | 2630 | C | ALEU A 332 | 0.209 | 5.363 | 29.404 | 0.50 | 16.24 | B | C |
| ATOM | 2631 | C | BLEU A 332 | 0.298 | 5.460 | 29.338 | 0.50 | 16.61 | B | C |
| ATOM | 2632 | O | ALEU A 332 | -0.377 | 4.407 | 28.892 | 0.50 | 17.59 | B | O |
| ATOM | 2633 | O | BLEU A 332 | -0.215 | 4.527 | 28.727 | 0.50 | 17.49 | B | O |
| ATOM | 2634 | N | VAL A 333 | -0.346 | 6.193 | 30.262 | 1.00 | 17.24 | B | N |
| ATOM | 2635 | CA | VAL A 333 | -1.657 | 5.875 | 30.842 | 1.00 | 18.05 | B | C |
| ATOM | 2636 | CB | VAL A 333 | -1.567 | 5.798 | 32.367 | 1.00 | 18.22 | B | C |
| ATOM | 2637 | CG1 | VAL A 333 | -2.892 | 5.400 | 32.959 | 1.00 | 20.88 | B | C |
| ATOM | 2638 | CG2 | VAL A 333 | -0.432 | 4.866 | 32.819 | 1.00 | 18.83 | B | C |
| ATOM | 2639 | C | VAL A 333 | -2.649 | 6.943 | 30.423 | 1.00 | 17.39 | B | C |
| ATOM | 2640 | O | VAL A 333 | -2.396 | 8.135 | 30.747 | 1.00 | 19.31 | B | O |
| ATOM | 2641 | N | PHE A 334 | -3.699 | 6.520 | 29.783 | 1.00 | 16.84 | B | N |
| ATOM | 2642 | CA | PHE A 334 | -4.789 | 7.413 | 29.301 | 1.00 | 17.69 | B | C |
| ATOM | 2643 | CB | PHE A 334 | -5.125 | 7.189 | 27.841 | 1.00 | 19.01 | B | C |
| ATOM | 2644 | CG | PHE A 334 | -3.979 | 7.451 | 26.913 | 1.00 | 18.89 | B | C |
| ATOM | 2645 | CD1 | PHE A 334 | -3.020 | 6.502 | 26.641 | 1.00 | 17.33 | B | C |
| ATOM | 2646 | CE1 | PHE A 334 | -1.982 | 6.789 | 25.764 | 1.00 | 18.63 | B | C |
| ATOM | 2647 | CZ | PHE A 334 | -1.874 | 8.029 | 25.195 | 1.00 | 20.26 | B | C |
| ATOM | 2648 | CD2 | PHE A 334 | -3.859 | 8.688 | 26.316 | 1.00 | 20.36 | B | C |
| ATOM | 2649 | CE2 | PHE A 334 | -2.844 | 8.953 | 25.437 | 1.00 | 20.30 | B | C |
| ATOM | 2650 | C | PHE A 334 | -6.011 | 7.090 | 30.148 | 1.00 | 19.57 | B | C |
| ATOM | 2651 | O | PHE A 334 | -6.542 | 5.962 | 30.064 | 1.00 | 19.83 | B | O |
| ATOM | 2652 | N | GLU A 335 | -6.430 | 8.058 | 30.948 | 1.00 | 22.41 | B | N |
| ATOM | 2653 | CA | GLU A 335 | -7.582 | 7.901 | 31.851 | 1.00 | 21.51 | B | C |
| ATOM | 2654 | CB | GLU A 335 | -7.238 | 8.304 | 33.258 | 1.00 | 22.44 | B | C |
| ATOM | 2655 | CG | GLU A 335 | -6.210 | 7.441 | 33.973 | 1.00 | 30.06 | B | C |
| ATOM | 2656 | CD | GLU A 335 | -5.523 | 8.171 | 35.117 | 1.00 | 37.25 | B | C |
| ATOM | 2657 | OE1 | GLU A 335 | -5.766 | 9.383 | 35.313 | 1.00 | 40.45 | B | O |
| ATOM | 2658 | OE2 | GLU A 335 | -4.705 | 7.522 | 35.798 | 1.00 | 50.58 | B | O |
| ATOM | 2659 | C | GLU A 335 | -8.772 | 8.738 | 31.395 | 1.00 | 22.52 | B | C |
| ATOM | 2660 | O | GLU A 335 | -8.579 | 9.962 | 31.203 | 1.00 | 22.93 | B | O |
| ATOM | 2661 | N | LYS A 336 | -9.927 | 8.106 | 31.256 | 1.00 | 24.49 | B | N |
| ATOM | 2662 | CA | LYS A 336 | -11.222 | 8.787 | 31.002 | 1.00 | 21.22 | B | C |
| ATOM | 2663 | CB | LYS A 336 | -12.123 | 7.976 | 30.103 | 1.00 | 22.65 | B | C |
| ATOM | 2664 | CG | LYS A 336 | -13.488 | 8.585 | 29.869 | 1.00 | 24.58 | B | C |
| ATOM | 2665 | CD | LYS A 336 | -14.374 | 7.694 | 29.082 | 1.00 | 28.09 | B | C |
| ATOM | 2666 | CE | LYS A 336 | -15.775 | 8.229 | 28.970 | 1.00 | 35.25 | B | C |

Fig. 5AT

```
ATOM   2667  NZ  LYS A 336     -16.537   7.381  28.031  1.00 40.46      B    N
ATOM   2668  C   LYS A 336     -11.918   9.051  32.322  1.00 22.10      B    C
ATOM   2669  O   LYS A 336     -12.251   8.118  33.048  1.00 21.83      B    O
ATOM   2670  N   TRP A 337     -12.080  10.343  32.594  1.00 22.06      B    N
ATOM   2671  CA  TRP A 337     -12.711  10.872  33.807  1.00 22.31      B    C
ATOM   2672  CB  TRP A 337     -11.812  11.847  34.559  1.00 24.24      B    C
ATOM   2673  CG  TRP A 337     -10.562  11.276  35.143  1.00 21.96      B    C
ATOM   2674  CD1 TRP A 337      -9.340  11.210  34.548  1.00 24.24      B    C
ATOM   2675  NE1 TRP A 337      -8.414  10.751  35.438  1.00 25.79      B    N
ATOM   2676  CE2 TRP A 337      -9.036  10.401  36.599  1.00 27.12      B    C
ATOM   2677  CD2 TRP A 337     -10.400  10.759  36.469  1.00 24.64      B    C
ATOM   2678  CE3 TRP A 337     -11.251  10.564  37.565  1.00 28.32      B    C
ATOM   2679  CZ3 TRP A 337     -10.741  10.012  38.718  1.00 32.16      B    C
ATOM   2680  CH2 TRP A 337      -9.385   9.688  38.827  1.00 30.53      B    C
ATOM   2681  CZ2 TRP A 337      -8.520   9.878  37.782  1.00 30.32      B    C
ATOM   2682  C   TRP A 337     -14.038  11.533  33.462  1.00 23.88      B    C
ATOM   2683  O   TRP A 337     -14.083  12.342  32.529  1.00 24.74      B    O
ATOM   2684  N   LYS A 338     -15.069  11.220  34.244  1.00 24.62      B    N
ATOM   2685  CA  LYS A 338     -16.383  11.910  34.106  1.00 24.45      B    C
ATOM   2686  CB  LYS A 338     -17.534  10.907  34.163  1.00 27.26      B    C
ATOM   2687  CG  LYS A 338     -18.918  11.558  34.011  1.00 31.83      B    C
ATOM   2688  CD  LYS A 338     -20.037  10.673  33.489  1.00 39.55      B    C
ATOM   2689  CE  LYS A 338     -20.338  10.864  32.018  1.00 44.51      B    C
ATOM   2690  NZ  LYS A 338     -19.610   9.867  31.192  1.00 56.49      B    N
ATOM   2691  C   LYS A 338     -16.475  12.986  35.167  1.00 24.76      B    C
ATOM   2692  O   LYS A 338     -16.285  12.660  36.352  1.00 26.46      B    O
ATOM   2693  N   ARG A 339     -16.761  14.230  34.743  1.00 24.06      B    N
ATOM   2694  CA  ARG A 339     -17.053  15.316  35.716  1.00 27.27      B    C
ATOM   2695  CB  ARG A 339     -16.616  16.678  35.170  1.00 28.86      B    C
ATOM   2696  CG  ARG A 339     -17.072  17.863  36.014  1.00 33.24      B    C
ATOM   2697  CD  ARG A 339     -17.226  19.111  35.119  1.00 39.64      B    C
ATOM   2698  NE  ARG A 339     -15.941  19.710  35.009  1.00 39.87      B    N
ATOM   2699  CZ  ARG A 339     -15.535  20.657  34.151  1.00 35.71      B    C
ATOM   2700  NH1 ARG A 339     -16.301  21.134  33.189  1.00 34.61      B    N
ATOM   2701  NH2 ARG A 339     -14.296  21.086  34.274  1.00 39.43      B    N
ATOM   2702  C   ARG A 339     -18.556  15.253  36.018  1.00 25.66      B    C
ATOM   2703  O   ARG A 339     -19.350  15.433  35.056  1.00 28.63      B    O
ATOM   2704  N   THR A 340     -18.930  14.852  37.238  1.00 30.31      B    N
ATOM   2705  CA  THR A 340     -20.320  14.452  37.579  1.00 30.30      B    C
ATOM   2706  CB  THR A 340     -20.356  13.556  38.822  1.00 32.71      B    C
ATOM   2707  OG1 THR A 340     -19.630  14.214  39.843  1.00 36.55      B    O
ATOM   2708  CG2 THR A 340     -19.698  12.222  38.554  1.00 35.47      B    C
ATOM   2709  C   THR A 340     -21.252  15.682  37.660  1.00 34.40      B    C
ATOM   2710  O   THR A 340     -22.429  15.512  37.331  1.00 39.32      B    O
ATOM   2711  N   SER A 341     -20.766  16.879  37.953  1.00 36.28      B    N
ATOM   2712  CA  SER A 341     -21.652  18.089  37.930  1.00 35.06      B    C
ATOM   2713  CB  SER A 341     -20.900  19.285  38.327  1.00 38.32      B    C
ATOM   2714  OG  SER A 341     -19.880  19.552  37.382  1.00 41.13      B    O
ATOM   2715  C   SER A 341     -22.325  18.289  36.556  1.00 40.42      B    C
ATOM   2716  O   SER A 341     -23.582  18.433  36.497  1.00 37.14      B    O
ATOM   2717  N   ASP A 342     -21.553  18.306  35.463  1.00 34.29      B    N
ATOM   2718  CA  ASP A 342     -22.099  18.689  34.136  1.00 37.27      B    C
ATOM   2719  CB  ASP A 342     -21.410  19.961  33.619  1.00 39.31      B    C
ATOM   2720  CG  ASP A 342     -19.911  19.829  33.446  1.00 42.15      B    C
ATOM   2721  OD1 ASP A 342     -19.410  18.712  33.686  1.00 35.99      B    O
ATOM   2722  OD2 ASP A 342     -19.244  20.830  33.090  1.00 38.92      B    O
ATOM   2723  C   ASP A 342     -22.058  17.470  33.220  1.00 34.29      B    C
ATOM   2724  O   ASP A 342     -22.421  17.625  32.050  1.00 36.13      B    O
```

Fig. 5AU

```
ATOM   2725  N   ASN A 343     -21.670  16.283  33.729  1.00 36.03      B    N
ATOM   2726  CA  ASN A 343     -21.695  15.049  32.898  1.00 38.73      B    C
ATOM   2727  CB  ASN A 343     -23.105  14.711  32.405  1.00 49.42      B    C
ATOM   2728  CG  ASN A 343     -23.362  13.228  32.475  1.00 54.84      B    C
ATOM   2729  OD1 ASN A 343     -23.368  12.664  33.567  1.00 63.56      B    O
ATOM   2730  ND2 ASN A 343     -23.547  12.595  31.332  1.00 64.38      B    N
ATOM   2731  C   ASN A 343     -20.771  15.234  31.685  1.00 36.68      B    C
ATOM   2732  O   ASN A 343     -21.089  14.746  30.587  1.00 39.47      B    O
ATOM   2733  N   THR A 344     -19.618  15.866  31.879  1.00 30.12      B    N
ATOM   2734  CA  THR A 344     -18.631  16.046  30.786  1.00 26.24      B    C
ATOM   2735  CB  THR A 344     -18.124  17.493  30.732  1.00 25.05      B    C
ATOM   2736  OG1 THR A 344     -17.554  17.892  31.974  1.00 25.23      B    O
ATOM   2737  CG2 THR A 344     -19.223  18.451  30.291  1.00 28.45      B    C
ATOM   2738  C   THR A 344     -17.489  15.030  30.980  1.00 25.63      B    C
ATOM   2739  O   THR A 344     -17.150  14.714  32.114  1.00 24.15      B    O
ATOM   2740  N   ASP A 345     -16.874  14.642  29.879  1.00 25.15      B    N
ATOM   2741  CA  ASP A 345     -15.784  13.640  29.930  1.00 23.43      B    C
ATOM   2742  CB  ASP A 345     -16.119  12.475  29.038  1.00 26.84      B    C
ATOM   2743  CG  ASP A 345     -17.397  11.756  29.444  1.00 31.44      B    C
ATOM   2744  OD1 ASP A 345     -17.519  11.430  30.603  1.00 34.31      B    O
ATOM   2745  OD2 ASP A 345     -18.215  11.511  28.559  1.00 39.90      B    O
ATOM   2746  C   ASP A 345     -14.458  14.303  29.581  1.00 22.26      B    C
ATOM   2747  O   ASP A 345     -14.383  15.089  28.639  1.00 22.13      B    O
ATOM   2748  N   TRP A 346     -13.403  13.780  30.178  1.00 21.69      B    N
ATOM   2749  CA  TRP A 346     -12.051  14.370  30.152  1.00 21.52      B    C
ATOM   2750  CB  TRP A 346     -11.843  15.221  31.398  1.00 21.39      B    C
ATOM   2751  CG  TRP A 346     -12.886  16.294  31.471  1.00 22.93      B    C
ATOM   2752  CD1 TRP A 346     -14.068  16.229  32.151  1.00 23.76      B    C
ATOM   2753  NE1 TRP A 346     -14.770  17.396  31.936  1.00 25.13      B    N
ATOM   2754  CE2 TRP A 346     -14.044  18.225  31.127  1.00 23.86      B    C
ATOM   2755  CD2 TRP A 346     -12.832  17.584  30.822  1.00 24.38      B    C
ATOM   2756  CE3 TRP A 346     -11.897  18.229  29.995  1.00 24.68      B    C
ATOM   2757  CZ3 TRP A 346     -12.173  19.516  29.569  1.00 26.16      B    C
ATOM   2758  CH2 TRP A 346     -13.395  20.118  29.873  1.00 25.30      B    C
ATOM   2759  CZ2 TRP A 346     -14.333  19.521  30.678  1.00 25.95      B    C
ATOM   2760  C   TRP A 346     -11.032  13.237  30.046  1.00 22.07      B    C
ATOM   2761  O   TRP A 346     -11.309  12.145  30.558  1.00 22.47      B    O
ATOM   2762  N   VAL A 347      -9.880  13.542  29.483  1.00 21.39      B    N
ATOM   2763  CA  VAL A 347      -8.780  12.555  29.329  1.00 20.88      B    C
ATOM   2764  CB  VAL A 347      -8.473  12.281  27.864  1.00 21.80      B    C
ATOM   2765  CG1 VAL A 347      -7.298  11.320  27.774  1.00 23.79      B    C
ATOM   2766  CG2 VAL A 347      -9.664  11.742  27.128  1.00 24.94      B    C
ATOM   2767  C   VAL A 347      -7.569  13.094  30.065  1.00 21.99      B    C
ATOM   2768  O   VAL A 347      -7.079  14.237  29.778  1.00 21.91      B    O
ATOM   2769  N   GLN A 348      -7.055  12.321  30.993  1.00 22.92      B    N
ATOM   2770  CA  GLN A 348      -5.801  12.631  31.691  1.00 21.70      B    C
ATOM   2771  CB  GLN A 348      -5.957  12.518  33.180  1.00 22.98      B    C
ATOM   2772  CG  GLN A 348      -4.679  12.880  33.898  1.00 26.42      B    C
ATOM   2773  CD  GLN A 348      -4.984  13.396  35.270  1.00 33.74      B    C
ATOM   2774  OE1 GLN A 348      -5.384  12.623  36.129  1.00 35.76      B    O
ATOM   2775  NE2 GLN A 348      -4.884  14.700  35.448  1.00 34.83      B    N
ATOM   2776  C   GLN A 348      -4.735  11.677  31.192  1.00 21.66      B    C
ATOM   2777  O   GLN A 348      -5.044  10.488  31.018  1.00 22.49      B    O
ATOM   2778  N   VAL A 349      -3.570  12.189  30.949  1.00 19.76      B    N
ATOM   2779  CA  VAL A 349      -2.415  11.378  30.453  1.00 19.13      B    C
ATOM   2780  CB  VAL A 349      -1.965  11.816  29.048  1.00 20.92      B    C
ATOM   2781  CG1 VAL A 349      -0.915  10.876  28.460  1.00 23.30      B    C
ATOM   2782  CG2 VAL A 349      -3.137  11.930  28.090  1.00 23.40      B    C
```

Fig. 5AV

```
ATOM   2783  C    VAL A 349      -1.312  11.474  31.488  1.00 19.38      B  C
ATOM   2784  O    VAL A 349      -1.015  12.550  32.041  1.00 19.81      B  O
ATOM   2785  N   ASER A 350      -0.709  10.321  31.803  0.50 19.25      B  N
ATOM   2786  N   BSER A 350      -0.703  10.325  31.796  0.50 18.28      B  N
ATOM   2787  CA  ASER A 350       0.388  10.200  32.783  0.50 19.08      B  C
ATOM   2788  CA  BSER A 350       0.429  10.250  32.735  0.50 17.35      B  C
ATOM   2789  CB  ASER A 350      -0.106   9.778  34.126  0.50 21.35      B  C
ATOM   2790  CB  BSER A 350      -0.010   9.979  34.144  0.50 17.62      B  C
ATOM   2791  OG  ASER A 350      -1.175  10.599  34.546  0.50 23.35      B  O
ATOM   2792  OG  BSER A 350      -0.820   8.810  34.215  0.50 17.13      B  O
ATOM   2793  C   ASER A 350       1.404   9.175  32.288  0.50 17.12      B  C
ATOM   2794  C   BSER A 350       1.415   9.179  32.274  0.50 16.36      B  C
ATOM   2795  O   ASER A 350       1.053   8.353  31.448  0.50 17.52      B  O
ATOM   2796  O   BSER A 350       1.077   8.361  31.420  0.50 17.12      B  O
ATOM   2797  N    PHE A 351       2.609   9.278  32.801  1.00 16.96      B  N
ATOM   2798  CA   PHE A 351       3.662   8.254  32.578  1.00 16.57      B  C
ATOM   2799  CB   PHE A 351       4.932   8.839  31.976  1.00 15.47      B  C
ATOM   2800  CG   PHE A 351       5.722   7.770  31.262  1.00 16.59      B  C
ATOM   2801  CD1  PHE A 351       6.607   6.954  31.939  1.00 16.26      B  C
ATOM   2802  CE1  PHE A 351       7.258   5.906  31.285  1.00 15.30      B  C
ATOM   2803  CZ   PHE A 351       7.052   5.666  29.963  1.00 16.09      B  C
ATOM   2804  CD2  PHE A 351       5.472   7.460  29.938  1.00 17.52      B  C
ATOM   2805  CE2  PHE A 351       6.131   6.427  29.297  1.00 16.90      B  C
ATOM   2806  C    PHE A 351       3.942   7.599  33.913  1.00 17.58      B  C
ATOM   2807  O    PHE A 351       4.360   8.249  34.851  1.00 17.55      B  O
ATOM   2808  N    VAL A 352       3.709   6.270  33.976  1.00 16.95      B  N
ATOM   2809  CA   VAL A 352       3.883   5.469  35.214  1.00 17.51      B  C
ATOM   2810  CB   VAL A 352       2.626   4.709  35.571  1.00 16.94      B  C
ATOM   2811  CG1  VAL A 352       2.950   3.736  36.723  1.00 19.47      B  C
ATOM   2812  CG2  VAL A 352       1.529   5.702  35.976  1.00 19.87      B  C
ATOM   2813  C    VAL A 352       5.098   4.574  35.021  1.00 17.01      B  C
ATOM   2814  O    VAL A 352       5.231   3.953  33.957  1.00 17.85      B  O
ATOM   2815  N    TYR A 353       6.007   4.539  35.963  1.00 16.30      B  N
ATOM   2816  CA   TYR A 353       7.301   3.878  35.765  1.00 17.33      B  C
ATOM   2817  CB   TYR A 353       8.208   4.793  34.953  1.00 17.49      B  C
ATOM   2818  CG   TYR A 353       8.676   6.004  35.695  1.00 16.35      B  C
ATOM   2819  CD1  TYR A 353       7.836   7.074  35.902  1.00 16.74      B  C
ATOM   2820  CE1  TYR A 353       8.228   8.158  36.676  1.00 18.24      B  C
ATOM   2821  CZ   TYR A 353       9.487   8.210  37.220  1.00 17.25      B  C
ATOM   2822  OH   TYR A 353       9.888   9.283  37.991  1.00 19.82      B  O
ATOM   2823  CE2  TYR A 353      10.357   7.146  37.028  1.00 17.63      B  C
ATOM   2824  CD2  TYR A 353       9.930   6.083  36.244  1.00 16.28      B  C
ATOM   2825  C    TYR A 353       7.945   3.538  37.100  1.00 17.72      B  C
ATOM   2826  O    TYR A 353       7.444   4.019  38.172  1.00 18.14      B  O
ATOM   2827  N    GLN A 354       9.009   2.759  37.039  1.00 16.58      B  N
ATOM   2828  CA   GLN A 354       9.903   2.568  38.178  1.00 16.41      B  C
ATOM   2829  CB   GLN A 354      10.144   1.056  38.315  1.00 17.64      B  C
ATOM   2830  CG   GLN A 354       8.898   0.327  38.802  1.00 17.79      B  C
ATOM   2831  CD   GLN A 354       8.721  -1.036  38.165  1.00 18.24      B  C
ATOM   2832  OE1  GLN A 354       8.740  -1.153  36.920  1.00 19.69      B  O
ATOM   2833  NE2  GLN A 354       8.371  -2.018  39.002  1.00 19.45      B  N
ATOM   2834  C    GLN A 354      11.187   3.312  37.965  1.00 15.26      B  C
ATOM   2835  O    GLN A 354      11.792   3.298  36.899  1.00 16.12      B  O
ATOM   2836  N    THR A 355      11.677   3.928  39.041  1.00 17.12      B  N
ATOM   2837  CA   THR A 355      13.009   4.508  39.027  1.00 16.94      B  C
ATOM   2838  CB   THR A 355      13.351   5.253  40.325  1.00 18.61      B  C
ATOM   2839  OG1  THR A 355      13.448   4.284  41.380  1.00 20.07      B  O
ATOM   2840  CG2  THR A 355      12.377   6.354  40.656  1.00 18.83      B  C
```

Fig. 5AW

```
ATOM   2841  C   THR A 355      14.058   3.415  38.836  1.00 16.20           B  C
ATOM   2842  O   THR A 355      13.787   2.192  39.110  1.00 18.27           B  O
ATOM   2843  N   LEU A 356      15.194   3.773  38.324  1.00 17.17           B  N
ATOM   2844  CA  LEU A 356      16.239   2.783  38.037  1.00 19.22           B  C
ATOM   2845  CB  LEU A 356      17.427   3.465  37.374  1.00 18.37           B  C
ATOM   2846  CG  LEU A 356      18.530   2.545  36.871  1.00 19.21           B  C
ATOM   2847  CD1 LEU A 356      17.991   1.443  35.971  1.00 19.58           B  C
ATOM   2848  CD2 LEU A 356      19.612   3.337  36.167  1.00 20.34           B  C
ATOM   2849  C   LEU A 356      16.630   2.089  39.348  1.00 20.96           B  C
ATOM   2850  O   LEU A 356      16.839   0.874  39.346  1.00 19.94           B  O
ATOM   2851  N   ARG A 357      16.700   2.831  40.433  1.00 20.92           B  N
ATOM   2852  CA  ARG A 357      17.001   2.211  41.744  1.00 21.97           B  C
ATOM   2853  CB  ARG A 357      17.168   3.352  42.747  1.00 27.09           B  C
ATOM   2854  CG  ARG A 357      17.467   2.825  44.144  1.00 32.94           B  C
ATOM   2855  CD  ARG A 357      18.956   2.727  44.340  1.00 42.99           B  C
ATOM   2856  NE  ARG A 357      19.463   1.368  44.267  1.00 55.08           B  N
ATOM   2857  CZ  ARG A 357      20.599   1.007  43.676  1.00 56.61           B  C
ATOM   2858  NH1 ARG A 357      21.345   1.904  43.054  1.00 54.58           B  N
ATOM   2859  NH2 ARG A 357      20.971  -0.262  43.701  1.00 59.97           B  N
ATOM   2860  C   ARG A 357      15.886   1.278  42.192  1.00 22.41           B  C
ATOM   2861  O   ARG A 357      16.230   0.186  42.732  1.00 22.44           B  O
ATOM   2862  N   ASP A 358      14.608   1.584  41.997  1.00 20.61           B  N
ATOM   2863  CA  ASP A 358      13.493   0.694  42.362  1.00 20.74           B  C
ATOM   2864  CB  ASP A 358      12.160   1.423  42.287  1.00 22.91           B  C
ATOM   2865  CG  ASP A 358      11.888   2.298  43.525  1.00 24.26           B  C
ATOM   2866  OD1 ASP A 358      12.745   2.272  44.483  1.00 26.29           B  O
ATOM   2867  OD2 ASP A 358      10.803   2.878  43.566  1.00 27.45           B  O
ATOM   2868  C   ASP A 358      13.547  -0.579  41.506  1.00 21.63           B  C
ATOM   2869  O   ASP A 358      12.960  -1.626  41.931  1.00 22.40           B  O
ATOM   2870  N   MET A 359      14.052  -0.487  40.266  1.00 18.94           B  N
ATOM   2871  CA  MET A 359      14.201  -1.720  39.468  1.00 19.32           B  C
ATOM   2872  CB  MET A 359      14.518  -1.326  38.020  1.00 20.32           B  C
ATOM   2873  CG  MET A 359      13.362  -0.672  37.302  1.00 19.98           B  C
ATOM   2874  SD  MET A 359      13.850  -0.119  35.625  1.00 20.05           B  S
ATOM   2875  CE  MET A 359      12.292   0.450  34.993  1.00 21.34           B  C
ATOM   2876  C   MET A 359      15.330  -2.546  40.068  1.00 20.98           B  C
ATOM   2877  O   MET A 359      15.133  -3.758  40.277  1.00 21.04           B  O
ATOM   2878  N   ARG A 360      16.477  -1.962  40.294  1.00 19.55           B  N
ATOM   2879  CA  ARG A 360      17.682  -2.696  40.735  1.00 21.52           B  C
ATOM   2880  CB  ARG A 360      18.855  -1.734  40.843  1.00 21.48           B  C
ATOM   2881  CG  ARG A 360      20.098  -2.488  41.297  1.00 25.76           B  C
ATOM   2882  CD  ARG A 360      21.312  -1.777  40.874  1.00 26.28           B  C
ATOM   2883  NE  ARG A 360      22.541  -2.483  41.233  1.00 31.25           B  N
ATOM   2884  CZ  ARG A 360      23.180  -3.396  40.479  1.00 27.91           B  C
ATOM   2885  NH1 ARG A 360      22.807  -3.675  39.249  1.00 25.80           B  N
ATOM   2886  NH2 ARG A 360      24.292  -3.942  40.927  1.00 33.13           B  N
ATOM   2887  C   ARG A 360      17.336  -3.346  42.091  1.00 23.50           B  C
ATOM   2888  O   ARG A 360      17.694  -4.553  42.307  1.00 24.88           B  O
ATOM   2889  N   ASP A 361      16.653  -2.637  42.971  1.00 23.23           B  N
ATOM   2890  CA  ASP A 361      16.285  -3.130  44.329  1.00 25.02           B  C
ATOM   2891  CB  ASP A 361      16.085  -1.940  45.265  1.00 28.72           B  C
ATOM   2892  CG  ASP A 361      17.321  -1.127  45.562  1.00 33.07           B  C
ATOM   2893  OD1 ASP A 361      18.456  -1.607  45.312  1.00 35.24           B  O
ATOM   2894  OD2 ASP A 361      17.128   0.023  46.071  1.00 41.97           B  O
ATOM   2895  C   ASP A 361      15.034  -4.029  44.313  1.00 30.46           B  C
ATOM   2896  O   ASP A 361      14.701  -4.542  45.382  1.00 29.89           B  O
ATOM   2897  N   ILE A 362      14.302  -4.228  43.197  1.00 27.58           B  N
ATOM   2898  CA  ILE A 362      12.953  -4.903  43.126  1.00 27.50           B  C
```

Fig. 5AX

```
ATOM   2899  CB   ILE A 362      12.991  -6.461  43.053  1.00 27.48           B  C
ATOM   2900  CG1  ILE A 362      14.170  -6.848  42.184  1.00 30.29           B  C
ATOM   2901  CG2  ILE A 362      11.700  -7.041  42.490  1.00 30.49           B  C
ATOM   2902  CD1  ILE A 362      13.905  -6.745  40.702  1.00 34.10           B  C
ATOM   2903  C    ILE A 362      12.081  -4.403  44.271  1.00 26.27           B  C
ATOM   2904  O    ILE A 362      11.523  -5.184  45.043  1.00 28.51           B  O
ATOM   2905  N    GLN A 363      11.847  -3.094  44.291  1.00 25.69           B  N
ATOM   2906  CA   GLN A 363      11.112  -2.427  45.378  1.00 28.87           B  C
ATOM   2907  CB   GLN A 363      11.378  -0.936  45.307  1.00 30.35           B  C
ATOM   2908  CG   GLN A 363      10.393  -0.124  46.124  1.00 33.00           B  C
ATOM   2909  CD   GLN A 363      10.647  -0.345  47.591  1.00 37.15           B  C
ATOM   2910  OE1  GLN A 363      11.774  -0.226  48.059  1.00 35.56           B  O
ATOM   2911  NE2  GLN A 363       9.594  -0.687  48.314  1.00 35.70           B  N
ATOM   2912  C    GLN A 363       9.628  -2.716  45.214  1.00 29.46           B  C
ATOM   2913  O    GLN A 363       9.028  -2.320  44.202  1.00 26.09           B  O
ATOM   2914  N    PRO A 364       8.946  -3.335  46.218  1.00 30.38           B  N
ATOM   2915  CA   PRO A 364       7.503  -3.539  46.176  1.00 30.50           B  C
ATOM   2916  CB   PRO A 364       7.179  -4.238  47.515  1.00 33.81           B  C
ATOM   2917  CG   PRO A 364       8.476  -4.851  47.929  1.00 38.54           B  C
ATOM   2918  CD   PRO A 364       9.535  -3.881  47.459  1.00 35.40           B  C
ATOM   2919  C    PRO A 364       6.792  -2.188  46.073  1.00 31.56           B  C
ATOM   2920  O    PRO A 364       7.233  -1.196  46.676  1.00 29.88           B  O
ATOM   2921  N    LEU A 365       5.696  -2.159  45.302  1.00 31.14           B  N
ATOM   2922  CA   LEU A 365       4.894  -0.938  45.071  1.00 31.26           B  C
ATOM   2923  CB   LEU A 365       4.785  -0.746  43.549  1.00 30.26           B  C
ATOM   2924  CG   LEU A 365       6.141  -0.668  42.851  1.00 29.51           B  C
ATOM   2925  CD1  LEU A 365       5.974  -0.535  41.334  1.00 26.40           B  C
ATOM   2926  CD2  LEU A 365       6.958   0.500  43.367  1.00 27.73           B  C
ATOM   2927  C    LEU A 365       3.527  -1.075  45.744  1.00 31.92           B  C
ATOM   2928  O    LEU A 365       2.942  -2.161  45.688  1.00 36.85           B  O
ATOM   2929  N    SER A 366       3.040   0.009  46.331  1.00 32.82           B  N
ATOM   2930  CA   SER A 366       1.762   0.074  47.078  1.00 34.03           B  C
ATOM   2931  CB   SER A 366       2.043  -0.297  48.523  1.00 36.45           B  C
ATOM   2932  OG   SER A 366       2.813   0.717  49.136  1.00 40.16           B  O
ATOM   2933  C    SER A 366       1.210   1.494  46.943  1.00 35.67           B  C
ATOM   2934  O    SER A 366       1.930   2.359  46.361  1.00 36.28           B  O
ATOM   2935  N    LEU A 367       0.028   1.798  47.488  1.00 35.52           B  N
ATOM   2936  CA   LEU A 367      -0.463   3.209  47.443  1.00 41.28           B  C
ATOM   2937  CB   LEU A 367      -1.940   3.303  47.844  1.00 40.37           B  C
ATOM   2938  CG   LEU A 367      -2.902   2.439  47.030  1.00 43.19           B  C
ATOM   2939  CD1  LEU A 367      -4.292   2.481  47.642  1.00 43.08           B  C
ATOM   2940  CD2  LEU A 367      -2.942   2.873  45.571  1.00 42.86           B  C
ATOM   2941  C    LEU A 367       0.445   4.073  48.342  1.00 44.36           B  C
ATOM   2942  O    LEU A 367       0.586   5.268  48.025  1.00 43.86           B  O
ATOM   2943  N    GLU A 368       1.059   3.468  49.369  1.00 49.44           B  N
ATOM   2944  CA   GLU A 368       2.013   4.098  50.332  1.00 58.52           B  C
ATOM   2945  CB   GLU A 368       2.208   3.203  51.566  1.00 66.96           B  C
ATOM   2946  CG   GLU A 368       0.930   2.897  52.332  1.00 73.32           B  C
ATOM   2947  CD   GLU A 368       0.022   4.092  52.564  1.00 85.37           B  C
ATOM   2948  OE1  GLU A 368       0.542   5.173  52.932  1.00 92.25           B  O
ATOM   2949  OE2  GLU A 368      -1.204   3.943  52.356  1.00 93.13           B  O
ATOM   2950  C    GLU A 368       3.387   4.340  49.687  1.00 55.00           B  C
ATOM   2951  O    GLU A 368       3.997   5.383  49.980  1.00 50.38           B  O
ATOM   2952  N    LYS A 369       3.881   3.384  48.894  1.00 52.24           B  N
ATOM   2953  CA   LYS A 369       5.191   3.445  48.191  1.00 52.07           B  C
ATOM   2954  CB   LYS A 369       6.123   2.338  48.703  1.00 62.62           B  C
ATOM   2955  CG   LYS A 369       5.914   1.973  50.170  1.00 76.15           B  C
ATOM   2956  CD   LYS A 369       6.977   1.078  50.784  1.00 80.58           B  C
```

Fig. 5AY

```
ATOM   2957  CE  LYS A 369       6.454   0.314  51.987  1.00 81.43           B  C
ATOM   2958  NZ  LYS A 369       7.553  -0.171  52.856  1.00 84.93           B  N
ATOM   2959  C   LYS A 369       4.894   3.309  46.698  1.00 37.41           B  C
ATOM   2960  O   LYS A 369       5.070   2.234  46.137  1.00 35.00           B  O
ATOM   2961  N   PRO A 370       4.364   4.381  46.058  1.00 38.27           B  N
ATOM   2962  CA  PRO A 370       3.823   4.270  44.706  1.00 31.85           B  C
ATOM   2963  CB  PRO A 370       2.993   5.545  44.527  1.00 33.39           B  C
ATOM   2964  CG  PRO A 370       3.712   6.554  45.421  1.00 38.62           B  C
ATOM   2965  CD  PRO A 370       4.223   5.746  46.596  1.00 39.11           B  C
ATOM   2966  C   PRO A 370       4.909   4.136  43.637  1.00 29.73           B  C
ATOM   2967  O   PRO A 370       6.048   4.503  43.844  1.00 30.98           B  O
ATOM   2968  N   ALA A 371       4.491   3.589  42.501  1.00 26.08           B  N
ATOM   2969  CA  ALA A 371       5.305   3.724  41.277  1.00 24.14           B  C
ATOM   2970  CB  ALA A 371       4.557   3.168  40.139  1.00 24.59           B  C
ATOM   2971  C   ALA A 371       5.595   5.215  41.080  1.00 23.68           B  C
ATOM   2972  O   ALA A 371       4.809   6.106  41.522  1.00 24.23           B  O
ATOM   2973  N   GLY A 372       6.604   5.498  40.286  1.00 20.97           B  N
ATOM   2974  CA  GLY A 372       6.780   6.869  39.792  1.00 21.28           B  C
ATOM   2975  C   GLY A 372       5.654   7.243  38.861  1.00 21.18           B  C
ATOM   2976  O   GLY A 372       5.073   6.404  38.139  1.00 18.75           B  O
ATOM   2977  N   LYS A 373       5.274   8.523  38.836  1.00 22.93           B  N
ATOM   2978  CA  LYS A 373       4.161   8.956  37.994  1.00 21.09           B  C
ATOM   2979  CB  LYS A 373       2.841   8.838  38.714  1.00 24.90           B  C
ATOM   2980  CG  LYS A 373       1.651   9.225  37.867  1.00 27.08           B  C
ATOM   2981  CD  LYS A 373       0.384   8.751  38.488  1.00 30.00           B  C
ATOM   2982  CE  LYS A 373      -0.864   9.301  37.880  1.00 37.51           B  C
ATOM   2983  NZ  LYS A 373      -1.998   8.956  38.765  1.00 37.26           B  N
ATOM   2984  C   LYS A 373       4.429  10.407  37.607  1.00 24.18           B  C
ATOM   2985  O   LYS A 373       4.777  11.242  38.524  1.00 29.33           B  O
ATOM   2986  N   VAL A 374       4.453  10.669  36.326  1.00 20.30           B  N
ATOM   2987  CA  VAL A 374       4.658  12.056  35.827  1.00 19.77           B  C
ATOM   2988  CB  VAL A 374       5.880  12.103  34.889  1.00 21.41           B  C
ATOM   2989  CG1 VAL A 374       5.953  13.442  34.150  1.00 24.13           B  C
ATOM   2990  CG2 VAL A 374       7.160  11.824  35.619  1.00 22.46           B  C
ATOM   2991  C   VAL A 374       3.369  12.434  35.119  1.00 22.53           B  C
ATOM   2992  O   VAL A 374       2.885  11.771  34.200  1.00 20.93           B  O
ATOM   2993  N   ASP A 375       2.844  13.614  35.492  1.00 22.77           B  N
ATOM   2994  CA  ASP A 375       1.652  14.167  34.830  1.00 25.10           B  C
ATOM   2995  CB  ASP A 375       1.109  15.341  35.682  1.00 31.58           B  C
ATOM   2996  CG  ASP A 375      -0.383  15.694  35.607  1.00 47.73           B  C
ATOM   2997  OD1 ASP A 375      -0.937  15.894  34.494  1.00 43.48           B  O
ATOM   2998  OD2 ASP A 375      -1.001  15.814  36.703  1.00 69.61           B  O
ATOM   2999  C   ASP A 375       2.061  14.702  33.454  1.00 23.05           B  C
ATOM   3000  O   ASP A 375       3.101  15.378  33.375  1.00 26.54           B  O
ATOM   3001  N   ALEU A 376      1.370  14.316  32.428  0.50 20.82           B  N
ATOM   3002  N   BLEU A 376      1.331  14.377  32.379  0.50 20.28           B  N
ATOM   3003  CA  ALEU A 376      1.661  14.819  31.091  0.50 20.38           B  C
ATOM   3004  CA  BLEU A 376      1.631  14.682  30.943  0.50 19.85           B  C
ATOM   3005  CB  ALEU A 376      1.727  13.663  30.102  0.50 19.55           B  C
ATOM   3006  CB  BLEU A 376      1.716  13.419  30.083  0.50 20.59           B  C
ATOM   3007  CG  ALEU A 376      2.751  12.586  30.476  0.50 19.32           B  C
ATOM   3008  CG  BLEU A 376      2.846  12.429  30.373  0.50 20.12           B  C
ATOM   3009  CD1 ALEU A 376      2.816  11.492  29.435  0.50 19.57           B  C
ATOM   3010  CD1 BLEU A 376      2.835  11.274  29.388  0.50 21.20           B  C
ATOM   3011  CD2 ALEU A 376      4.126  13.193  30.711  0.50 19.11           B  C
ATOM   3012  CD2 BLEU A 376      4.208  13.099  30.368  0.50 20.77           B  C
ATOM   3013  C   ALEU A 376      0.552  15.818  30.783  0.50 25.37           B  C
ATOM   3014  C   BLEU A 376      0.529  15.567  30.318  0.50 21.85           B  C
```

Fig. 5AZ

```
ATOM   3015  O   ALEU A 376      -0.494  15.760  31.442  0.50 22.62      B   O
ATOM   3016  O   BLEU A 376      -0.592  15.110  30.154  0.50 20.64      B   O
ATOM   3017  N   LYS  A 377       0.881  16.793  29.938  1.00 25.17      B   N
ATOM   3018  CA  LYS  A 377      -0.125  17.704  29.357  1.00 25.69      B   C
ATOM   3019  CB  LYS  A 377       0.192  19.166  29.651  1.00 29.60      B   C
ATOM   3020  CG  LYS  A 377       0.434  19.501  31.100  1.00 33.80      B   C
ATOM   3021  CD  LYS  A 377      -0.766  19.365  31.958  1.00 37.01      B   C
ATOM   3022  CE  LYS  A 377      -0.393  19.796  33.355  1.00 41.84      B   C
ATOM   3023  NZ  LYS  A 377      -1.256  19.125  34.344  1.00 46.68      B   N
ATOM   3024  C   LYS  A 377      -0.105  17.532  27.861  1.00 24.72      B   C
ATOM   3025  O   LYS  A 377       0.967  17.565  27.187  1.00 25.32      B   O
ATOM   3026  N   LEU  A 378      -1.278  17.395  27.304  1.00 26.82      B   N
ATOM   3027  CA  LEU  A 378      -1.486  17.463  25.860  1.00 28.00      B   C
ATOM   3028  CB  LEU  A 378      -2.656  16.550  25.482  1.00 31.83      B   C
ATOM   3029  CG  LEU  A 378      -2.269  15.189  24.943  1.00 34.63      B   C
ATOM   3030  CD1 LEU  A 378      -3.451  14.393  24.449  1.00 36.32      B   C
ATOM   3031  CD2 LEU  A 378      -1.278  15.351  23.838  1.00 42.30      B   C
ATOM   3032  C   LEU  A 378      -1.804  18.914  25.518  1.00 32.07      B   C
ATOM   3033  O   LEU  A 378      -2.993  19.254  25.596  1.00 30.90      B   O
ATOM   3034  N   ILE  A 379      -0.806  19.676  25.053  1.00 37.84      B   N
ATOM   3035  CA  ILE  A 379      -0.968  21.119  24.691  1.00 42.67      B   C
ATOM   3036  CB  ILE  A 379       0.374  21.859  24.479  1.00 51.82      B   C
ATOM   3037  CG1 ILE  A 379       1.366  21.659  25.628  1.00 55.73      B   C
ATOM   3038  CG2 ILE  A 379       0.118  23.346  24.270  1.00 52.33      B   C
ATOM   3039  CD1 ILE  A 379       2.817  21.905  25.242  1.00 57.06      B   C
ATOM   3040  C   ILE  A 379      -1.874  21.260  23.461  1.00 37.18      B   C
ATOM   3041  O   ILE  A 379      -2.583  22.258  23.413  1.00 42.18      B   O
ATOM   3042  N   ALA  A 380      -1.926  20.330  22.503  1.00 31.98      B   N
ATOM   3043  CA  ALA  A 380      -2.586  20.524  21.196  1.00 35.89      B   C
ATOM   3044  CB  ALA  A 380      -2.021  19.616  20.117  1.00 42.28      B   C
ATOM   3045  C   ALA  A 380      -4.104  20.369  21.242  1.00 33.84      B   C
ATOM   3046  O   ALA  A 380      -4.742  20.650  20.238  1.00 39.21      B   O
ATOM   3047  N   ACYS A 381      -4.728  19.796  22.268  0.50 34.04      B   N
ATOM   3048  N   BCYS A 381      -4.646  19.991  22.407  0.50 34.87      B   N
ATOM   3049  CA  ACYS A 381      -6.205  19.677  22.182  0.50 30.59      B   C
ATOM   3050  CA  BCYS A 381      -6.102  19.800  22.626  0.50 31.64      B   C
ATOM   3051  CB  ACYS A 381      -6.808  18.610  23.081  0.50 27.32      B   C
ATOM   3052  CB  BCYS A 381      -6.336  19.061  23.937  0.50 26.77      B   C
ATOM   3053  SG  ACYS A 381      -6.433  18.967  24.801  0.50 26.92      B   S
ATOM   3054  SG  BCYS A 381      -6.226  17.264  23.780  0.50 36.50      B   S
ATOM   3055  C   ACYS A 381      -6.802  21.056  22.495  0.50 29.03      B   C
ATOM   3056  C   BCYS A 381      -6.820  21.159  22.601  0.50 28.09      B   C
ATOM   3057  O   ACYS A 381      -6.221  21.806  23.302  0.50 33.35      B   O
ATOM   3058  O   BCYS A 381      -6.314  22.050  23.296  0.50 35.54      B   O
ATOM   3059  N   GLU  A 382      -7.949  21.266  21.875  1.00 31.70      B   N
ATOM   3060  CA  GLU  A 382      -8.687  22.562  21.763  1.00 33.50      B   C
ATOM   3061  CB  GLU  A 382      -9.665  22.458  20.594  1.00 39.93      B   C
ATOM   3062  CG  GLU  A 382      -8.925  22.281  19.265  1.00 49.34      B   C
ATOM   3063  CD  GLU  A 382      -9.495  22.928  18.016  1.00 57.32      B   C
ATOM   3064  OE1 GLU  A 382      -8.713  23.124  17.052  1.00 62.20      B   O
ATOM   3065  OE2 GLU  A 382     -10.717  23.196  17.987  1.00 65.17      B   O
ATOM   3066  C   GLU  A 382      -9.361  22.921  23.095  1.00 38.49      B   C
ATOM   3067  O   GLU  A 382      -9.341  24.104  23.430  1.00 40.86      B   O
ATOM   3068  N   GLU  A 383      -9.846  21.951  23.872  1.00 28.98      B   N
ATOM   3069  CA  GLU  A 383     -10.672  22.200  25.084  1.00 29.31      B   C
ATOM   3070  CB  GLU  A 383     -12.079  21.615  24.901  1.00 32.00      B   C
ATOM   3071  CG  GLU  A 383     -12.839  21.986  23.607  1.00 37.11      B   C
ATOM   3072  CD  GLU  A 383     -14.109  21.200  23.226  1.00 41.13      B   C
```

Fig. 5BA

| | | | | | | | | | | | |
|---|---|---|---|---|---|---|---|---|---|---|---|
| ATOM | 3073 | OE1 | GLU | A | 383 | -14.324 | 20.040 | 23.712 | 1.00 | 36.48 | B O |
| ATOM | 3074 | OE2 | GLU | A | 383 | -14.939 | 21.740 | 22.412 | 1.00 | 39.25 | B O |
| ATOM | 3075 | C | GLU | A | 383 | -9.967 | 21.515 | 26.257 | 1.00 | 28.95 | B C |
| ATOM | 3076 | O | GLU | A | 383 | -9.767 | 20.293 | 26.195 | 1.00 | 28.22 | B O |
| ATOM | 3077 | N | LYS | A | 384 | -9.520 | 22.234 | 27.258 | 1.00 | 26.94 | B N |
| ATOM | 3078 | CA | LYS | A | 384 | -8.861 | 21.666 | 28.452 | 1.00 | 27.38 | B C |
| ATOM | 3079 | CB | LYS | A | 384 | -7.401 | 22.098 | 28.593 | 1.00 | 31.54 | B C |
| ATOM | 3080 | CG | LYS | A | 384 | -6.492 | 21.617 | 27.479 | 1.00 | 37.81 | B C |
| ATOM | 3081 | CD | LYS | A | 384 | -5.482 | 22.670 | 27.112 | 1.00 | 42.63 | B C |
| ATOM | 3082 | CE | LYS | A | 384 | -4.326 | 22.152 | 26.300 | 1.00 | 45.00 | B C |
| ATOM | 3083 | NZ | LYS | A | 384 | -3.737 | 23.286 | 25.566 | 1.00 | 48.49 | B N |
| ATOM | 3084 | C | LYS | A | 384 | -9.639 | 22.085 | 29.683 | 1.00 | 29.15 | B C |
| ATOM | 3085 | O | LYS | A | 384 | -10.221 | 23.189 | 29.668 | 1.00 | 31.92 | B O |
| ATOM | 3086 | N | ASN | A | 385 | -9.575 | 21.303 | 30.749 | 1.00 | 28.65 | B N |
| ATOM | 3087 | CA | ASN | A | 385 | -10.120 | 21.725 | 32.062 | 1.00 | 26.25 | B C |
| ATOM | 3088 | CB | ASN | A | 385 | -10.863 | 20.583 | 32.743 | 1.00 | 25.02 | B C |
| ATOM | 3089 | CG | ASN | A | 385 | -9.963 | 19.470 | 33.234 | 1.00 | 26.15 | B C |
| ATOM | 3090 | OD1 | ASN | A | 385 | -8.724 | 19.569 | 33.296 | 1.00 | 25.85 | B O |
| ATOM | 3091 | ND2 | ASN | A | 385 | -10.630 | 18.385 | 33.611 | 1.00 | 28.30 | B N |
| ATOM | 3092 | C | ASN | A | 385 | -9.008 | 22.375 | 32.881 | 1.00 | 25.18 | B C |
| ATOM | 3093 | O | ASN | A | 385 | -7.875 | 22.522 | 32.387 | 1.00 | 25.81 | B O |
| ATOM | 3094 | N | SER | A | 386 | -9.278 | 22.713 | 34.136 | 1.00 | 26.74 | B N |
| ATOM | 3095 | CA | SER | A | 386 | -8.352 | 23.451 | 35.013 | 1.00 | 29.85 | B C |
| ATOM | 3096 | CB | SER | A | 386 | -9.065 | 23.921 | 36.256 | 1.00 | 33.18 | B C |
| ATOM | 3097 | OG | SER | A | 386 | -8.970 | 22.945 | 37.285 | 1.00 | 37.55 | B O |
| ATOM | 3098 | C | SER | A | 386 | -7.141 | 22.588 | 35.353 | 1.00 | 32.17 | B C |
| ATOM | 3099 | O | SER | A | 386 | -6.065 | 23.141 | 35.566 | 1.00 | 29.39 | B O |
| ATOM | 3100 | N | GLN | A | 387 | -7.289 | 21.246 | 35.323 | 1.00 | 30.09 | B N |
| ATOM | 3101 | CA | GLN | A | 387 | -6.155 | 20.321 | 35.591 | 1.00 | 29.72 | B C |
| ATOM | 3102 | CB | GLN | A | 387 | -6.678 | 19.047 | 36.241 | 1.00 | 35.37 | B C |
| ATOM | 3103 | CG | GLN | A | 387 | -7.339 | 19.312 | 37.585 | 1.00 | 40.24 | B C |
| ATOM | 3104 | CD | GLN | A | 387 | -8.195 | 18.136 | 37.967 | 1.00 | 47.85 | B C |
| ATOM | 3105 | OE1 | GLN | A | 387 | -9.386 | 18.078 | 37.651 | 1.00 | 51.93 | B O |
| ATOM | 3106 | NE2 | GLN | A | 387 | -7.556 | 17.151 | 38.577 | 1.00 | 59.07 | B N |
| ATOM | 3107 | C | GLN | A | 387 | -5.391 | 19.996 | 34.312 | 1.00 | 26.98 | B C |
| ATOM | 3108 | O | GLN | A | 387 | -4.451 | 19.213 | 34.394 | 1.00 | 30.15 | B O |
| ATOM | 3109 | N | GLY | A | 388 | -5.749 | 20.581 | 33.176 | 1.00 | 23.30 | B N |
| ATOM | 3110 | CA | GLY | A | 388 | -5.052 | 20.402 | 31.897 | 1.00 | 26.00 | B C |
| ATOM | 3111 | C | GLY | A | 388 | -5.442 | 19.123 | 31.215 | 1.00 | 24.59 | B C |
| ATOM | 3112 | O | GLY | A | 388 | -4.841 | 18.790 | 30.200 | 1.00 | 24.74 | B O |
| ATOM | 3113 | N | MET | A | 389 | -6.521 | 18.478 | 31.662 | 1.00 | 23.36 | B N |
| ATOM | 3114 | CA | MET | A | 389 | -7.062 | 17.325 | 30.936 | 1.00 | 21.73 | B C |
| ATOM | 3115 | CB | MET | A | 389 | -8.110 | 16.614 | 31.785 | 1.00 | 22.73 | B C |
| ATOM | 3116 | CG | MET | A | 389 | -7.645 | 16.164 | 33.082 | 1.00 | 22.83 | B C |
| ATOM | 3117 | SD | MET | A | 389 | -8.984 | 15.133 | 33.869 | 1.00 | 26.03 | B S |
| ATOM | 3118 | CE | MET | A | 389 | -8.331 | 14.880 | 35.513 | 1.00 | 29.93 | B C |
| ATOM | 3119 | C | MET | A | 389 | -7.773 | 17.821 | 29.680 | 1.00 | 24.40 | B C |
| ATOM | 3120 | O | MET | A | 389 | -8.476 | 18.863 | 29.715 | 1.00 | 24.18 | B O |
| ATOM | 3121 | N | ACYS | A | 390 | -7.590 | 17.154 | 28.554 | 0.50 | 22.26 | B N |
| ATOM | 3122 | N | BCYS | A | 390 | -7.630 | 17.095 | 28.617 | 0.50 | 24.28 | B N |
| ATOM | 3123 | CA | ACYS | A | 390 | -8.344 | 17.403 | 27.308 | 0.50 | 21.52 | B C |
| ATOM | 3124 | CA | BCYS | A | 390 | -8.305 | 17.323 | 27.344 | 0.50 | 24.37 | B C |
| ATOM | 3125 | CB | ACYS | A | 390 | -7.805 | 16.651 | 26.102 | 0.50 | 23.03 | B C |
| ATOM | 3126 | CB | BCYS | A | 390 | -7.539 | 16.469 | 26.367 | 0.50 | 30.04 | B C |
| ATOM | 3127 | SG | ACYS | A | 390 | -6.109 | 17.085 | 25.637 | 0.50 | 23.88 | B S |
| ATOM | 3128 | SG | BCYS | A | 390 | -7.999 | 16.846 | 24.677 | 0.50 | 35.42 | B S |
| ATOM | 3129 | C | ACYS | A | 390 | -9.800 | 16.947 | 27.446 | 0.50 | 20.91 | B C |
| ATOM | 3130 | C | BCYS | A | 390 | -9.789 | 16.911 | 27.409 | 0.50 | 22.63 | B C |

Fig. 5BB

| | | | | | | | | | | |
|---|---|---|---|---|---|---|---|---|---|---|
| ATOM | 3131 | O   | ACYS | A 390 | -10.061 | 15.839 | 27.944 | 0.50 21.45 | B | O |
| ATOM | 3132 | O   | BCYS | A 390 | -10.069 | 15.809 | 27.895 | 0.50 22.57 | B | O |
| ATOM | 3133 | N   | SER  | A 391 | -10.754 | 17.686 | 26.884 | 1.00 22.68 | B | N |
| ATOM | 3134 | CA  | SER  | A 391 | -12.124 | 17.156 | 26.749 | 1.00 22.53 | B | C |
| ATOM | 3135 | CB  | SER  | A 391 | -13.093 | 18.152 | 26.120 | 1.00 24.35 | B | C |
| ATOM | 3136 | OG  | SER  | A 391 | -12.849 | 18.328 | 24.714 | 1.00 27.41 | B | O |
| ATOM | 3137 | C   | SER  | A 391 | -12.088 | 15.871 | 25.912 | 1.00 22.93 | B | C |
| ATOM | 3138 | O   | SER  | A 391 | -11.286 | 15.764 | 24.963 | 1.00 22.12 | B | O |
| ATOM | 3139 | N   | LEU  | A 392 | -12.943 | 14.886 | 26.204 | 1.00 23.43 | B | N |
| ATOM | 3140 | CA  | LEU  | A 392 | -12.940 | 13.628 | 25.450 | 1.00 23.80 | B | C |
| ATOM | 3141 | CB  | LEU  | A 392 | -14.020 | 12.696 | 26.002 | 1.00 26.58 | B | C |
| ATOM | 3142 | CG  | LEU  | A 392 | -14.075 | 11.314 | 25.338 | 1.00 28.13 | B | C |
| ATOM | 3143 | CD1 | LEU  | A 392 | -12.824 | 10.510 | 25.669 | 1.00 30.97 | B | C |
| ATOM | 3144 | CD2 | LEU  | A 392 | -15.357 | 10.555 | 25.697 | 1.00 31.67 | B | C |
| ATOM | 3145 | C   | LEU  | A 392 | -13.171 | 13.943 | 23.978 | 1.00 24.44 | B | C |
| ATOM | 3146 | O   | LEU  | A 392 | -12.493 | 13.380 | 23.090 | 1.00 26.22 | B | O |
| ATOM | 3147 | N   | LYS  | A 393 | -14.156 | 14.790 | 23.650 | 1.00 25.61 | B | N |
| ATOM | 3148 | CA  | LYS  | A 393 | -14.459 | 15.041 | 22.224 | 1.00 27.16 | B | C |
| ATOM | 3149 | CB  | LYS  | A 393 | -15.802 | 15.783 | 22.125 | 1.00 31.03 | B | C |
| ATOM | 3150 | CG  | LYS  | A 393 | -17.012 | 14.958 | 22.556 | 1.00 38.60 | B | C |
| ATOM | 3151 | CD  | LYS  | A 393 | -18.407 | 15.499 | 22.152 | 1.00 47.03 | B | C |
| ATOM | 3152 | CE  | LYS  | A 393 | -18.552 | 17.006 | 22.239 | 1.00 55.44 | B | C |
| ATOM | 3153 | NZ  | LYS  | A 393 | -19.741 | 17.486 | 21.490 | 1.00 62.06 | B | N |
| ATOM | 3154 | C   | LYS  | A 393 | -13.287 | 15.769 | 21.558 | 1.00 24.91 | B | C |
| ATOM | 3155 | O   | LYS  | A 393 | -13.032 | 15.421 | 20.392 | 1.00 28.59 | B | O |
| ATOM | 3156 | N   | SER  | A 394 | -12.570 | 16.680 | 22.219 | 1.00 25.06 | B | N |
| ATOM | 3157 | CA  | SER  | A 394 | -11.424 | 17.397 | 21.609 | 1.00 26.34 | B | C |
| ATOM | 3158 | CB  | SER  | A 394 | -11.118 | 18.710 | 22.198 | 1.00 31.89 | B | C |
| ATOM | 3159 | OG  | SER  | A 394 | -10.298 | 18.632 | 23.321 | 1.00 33.52 | B | O |
| ATOM | 3160 | C   | SER  | A 394 | -10.201 | 16.474 | 21.527 | 1.00 27.20 | B | C |
| ATOM | 3161 | O   | SER  | A 394 | -9.472  | 16.569 | 20.558 | 1.00 24.28 | B | O |
| ATOM | 3162 | N   | PHE  | A 395 | -10.035 | 15.524 | 22.453 | 1.00 24.08 | B | N |
| ATOM | 3163 | CA  | PHE  | A 395 | -8.985  | 14.477 | 22.286 | 1.00 23.08 | B | C |
| ATOM | 3164 | CB  | PHE  | A 395 | -8.932  | 13.682 | 23.573 | 1.00 22.06 | B | C |
| ATOM | 3165 | CG  | PHE  | A 395 | -8.005  | 12.489 | 23.579 | 1.00 21.21 | B | C |
| ATOM | 3166 | CD1 | PHE  | A 395 | -6.669  | 12.680 | 23.839 | 1.00 24.21 | B | C |
| ATOM | 3167 | CE1 | PHE  | A 395 | -5.811  | 11.584 | 23.913 | 1.00 23.23 | B | C |
| ATOM | 3168 | CZ  | PHE  | A 395 | -6.303  | 10.343 | 23.683 | 1.00 21.40 | B | C |
| ATOM | 3169 | CD2 | PHE  | A 395 | -8.478  | 11.215 | 23.362 | 1.00 25.57 | B | C |
| ATOM | 3170 | CE2 | PHE  | A 395 | -7.616  | 10.124 | 23.399 | 1.00 24.10 | B | C |
| ATOM | 3171 | C   | PHE  | A 395 | -9.269  | 13.657 | 21.026 | 1.00 22.50 | B | C |
| ATOM | 3172 | O   | PHE  | A 395 | -8.348  | 13.383 | 20.206 | 1.00 22.37 | B | O |
| ATOM | 3173 | N   | SER  | A 396 | -10.500 | 13.244 | 20.825 | 1.00 23.85 | B | N |
| ATOM | 3174 | CA  | SER  | A 396 | -10.915 | 12.406 | 19.680 | 1.00 23.75 | B | C |
| ATOM | 3175 | CB  | SER  | A 396 | -12.296 | 11.866 | 19.861 | 1.00 26.15 | B | C |
| ATOM | 3176 | OG  | SER  | A 396 | -12.595 | 10.947 | 18.844 | 1.00 29.23 | B | O |
| ATOM | 3177 | C   | SER  | A 396 | -10.728 | 13.216 | 18.392 | 1.00 26.49 | B | C |
| ATOM | 3178 | O   | SER  | A 396 | -10.161 | 12.699 | 17.387 | 1.00 25.78 | B | O |
| ATOM | 3179 | N   | ARG  | A 397 | -11.074 | 14.505 | 18.441 | 1.00 27.05 | B | N |
| ATOM | 3180 | CA  | ARG  | A 397 | -10.904 | 15.351 | 17.227 | 1.00 30.25 | B | C |
| ATOM | 3181 | CB  | ARG  | A 397 | -11.650 | 16.674 | 17.403 | 1.00 36.60 | B | C |
| ATOM | 3182 | CG  | ARG  | A 397 | -13.170 | 16.531 | 17.337 | 1.00 47.03 | B | C |
| ATOM | 3183 | CD  | ARG  | A 397 | -13.877 | 17.875 | 17.478 | 1.00 55.08 | B | C |
| ATOM | 3184 | NE  | ARG  | A 397 | -12.916 | 18.881 | 17.042 | 1.00 60.38 | B | N |
| ATOM | 3185 | CZ  | ARG  | A 397 | -12.174 | 19.655 | 17.837 | 1.00 61.10 | B | C |
| ATOM | 3186 | NH1 | ARG  | A 397 | -12.323 | 19.642 | 19.153 | 1.00 65.91 | B | N |
| ATOM | 3187 | NH2 | ARG  | A 397 | -11.289 | 20.469 | 17.292 | 1.00 58.64 | B | N |
| ATOM | 3188 | C   | ARG  | A 397 | -9.419  | 15.508 | 16.909 | 1.00 27.57 | B | C |

Fig. 5BC

```
ATOM   3189  O    ARG A 397      -9.052  15.440  15.693  1.00  28.12      B  O
ATOM   3190  N    LEU A 398      -8.565  15.677  17.908  1.00  24.64      B  N
ATOM   3191  CA   LEU A 398      -7.093  15.756  17.707  1.00  24.12      B  C
ATOM   3192  CB   LEU A 398      -6.389  15.999  19.041  1.00  26.55      B  C
ATOM   3193  CG   LEU A 398      -4.871  15.972  19.018  1.00  28.32      B  C
ATOM   3194  CD1  LEU A 398      -4.313  17.079  18.142  1.00  31.35      B  C
ATOM   3195  CD2  LEU A 398      -4.283  16.088  20.419  1.00  29.95      B  C
ATOM   3196  C    LEU A 398      -6.591  14.476  17.010  1.00  24.80      B  C
ATOM   3197  O    LEU A 398      -5.807  14.554  16.036  1.00  25.02      B  O
ATOM   3198  N    ILE A 399      -6.951  13.309  17.508  1.00  24.19      B  N
ATOM   3199  CA   ILE A 399      -6.570  12.031  16.854  1.00  23.73      B  C
ATOM   3200  CB   ILE A 399      -7.083  10.830  17.668  1.00  24.61      B  C
ATOM   3201  CG1  ILE A 399      -6.264  10.747  18.955  1.00  24.75      B  C
ATOM   3202  CG2  ILE A 399      -6.976   9.551  16.867  1.00  24.92      B  C
ATOM   3203  CD1  ILE A 399      -6.742   9.712  19.975  1.00  26.56      B  C
ATOM   3204  C    ILE A 399      -7.030  12.048  15.394  1.00  25.30      B  C
ATOM   3205  O    ILE A 399      -6.237  11.606  14.507  1.00  25.26      B  O
ATOM   3206  N    LYS A 400      -8.284  12.451  15.137  1.00  27.19      B  N
ATOM   3207  CA   LYS A 400      -8.816  12.444  13.739  1.00  29.61      B  C
ATOM   3208  CB   LYS A 400     -10.236  12.999  13.658  1.00  36.36      B  C
ATOM   3209  CG   LYS A 400     -11.294  12.169  14.339  1.00  46.59      B  C
ATOM   3210  CD   LYS A 400     -11.456  10.778  13.744  1.00  53.91      B  C
ATOM   3211  CE   LYS A 400     -11.121   9.700  14.740  1.00  55.39      B  C
ATOM   3212  NZ   LYS A 400     -11.678  10.037  16.080  1.00  50.62      B  N
ATOM   3213  C    LYS A 400      -7.930  13.314  12.855  1.00  26.35      B  C
ATOM   3214  O    LYS A 400      -7.708  12.944  11.675  1.00  28.80      B  O
ATOM   3215  N    GLU A 401      -7.460  14.430  13.371  1.00  28.47      B  N
ATOM   3216  CA   GLU A 401      -6.617  15.397  12.623  1.00  31.95      B  C
ATOM   3217  CB   GLU A 401      -6.614  16.724  13.382  1.00  36.95      B  C
ATOM   3218  CG   GLU A 401      -5.490  17.682  13.054  1.00  47.91      B  C
ATOM   3219  CD   GLU A 401      -5.548  18.886  13.990  1.00  58.43      B  C
ATOM   3220  OE1  GLU A 401      -6.689  19.372  14.260  1.00  62.50      B  O
ATOM   3221  OE2  GLU A 401      -4.479  19.290  14.515  1.00  61.24      B  O
ATOM   3222  C    GLU A 401      -5.223  14.816  12.360  1.00  33.03      B  C
ATOM   3223  O    GLU A 401      -4.709  15.030  11.239  1.00  35.99      B  O
ATOM   3224  N    ILE A 402      -4.600  14.117  13.317  1.00  27.00      B  N
ATOM   3225  CA   ILE A 402      -3.148  13.780  13.213  1.00  25.64      B  C
ATOM   3226  CB   ILE A 402      -2.399  13.941  14.543  1.00  27.41      B  C
ATOM   3227  CG1  ILE A 402      -2.856  12.877  15.553  1.00  27.91      B  C
ATOM   3228  CG2  ILE A 402      -2.535  15.367  15.055  1.00  29.82      B  C
ATOM   3229  CD1  ILE A 402      -2.201  12.957  16.941  1.00  31.33      B  C
ATOM   3230  C    ILE A 402      -2.948  12.375  12.648  1.00  23.96      B  C
ATOM   3231  O    ILE A 402      -1.889  12.160  12.125  1.00  25.88      B  O
ATOM   3232  N    ARG A 403      -3.947  11.513  12.685  1.00  24.21      B  N
ATOM   3233  CA   ARG A 403      -3.810  10.113  12.209  1.00  23.94      B  C
ATOM   3234  CB   ARG A 403      -5.040   9.293  12.569  1.00  25.09      B  C
ATOM   3235  CG   ARG A 403      -6.333   9.736  11.885  1.00  24.99      B  C
ATOM   3236  CD   ARG A 403      -7.525   8.982  12.390  1.00  26.39      B  C
ATOM   3237  NE   ARG A 403      -7.485   7.549  12.087  1.00  26.41      B  N
ATOM   3238  CZ   ARG A 403      -7.939   6.982  10.973  1.00  27.56      B  C
ATOM   3239  NH1  ARG A 403      -8.450   7.730   9.997  1.00  30.13      B  N
ATOM   3240  NH2  ARG A 403      -7.893   5.686  10.791  1.00  27.67      B  N
ATOM   3241  C    ARG A 403      -3.596  10.084  10.693  1.00  25.92      B  C
ATOM   3242  O    ARG A 403      -3.981  11.050   9.968  1.00  27.01      B  O
ATOM   3243  N    VAL A 404      -3.018   9.001  10.209  1.00  23.88      B  N
ATOM   3244  CA   VAL A 404      -2.707   8.827   8.769  1.00  23.27      B  C
ATOM   3245  CB   VAL A 404      -1.207   8.580   8.602  1.00  24.45      B  C
ATOM   3246  CG1  VAL A 404      -0.848   8.318   7.155  1.00  24.23      B  C
```

Fig. 5BD

```
ATOM   3247  CG2 VAL A 404      -0.385   9.704   9.138  1.00 23.43      B    C
ATOM   3248  C   VAL A 404      -3.536   7.644   8.310  1.00 26.29      B    C
ATOM   3249  O   VAL A 404      -3.233   6.507   8.669  1.00 24.13      B    O
ATOM   3250  N   PRO A 405      -4.639   7.860   7.553  1.00 23.90      B    N
ATOM   3251  CA  PRO A 405      -5.603   6.817   7.282  1.00 26.07      B    C
ATOM   3252  CB  PRO A 405      -6.651   7.490   6.359  1.00 28.37      B    C
ATOM   3253  CG  PRO A 405      -6.366   8.960   6.393  1.00 33.29      B    C
ATOM   3254  CD  PRO A 405      -5.080   9.204   7.134  1.00 27.65      B    C
ATOM   3255  C   PRO A 405      -4.989   5.570   6.629  1.00 23.70      B    C
ATOM   3256  O   PRO A 405      -5.500   4.482   6.859  1.00 27.47      B    O
ATOM   3257  N   GLU A 406      -3.973   5.760   5.803  1.00 26.12      B    N
ATOM   3258  CA  GLU A 406      -3.285   4.687   5.042  1.00 26.73      B    C
ATOM   3259  CB  GLU A 406      -2.259   5.282   4.060  1.00 28.27      B    C
ATOM   3260  CG  GLU A 406      -2.884   6.183   2.972  1.00 34.74      B    C
ATOM   3261  CD  GLU A 406      -3.180   7.635   3.346  1.00 38.21      B    C
ATOM   3262  OE1 GLU A 406      -2.717   8.072   4.370  1.00 33.43      B    O
ATOM   3263  OE2 GLU A 406      -3.871   8.358   2.554  1.00 42.13      B    O
ATOM   3264  C   GLU A 406      -2.570   3.740   6.027  1.00 27.19      B    C
ATOM   3265  O   GLU A 406      -2.281   2.559   5.697  1.00 25.65      B    O
ATOM   3266  N   CYS A 407      -2.341   4.226   7.254  1.00 23.60      B    N
ATOM   3267  CA  CYS A 407      -1.591   3.462   8.289  1.00 24.48      B    C
ATOM   3268  CB  CYS A 407      -0.486   4.331   8.858  1.00 22.76      B    C
ATOM   3269  SG  CYS A 407       0.786   4.693   7.625  1.00 25.56      B    S
ATOM   3270  C   CYS A 407      -2.523   2.893   9.337  1.00 23.71      B    C
ATOM   3271  O   CYS A 407      -2.002   2.331  10.342  1.00 24.80      B    O
ATOM   3272  N   ALA A 408      -3.836   2.961   9.144  1.00 24.46      B    N
ATOM   3273  CA  ALA A 408      -4.827   2.266   9.970  1.00 24.35      B    C
ATOM   3274  CB  ALA A 408      -6.209   2.794   9.731  1.00 26.57      B    C
ATOM   3275  C   ALA A 408      -4.775   0.769   9.677  1.00 27.52      B    C
ATOM   3276  O   ALA A 408      -4.509   0.360   8.534  1.00 28.11      B    O
ATOM   3277  N   VAL A 409      -5.045  -0.031  10.701  1.00 27.60      B    N
ATOM   3278  CA  VAL A 409      -5.177  -1.504  10.599  1.00 29.06      B    C
ATOM   3279  CB  VAL A 409      -4.448  -2.198  11.763  1.00 29.87      B    C
ATOM   3280  CG1 VAL A 409      -2.973  -1.928  11.682  1.00 27.47      B    C
ATOM   3281  CG2 VAL A 409      -4.978  -1.825  13.131  1.00 31.86      B    C
ATOM   3282  C   VAL A 409      -6.659  -1.876  10.581  1.00 35.68      B    C
ATOM   3283  O   VAL A 409      -7.609  -1.091  10.730  1.00 40.47      B    O
ATOM   3284  OXT VAL A 409      -6.876  -3.047  10.439  1.00 37.84           O
TER
```

Fig. 5BE

SEQUENCE LISTING

<160> NUMBER OF SEQ ID NOS: 22

<210> SEQ ID NO 1
<211> LENGTH: 1233
<212> TYPE: DNA
<213> ORGANISM: Citrobacter braakii
<220> FEATURE:
<221> NAME/KEY: mat_peptide
<222> LOCATION: (1)..(1233)
<220> FEATURE:
<221> NAME/KEY: CDS
<222> LOCATION: (1)..(1233)

<400> SEQUENCE: 1

| | | | | | | | | | | | | | | | | |
|---|---|---|---|---|---|---|---|---|---|---|---|---|---|---|---|---|
| gaa | gag | cag | aat | ggt | atg | aaa | ctt | gag | cgg | gtt | gtg | ata | gtg | agt | cgt | 48 |
| Glu | Glu | Gln | Asn | Gly | Met | Lys | Leu | Glu | Arg | Val | Val | Ile | Val | Ser | Arg | |
| 1 | | | | 5 | | | | | 10 | | | | | 15 | | |
| cat | gga | gta | aga | gca | cct | acg | aag | ttc | act | cca | ata | atg | aaa | aat | gtc | 96 |
| His | Gly | Val | Arg | Ala | Pro | Thr | Lys | Phe | Thr | Pro | Ile | Met | Lys | Asn | Val | |
| | | | 20 | | | | | 25 | | | | | 30 | | | |
| aca | ccc | gat | caa | tgg | cca | caa | tgg | gat | gtg | ccg | tta | gga | tgg | cta | acg | 144 |
| Thr | Pro | Asp | Gln | Trp | Pro | Gln | Trp | Asp | Val | Pro | Leu | Gly | Trp | Leu | Thr | |
| | | | 35 | | | | | 40 | | | | | 45 | | | |
| cct | cgt | ggg | gga | gaa | ctt | gtt | tct | gaa | tta | ggt | cag | tat | caa | cgt | tta | 192 |
| Pro | Arg | Gly | Gly | Glu | Leu | Val | Ser | Glu | Leu | Gly | Gln | Tyr | Gln | Arg | Leu | |
| | 50 | | | | | 55 | | | | | 60 | | | | | |
| tgg | ttc | acg | agc | aaa | ggt | ctg | ttg | aat | aat | caa | acg | tgc | cca | tct | cca | 240 |
| Trp | Phe | Thr | Ser | Lys | Gly | Leu | Leu | Asn | Asn | Gln | Thr | Cys | Pro | Ser | Pro | |
| 65 | | | | | 70 | | | | | 75 | | | | | 80 | |
| ggg | cag | gtt | gct | gtt | att | gca | gac | acg | gat | caa | cgc | acc | cgt | aaa | acg | 288 |
| Gly | Gln | Val | Ala | Val | Ile | Ala | Asp | Thr | Asp | Gln | Arg | Thr | Arg | Lys | Thr | |
| | | | | 85 | | | | | 90 | | | | | 95 | | |
| ggt | gag | gcg | ttt | ctg | gct | ggg | tta | gca | cca | aaa | tgt | caa | att | caa | gtg | 336 |
| Gly | Glu | Ala | Phe | Leu | Ala | Gly | Leu | Ala | Pro | Lys | Cys | Gln | Ile | Gln | Val | |
| | | | 100 | | | | | 105 | | | | | 110 | | | |
| cat | tat | cag | aag | gat | gaa | gaa | aaa | aat | gat | cct | ctt | ttt | aat | ccg | gta | 384 |
| His | Tyr | Gln | Lys | Asp | Glu | Glu | Lys | Asn | Asp | Pro | Leu | Phe | Asn | Pro | Val | |
| | | | 115 | | | | | 120 | | | | | 125 | | | |
| aaa | atg | ggg | aaa | tgt | tcg | ttt | aac | aca | ttg | cag | gtt | aaa | aac | gct | att | 432 |
| Lys | Met | Gly | Lys | Cys | Ser | Phe | Asn | Thr | Leu | Gln | Val | Lys | Asn | Ala | Ile | |
| | 130 | | | | | 135 | | | | | 140 | | | | | |
| ctg | gaa | cgg | gcc | gga | gga | aat | att | gaa | ctg | tat | acc | caa | cgc | tat | caa | 480 |
| Leu | Glu | Arg | Ala | Gly | Gly | Asn | Ile | Glu | Leu | Tyr | Thr | Gln | Arg | Tyr | Gln | |
| 145 | | | | | 150 | | | | | 155 | | | | | 160 | |
| tct | tca | ttt | cgg | acc | ctg | gaa | aat | gtt | tta | aat | ttc | tca | caa | tcg | gag | 528 |
| Ser | Ser | Phe | Arg | Thr | Leu | Glu | Asn | Val | Leu | Asn | Phe | Ser | Gln | Ser | Glu | |
| | | | 165 | | | | | 170 | | | | | 175 | | | |
| aca | tgt | aag | act | aca | gaa | aag | tct | acg | aaa | tgc | aca | tta | cca | gag | gct | 576 |
| Thr | Cys | Lys | Thr | Thr | Glu | Lys | Ser | Thr | Lys | Cys | Thr | Leu | Pro | Glu | Ala | |
| | | | | 180 | | | | | 185 | | | | | 190 | | |
| tta | ccg | tct | gaa | ctt | aag | gta | act | cct | gac | aat | gta | tca | tta | cct | ggt | 624 |
| Leu | Pro | Ser | Glu | Leu | Lys | Val | Thr | Pro | Asp | Asn | Val | Ser | Leu | Pro | Gly | |
| | | | 195 | | | | | 200 | | | | | 205 | | | |
| gcc | tgg | agt | ctt | tct | tcc | acg | ctg | act | gag | ata | ttt | ctg | ttg | caa | gag | 672 |
| Ala | Trp | Ser | Leu | Ser | Ser | Thr | Leu | Thr | Glu | Ile | Phe | Leu | Leu | Gln | Glu | |
| | 210 | | | | | 215 | | | | | 220 | | | | | |
| gcc | cag | gga | atg | cca | cag | gta | gcc | tgg | ggg | cgt | att | acg | gga | gaa | aaa | 720 |
| Ala | Gln | Gly | Met | Pro | Gln | Val | Ala | Trp | Gly | Arg | Ile | Thr | Gly | Glu | Lys | |
| 225 | | | | | 230 | | | | | 235 | | | | | 240 | |
| gaa | tgg | aga | gat | ttg | tta | agt | ctg | cat | aac | gct | cag | ttt | gat | ctt | ttg | 768 |
| Glu | Trp | Arg | Asp | Leu | Leu | Ser | Leu | His | Asn | Ala | Gln | Phe | Asp | Leu | Leu | |
| | | | 245 | | | | | 250 | | | | | 255 | | | |

```
caa aga act cca gaa gtt gcc cgt agt agg gcc aca cca tta ctc gat        816
Gln Arg Thr Pro Glu Val Ala Arg Ser Arg Ala Thr Pro Leu Leu Asp
        260                 265                 270 atg ata gac act gca tta ttg aca aat ggt aca aca gaa aac agg tat        864
Met Ile Asp Thr Ala Leu Leu Thr Asn Gly Thr Thr Glu Asn Arg Tyr
            275                 280                 285 ggc ata aaa tta ccc gta tct ctg ttg ttt att gct ggt cat gat acc        912
Gly Ile Lys Leu Pro Val Ser Leu Leu Phe Ile Ala Gly His Asp Thr
290                 295                 300 aat ctt gca aat tta agc ggg gct tta gat ctt aac tgg tcg cta ccc        960
Asn Leu Ala Asn Leu Ser Gly Ala Leu Asp Leu Asn Trp Ser Leu Pro
305                 310                 315                 320 ggt caa ccc gat aat acc cct cct ggt ggg gag ctt gta ttc gaa aag       1008
Gly Gln Pro Asp Asn Thr Pro Pro Gly Gly Glu Leu Val Phe Glu Lys
                325                 330                 335 tgg aaa aga acc agt gat aat acg gat tgg gtt cag gtt tca ttt gtt       1056
Trp Lys Arg Thr Ser Asp Asn Thr Asp Trp Val Gln Val Ser Phe Val
            340                 345                 350 tat cag acg ctg aga gat atg agg gat ata caa ccg ttg tcg tta gaa       1104
Tyr Gln Thr Leu Arg Asp Met Arg Asp Ile Gln Pro Leu Ser Leu Glu
        355                 360                 365 aaa cct gct ggc aaa gtt gat tta aaa tta att gca tgt gaa gag aaa       1152
Lys Pro Ala Gly Lys Val Asp Leu Lys Leu Ile Ala Cys Glu Glu Lys
370                 375                 380 aat agt cag gga atg tgt tcg tta aaa agt ttt tcc agg ctc att aag       1200
Asn Ser Gln Gly Met Cys Ser Leu Lys Ser Phe Ser Arg Leu Ile Lys
385                 390                 395                 400 gaa att cgc gtg cca gag tgt gca gtt acg gaa                           1233
Glu Ile Arg Val Pro Glu Cys Ala Val Thr Glu
                405                 410

<210> SEQ ID NO 2
<211> LENGTH: 411
<212> TYPE: PRT
<213> ORGANISM: Citrobacter braakii

<400> SEQUENCE: 2

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asn Val
            20                  25                  30

Thr Pro Asp Gln Trp Pro Gln Trp Asp Val Pro Leu Gly Trp Leu Thr
        35                  40                  45

Pro Arg Gly Gly Glu Leu Val Ser Glu Leu Gly Gln Tyr Gln Arg Leu
    50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
            100                 105                 110

His Tyr Gln Lys Asp Glu Glu Lys Asn Asp Pro Leu Phe Asn Pro Val
        115                 120                 125

Lys Met Gly Lys Cys Ser Phe Asn Thr Leu Gln Val Lys Asn Ala Ile
    130                 135                 140

Leu Glu Arg Ala Gly Gly Asn Ile Glu Leu Tyr Thr Gln Arg Tyr Gln
145                 150                 155                 160
```

```
Ser Ser Phe Arg Thr Leu Glu Asn Val Leu Asn Phe Ser Gln Ser Glu
            165                 170                 175

Thr Cys Lys Thr Thr Glu Lys Ser Thr Lys Cys Thr Leu Pro Glu Ala
        180                 185                 190

Leu Pro Ser Glu Leu Lys Val Thr Pro Asp Asn Val Ser Leu Pro Gly
    195                 200                 205

Ala Trp Ser Leu Ser Ser Thr Leu Thr Glu Ile Phe Leu Leu Gln Glu
210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
            245                 250                 255

Gln Arg Thr Pro Glu Val Ala Arg Ser Arg Ala Thr Pro Leu Leu Asp
        260                 265                 270

Met Ile Asp Thr Ala Leu Leu Thr Asn Gly Thr Thr Glu Asn Arg Tyr
    275                 280                 285

Gly Ile Lys Leu Pro Val Ser Leu Leu Phe Ile Ala Gly His Asp Thr
290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Lys
            325                 330                 335

Trp Lys Arg Thr Ser Asp Asn Thr Asp Trp Val Gln Val Ser Phe Val
        340                 345                 350

Tyr Gln Thr Leu Arg Asp Met Arg Asp Ile Gln Pro Leu Ser Leu Glu
    355                 360                 365

Lys Pro Ala Gly Lys Val Asp Leu Lys Leu Ile Ala Cys Glu Glu Lys
370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
            405                 410

<210> SEQ ID NO 3
<211> LENGTH: 411
<212> TYPE: PRT
<213> ORGANISM: Citrobacter braakii
<220> FEATURE:
<221> NAME/KEY: mat_peptide
<222> LOCATION: (1)..(411)

<400> SEQUENCE: 3

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asp Val
            20                  25                  30

Thr Pro Asp Gln Trp Pro Gln Trp Asp Val Pro Leu Gly Trp Leu Thr
        35                  40                  45

Pro Arg Gly Gly Glu Leu Val Ser Glu Leu Gly Gln Tyr Gln Arg Leu
    50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
            85                  90                  95

Gly Glu Ala Phe Leu Ala Gly Leu Ala Pro Lys Cys Gln Ile Gln Val
        100                 105                 110
```

His Tyr Gln Lys Asp Glu Glu Lys Asn Asp Pro Leu Phe Asn Pro Val
            115                 120                 125

Lys Met Gly Lys Cys Ser Phe Asn Thr Leu Lys Val Lys Asn Ala Ile
130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Phe Lys Val Thr Pro Asp Asn Val Ser Leu Pro Gly
            195                 200                 205

Ala Trp Ser Leu Ser Ser Thr Leu Thr Glu Ile Phe Leu Leu Gln Glu
210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
            275                 280                 285

Gly Ile Lys Leu Pro Val Ser Leu Leu Phe Ile Ala Gly His Asp Thr
290                 295                 300

Asn Leu Ala Asn Leu Ser Gly Ala Leu Asp Leu Lys Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
            355                 360                 365

Lys Pro Ala Gly Lys Val Asp Leu Lys Leu Ile Ala Cys Glu Glu Lys
370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 4
<211> LENGTH: 411
<212> TYPE: PRT
<213> ORGANISM: citronbacter freundii
<220> FEATURE:
<221> NAME/KEY: mat_peptide
<222> LOCATION: (1)..(411)

<400> SEQUENCE: 4

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asp Val
                20                  25                  30

Thr Pro Asp Gln Trp Pro Gln Trp Asp Val Pro Leu Gly Trp Leu Thr
            35                  40                  45

Pro Arg Gly Gly Glu Leu Val Ser Glu Leu Gly Gln Tyr Gln Arg Leu

```
                50                  55                  60
Trp Phe Thr Ser Lys Gly Leu Leu Asn Asn Gln Thr Cys Pro Ser Pro
 65                  70                  75                  80

Gly Gln Val Ala Val Ile Ala Asp Thr Asp Gln Arg Thr Arg Lys Thr
                 85                  90                  95

Gly Glu Ala Phe Leu Ala Gly Leu Ala Pro Lys Cys Gln Ile Gln Val
            100                 105                 110

His Tyr Gln Lys Asp Glu Glu Lys Thr Asp Pro Leu Phe Asn Pro Val
            115                 120                 125

Lys Met Gly Thr Cys Ser Phe Asn Thr Leu Lys Val Lys Asn Ala Ile
130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Leu Lys Val Thr Pro Asp Asn Val Ser Leu Pro Gly
            195                 200                 205

Ala Trp Ser Leu Ser Ser Thr Leu Thr Glu Ile Phe Leu Leu Gln Glu
210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
            275                 280                 285

Gly Ile Lys Leu Pro Val Ser Leu Leu Phe Ile Ala Gly His Asp Thr
290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
            355                 360                 365

Lys Pro Ala Gly Lys Val Asp Leu Lys Leu Ile Ala Cys Glu Glu Lys
370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 5
<211> LENGTH: 1236
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1233)
<220> FEATURE:
```

<220> NAME/KEY: mat_peptide
<222> LOCATION: (1)..(1233)

<400> SEQUENCE: 5

```
gaa gag cag aat ggt atg aaa ctt gag cgg gtt gtg ata gtg agt cgt      48
Glu Glu Gln Asn Gly Met Lys Leu Glu Arg Val Val Ile Val Ser Arg
1               5                  10                  15 cat ggr gta aga gca cct acg aag ttc act cca ata atg aaa aat gtc      96
His Xaa Val Arg Ala Pro Thr Lys Phe Thr Pro Ile Met Lys Asn Val
            20                  25                  30 aca ccc gat caa tgg cca caa tgg gat gtg ccg tta gga tgg cta acg     144
Thr Pro Asp Gln Trp Pro Gln Trp Asp Val Pro Leu Gly Trp Leu Thr
        35                  40                  45 cct cgt ggg gga gaa ctt gtt tct gaa tta ggt cag tat caa cgt tta     192
Pro Arg Gly Gly Glu Leu Val Ser Glu Leu Gly Gln Tyr Gln Arg Leu
    50                  55                  60 tgg ttc acg agc aaa ggt ctg ttg aat aat caa acg tgc cca tct cca     240
Trp Phe Thr Ser Lys Gly Leu Leu Asn Asn Gln Thr Cys Pro Ser Pro
65                  70                  75                  80 ggg cag gtt gct gtt att gca gac acg gat caa cgc acc cgt aaa acg     288
Gly Gln Val Ala Val Ile Ala Asp Thr Asp Gln Arg Thr Arg Lys Thr
                85                  90                  95 ggt gag gcg ttt ctg gct ggg tta gca cca aaa tgt caa att caa gtg     336
Gly Glu Ala Phe Leu Ala Gly Leu Ala Pro Lys Cys Gln Ile Gln Val
            100                 105                 110 cat tat cag aag gat gaa gaa aaa aat gat cct ctt ttt aat ccg gta     384
His Tyr Gln Lys Asp Glu Glu Lys Asn Asp Pro Leu Phe Asn Pro Val
        115                 120                 125 aaa atg ggg aaa tgt tcg ttt aac aca ttg cag gtt aaa aac gct att     432
Lys Met Gly Lys Cys Ser Phe Asn Thr Leu Gln Val Lys Asn Ala Ile
    130                 135                 140 ctg gaa cgg gcc gga gga aat att gaa ctg tat acc caa cgc tat caa     480
Leu Glu Arg Ala Gly Gly Asn Ile Glu Leu Tyr Thr Gln Arg Tyr Gln
145                 150                 155                 160 tct tca ttt cgg acc ctg gaa aat gtt tta aat ttc tca caa tcg gag     528
Ser Ser Phe Arg Thr Leu Glu Asn Val Leu Asn Phe Ser Gln Ser Glu
                165                 170                 175 aca tgt aag act aca gaa aag tct acg aaa tgc aca tta cca gag gct     576
Thr Cys Lys Thr Thr Glu Lys Ser Thr Lys Cys Thr Leu Pro Glu Ala
            180                 185                 190 tta ccg tct gaa ctt aag gta act cct gac aat gta tca tta cct ggt     624
Leu Pro Ser Glu Leu Lys Val Thr Pro Asp Asn Val Ser Leu Pro Gly
        195                 200                 205 gcc tgg agt ctt tct tcc acg ctg act gag ata ttt ctg ttg caa gag     672
Ala Trp Ser Leu Ser Ser Thr Leu Thr Glu Ile Phe Leu Leu Gln Glu
    210                 215                 220 gcc cag gga atg cca cag gta gcc tgg ggg cgt att acg gga gaa aaa     720
Ala Gln Gly Met Pro Gln Val Ala Trp Gly Arg Ile Thr Gly Glu Lys
225                 230                 235                 240 gaa tgg aga gat ttg tta agt ctg cat aac gct cag ttt gat ctt ttg     768
Glu Trp Arg Asp Leu Leu Ser Leu His Asn Ala Gln Phe Asp Leu Leu
                245                 250                 255 caa aga act cca gaa gtt gcc cgt agt agg gcc aca cca tta ctc gat     816
Gln Arg Thr Pro Glu Val Ala Arg Ser Arg Ala Thr Pro Leu Leu Asp
            260                 265                 270 atg ata gac act gca tta ttg aca aat ggt aca aca gaa aac agg tat     864
Met Ile Asp Thr Ala Leu Leu Thr Asn Gly Thr Thr Glu Asn Arg Tyr
        275                 280                 285 ggc ata aaa tta ccc gta tct ctg ttg ttt att gct ggt cat gat acc     912
Gly Ile Lys Leu Pro Val Ser Leu Leu Phe Ile Ala Gly His Asp Thr
```

```
                290                 295                 300
aat ctt gca aat tta agc ggg gct tta gat ctt aac tgg tcg cta ccc         960
Asn Leu Ala Asn Leu Ser Gly Ala Leu Asp Leu Asn Trp Ser Leu Pro
305                 310                 315                 320 ggt caa ccs gat aay acc ccg ccg ggc gac aag ctt gta ttc gaa aag        1008
Gly Gln Xaa Asp Asn Thr Pro Pro Gly Asp Lys Leu Val Phe Glu Lys
                325                 330                 335 tgg aaa aga acc agt gat aat acg gat tgg gtt cag gtt tca ttt gtt        1056
Trp Lys Arg Thr Ser Asp Asn Thr Asp Trp Val Gln Val Ser Phe Val
                340                 345                 350 tat cag acg ctg aga gat atg agg gat ata caa ccg ttg tcg tta gaa        1104
Tyr Gln Thr Leu Arg Asp Met Arg Asp Ile Gln Pro Leu Ser Leu Glu
                355                 360                 365 aaa cct gct ggc aaa gtt gat tta aaa tta att gca tgt gaa gag aaa        1152
Lys Pro Ala Gly Lys Val Asp Leu Lys Leu Ile Ala Cys Glu Glu Lys
370                 375                 380 aat agt cag gga atg tgt tcg tta aaa agt ttt tcc agg ctc att aag        1200
Asn Ser Gln Gly Met Cys Ser Leu Lys Ser Phe Ser Arg Leu Ile Lys
385                 390                 395                 400 gaa att cgc gtg cca gag tgt gca gtt acg gaa taa                        1236
Glu Ile Arg Val Pro Glu Cys Ala Val Thr Glu
                405                 410
```

<210> SEQ ID NO 6
<211> LENGTH: 411
<212> TYPE: PRT
<213> ORGANISM: Artificial sequence
<220> FEATURE:
<221> NAME/KEY: misc_feature
<222> LOCATION: (18)..(18)
<223> OTHER INFORMATION: The 'Xaa' at location 18 stands for Gly.
<220> FEATURE:
<221> NAME/KEY: misc_feature
<222> LOCATION: (323)..(323)
<223> OTHER INFORMATION: The 'Xaa' at location 323 stands for Pro.
<220> FEATURE:
<223> OTHER INFORMATION: Synthetic Construct

<400> SEQUENCE: 6

```
Glu Glu Gln Asn Gly Met Lys Leu Glu Arg Val Val Ile Val Ser Arg
1               5                   10                  15

His Xaa Val Arg Ala Pro Thr Lys Phe Thr Pro Ile Met Lys Asn Val
            20                  25                  30

Thr Pro Asp Gln Trp Pro Gln Trp Asp Val Pro Leu Gly Trp Leu Thr
                35                  40                  45

Pro Arg Gly Gly Glu Leu Val Ser Glu Leu Gly Gln Tyr Gln Arg Leu
50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
                100                 105                 110

His Tyr Gln Lys Asp Glu Glu Lys Asn Asp Pro Leu Phe Asn Pro Val
            115                 120                 125

Lys Met Gly Lys Cys Ser Phe Asn Thr Leu Gln Val Lys Asn Ala Ile
            130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
```

```
                    165                 170                 175
Thr Cys Lys Thr Thr Glu Lys Ser Thr Lys Cys Thr Leu Pro Glu Ala
                180                 185                 190
Leu Pro Ser Glu Leu Lys Val Thr Pro Asp Asn Val Ser Leu Pro Gly
            195                 200                 205
Ala Trp Ser Leu Ser Ser Thr Leu Thr Glu Ile Phe Leu Leu Gln Glu
        210                 215                 220
Ala Gln Gly Met Pro Gln Val Ala Trp Gly Arg Ile Thr Gly Glu Lys
225                 230                 235                 240
Glu Trp Arg Asp Leu Leu Ser Leu His Asn Ala Gln Phe Asp Leu Leu
                245                 250                 255
Gln Arg Thr Pro Glu Val Ala Arg Ser Arg Ala Thr Pro Leu Leu Asp
            260                 265                 270
Met Ile Asp Thr Ala Leu Leu Thr Asn Gly Thr Thr Glu Asn Arg Tyr
        275                 280                 285
Gly Ile Lys Leu Pro Val Ser Leu Leu Phe Ile Ala Gly His Asp Thr
    290                 295                 300
Asn Leu Ala Asn Leu Ser Gly Ala Leu Asp Leu Asn Trp Ser Leu Pro
305                 310                 315                 320
Gly Gln Xaa Asp Asn Thr Pro Pro Gly Asp Lys Leu Val Phe Glu Lys
                325                 330                 335
Trp Lys Arg Thr Ser Asp Asn Thr Asp Trp Val Gln Val Ser Phe Val
            340                 345                 350
Tyr Gln Thr Leu Arg Asp Met Arg Asp Ile Gln Pro Leu Ser Leu Glu
        355                 360                 365
Lys Pro Ala Gly Lys Val Asp Leu Lys Leu Ile Ala Cys Glu Glu Lys
    370                 375                 380
Asn Ser Gln Gly Met Cys Ser Leu Lys Ser Phe Ser Arg Leu Ile Lys
385                 390                 395                 400
Glu Ile Arg Val Pro Glu Cys Ala Val Thr Glu
                405                 410

<210> SEQ ID NO 7
<211> LENGTH: 66
<212> TYPE: DNA
<213> ORGANISM: Citrobacter braakii
<220> FEATURE:
<221> NAME/KEY: sig_peptide
<222> LOCATION: (1)..(66)
<220> FEATURE:
<221> NAME/KEY: CDS
<222> LOCATION: (1)..(66)

<400> SEQUENCE: 7 atg agt aca ttc atc att cgt tta tta ttt ttt tct ctc tta tgc ggt    48
Met Ser Thr Phe Ile Ile Arg Leu Leu Phe Phe Ser Leu Leu Cys Gly
1               5                   10                  15 tct ttc tca ata cat gct                                            66
Ser Phe Ser Ile His Ala
            20

<210> SEQ ID NO 8
<211> LENGTH: 22
<212> TYPE: PRT
<213> ORGANISM: Citrobacter braakii

<400> SEQUENCE: 8

Met Ser Thr Phe Ile Ile Arg Leu Leu Phe Phe Ser Leu Leu Cys Gly
1               5                   10                  15
```

-continued

Ser Phe Ser Ile His Ala
            20

<210> SEQ ID NO 9
<211> LENGTH: 433
<212> TYPE: PRT
<213> ORGANISM: Citrobacter freundii
<220> FEATURE:
<221> NAME/KEY: mat_peptide
<222> LOCATION: (1)..(433)

<400> SEQUENCE: 9

Met Ser Thr Phe Ile Ile Arg Leu Leu Phe Ser Leu Leu Cys Gly
1               5                   10                  15

Ser Phe Ser Ile His Ala Glu Glu Pro Asn Gly Met Lys Leu Glu Arg
            20                  25                  30

Val Val Ile Val Ser Arg His Gly Val Arg Ala Pro Thr Lys Phe Thr
        35                  40                  45

Pro Ile Met Lys Asp Val Thr Pro Asp Gln Trp Pro Gln Trp Asp Val
    50                  55                  60

Pro Leu Gly Trp Leu Thr Pro Arg Gly Gly Glu Leu Val Ser Glu Leu
65                  70                  75                  80

Gly Gln Tyr Gln Arg Leu Trp Phe Thr Ser Lys Gly Leu Leu Asn Asn
                85                  90                  95

Gln Thr Cys Pro Ser Pro Gly Gln Val Ala Val Ile Ala Asp Thr Asp
            100                 105                 110

Gln Arg Thr Arg Lys Thr Gly Glu Ala Phe Leu Ala Gly Leu Ala Pro
        115                 120                 125

Lys Cys Gln Ile Gln Val His Tyr Gln Lys Asp Glu Glu Lys Thr Asp
    130                 135                 140

Pro Leu Phe Asn Pro Val Lys Met Gly Thr Cys Ser Phe Asn Thr Leu
145                 150                 155                 160

Lys Val Lys Asn Ala Ile Leu Glu Arg Ala Gly Gly Asn Ile Glu Leu
                165                 170                 175

Tyr Thr Gln Arg Tyr Gln Ser Ser Phe Arg Thr Leu Glu Asn Val Leu
            180                 185                 190

Asn Phe Ser Gln Ser Glu Thr Cys Lys Thr Thr Glu Lys Ser Thr Lys
        195                 200                 205

Cys Thr Leu Pro Glu Ala Leu Pro Ser Glu Leu Lys Val Thr Pro Asp
    210                 215                 220

Asn Val Ser Leu Pro Gly Ala Trp Ser Leu Ser Ser Thr Leu Thr Glu
225                 230                 235                 240

Ile Phe Leu Leu Gln Glu Ala Gln Gly Met Pro Gln Val Ala Trp Gly
                245                 250                 255

Arg Ile Thr Gly Glu Lys Glu Trp Arg Asp Leu Leu Ser Leu His Asn
            260                 265                 270

Ala Gln Phe Asp Leu Leu Gln Arg Thr Pro Glu Val Ala Arg Ser Arg
        275                 280                 285

Ala Thr Pro Leu Leu Asp Met Ile Asp Thr Ala Leu Leu Thr Asn Gly
    290                 295                 300

Thr Thr Glu Asn Arg Tyr Gly Ile Lys Leu Pro Val Ser Leu Leu Phe
305                 310                 315                 320

Ile Ala Gly His Asp Thr Asn Leu Ala Asn Leu Ser Gly Ala Leu Asp
                325                 330                 335

Leu Asn Trp Ser Leu Pro Gly Gln Pro Asp Asn Thr Pro Pro Gly Gly

```
                    340                 345                 350
Glu Leu Val Phe Glu Lys Trp Lys Arg Thr Ser Asp Asn Thr Asp Trp
                355                 360                 365

Val Gln Val Ser Phe Val Tyr Gln Thr Leu Arg Asp Met Arg Asp Ile
                370                 375             380

Gln Pro Leu Ser Leu Glu Lys Pro Ala Gly Lys Val Asp Leu Lys Leu
385                 390                 395                 400

Ile Ala Cys Glu Glu Lys Asn Ser Gln Gly Met Cys Ser Leu Lys Ser
                405                 410                 415

Phe Ser Arg Leu Ile Lys Glu Ile Arg Val Pro Glu Cys Ala Val Thr
                420                 425                 430

Glu

<210> SEQ ID NO 10
<211> LENGTH: 411
<212> TYPE: PRT
<213> ORGANISM: Citrobacter braakii
<220> FEATURE:
<221> NAME/KEY: mat_peptide
<222> LOCATION: (1)..(411)

<400> SEQUENCE: 10

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Cys Val
                20                  25                  30

Thr Pro Asp Gln Trp Pro Gln Trp Asp Val Pro Leu Gly Trp Leu Thr
                35                  40                  45

Pro Arg Gly Cys Glu Leu Val Ser Glu Leu Gly Gln Tyr Gln Arg Leu
            50                  55                  60

Trp Phe Thr Ser Lys Gly Leu Leu Asn Asn Gln Thr Cys Pro Ser Pro
65              70                  75                  80

Gly Gln Val Ala Val Ile Ala Asp Thr Asp Gln Arg Thr Arg Lys Thr
                85                  90                  95

Gly Glu Cys Phe Leu Ala Gly Leu Ala Pro Lys Cys Gln Ile Gln Val
                100                 105                 110

His Tyr Gln Lys Asp Glu Glu Lys Asn Asp Pro Leu Phe Asn Pro Val
                115                 120                 125

Lys Met Gly Lys Cys Ser Phe Asn Thr Leu Gln Val Cys Asn Ala Ile
                130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Cys Cys Lys Thr Thr Glu Lys Ser Thr Lys Cys Thr Leu Pro Glu Ala
                180                 185                 190

Leu Pro Ser Glu Leu Lys Cys Thr Pro Asp Leu Val Ser Leu Pro Gly
                195                 200                 205

Ala Trp Ser Leu Ser Ser Thr Leu Thr Glu Ile Phe Leu Leu Gln Glu
                210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
```

```
                260               265               270
Met Ile Asp Thr Ala Leu Leu Thr Asn Gly Thr Thr Glu Asn Arg Tyr
            275               280               285
Gly Ile Lys Leu Pro Val Ser Leu Leu Phe Ile Ala Gly His Asp Thr
        290               295               300
Asn Leu Ala Asn Leu Ser Gly Ala Leu Asp Leu Asn Trp Ser Leu Pro
305               310               315               320
Gly Gln Pro Asp Asn Thr Pro Pro Gly Gly Glu Leu Val Phe Glu Lys
                325               330               335
Trp Lys Arg Thr Ser Asp Asn Thr Asp Trp Val Gln Val Ser Phe Val
            340               345               350
Tyr Gln Thr Leu Arg Asp Met Arg Asp Ile Gln Pro Leu Ser Leu Glu
        355               360               365
Lys Pro Ala Gly Lys Val Asp Leu Lys Leu Ile Ala Cys Glu Glu Lys
        370               375               380
Asn Ser Gln Gly Met Cys Ser Leu Lys Ser Phe Ser Arg Leu Ile Lys
385               390               395               400
Glu Ile Arg Val Pro Glu Cys Ala Val Thr Glu
                405               410
```

<210> SEQ ID NO 11
<211> LENGTH: 1396
<212> TYPE: DNA
<213> ORGANISM: Citrobacter braakii
<220> FEATURE:
<221> NAME/KEY: gene
<222> LOCATION: (1)..(1396)

<400> SEQUENCE: 11

```
atgaagttct tcaccaccat cctcagcacc gccagccttg ttgctgctct cccgccgct      60
gttgactcga accataccc ggccgctcct gaacttgttg cccgggaaga gcagaacgga     120
atgaagttgg agcgagtcgt gattgtctcc aggcacggag tccgcgcccc tactaagttc     180
acgcctatca tgaagtgcgt caccccgac cagtggcctc agtgggacgt gcctttggga     240
tggctcacgc cgcggggatg cgagctcgtc tccgaactcg gccagtacca cgcctctgg      300
ttcacatcga aaggactctt gaacaaccag acttgtcctt cgccgggaca ggtcgcggtc     360
attgcggata ccgaccagcg cacaaggaag accggtgagt gcttcctcgc cggtttggcg     420
cccaaatgtc agatccaggt ccattaccag aaagacgagg agaaaaacga tcctttgttc     480
aacccggtca aatgggcaa atgttcgttc aacactttgc aggtctgcaa cgcaatcttg      540
gaacgcgcag gaggtaacat tgagctctat acacagcgat accagtcgtc gttcaggacc     600
ctcgaaaacg tcttgaactt ctcgcagtcg gaatgctgta agacgaccga gaagtcgact     660
aaatgtaccc tcccggaggc attgccttcc gagttgaagt gcactcccga tctcgtgtcg     720
ctccccggcg cgtggtcgtt gtcgtcgaca ttgacggaga tcttcctcct ccaggaggcc     780
cagggcatgc cccaggtcgc gtggggtagg atcaccggcg agaaggagtg gagggacctc     840
ttgtcctgc ataacgcaca gttcgacttg ttgcagcgca cccccgaagt ggcaaggtcg      900
agggcaactc cccttgctcga tatgatcgat actgccctct tgaccaacgg caccaccgaa     960
aaccggtacg gtatcaaatt gccgtgtcc ctcttgttca tcgccggcca cgataccaac      1020
ttggcaaacc tctccggcgc cctcgatctc aactggtccc tcctggtca gccggataac      1080
accccgcctg gcgagagct cgtcttcgag aaatggaagc ggacgtcgga taacacggac      1140
tgggtccagg tctccttcgt ctatcagacc ttgagggata tgcgtgacat ccagcccctc     1200
```

```
tcgctggaga agcccgccgg taaggtggac ttgaaactca tcgcctgtga ggaaaagaac    1260
tcgcagggta tgtgttcgct caagtccttc tcgcggctca ttaaggagat ccgtgtgccc    1320
gagtgtgccg tcacagagta gctcgagatc tagagggtga ctgacacctg gcggtagaca    1380
atcaatccat ttcatc                                                   1396

<210> SEQ ID NO 12
<211> LENGTH: 411
<212> TYPE: PRT
<213> ORGANISM: Citrobacter braakii
<220> FEATURE:
<221> NAME/KEY: mat_peptide
<222> LOCATION: (1)..(411)

<400> SEQUENCE: 12
```

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Cys Val
            20                  25                  30

Thr Pro Asp Gln Trp Pro Gln Trp Asp Val Pro Leu Gly Trp Leu Thr
        35                  40                  45

Pro Arg Gly Cys Glu Leu Val Ser Tyr Leu Gly Gln Tyr Gln Arg Leu
    50                  55                  60

Trp Phe Thr Ser Lys Gly Leu Leu Pro Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Cys Phe Leu Ala Gly Leu Ala Pro Lys Cys Gln Ile Gln Val
            100                 105                 110

His Tyr Gln Lys Asp Glu Glu Lys Pro Asp Pro Leu Phe Asn Pro Val
        115                 120                 125

Lys Met Gly Lys Cys Gln Phe Asn Thr Leu Gln Val Cys Asn Ala Ile
130                 135                 140

Leu Glu Arg Ala Gly Gly Asn Ile Glu Leu Phe Thr Gln Arg Tyr Gln
145                 150                 155                 160

Ser Ser Phe Arg Thr Leu Glu Asn Val Leu Asn Phe Ser Gln Ser Glu
                165                 170                 175

Cys Cys Lys Thr Thr Glu Lys Ser Thr Lys Cys Thr Leu Pro Glu Ala
            180                 185                 190

Leu Pro Ser Glu Leu Lys Cys Thr Pro Asp Leu Val Ser Leu Thr Gly
        195                 200                 205

Ala Trp Ser Leu Ser Ser Thr Leu Thr Glu Ile Phe Leu Leu Gln Glu
    210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Leu Ile Asp Thr Ala Leu Leu Thr Asn Gly Thr Thr Glu Asn Arg Tyr
        275                 280                 285

Gly Ile Lys Leu Pro Val Ser Leu Leu Phe Ile Ala Gly His Asp Thr
    290                 295                 300

Asn Leu Ala Asn Leu Ser Gly Ala Leu Asp Leu Asn Trp Ser Leu Pro
305                 310                 315                 320

```
Gly Gln Pro Asp Asn Thr Pro Gly Gly Glu Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
        355                 360                 365

Lys Pro Ala Gly Lys Val Asp Leu Lys Leu Ile Ala Cys Glu Glu Lys
    370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 13
<211> LENGTH: 1360
<212> TYPE: DNA
<213> ORGANISM: Citrobacter braakii
<220> FEATURE:
<221> NAME/KEY: gene
<222> LOCATION: (1)..(1360)

<400> SEQUENCE: 13
gggatccacc atgaagttct tcaccaccat cctcagcacc gccagccttg ttgctgctct      60
ccccgccgct gttgactcga accataccccc ggccgctcct gaacttgttg cccgggaaga    120
gcagaacgga atgaagttgg agcgagtcgt gattgtctcc aggcacggag tccgcgcccc    180
tactaagttc acgcctatca tgaagtgcgt caccccccgac cagtggcctc agtgggacgt    240
gcctttggga tggctcacgc cgcggggatg cgagctcgtc tcctacctcg gccagtacca    300
gcgcctctgg ttcacatcga aaggactctt gcccaaccag acttgtcctt cgcccggaca    360
ggtcgcggtc attgcggata ccgaccagcg cacaaggaag accggtgagt gcttcctcgc    420
cggtttggcg cccaaatgtc agatccaggt ccattaccag aaagacgagg agaaacccga    480
tcctttgttc aacccggtca aatgggcaa atgtcagttc aacactttgc aggtctgcaa    540
cgcaatcttg aacgcgcag gaggtaacat tgagctcttc acacagcgat accagtcgtc    600
gttcaggacc ctcgaaaacg tcttgaactt ctcgcagtcg gaatgctgta agacgaccga    660
gaagtcgact aaatgtaccc tcccggaggc attgccttcc gagttgaagt gcactcccga    720
tctcgtgtcg ctcaccggcg cgtggtcgtt gtcgtcgaca ttgacggaga tcttcctcct    780
ccaggaggcc cagggcatgc cccaggtcgc gtggggtagg atcaccggcg agaaggagtg    840
gagggacctc ttgtccttgc ataacgcaca gttcgacttg ttgcagcgca ccccgaagt    900
ggcaaggtcg agggcaactc ccttgctcga tctcatcgat actgccctct tgaccaacgg    960
caccaccgaa aaccggtacg gtatcaaatt gcccgtgtcc ctcttgttca tcgccggcca   1020
cgataccaac ttggcaaacc ctccggcgc cctcgatctc aactggtccc tccctggtca   1080
gccggataac ccccgcctg gcggagagct cgtcttcgag aaatggaagc ggacgtcgga   1140
taacacggac tgggtccagg tctccttcgt ctatcagacc ttgagggata tgcgtgacat   1200
ccagcccctc tcgctggaga agcccgccgg taaggtggac ttgaaactca tcgcctgtga   1260
ggaaaagaac tcgcagggta tgtgttcgct caagtccttc tcgcggctca ttaaggagat   1320
ccgtgtgccc gagtgtgccg tcacagagta gctcgagatc                        1360

<210> SEQ ID NO 14
<211> LENGTH: 411
```

```
<212> TYPE: PRT
<213> ORGANISM: Citrobacter braakii
<220> FEATURE:
<221> NAME/KEY: mat_peptide
<222> LOCATION: (1)..(411)

<400> SEQUENCE: 14
```

| | | | | | | | | | | | | | |
|---|---|---|---|---|---|---|---|---|---|---|---|---|---|
|Glu|Glu|Gln|Asn|Gly|Met|Lys|Leu|Glu|Arg|Val|Val|Ile|Val|Ser|Arg|
|1| | | |5| | | | |10| | | | |15| |

| | | | | | | | | | | | | |
|---|---|---|---|---|---|---|---|---|---|---|---|---|
|His|Gly|Val|Arg|Ala|Pro|Thr|Lys|Phe|Thr|Pro|Ile|Met|Lys|Cys|Val|
| | | | |20| | | | |25| | | | |30| |

Thr Pro Asp Ala Trp Pro Gln Trp Asp Val Pro Leu Gly Trp Leu Thr
                35                  40                  45

Pro Arg Gly Cys Glu Leu Val Ser Tyr Leu Gly His Tyr Gln Arg Gln
 50                  55                  60

Trp Phe Thr Ser Lys Gly Leu Leu Pro Asn Gln Thr Cys Pro Ser Pro
 65                  70                  75                  80

Gly Gln Val Ala Val Ile Ala Asp Thr Asp Gln Arg Thr Arg Lys Thr
                 85                  90                  95

Gly Glu Cys Phe Leu Ala Gly Leu Ala Pro Lys Cys Gln Ile Gln Val
                100                 105                 110

His Tyr Gln Lys Asp Glu Ser Lys Pro Asp Pro Leu Phe Asn Pro Val
                115                 120                 125

Lys Thr Gly Lys Cys Gln Phe Asn Thr Ala Gln Val Cys Asn Ala Ile
130                 135                 140

Leu Glu Arg Ala Gly Gly Asn Ile Glu Leu Phe Thr Gln Arg Tyr Gln
145                 150                 155                 160

Thr Ala Phe Arg Thr Leu Glu Asn Val Leu Asn Phe Ser Gln Ser Pro
                165                 170                 175

Cys Cys Lys Asn Thr Glu Lys Gln Thr Lys Cys Thr Leu Thr Glu Ala
                180                 185                 190

Leu Pro Ser Glu Leu Lys Cys Thr Pro Asp Leu Val Ser Leu Thr Gly
                195                 200                 205

Ala Trp Ser Leu Ser Ser Thr Leu Thr Glu Ile Phe Leu Leu Gln Gln
210                 215                 220

Ala Gln Gly Met Pro Glu Val Ala Trp Gly Arg Ile Thr Gly Glu Lys
225                 230                 235                 240

Glu Trp Asn Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
                260                 265                 270

Leu Ile Asp Thr Ala Leu Leu Thr Asn Gly Thr Thr Glu Asn Arg Tyr
                275                 280                 285

Gly Ile Lys Leu Pro Val Ser Leu Leu Phe Ile Ala Gly His Asp Thr
                290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Gly Gly Glu Leu Val Phe Glu Arg
                325                 330                 335

Trp Lys Arg Leu Ser Asp Asn Thr Asp Trp Val Gln Val Ser Phe Val
                340                 345                 350

Tyr Gln Thr Leu Arg Asp Met Arg Asp Ile Gln Pro Leu Ser Leu Glu
                355                 360                 365

Lys Pro Ala Gly Lys Val Asp Leu Lys Leu Ile Ala Cys Glu Glu Lys
370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 15
<211> LENGTH: 1360
<212> TYPE: DNA
<213> ORGANISM: Citrobacter braakii
<220> FEATURE:
<221> NAME/KEY: gene
<222> LOCATION: (1)..(1360)

<400> SEQUENCE: 15
gggatccacc atgaagttct tcaccaccat cctcagcacc gccagccttg ttgctgctct     60
ccccgccgct gttgactcga accatacccc ggccgctcct gaacttgttg cccgggaaga    120
gcagaacgga atgaagttgg agcgagtcgt gattgtctcc aggcacggag tccgcgcccc    180
tactaagttc acgcctatca tgaagtgcgt caccccgac gcctggcctc agtgggacgt     240
gcctttggga tggctcacgc cgcggggatg cgagctcgtc tcctacctcg ccactacca     300
gcgccagtgg ttcacatcga aaggactctt gcccaaccag acttgtcctt cgcccggaca    360
ggtcgcggtc attgcggata ccgaccagcg cacaaggaag accggtgagt gcttcctcgc    420
cggtttggcg cccaaatgtc agatccaggt ccattaccag aaagacgagt cgaaacccga    480
tcctttgttc aacccggtca aaaccggcaa atgtcagttc aacactgcgc aggtctgcaa    540
cgcaatcttg aacgcgcag gaggtaacat tgagctcttc acacagcgat accagacggc     600
gttcaggacc ctcgaaaacg tcttgaactt ctcgcagtcg ccgtgctgta agaacaccga    660
gaagcagact aaatgtaccc tcacggaggc attgccttcc gagttgaagt gcactcccga    720
tctcgtgtcg ctcaccggcg cgtggtcgtt gtcgtcgaca ttgacggaga tcttcctcct    780
ccagcaggcc cagggcatgc ccgaggtcgc gtggggtagg atcaccggcg agaaggagtg    840
gaacgacctc ttgtccttgc ataacgcaca gttcgacttg ttgcagcgca ccccgaagt    900
ggcaaggtcg agggcaactc ccttgctcga tctcatcgat actgccctct tgaccaacgg    960
caccaccgaa aaccggtacg gtatcaaatt gcccgtgtcc ctcttgttca tcgccggcca   1020
cgataccaac ttggcaaacc tctccggcgc cctcgatctc aactggtccc tcctggtca    1080
gccggataac accccgcctg cgggagagct cgtcttcgag cgctggaagc ggctgtcgga   1140
taacacggac tgggtccagg tctccttcgt ctatcagacc ttgagggata tgcgtgacat   1200
ccagccctc tcgctggaga agcccgccgg taaggtggac ttgaaactca tcgcctgtga    1260
ggaaaagaac tcgcagggta tgtgttcgct caagtccttc tcgcggctca ttaaggagat   1320
ccgtgtgccc gagtgtgccg tcacagagta gctcgagatc                         1360

<210> SEQ ID NO 16
<211> LENGTH: 411
<212> TYPE: PRT
<213> ORGANISM: Citrobacter braakii
<220> FEATURE:
<221> NAME/KEY: mat_peptide
<222> LOCATION: (1)..(411)

<400> SEQUENCE: 16

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Cys Val

```
            20                  25                  30
Thr Pro Asp Ala Trp Pro Gln Trp Asp Val Cys Leu Gly Cys Leu Thr
        35                  40                  45
Pro Arg Gly Cys Glu Leu Val Ser Tyr Leu Gly His Tyr Gln Arg Gln
    50                  55                  60
Trp Phe Thr Ser Lys Gly Leu Leu Pro Asn Gln Thr Cys Pro Ser Pro
65                  70                  75                  80
Gly Gln Val Ala Val Ile Ala Asp Thr Asp Gln Arg Thr Arg Lys Thr
                85                  90                  95
Gly Glu Cys Phe Leu Ala Gly Leu Ala Pro Lys Cys Gln Ile Gln Val
            100                 105                 110
His Tyr Gln Lys Asp Glu Ser Lys Pro Asp Pro Leu Phe Asn Pro Val
        115                 120                 125
Lys Thr Gly Lys Cys Gln Phe Asn Thr Ala Gln Val Cys Asn Ala Ile
    130                 135                 140
Leu Glu Arg Ala Gly Gly Asn Ile Glu Leu Phe Thr Gln Arg Tyr Gln
145                 150                 155                 160
Thr Ala Phe Arg Thr Leu Glu Asn Val Leu Asn Phe Ser Gln Ser Pro
                165                 170                 175
Cys Cys Lys Asn Thr Glu Lys Gln Thr Lys Cys Thr Leu Thr Glu Ala
            180                 185                 190
Leu Pro Ser Glu Leu Lys Cys Thr Pro Asp Leu Val Ser Leu Thr Gly
        195                 200                 205
Ala Trp Ser Leu Ser Ser Thr Leu Thr Glu Ile Phe Leu Leu Gln Gln
    210                 215                 220
Ala Gln Gly Met Pro Glu Val Ala Trp Gly Arg Ile Thr Gly Glu Lys
225                 230                 235                 240
Glu Trp Asn Asp Leu Leu Ser Leu His Asn Ala Gln Phe Asp Leu Leu
                245                 250                 255
Gln Arg Thr Pro Glu Val Ala Arg Ser Arg Ala Thr Pro Leu Leu Asp
            260                 265                 270
Leu Ile Asp Thr Ala Leu Leu Thr Asn Gly Thr Thr Glu Ser Arg Tyr
        275                 280                 285
Gly Ile Lys Leu Pro Val Ser Leu Leu Phe Ile Ala Gly His Asp Thr
    290                 295                 300
Asn Leu Ala Asn Leu Ser Gly Ala Leu Asp Leu Asn Trp Ser Leu Pro
305                 310                 315                 320
Gly Gln Pro Asp Asn Thr Pro Pro Gly Gly Glu Leu Val Phe Glu Arg
                325                 330                 335
Trp Lys Arg Leu Ser Asp Asn Thr Asp Trp Val Gln Val Ser Phe Val
            340                 345                 350
Tyr Gln Thr Leu Arg Asp Met Arg Asp Ile Gln Pro Leu Ser Leu Glu
        355                 360                 365
Lys Pro Ala Gly Lys Val Asp Leu Lys Leu Ile Ala Cys Glu Glu Lys
    370                 375                 380
Asn Ser Gln Gly Met Cys Ser Leu Lys Ser Phe Ser Arg Leu Ile Lys
385                 390                 395                 400
Glu Ile Arg Val Pro Glu Cys Ala Val Thr Glu
                405                 410

<210> SEQ ID NO 17
<211> LENGTH: 1360
<212> TYPE: DNA
<213> ORGANISM: Citrobacter braakii
```

<220> FEATURE:
<221> NAME/KEY: gene
<222> LOCATION: (1)..(1360)

<400> SEQUENCE: 17

```
gggatccacc atgaagttct tcaccaccat cctcagcacc gccagccttg ttgctgctct      60
ccccgccgct gttgactcga accataccccc ggccgctcct gaacttgttg cccgggaaga   120
gcagaacgga atgaagttgg agcgagtcgt gattgtctcc aggcacggag tccgcgcccc   180
tactaagttc acgcctatca tgaagtgcgt caccccccgac gcctggcctc agtgggacgt   240
gtgtttggga tgtctcacgc cgcggggatg cgagctcgtc tcctacctcg gccactacca   300
gcgccagtgg ttcacatcga aaggactctt gcccaaccag acttgtcctt cgcccggaca   360
ggtcgcggtc attgcggata ccgaccagcg cacaaggaag accggtgagt gcttcctcgc   420
cggtttggcg cccaaatgtc agatccaggt ccattaccag aaagacgagt cgaaacccga   480
tcctttgttc aacccggtca aaaccggcaa atgtcagttc aacactgcgc aggtctgcaa   540
cgcaatcttg gaacgcgcag gaggtaacat tgagctcttc acacagcgat accagacggc   600
gttcaggacc ctcgaaaacg tcttgaactt ctcgcagtcg ccgtgctgta agaacaccga   660
gaagcagact aaatgtaccc tcacggaggc attgccttcc gagttgaagt gcactcccga   720
tctcgtgtcg ctcaccggcg cgtggtcgtt gtcgtcgaca ttgacggaga tcttcctcct   780
ccagcaggcc cagggcatgc ccgaggtcgc gtggggtagg atcaccggcg agaaggagtg   840
gaacgacctc ttgtccttgc ataacgcaca gttcgacttg ttgcagcgca ccccgaagt    900
ggcaaggtcg agggcaactc ccttgctcga tctcatcgat actgccctct tgaccaacgg   960
caccaccgaa agccggtacg gtatcaaatt gcccgtgtcc ctcttgttca cgccggcca  1020
cgataccaac ttggcaaacc tctccggcgc cctcgatctc aactggtccc tccctggtca  1080
gccggataac accccgcctg gcggagagct cgtcttcgag cgctggaagc ggctgtcgga  1140
taacacggac tgggtccagg tctccttcgt ctatcagacc ttgagggata tgcgtgacat  1200
ccagccccctc tcgctggaga gcccgccgg taaggtggac ttgaaactca tcgcctgtga  1260
ggaaaagaac tcgcagggta tgtgttcgct caagtccttc tcgcggctca ttaaggagat  1320
ccgtgtgccc gagtgtgccg tcacagagta gctcgagatc                      1360
```

<210> SEQ ID NO 18
<211> LENGTH: 411
<212> TYPE: PRT
<213> ORGANISM: Citrobacter braakii
<220> FEATURE:
<221> NAME/KEY: mat_peptide
<222> LOCATION: (1)..(411)

<400> SEQUENCE: 18

```
Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Cys Val
            20                  25                  30

Thr Pro Asp Ala Trp Pro Gln Trp Asp Val Pro Leu Gly Trp Leu Thr
        35                  40                  45

Pro Arg Gly Cys Glu Leu Val Ser Tyr Leu Gly His Tyr Gln Arg Gln
    50                  55                  60

Trp Phe Thr Ser Lys Gly Leu Leu Pro Asn Gln Thr Cys Pro Ser Pro
65                  70                  75                  80

Gly Gln Val Ala Val Ile Ala Asp Thr Asp Gln Arg Thr Arg Lys Thr
```

```
            85                  90                  95
Gly Glu Cys Phe Leu Ala Gly Leu Ala Pro Lys Cys Gln Ile Gln Val
            100                 105                 110

His Tyr Gln Lys Asp Glu Ser Lys Pro Asp Cys Leu Phe Asn Pro Val
            115                 120                 125

Lys Cys Gly Lys Cys Gln Phe Asn Thr Ala Gln Val Cys Asn Ala Ile
130                 135                 140

Leu Glu Arg Ala Gly Gly Ser Ile Glu Leu Phe Thr Gln Arg Tyr Gln
145                 150                 155                 160

Thr Ala Phe Arg Thr Leu Glu Asn Val Leu Asn Phe Ser Gln Ser Pro
                165                 170                 175

Cys Cys Lys Asn Thr Glu Lys Gln Thr Lys Cys Thr Leu Thr Glu Ala
                180                 185                 190

Leu Pro Ser Glu Leu Lys Cys Thr Pro Asp Leu Val Ser Leu Thr Gly
                195                 200                 205

Ala Trp Ser Leu Ser Ser Thr Leu Thr Glu Ile Phe Leu Leu Gln Gln
210                 215                 220

Ala Gln Gly Met Pro Glu Val Ala Trp Gly Arg Ile Thr Gly Glu Lys
225                 230                 235                 240

Glu Trp Asn Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
                260                 265                 270

Leu Ile Asp Thr Ala Leu Leu Thr Asn Gly Thr Thr Glu Asn Arg Tyr
                275                 280                 285

Gly Ile Lys Leu Pro Val Ser Leu Leu Phe Ile Ala Gly His Asp Thr
                290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Arg
                325                 330                 335

Trp Lys Arg Leu Ser Asp Asn Thr Asp Trp Val Gln Val Ser Phe Val
                340                 345                 350

Tyr Gln Thr Leu Arg Asp Met Arg Asp Ile Gln Pro Leu Ser Leu Glu
                355                 360                 365

Lys Pro Ala Gly Lys Val Asp Leu Lys Leu Ile Ala Cys Glu Glu Lys
                370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410
```

<210> SEQ ID NO 19
<211> LENGTH: 1360
<212> TYPE: DNA
<213> ORGANISM: Citrobacter braakii
<220> FEATURE:
<221> NAME/KEY: gene
<222> LOCATION: (1)..(1360)

<400> SEQUENCE: 19
gggatccacc atgaagttct tcaccaccat cctcagcacc gccagccttg ttgctgctct    60
ccccgccgct gttgactcga accataccec ggccgctcct gaacttgttg cccgggaaga   120
gcagaacgga atgaagttgg agcgagtcgt gattgtctcc aggcacggag tccgcgcccc   180

-continued

| | |
|---|---|
| tactaagttc acgcctatca tgaagtgcgt caccccgac gcctggcctc agtgggacgt | 240 |
| gcctttggga tggctcacgc cgcggggatg cgagctcgtc tcctacctcg gccactacca | 300 |
| gcgccagtgg ttcacatcga aaggactctt gcccaaccag acttgtcctt cgcccggaca | 360 |
| ggtcgcggtc attgcggata ccgaccagcg cacaaggaag accggtgagt gcttcctcgc | 420 |
| cggtttggcg cccaaatgtc agatccaggt ccattaccag aaagacgagt cgaaacccga | 480 |
| ttgtttgttc aacccggtca atgtggcaa atgtcagttc aacactgcgc aggtctgcaa | 540 |
| cgcaatcttg gaacgcgcag gaggtagcat tgagctcttc acacagcgat accagacggc | 600 |
| gttcaggacc ctcgaaaacg tcttgaactt ctcgcagtcg ccgtgctgta agaacaccga | 660 |
| gaagcagact aaatgtaccc tcacggaggc attgccttcc gagttgaagt gcactcccga | 720 |
| tctcgtgtcg ctcaccggcg cgtggtcgtt gtcgtcgaca ttgacggaga tcttcctcct | 780 |
| ccagcaggcc cagggcatgc ccgaggtcgc gtggggtagg atcaccggcg agaaggagtg | 840 |
| gaacgacctc ttgtccttgc ataacgcaca gttcgacttg ttgcagcgca ccccgaagt | 900 |
| ggcaaggtcg agggcaactc ccttgctcga tctcatcgat actgccctct tgaccaacgg | 960 |
| caccaccgaa aaccggtacg gtatcaaatt gcccgtgtcc ctcttgttca tcgccggcca | 1020 |
| cgataccaac ttggcaaacc tctccggcgc cctcgatctc aactggtccc tccctggtca | 1080 |
| gccggataac accccgcctg gcggagagct cgtcttcgag cgctggaagc ggctgtcgga | 1140 |
| taacacggac tgggtccagg tctccttcgt ctatcagacc ttgagggata tgcgtgacat | 1200 |
| ccagccctc tcgctggaga agcccgccgg taaggtggac ttgaaactca tcgcctgtga | 1260 |
| ggaaaagaac tcgcagggta tgtgttcgct caagtccttc tcgcggctca ttaaggagat | 1320 |
| ccgtgtgccc gagtgtgccg tcacagagta gctcgagatc | 1360 |

<210> SEQ ID NO 20
<211> LENGTH: 411
<212> TYPE: PRT
<213> ORGANISM: Citrobacter braakii

<400> SEQUENCE: 20

```
Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Cys Val
            20                  25                  30

Thr Pro Asp Ala Trp Pro Gln Trp Asp Val Cys Leu Gly Cys Leu Thr
        35                  40                  45

Pro Arg Gly Cys Glu Leu Val Ser Tyr Leu Gly His Tyr Gln Arg Gln
    50                  55                  60

Trp Phe Thr Ser Lys Gly Leu Leu Pro Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Cys Phe Leu Ala Gly Leu Ala Pro Lys Cys Gln Ile Gln Val
            100                 105                 110

His Tyr Gln Lys Asp Glu Ser Lys Pro Asp Cys Leu Phe Asn Pro Val
        115                 120                 125

Lys Cys Gly Lys Cys Gln Phe Asn Thr Ala Gln Val Cys Asn Ala Ile
    130                 135                 140

Leu Glu Arg Ala Gly Gly Asn Ile Glu Leu Phe Thr Gln Arg Tyr Gln
145                 150                 155                 160

Thr Ala Phe Arg Thr Leu Glu Asn Val Leu Asn Phe Ser Gln Ser Pro
```

```
                    165                 170                 175
Cys Cys Lys Asn Thr Glu Lys Gln Thr Lys Cys Thr Leu Thr Glu Ala
                180                 185                 190

Leu Pro Ser Glu Leu Lys Cys Thr Pro Asp Leu Val Ser Leu Thr Gly
            195                 200                 205

Ala Trp Ser Leu Ser Ser Thr Leu Thr Glu Ile Phe Leu Leu Gln Gln
        210                 215                 220

Ala Gln Gly Met Pro Glu Val Ala Trp Gly Arg Ile Thr Gly Glu Lys
225                 230                 235                 240

Glu Trp Asn Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Leu Ile Asp Thr Ala Leu Leu Thr Asn Gly Thr Thr Glu Ser Arg Tyr
        275                 280                 285

Gly Ile Lys Leu Pro Val Ser Leu Leu Phe Ile Ala Gly His Asp Thr
290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Arg
                325                 330                 335

Trp Lys Arg Leu Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
        355                 360                 365

Lys Pro Ala Gly Lys Val Asp Leu Lys Leu Ile Ala Cys Glu Glu Lys
    370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 21
<211> LENGTH: 1341
<212> TYPE: DNA
<213> ORGANISM: Citrobacter braakii
<220> FEATURE:
<221> NAME/KEY: gene
<222> LOCATION: (1)..(1341)

<400> SEQUENCE: 21
atgaagttct tcaccaccat cctcagcacc gccagccttg ttgctgctct ccccgccgct      60
gttgactcga accataccCC ggccgctcct gaacttgttg cccgggaaga gcagaacgga     120
atgaagttgg agcgagtcgt gattgtctcc aggcacggag tccgcgcccc tactaagttc     180
acgcctatca tgaagtgcgt caccccccgac gcctggcctc agtgggacgt gtgtttggga     240
tgtctcacgc cgcggggatg cgagctcgtc tcctacctcg ccactacca gcgccagtgg     300 ttcacatcga aaggactctt gcccaaccag acttgtcctt cgcccggaca ggtcgcggtc     360
attgcggata ccgaccagcg cacaaggaag accggtgagt gcttcctcgc cggtttggcg     420
cccaaatgtc agatccaggt ccattaccag aaagacgagt cgaaacccga ttgcttgttc     480
aacccggtca atgtggcaa atgtcagttc aacactgcgc aggtctgcaa cgcaatcttg     540
gaacgcgcag gaggtaacat tgagctcttc acacagcgat accagacggc gttcaggacc     600
ctcgaaaacg tcttgaactt ctcgcagtcg ccgtgctgta agaacaccga gaagcagact     660
```

-continued

```
aaatgtaccc tcacggaggc attgccttcc gagttgaagt gcactcccga tctcgtgtcg      720
ctcaccggcg cgtggtcgtt gtcgtcgaca ttgacgagaa tcttcctcct ccagcaggcc      780
cagggcatgc ccgaggtcgc gtggggtagg atcaccggcg agaaggagtg gaacgacctc      840
ttgtccttgc ataacgcaca gttcgacttg ttgcagcgca cccccgaagt ggcaaggtcg      900
agggcaactc ccttgctcga tctcatcgat actgccctct tgaccaacgg caccaccgaa      960
agccggtacg gtatcaaatt gcccgtgtcc ctcttgttca tcgccggcca cgataccaac     1020
ttggcaaacc tctccggcgc cctcgatctc aactggtccc tccctggtca gccggataac     1080
accccgcctg gcggagagct cgtcttcgag cgctggaagc ggctgtcgga taacacggac     1140
tgggtccagg tctccttcgt ctatcagacc ttgagggata tgcgtgacat ccagcccctc     1200
tcgctggaga agcccgccgg taaggtggac ttgaaactca tcgcctgtga ggaaaagaac     1260
tcgcagggta tgtgttcgct caagtccttc tcgcggctca ttaaggagat ccgtgtgccc     1320
gagtgtgccg tcacagagta g                                                1341
```

<210> SEQ ID NO 22
<211> LENGTH: 311
<212> TYPE: PRT
<213> ORGANISM: Artificial Sequence
<220> FEATURE:
<223> OTHER INFORMATION: Synthetic construct

<400> SEQUENCE: 22

```
Ala Val Pro Ser Thr Gln Thr Pro Trp Gly Ile Lys Ser Ile Tyr Asn
1               5                   10                  15

Asp Gln Ser Ile Thr Lys Thr Thr Gly Gly Lys Gly Ile Lys Val Ala
            20                  25                  30

Val Leu Asp Thr Gly Val Tyr Thr Ser His Leu Asp Leu Ala Gly Ser
        35                  40                  45

Ala Glu Gln Cys Lys Asp Phe Thr Gln Ser Asn Pro Leu Val Asp Gly
    50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Lys Gly Glu Gly
            100                 105                 110

Tyr Ser Asp Asp Ile Ala Ala Ala Ile Arg His Val Ala Asp Glu Ala
        115                 120                 125

Ser Arg Thr Gly Ser Lys Val Val Ile Asn Met Ser Leu Gly Ser Ser
    130                 135                 140

Ala Lys Asp Ser Leu Ile Ala Ser Ala Val Asp Tyr Ala Tyr Gly Lys
145                 150                 155                 160

Gly Val Leu Ile Val Ala Ala Ala Gly Asn Glu Gly Pro Lys Pro Asn
                165                 170                 175

Thr Ile Gly Tyr Pro Ala Gly Phe Val Asn Ala Val Ala Val Ala Ala
            180                 185                 190

Leu Glu Asn Val Gln Glu Lys Gly Thr Tyr Arg Val Ala Asp Phe Ser
        195                 200                 205

Ser Arg Gly Asn Pro Ala Thr Ala Gly Asp Tyr Ile Ile Gln Glu Arg
    210                 215                 220

Asp Ile Glu Val Ser Ala Pro Gly Ala Ser Val Glu Ser Thr Trp Tyr
225                 230                 235                 240
```

```
Thr Gly Gly Tyr Asn Thr Ile Ser Gly Thr Ser Met Ala Thr Pro His
            245                 250                 255

Val Ala Gly Leu Ala Ala Lys Ile Trp Ser Ala Asn Thr Ser Leu Ser
            260                 265                 270

His Ser Gln Leu Arg Thr Glu Leu Gln Asn Arg Ala Lys Val Tyr Asp
        275                 280                 285

Ile Lys Gly Gly Ile Gly Ala Gly Pro Gly Asp Asp Tyr Ala Ser Gly
    290                 295                 300

Phe Gly Tyr Pro Arg Val Lys
305                 310
```

PHYTASE VARIANTS AND POLYNUCLEOTIDES ENCODING SAME

CROSS-REFERENCE TO RELATED APPLICATIONS

This application claims priority under 35 U.S.C. 119 of European application nos. 20190917.3, 20201328.0 and 21172706.0 filed on Aug. 13, 2020, Oct. 12, 2020 and May 7, 2021, respectively, and of international application no. PCT/CN2021/081613 filed on Mar. 18, 2021. The content of each application is fully incorporated herein by reference.

REFERENCE TO A SEQUENCE LISTING

This application contains a Sequence Listing in computer readable form, which is incorporated herein by reference. The name of the file containing the Sequence Listing is SQ.txt, which was created on Sep. 9, 2021 and has 66.4 KB.

REFERENCE TO ATOMIC COORDINATES

This application sets forth in FIG. 5, the atomic coordinates of the three-dimensional structure of the phytase variant (var400).

FIELD OF THE INVENTION

The present invention relates to phytase variants, polynucleotides encoding the variants, methods of producing the variants, and methods of using the variants.

BACKGROUND OF THE INVENTION

Phytases are well-known enzymes, as are the advantages of adding them to foodstuffs for animals, including humans. Phytases have been isolated from various sources, including a number of fungal and bacterial strains.

It is an object of the present invention to provide alternative polypeptides having phytase activity (phytases) and polynucleotides encoding the polypeptides. The phytase variants of the invention exhibit modified or altered preferably improved properties as compared to the parent phytase. Non-limiting examples of such properties are: stability (such as acid-stability, heat-stability, steam stability, pelleting stability, and/or protease stability, in particular pepsin stability), temperature profile, pH profile, specific activity, substrate specificity, performance in animal feed (such as an improved release and/or degradation of phytate), susceptibility to glycation, and/or glycosylation pattern.

As described herein, mutagenesis of a parent polynucleotide encoding a phytase is employed to prepare variant (synthetic) DNAs encoding a phytase having improved properties relative to the phytase encoded by the parent polynucleotide.

*Citrobacter*

The sequence of the phyA gene from a strain of *Citrobacter freundii* has been submitted by Zinin et al to the EMBL/GenBank/DDBJ databases with accession no. AY390262. The corresponding phytase amino acid sequence is found in the UniProt/TrEMBL databases with accession no. Q676V7. The expected mature part of Q676V7 is included in the present sequence listing as SEQ ID NO: 4.

WO 2004/085638 (Republic of National Fisheries Research and Development Institute of Korea) discloses, as SEQ ID NO: 7, the amino acid sequence of a phytase from *Citrobacter braakii* YH-15, deposited as KCCM 10427. The mature part of this amino acid sequence is included herein as SEQ ID NO: 3. This sequence is also found in the database Geneseqp with accession no. ADU50737.

WO 2006/037328 (Novozymes A/S) discloses the wild-type phytase of *Citrobacter braakii* ATCC 51113 (i.e., SEQ ID NO: 2 herein), as well as a variant thereof, which is also included in the present sequence listing, viz. as SEQ ID NO: 6.

WO 2006/038062 and WO 2006/038128 (Danisco A/S) both disclose the amino acid sequence of the phytase gene of *Citrobacter freundii* P3-42, deposited under accession number NCIMB 41247 and a number of variants thereof. This amino acid sequence is included herein as SEQ ID NO: 9. These applications disclose only one substitution in position 233 to a cysteine (S233C) according to the numbering used herein this would be S211C. The texts of WO 2006/038062 and WO 2006/038128 seem to be identical.

WO 2007/112739 (Novozymes A/S) discloses a large number of phytase variants with exemplification using *Citrobacter braakii* ATCC 51113 phytase as parent. WO 2007/112739 indicates, inter alia, the creation of disulfide bridges.

WO 2011/117396 (Novozymes A/S) discloses additional phytase variants with exemplification using *Citrobacter braakii* ATCC 51113 phytase as variant by introducing two or more disulfide bridges in the molecule.

SUMMARY OF THE INVENTION

The present invention is directed, in one aspect, to phytase variants which have at least 70% identity to SEQ ID NO: 2 and which comprise the alterations N31C+G52C+A99C+K141C+T177C+V199C as compared to SEQ ID NO: 2, so as to form disulfide bridges between positions 52 and 99, 31 and 177, and 141 and 199 and further comprise a substitution in one or more position(s) selected from the following: 30, 36, 43, 46, 57, 60, 64, 73, 79, 119, 121, 123, 130, 134,138, 151, 155, 161, 162, 168, 176, 180, 184, 190, 207, 224, 230, 243, 273, 286, 336, 340, 358 and 375 using SEQ ID NO: 2 for numbering.

The present invention relates to phytase variants which have at least 70%, at least 75%, at least 80%, at least 85%, at least 90%, at least 95%, at least 98%, or at least 99% identity, but less than 100% identity, to SEQ ID NO: 2 and which comprise the alterations N31C+G52C+A99C+K141C+T177C+V199C+N203L as compared to SEQ ID NO: 2 and further comprises a substitution in one or more position(s) selected from the following: 30, 36, 43, 46, 57, 60, 64, 73, 79, 119, 121, 123, 130, 134,138, 151, 155, 161, 162, 168, 176, 180, 184, 190, 207, 224, 230, 243, 273, 286, 336, 340, 358 and 375 using SEQ ID NO: 2 for numbering, and which have phytase activity.

A further aspect is directed to an isolated polypeptide having phytase activity, selected from the group consisting of a) a polypeptide having at least 70%, at least 75%, at least 80%, at least 85%, at least 90%, at least 95%, at least 98%, at least 99% or 100% identity to SEQ ID NO: 12;

b) a polypeptide having at least 70%, at least 75%, at least 80%, at least 85%, at least 90%, at least 95%, at least 98%, at least 99% or 100% identity to SEQ ID NO: 14;

c) a polypeptide having at least 70%, at least 75%, at least 80%, at least 85%, at least 90%, at least 95%, at least 98%, at least 99% or 100% identity to SEQ ID NO: 16;

d) a polypeptide having at least 70%, at least 75%, at least 80%, at least 85%, at least 90%, at least 95%, at least 98%, at least 99% or 100% identity to SEQ ID NO: 18; and e) a polypeptide having at least 70%, at least 75%, at least 80%, at least 85%, at least 90%, at least 95%, at least 98%, at least 99% or 100% identity to SEQ ID NO: 20.

Typically said polypeptide is pH stable and thermostable such that it comprises one or more of the following properties
i. an unfolding temperature at pH 4 of at least 75° C.;
ii. an unfolding temperature at pH 3 of at least 70° C.; and
iii. an unfolding temperature at pH 2 of at least 55° C.

Alternatively defined, the polypeptide is acid stable such that it maintains a residual activity level above 90% after 24 hours at each of pH 2, 3, 4, 5, 6, 7 and 8.

The present invention also relates to polynucleotides encoding the variants; nucleic acid constructs, vectors, and host cells comprising the polynucleotides; and methods of producing the variants.

The invention accordingly relates to method of preparing a recombinant polypeptide having phytase activity comprising:
(a) cultivating a recombinant host cell comprising an exogenous polynucleotide selected from the group consisting of
  a. a polynucleotide having at least 70%, at least 75%, at least 80%, at least 85%, at least 90%, at least 95%, at least 98%, at least 99% or 100% identity to SEQ ID NO: 13;
  b. a polynucleotide having at least 70%, at least 75%, at least 80%, at least 85%, at least 90%, at least 95%, at least 98%, at least 99% or 100% identity to SEQ ID NO: 15;
  c. a polynucleotide having at least 70%, at least 75%, at least 80%, at least 85%, at least 90%, at least 95%, at least 98%, at least 99% or 100% identity to SEQ ID NO: 17;
  d. a polynucleotide having at least 70%, at least 75%, at least 80%, at least 85%, at least 90%, at least 95%, at least 98%, at least 99% or 100% identity to SEQ ID NO: 19;
  e. a polynucleotide having at least 70%, at least 75%, at least 80%, at least 85%, at least 90%, at least 95%, at least 98%, at least 99% or 100% identity to SEQ ID NO: 21;
wherein the polynucleotide is expressed and the polypeptide is produced;
(b) optionally isolating the polypeptide; and
(c) optionally recovering the polypeptide.

The invention further relates to a method of producing a polypeptide of the present invention, said method comprising:
(a) cultivating a recombinant host cell comprising an exogenous polynucleotide encoding the polypeptide having phytase activity selected from the group consisting of
  a. a polypeptide having at least 70%, at least 75%, at least 80%, at least 85%, at least 90%, at least 95%, at least 97%, at least 98%, at least 99% or 100 identity to SEQ ID NO: 12;
  b. a polypeptide having at least 70%, at least 75%, at least 80%, at least 85%, at least 90%, at least 95%, at least 97%, at least 98%, at least 99% or 100 identity to SEQ ID NO: 14;
  c. a polypeptide having at least 70%, at least 75%, at least 80%, at least 85%, at least 90%, at least 95%, at least 97%, at least 98%, at least 99% or 100 identity to SEQ ID NO: 16;
  d. a polypeptide having at least 70%, at least 75%, at least 80%, at least 85%, at least 90%, at least 95%, at least 97%, at least 98%, at least 99% or 100 identity to SEQ ID NO: 18; and
  e. a polypeptide having at least 70%, at least 75%, at least 80%, at least 85%, at least 90%, at least 95%, at least 98%, at least 99% or 100% identity to SEQ ID NO: 20;
wherein the polynucleotide is expressed and the polypeptide is produced;
(b) optionally isolating the polypeptide; and
(c) optionally recovering the polypeptide.

The present invention further relates to compositions, in particular animal feed compositions comprising the variants of the invention, and the use of such compositions for improving the nutritional value of an animal feed; reducing the phytate levels in animal manure; treating vegetable proteins; for liberating phosphorous from a phytate substrate; or for increasing weight gain, improving specific growth rate and/or improving Feed Conversion Ratio of an animal; or for improving nutrient retention, and/or nutrient digestibility in an animal.

BRIEF DESCRIPTION OF THE SEQUENCE LISTING

In the Sequence listing the sequences apply as follows:
SEQ ID NO: 1 represents the polynucleotide sequence of the phytase from *Citrobacter braakii* ATCC 51113 (WO 2006/037328).
SEQ ID NO: 2 represents the polypeptide sequence of the phytase from *Citrobacter braakii* ATCC 51113 (WO 2006/037328).
SEQ ID NO: 3 represents the polypeptide sequence of the phytase from *Citrobacter braakii* YH-15 (WO-2004/085638).
SEQ ID NO: 4 represents the polypeptide sequence of the phytase from *Citrobacter freundii* (UniProt/TrEMBL accession no. Q676V7).
SEQ ID NO: 5 represents a variant of SEQ ID NO: 2 (18 is Xaa and 323 are Xaa).
SEQ ID NO: 6 represents a variant of SEQ ID NO: 2 (18 is Gly and 323 is Pro).
SEQ ID NO: 7 represents *Citrobacter braakii* ATCC 51113 signal peptide.
SEQ ID NO: 8 represents *Citrobacter braakii* ATCC 51113 pro-peptide.
SEQ ID NO: 9 represents the polypeptide sequence of the phytase from *Citrobacter freundii* NCIMB 41247 (WO 2006/038062 and WO 2006/038128).
SEQ ID NO: 10 represents the mature polypeptide sequence of a variant of SEQ ID NO: 2, entitled var300.
SEQ ID NO: 11 represents the polynucleotide sequence encoding for SEQ ID NO: 10 with coding sequence (CDS) from nucleotide 11 to nucleotide 1351.
SEQ ID NO: 12 represents the mature polypeptide sequence of a variant of SEQ ID NO: 2, entitled var400.
SEQ ID NO: 13 represents the polynucleotide sequence encoding for SEQ ID NO: 12 with CDS from nucleotide 11 to nucleotide 1351.
SEQ ID NO: 14 represents the mature polypeptide sequence of a variant of SEQ ID NO: 2, entitled var404.
SEQ ID NO: 15 represents the polynucleotide sequence encoding for SEQ ID NO: 14 with CDS from nucleotide 11 to nucleotide 1351.
SEQ ID NO: 16 represents the mature polypeptide sequence of a variant of SEQ ID NO: 2, entitled var405.

SEQ ID NO: 17 represents the polynucleotide sequence encoding for SEQ ID NO: 16 with CDS from nucleotide 11 to nucleotide 1351.

SEQ ID NO: 18 represents the mature polypeptide sequence of a variant of SEQ ID NO: 2, entitled var406.

SEQ ID NO: 19 represents the polynucleotide sequence encoding for SEQ ID NO: 18 with CDS from nucleotide 11 to nucleotide 1351.

SEQ ID NO: 20 represents the mature polypeptide sequence of a variant of SEQ ID NO: 2, entitled var411.

SEQ ID NO: 21 represents the polynucleotide sequence encoding for SEQ ID NO: 20 with CDS from nucleotide 1 to nucleotide 1341.

SEQ ID NO: 22 represents a polypeptide sequence of a protease.

BRIEF DESCRIPTION OF THE DRAWINGS

FIG. 1 shows an example of an alignment of the phytase of SEQ ID NO: 2 and the phytase of SEQ ID NO: 9.

FIGS. 5A-5BE set forth the atomic coordinates of the three-dimensional structure of the phytase variant (var400). These atomic coordinates can aid in generating a three-dimensional model depicting the structure of the phytase variant (var400) and a three-dimensional model of homologous structures, such as variants of the aforementioned phytase variant.

DETAILED DESCRIPTION OF THE INVENTION

Figure 2:
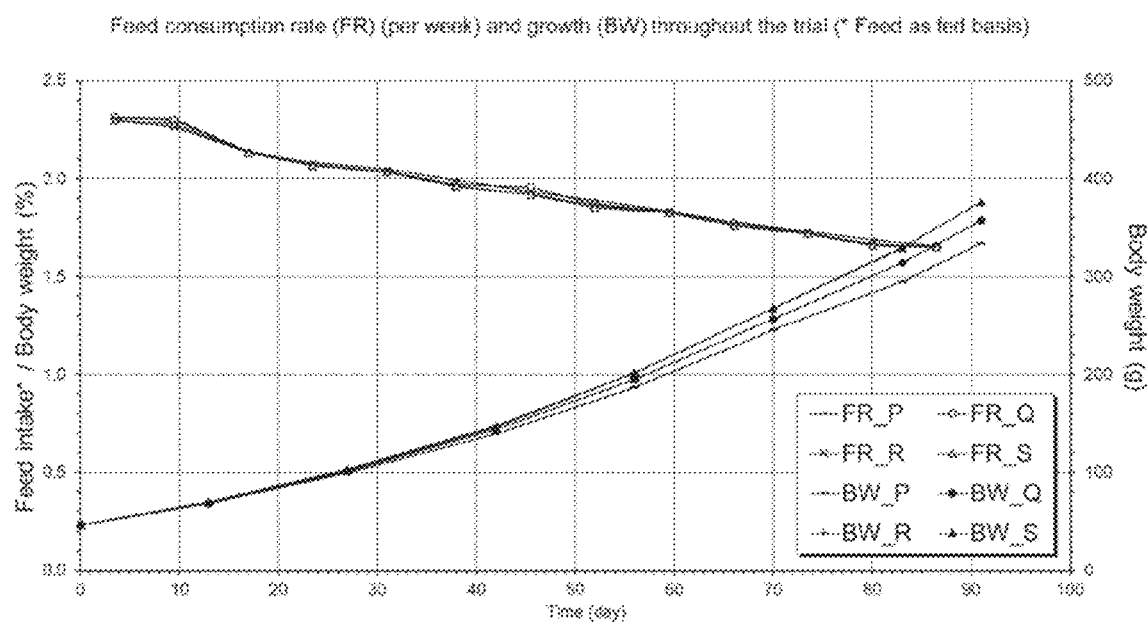
FIG. 2 shows feed consumption ratio (FR) and body weight (BW) evolution during the experimental trial.

A phytase with improved properties, including improved instrinsic temperature and pH stability and improved in vivo efficacy per enzyme unit (FYT) is herein described. As known to the person skilled in the art, these types of improvements not only allow for flexibility in the formulation of the product and the consequent cost-savings with this flexibility, it provides for improved removal of phytate and anti-nutritional factors, improved release of phosphorous, calcium and myo-inositol and increased digestibility of phosphorous, improved muscle protein accretion by myo-inositol release and minimized P excretion for improved sustainability.

The present invention is directed, in one aspect, to phytase variants which has at least 70% identity to SEQ ID NO: 2 and which comprises the alterations N31C+G52C+A99C+K141C+T177C+V199C as compared to SEQ ID NO: 2, so as to form disulfide bridges between positions 52 and 99, 31 and 177, and 141 and 199.

The present invention relates to phytase variants which have at least 70%, at least 75%, at least 80%, at least 85%, at least 90% or at least 95% identity to SEQ ID NO: 2 and which comprise the alterations N31C/G52C/A99C/K141C/T177C/V199C as compared to SEQ ID NO: 2 and further comprise a substitution in one or more position(s) selected from the following: 30, 36, 43, 46, 57, 60, 64, 73, 79, 119, 121, 123, 130, 134,138, 151, 155, 161, 162, 168, 176, 180, 184, 190, 207, 224, 230, 243, 273, 286, 336, 340, 358 and 375 using SEQ ID NO: 2 for numbering, wherein the variants have phytase activity.

Variants

The present invention is directed, in one aspect, to phytase variants which have at least 70% identity to SEQ ID NO: 2 and which comprise the alterations N31C+G52C+A99C+K141C+T177C+V199C as compared to SEQ ID NO: 2, so as to form disulfide bridges between positions 52 and 99, 31 and 177, and 141 and 199.

The present invention provides phytase variants, comprising the substitutions N31C/G52C/A99C/K141C/T177C/V199C/N203L as compared to SEQ ID NO: 2 and further comprising an alteration in one or more position(s) selected from the following: 30, 36, 43, 46, 57, 60, 64, 73, 79, 119, 121, 123, 130, 134,138, 151, 155, 161, 162, 168, 176, 180, 184, 190, 207, 224, 230, 243, 273, 286, 336, 340, 358 and 375 using SEQ ID NO: 2 for numbering, wherein the variants have phytase activity.

In an embodiment, the alteration is a substitution.

In an embodiment, the variant has sequence identity of at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent phytase.

In another embodiment, the variant has at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 2.

In one aspect, the variants of the invention comprise the substitutions N31C/G52C/A99C/K141C/T177C/V199C/N203L as compared to SEQ ID NO: 2 and further comprise alterations, where the number of further alterations in the variants of the present invention is 1-30, e.g., 1-20, 1-10 and 1-5, such as 1, 2, 3, 4, 5, 6, 7, 8, 9 or 10 alterations.

In another aspect, the variants of the invention comprise the substitutions N31C/G52C/A99C/K141C/T177C/V199C/N203L as compared to SEQ ID NO: 2 and further comprise one or more substitution in positions corresponding to 57, 73, 121, 134, 155, 207 and 273 using SEQ ID NO: 2 for numbering. In a preferred embodiment, the variants comprise the substitutions N31C/G52C/A99C/K141C/T177C/V199C/N203L as compared to SEQ ID NO: 2 and further comprise two or more substitutions, e.g., 2, 3, 4, 5, 6 or 7 substitutions; in positions corresponding to 57, 73, 121, 134, 155, 207 and 273 using SEQ ID NO: 2 for numbering.

In another aspect, the variant comprises or consists of a substitution at a position corresponding to position 57. In another aspect, the amino acid at a position corresponding to position 57 is substituted with Ala, Arg, Asn, Asp, Cys, Gln, Gly, His, Ile, Leu, Lys, Met, Phe, Pro, Ser, Thr, Trp, Tyr, or Val, preferably with Tyr. In another aspect, the variant comprises or consists of the substitution E57Y of the mature polypeptide of SEQ ID NO: 2.

In another aspect, the variant comprises or consists of a substitution at a position corresponding to position 73. In another aspect, the amino acid at a position corresponding to position 73 is substituted with Ala, Arg, Asp, Cys, Gln, Giu, Gly, His, Ile, Leu, Lys, Met, Phe, Pro, Ser, Thr, Trp, Tyr, or Val, preferably with Pro. In another aspect, the variant comprises or consists of the substitution N73P of the mature polypeptide of SEQ ID NO: 2.

In another aspect, the variant comprises or consists of a substitution at a position corresponding to position 121. In another aspect, the amino acid at a position corresponding to position 121 is substituted with Ala, Arg, Asp, Cys, Gln, Giu, Gly, His, lie, Leu, Lys, Met, Phe, Pro, Ser, Thr, Trp, Tyr, or Val, preferably with Pro. In another aspect, the variant comprises or consists of the substitution N121P of the mature polypeptide of SEQ ID NO: 2.

In another aspect, the variant comprises or consists of a substitution at a position corresponding to position 134. In another aspect, the amino acid at a position corresponding to position 134 is substituted with Ala, Arg, Asp, Asn, Cys, Gln, Giu, Gly, His, lie, Leu, Lys, Met, Phe, Pro, Thr, Trp, Tyr, or Val, preferably with Gln. In another aspect, the variant comprises or consists of the substitution S134Q of the mature polypeptide of SEQ ID NO: 2.

In another aspect, the variant comprises or consists of a substitution at a position corresponding to position 155. In another aspect, the amino acid at a position corresponding to position 155 is substituted with Ala, Arg, Asp, Asn, Cys, Gln, Giu, Gly, His, lie, Leu, Lys, Met, Phe, Pro, Ser, Thr, Trp, or Val, preferably with Phe. In another aspect, the variant comprises or consists of the substitution Y155F of the mature polypeptide of SEQ ID NO: 2.

In another aspect, the variant comprises or consists of a substitution at a position corresponding to position 207. In another aspect, the amino acid at a position corresponding to position 207 is substituted with Ala, Arg, Asp, Asn, Cys, Gln, Giu, Gly, His, lie, Leu, Lys, Met, Phe, Ser, Thr, Trp, Tyr, or Val, preferably with Thr. In another aspect, the variant comprises or consists of the substitution P207T of the mature polypeptide of SEQ ID NO: 2.

In another aspect, the variant comprises or consists of a substitution at a position corresponding to position 273. In another aspect, the amino acid at a position corresponding to position 273 is substituted with Ala, Arg, Asp, Asn, Cys, Gln, Giu, Gly, His, lie, Leu, Lys, Phe, Pro, Ser, Thr, Trp, Tyr, or Val, preferably with Leu. In another aspect, the variant comprises or consists of the substitution M273L of the mature polypeptide of SEQ ID NO: 2.

In another aspect, the variant comprises or consists of an alteration at positions corresponding to positions 57 and 73, such as those described above.

In another aspect, the variant comprises or consists of alterations at positions corresponding to positions 57 and 121, such as those described above.

In another aspect, the variant comprises or consists of alterations at positions corresponding to positions 57 and 134, such as those described above.

In another aspect, the variant comprises or consists of an alteration at positions corresponding to positions 57 and 155, such as those described above.

In another aspect, the variant comprises or consists of alterations at positions corresponding to positions 57 and 207, such as those described above.

In another aspect, the variant comprises or consists of alterations at positions corresponding to positions 57 and 273, such as those described above.

In another aspect, the variant comprises or consists of alterations at positions corresponding to positions 73, and 121, such as those described above.

In another aspect, the variant comprises or consists of alterations at positions corresponding to positions 73 and 134, such as those described above.

In another aspect, the variant comprises or consists of alterations at positions corresponding to positions 73, and 155, such as those described above.

In another aspect, the variant comprises or consists of alterations at positions corresponding to positions 73 and 207, such as those described above.

In another aspect, the variant comprises or consists of alterations at positions corresponding to positions 73 and 273, such as those described above.

In another aspect, the variant comprises or consists of alterations at positions corresponding to positions 121 and 134, such as those described above.

In another aspect, the variant comprises or consists of alterations at positions corresponding to positions 121 and 155, such as those described above.

In another aspect, the variant comprises or consists of alterations at positions corresponding to positions 121 and 207, such as those described above.

In another aspect, the variant comprises or consists of alterations at positions corresponding to positions 121 and 273, such as those described above.

In another aspect, the variant comprises or consists of alterations at positions corresponding to positions 134 and 155, such as those described above.

In another aspect, the variant comprises or consists of alterations at positions corresponding to positions 134 and 207, such as those described above.

In another aspect, the variant comprises or consists of alterations at positions corresponding to positions 134 and 273, such as those described above.

In another aspect, the variant comprises or consists of alterations at positions corresponding to positions 155 and 207, such as those described above.

In another aspect, the variant comprises or consists of alterations at positions corresponding to positions 155 and 273, such as those described above.

In another aspect, the variant comprises or consists of alterations at positions corresponding to positions 207 and 273, such as those described above.

In another aspect, the variant comprises or consists of alterations at positions corresponding to positions 57, 73, and 121, such as those described above.

In another aspect, the variant comprises or consists of alterations at positions corresponding to positions 57, 73, and 134, such as those described above.

In another aspect, the variant comprises or consists of alterations at positions corresponding to positions 57, 73, and 155, such as those described above.

In another aspect, the variant comprises or consists of alterations at positions corresponding to positions 57, 73, and 207, such as those described above.

In another aspect, the variant comprises or consists of alterations at positions corresponding to positions 57, 73, and 273, such as those described above.

In another aspect, the variant comprises or consists of alterations at positions corresponding to positions 57, 121, and 134, such as those described above.

In another aspect, the variant comprises or consists of alterations at positions corresponding to positions 57, 121, and 155, such as those described above.

In another aspect, the variant comprises or consists of alterations at positions corresponding to positions 57, 121, and 207, such as those described above.

In another aspect, the variant comprises or consists of alterations at positions corresponding to positions 57, 121, and 273, such as those described above.

In another aspect, the variant comprises or consists of alterations at positions corresponding to positions 57, 155, and 207, such as those described above.

In another aspect, the variant comprises or consists of alterations at positions corresponding to positions 57, 155, and 273, such as those described above.

In another aspect, the variant comprises or consists of alterations at positions corresponding to positions 57, 207, and 273, such as those described above.

In another aspect, the variant comprises or consists of alterations at positions corresponding to positions 73, 121, and 134, such as those described above.

In another aspect, the variant comprises or consists of alterations at positions corresponding to positions 73, 121, and 155, such as those described above.

In another aspect, the variant comprises or consists of alterations at positions corresponding to positions 73, 121, and 207, such as those described above.

In another aspect, the variant comprises or consists of alterations at positions corresponding to positions 73, 121, and 273, such as those described above.

In another aspect, the variant comprises or consists of alterations at positions corresponding to positions 73, 134, and 155, such as those described above.

In another aspect, the variant comprises or consists of alterations at positions corresponding to positions 73, 134, and 207, such as those described above.

In another aspect, the variant comprises or consists of alterations at positions corresponding to positions 73, 134, and 273, such as those described above.

In another aspect, the variant comprises or consists of alterations at positions corresponding to positions 73, 155, and 207, such as those described above.

In another aspect, the variant comprises or consists of alterations at positions corresponding to positions 73, 134, and 207, such as those described above.

In another aspect, the variant comprises or consists of alterations at positions corresponding to positions 73, 134, and 273, such as those described above.

In another aspect, the variant comprises or consists of alterations at positions corresponding to positions 121, 134, and 155, such as those described above.

In another aspect, the variant comprises or consists of alterations at positions corresponding to positions 121, 134, and 207, such as those described above.

In another aspect, the variant comprises or consists of alterations at positions corresponding to positions 121, 134, and 273, such as those described above.

In another aspect, the variant comprises or consists of alterations at positions corresponding to positions 134, 155, and 207, such as those described above.

In another aspect, the variant comprises or consists of alterations at positions corresponding to positions 134, 155, and 273, such as those described above.

In another aspect, the variant comprises or consists of alterations at positions corresponding to positions 155, 207, and 273, such as those described above.

In another aspect, the variant comprises or consists of alterations at positions corresponding to positions 57, 73, 121, and 134, such as those described above.

In another aspect, the variant comprises or consists of alterations at positions corresponding to positions 57, 73, 121, and 155, such as those described above.

In another aspect, the variant comprises or consists of alterations at positions corresponding to positions 57, 73, 121, and 207, such as those described above.

In another aspect, the variant comprises or consists of alterations at positions corresponding to positions 57, 73, 121, and 273, such as those described above.

In another aspect, the variant comprises or consists of alterations at positions corresponding to positions 57, 73, 134, and 155, such as those described above.

In another aspect, the variant comprises or consists of alterations at positions corresponding to positions 57, 73, 134, and 207, such as those described above.

In another aspect, the variant comprises or consists of alterations at positions corresponding to positions 57, 73, 134, and 273, such as those described above.

In another aspect, the variant comprises or consists of alterations at positions corresponding to positions 57, 73, 155, and 207, such as those described above.

In another aspect, the variant comprises or consists of alterations at positions corresponding to positions 57, 73, 155, and 273, such as those described above.

In another aspect, the variant comprises or consists of alterations at positions corresponding to positions 57, 73, 207, and 273, such as those described above.

In another aspect, the variant comprises or consists of alterations at positions corresponding to positions 57, 121, 134, and 155, such as those described above.

In another aspect, the variant comprises or consists of alterations at positions corresponding to positions 57, 121, 134, and 207, such as those described above.

In another aspect, the variant comprises or consists of alterations at positions corresponding to positions 57, 121, 134, and 273, such as those described above.

In another aspect, the variant comprises or consists of alterations at positions corresponding to positions 57, 121, 155, and 207, such as those described above.

In another aspect, the variant comprises or consists of alterations at positions corresponding to positions 57, 121, 207, and 273, such as those described above.

In another aspect, the variant comprises or consists of alterations at positions corresponding to positions 57, 134, 155, and 207, such as those described above.

In another aspect, the variant comprises or consists of alterations at positions corresponding to positions 57, 134, 155, and 273, such as those described above.

In another aspect, the variant comprises or consists of alterations at positions corresponding to positions 57, 155, 207, and 273, such as those described above.

In another aspect, the variant comprises or consists of alterations at positions corresponding to positions 73, 121, 134, and 155, such as those described above.

In another aspect, the variant comprises or consists of alterations at positions corresponding to positions 73, 121, 134, and 207, such as those described above.

In another aspect, the variant comprises or consists of alterations at positions corresponding to positions 73, 121, 134, and 273, such as those described above.

In another aspect, the variant comprises or consists of alterations at positions corresponding to positions 73, 134, 155, and 207, such as those described above.

In another aspect, the variant comprises or consists of alterations at positions corresponding to positions 73, 134, 155, and 273, such as those described above.

In another aspect, the variant comprises or consists of alterations at positions corresponding to positions 73, 134, 207, and 273, such as those described above.

In another aspect, the variant comprises or consists of alterations at positions corresponding to positions 73, 155, 207, and 273, such as those described above.

In another aspect, the variant comprises or consists of alterations at positions corresponding to positions 121, 134, 155, and 207, such as those described above.

In another aspect, the variant comprises or consists of alterations at positions corresponding to positions 121, 134, 155, and 273, such as those described above.

In another aspect, the variant comprises or consists of alterations at positions corresponding to positions 121, 134, 207, and 273, such as those described above.

In another aspect, the variant comprises or consists of alterations at positions corresponding to positions 134, 155, 207, and 273, such as those described above.

In another aspect, the variant comprises or consists of alterations at positions corresponding to positions 57, 73, 121, 134, and 155, such as those described above.

In another aspect, the variant comprises or consists of alterations at positions corresponding to positions 57, 73, 121, 134, and 207, such as those described above.

In another aspect, the variant comprises or consists of alterations at positions corresponding to positions 57, 73, 121, 134, and 273, such as those described above.

In another aspect, the variant comprises or consists of alterations at positions corresponding to positions 57, 73, 121, 155, and 207, such as those described above.

In another aspect, the variant comprises or consists of alterations at positions corresponding to positions 57, 73, 121, 155, and 273, such as those described above.

In another aspect, the variant comprises or consists of alterations at positions corresponding to positions 57, 73, 121, 207, and 273, such as those described above.

In another aspect, the variant comprises or consists of alterations at positions corresponding to positions 57, 73, 134, 155, and 207, such as those described above.

In another aspect, the variant comprises or consists of alterations at positions corresponding to positions 57, 73, 134, 155, and 273, such as those described above.

In another aspect, the variant comprises or consists of alterations at positions corresponding to positions 57, 73, 134, 207, and 273, such as those described above.

In another aspect, the variant comprises or consists of alterations at positions corresponding to positions 57, 73, 155, 207, and 273, such as those described above.

In another aspect, the variant comprises or consists of alterations at positions corresponding to positions 57, 121, 134, 155, and 207, such as those described above.

In another aspect, the variant comprises or consists of alterations at positions corresponding to positions 57, 121, 134, 155, and 273, such as those described above.

In another aspect, the variant comprises or consists of alterations at positions corresponding to positions 57, 121, 134, 207, and 273, such as those described above.

In another aspect, the variant comprises or consists of alterations at positions corresponding to positions 57, 121, 155, 207, and 273, such as those described above.

In another aspect, the variant comprises or consists of alterations at positions corresponding to positions 57, 134, 155, 207, and 273, such as those described above.

In another aspect, the variant comprises or consists of alterations at positions corresponding to positions 73, 121, 134, 155, and 207, such as those described above.

In another aspect, the variant comprises or consists of alterations at positions corresponding to positions 73, 121, 134, 155, and 273, such as those described above.

In another aspect, the variant comprises or consists of alterations at positions corresponding to positions 73, 121, 134, 207, and 273, such as those described above.

In another aspect, the variant comprises or consists of alterations at positions corresponding to positions 73, 121, 155, 207, and 273, such as those described above.

In another aspect, the variant comprises or consists of alterations at positions corresponding to positions 73, 134, 155, 207, and 273, such as those described above.

In another aspect, the variant comprises or consists of alterations at positions corresponding to positions 121, 134, 155, 207, and 273, such as those described above.

In another aspect, the variant comprises or consists of alterations at positions corresponding to positions 57, 73, 121, 134, 155 and 207, such as those described above.

In another aspect, the variant comprises or consists of alterations at positions corresponding to positions 57, 73, 121, 134, 155, and 273, such as those described above.

In another aspect, the variant comprises or consists of alterations at positions corresponding to positions 57, 73, 121, 134, 207, and 273, such as those described above.

In another aspect, the variant comprises or consists of alterations at positions corresponding to positions 57, 73, 121, 155, 207 and 273, such as those described above.

In another aspect, the variant comprises or consists of alterations at positions corresponding to positions 57, 73, 134, 155, 207, and 273, such as those described above.

In another aspect, the variant comprises or consists of alterations at positions corresponding to positions 57, 121, 134, 155, 207, and 273, such as those described above.

In another aspect, the variant comprises or consists of alterations at positions corresponding to positions 73, 121, 134, 155, 207, and 273, such as those described above.

In another aspect, the variant comprises or consists of alterations at positions corresponding to positions 57, 73, 121, 134, 155, 207, and 273, such as those described above.

In another aspect, the variant comprises or consists of one or more (e.g., several) substitutions selected from the group consisting of 30Q, 36A, 43C, 46C, 57Y, 60H, 64Q, 73P, 79Q, 119P, 121P, 123C, 130T,C, 134Q, 138A, 151S, 155F, 161T, 162A, 176P, 180N, 184Q, 190T, 207T, 224Q, 230E, 243N, 273L, 286S, 336R, 340L,P, 358Q and 375K.

In another aspect, the variant comprises or consists of one or more (e.g., several) substitutions selected from the group consisting of K30Q, Q36A, P43C, W46C, E57Y, Q60H, L64Q, N73P, S79Q, E119P, N121P, P123C, M130T,C, S134Q, L138A, N151S, Y155F, S161T, S162A, N168R, E176P, T180N, S184Q, P190T, P207T, E224Q, Q230E, R243N, M273L, N286S, K336R, T340L,P, D358Q and D375K.

In another aspect, the variant comprises or consists of the substitutions.

In a preferred embodiment, the variants comprises the substitutions N31C/G52C/A99C/K141C/T177C/V199C/N203L as compared to SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 2 which has phytase activity, and further the variant comprises substitutions in the positions: 57, 73, 121, 134, 155, 207 and 273, preferably 57Y, 73P, 121P, 134Q, 155Y, 207T and 273L; and further comprises one or more substitutions in one or more of the positions: 30, 36, 43, 46, 60, 64, 79, 119, 123, 130, 138, 151, 161, 162, 168, 176, 180, 184, 190, 224, 230, 243, 286, 336, 340, 358 and 375.

If a variant comprises the substitution P43C as compared to SEQ ID NO: 2 it is preferred that it also comprises the substitution W46C. If a variant comprises the substitution W46C as compared to SEQ ID NO: 2 it is preferred that it also comprises the substitution P43C. If a variant comprises the substitution P123C as compared to SEQ ID NO: 2 it is preferred that it also comprises the substitution M130C. If a variant comprises the substitution M130C as compared to SEQ ID NO: 2 it is preferred that it also comprises the substitution P123C.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R.L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/11e, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for phytase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The crystal structure of the phytase variant (var400) was solved at a resolution of 1.33 A. The atomic coordinates of this structure are shown in FIG. 5. These atomic coordinates can be used to generate a three-dimensional model depicting the structure of the phytase variant (var400) or homologous structures (such as more variants of the present invention). The three-dimensional structure shows the molecular consequence of the introduced mutations, and it confirms that disulfide bridges between positions 52 and 99, 31 and 177, and 141 and 199 are formed.

In an embodiment, the variant has improved stability under storage conditions compared to the parent enzyme.

In an embodiment, the variant has improved thermostability compared to the parent enzyme.

Examples of variants according to the invention including variants having following substitution in comparison with SEQ ID NO: 2:

N31C/G52C/E57Y/N73P/A99C/N121 P/S134Q/K141C/Y155F/T177C/V199C/N203L/P207T/M273L;

N31C/Q36A/G52C/E57Y/Q60H/L64Q/N73P/A99C/E119S/N121 P/M130T/S134Q/L138A/K141C/Y155F/S161T/S162A/E176P/T177C/T180N/S184Q/P190T/V199C/N203L/P207T/E224Q/Q230E/R243N/M273L/K336R/T340L;

N31C/Q36A/P43C/W46C/G52C/E57Y/Q60H/L64Q/N73P/A99C/E119S/N121 P/M130T/S134Q/L138A/K141C/Y155F/S161T/S162A/E176P/T177C/T180N/S184Q/P190T/V199C/N203L/P207T/E224Q/Q230E/R243N/M273L/N286S/K336R/T340L;

N31C/Q36A/G52C/E57Y/Q60H/L64Q/N73P/A99C/E119S/N121P/P123C/M130C/S134Q/L138A/K141C/N151S/Y155F/S161T/S162A/E176P/T177C/T180N/S184Q/P190T/V199C/N203L/P207T/E224Q/Q230E/R243N/M273L/K336R/T340L; and N31C/Q36A/P43C+W46C+G52C+E57Y+Q60H+L64Q+N73P+A99C+E119S+N121P+P123C+M130C+S134Q+L138A/K141C/Y155F/S161T/S162A/E176P/T177C/T180N/S184Q/P190T/V199C/N203L/P207T/E224Q/Q230E/R243N/M273L/N286S/K336R/T340L.

Phytase Polypeptides, Percentage of Identity

In the present context a phytase is a polypeptide having phytase activity, i.e., an enzyme which catalyzes the hydrolysis of phytate (myo-inositol hexakisphosphate) to (1) myo-inositol and/or (2) mono-, di-, tri-, tetra- and/or pentaphosphates thereof and (3) inorganic phosphate.

In the present context the term a phytate substrate encompasses, i.e., phytic acid and any phytate (salt of phytic acid), as well as the phosphates listed under (2) above.

The ENZYME site at the internet (www.expasy.ch/enzyme/) is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch, 2000, "The ENZYME Database", *Nucleic Acids Res.* 28:304-305). See also the handbook Enzyme Nomenclature from NC-IUBMB, 1992).

According to the ENZYME site, three different types of phytases are known: a so-called 3-phytase (alternative name 1-phytase; a myo-inositol hexaphosphate 3-phosphohydrolase, EC 3.1.3.8), a so-called 4-phytase (alternative name 6-phytase, name based on 1L-numbering system and not 1D-numbering, EC 3.1.3.26), and a so-called 5-phytase (EC 3.1.3.72). For the purposes of the present invention, all three types are included in the definition of phytase.

In a particular embodiment, the phytases of the invention belong to the family of acid histidine phosphatases, which includes the *Escherichia coli* pH 2.5 acid phosphatase (gene appA) as well as fungal phytases such as *Aspergillus awamorii* phytases A and B (EC: 3.1.3.8) (gene phyA and phyB). The histidine acid phosphatases share two regions of sequence similarity, each centered around a conserved histidine residue. These two histidines seem to be involved in the enzymes' catalytic mechanism. The first histidine is located in the N-terminal section and forms a phosphor-histidine intermediate while the second is located in the C-terminal section and possibly acts as proton donor.

In a further particular embodiment, the phytases of the invention have a conserved active site motif, viz. R-H-G-X-R-X-P, wherein X designates any amino acid (see amino acids 16 to 22 of SEQ ID NOs: 2, 3, 4, 6 and amino acids 38-44 of SEQ ID NO: 9). In a preferred embodiment, the conserved active site motif is R-H-G-V-R-A-P, i.e., amino acids 16-22 (by reference to SEQ ID NO: 2) are RHGVRAP.

For the purposes of the present invention the phytase activity is determined in the unit of FYT, one FYT being the amount of enzyme that liberates 1 micro-mol inorganic ortho-phosphate per min. under the following conditions: pH 5.5; temperature 37° C.; substrate: sodium phytate ($C_6H_{24}O_{24}P_6Na_{12}$) in a concentration of 0.0050 mol/l. Suitable phytase assays are the FYT and FTU assays described in Example 1 of WO 00/20569. FTU is for determining phytase activity in feed and premix. Phytase activity may also be determined using the assays of Example 1 ("Determination of phosphatase activity" or "Determination of phytase activity").

In a particular embodiment the phytase of the invention is isolated. The term "isolated" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

The relatedness between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman and Wunsch, 1970, *J. Mol. Biol.* 48: 443-453. The substitution matrix used is BLOSUM62, gap opening penalty is 10, and gap extension penalty is 0.5.

The degree of identity between an amino acid sequence of the present invention ("invention sequence") and the amino acid sequence referred to in the claims (SEQ ID NO: 2) is calculated as the number of exact matches in an alignment of the two sequences, divided by the length of the "invention sequence," or the length of the SEQ ID NO: 2, whichever is the shortest. The result is expressed in percent identity.

An exact match occurs when the "invention sequence" and SEQ ID NO: 2 have identical amino acid residues in the same positions of the overlap (in the alignment example below this is represented by "I"). The length of a sequence is the number of amino acid residues in the sequence (e.g., the length of amino acids 1-411 of SEQ ID NO: 2 is 411).

Example 11 in WO 2011/117396 is an example of an alignment of the phytase of SEQ ID NO: 2 and the phytase of SEQ ID NO: 9, and the example illustrates how to calculate the percentage of identity between these two backbones.

In another, purely hypothetical, alignment example below, the overlap is the amino acid sequence "HTWGER-NL" of Sequence 1; or the amino acid sequence "HGWGEDANL" of Sequence 2. In the example a gap is indicated by a Hypothetical alignment example:

```
Sequence 1: ACMSHTWGER-NL
               | ||| ||
Sequence 2:    HGWGEDANLAMNPS
```

In a particular embodiment, the percentage of identity of an amino acid sequence of a polypeptide with, or to, SEQ ID NO: 2 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage.

In the above hypothetical example, the number of exact matches is 6, the length of the shortest one of the two amino acid sequences is 12; accordingly the percentage of identity is 50%.

In particular embodiments of the phytase of the invention, the degree of identity to SEQ ID NO: 2 is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%. In still further particular embodiments, the degree of identity is at least 98.0%, 98.2%, 98.4%, 98.6%, 98.8%, 99.0%, 99.1%, 99.2%, 99.3%, 99.4%, 99.5%, 99.6%, 99.7%, 99.8%, or at least 99.9%. In alternative embodiments, the degree of identity is at least 70%, 71%, 72%, or at least 73%.

In still further particular embodiments, the phytase of the invention has no more than 1, 2, 3, 4, 5, 6, 7, 8, 9, or no more than 10 modifications as compared to SEQ ID NO: 2 or any other parent phytase; no more than 11, 12, 13, 14, 15, 16, 17, 18, 19, or no more than 20 modifications as compared to SEQ ID NO: 2 or any other parent phytase; no more than 21, 22, 23, 24, 25, 26, 27, 28, 29, or no more than 30 modifications as compared to SEQ ID NO: 2 or any other parent phytase; no more than 31, 32, 33, 34, 35, 36, 37, 38, 39, or not more than 40 modifications as compared to SEQ ID NO: 2 or any other parent phytase; no more than 41, 42, 43, 44, 45, 46, 47, 48, 49, or no more than 50 modifications as compared to SEQ ID NO: 2 or any other parent phytase; no more than 51, 52, 53, 54, 55, 56, 57, 58, 59, or no more than 60 modifications as compared to SEQ ID NO: 2 or any other parent phytase; no more than 61, 62, 63, 64, 65, 66, 67, 68, 69, or no more than 70 modifications as compared to SEQ ID NO: 2 or any other parent phytase; no more than 71, 72, 73, 74, 75, 76, 77, 78, 79, or no more than 80 modifications as compared to SEQ ID NO: 2 or any other parent phytase; no more than 81, 82, 83, 84, 85, 86, 87, 88, 89, or no more than 90 modifications as compared to SEQ ID NO: 2 or any other parent phytase; no more than 91, 92, 93, 94, 95, 96, 97, 98, 99, or no more than 100 modifications as compared to SEQ ID NO: 2 or any other parent phytase; no more than 101, 102, 103, 104, 105, 106, 107, 108, 109, or no more than 110 modifications as compared to SEQ ID NO: 2 or any other parent phytase; no more than 111, 112, 113, 114, 115, 116, 117, 118, 119, or no more than 120 modifications as compared to SEQ ID NO: 2 or any other parent phytase; or no more than 121, 122, 123, or 124 modifications as compared to SEQ ID NO: 2 or any other parent phytase.

An aspect of the invention is directed to an isolated polypeptide having phytase activity, selected from the group consisting of a) a polypeptide having at least 70%, at least 75%, at least 80%, at least 85%, at least 90%, at least 95%, at least 98%, at least 99% or 100% identity to SEQ ID NO: 12;

b) a polypeptide having at least 70%, at least 75%, at least 80%, at least 85%, at least 90%, at least 95%, at least 98%, at least 99% or 100% identity to SEQ ID NO: 14;

c) a polypeptide having at least 70%, at least 75%, at least 80%, at least 85%, at least 90%, at least 95%, at least 98%, at least 99% or 100% identity to SEQ ID NO: 16; and d) a polypeptide having at least 70%, at least 75%, at least 80%, at least 85%, at least 90%, at least 95%, at least 98%, 99% identity or 100% identity to SEQ ID NO: 18; and e) a polypeptide having at least 70%, at least 75%, at least 80%, at least 85%, at least 90%, at least 95%, at least 98%, at least 99% or 100% identity to SEQ ID NO: 20.

Preferably, the polypeptide is obtained or obtainable from *Citrobacter* braakii.

An interesting aspect is directed to an isolated polypeptide having phytase activity, selected from the group consisting of a) a polypeptide having at least 70%, at least 75%, at least 80%, at least 85%, at least 90%, at least 95%, at least 98%, at least 99% or 100% identity to SEQ ID NO: 12;

b) a polypeptide having at least 70%, at least 75%, at least 80%, at least 85%, at least 90%, at least 95%, at least 98%, at least 99% or 100% identity to SEQ ID NO: 14;

c) a polypeptide having at least 70%, at least 75%, at least 80%, at least 85%, at least 90%, at least 95%, at least 98%, at least 99% or 100% identity to SEQ ID NO: 16;

d) a polypeptide having at least 70%, at least 75%, at least 80%, at least 85%, at least 90%, at least 95%, at least 98%, at least 99% or 100% identity to SEQ ID NO: 18; and e) a polypeptide having at least 70%, at least 75%, at least 80%, at least 85%, at least 90%, at least 95%, at least 98%, at least 99% or 100% identity to SEQ ID NO: 20;

wherein the polypeptide is pH and thermostable such that it comprises one or more of the following properties i. an unfolding temperature at pH 4 of at least 75° C.;
ii. an unfolding temperature at pH 3 of at least 70° C.; and
iii. an unfolding temperature at pH 2 of at least 55° C.

A further interesting aspect is directed to an isolated polypeptide having phytase activity, selected from the group consisting of a) a polypeptide having at least 70%, at least 75%, at least 80%, at least 85%, at least 90%, at least 95%, at least 98%, at least 99% or 100% identity to SEQ ID NO: 12;

b) a polypeptide having at least 70%, at least 75%, at least 80%, at least 85%, at least 90%, at least 95%, 98% identity, at least 99% identity or 100% identity to SEQ ID NO: 14;

c) a polypeptide having at least 70%, at least 75%, at least 80%, at least 85%, at least 90%, at least 95%, at least 98%, at least 99% identity or 100% identity to SEQ ID NO: 16;

d) a polypeptide having at least 70%, at least 75%, at least 80%, at least 85%, at least 90%, at least 95%, at least 98%, at least 99% or 100% identity to SEQ ID NO: 18; and e) a polypeptide having at least 70%, at least 75%, at least 80%, at least 85%, at least 90%, at least 95%, at least 98%, at least 99% or 100% identity to SEQ ID NO: 20;

wherein said polypeptide is acid stable such that it maintains a residual activity level above 90% after 24 hours at each of pH 2, 3, 4, 5, 6, 7 and 8.

Typically, the polypeptide comprises the alterations N31C/G52C/A99C/K141C/T177C/V199C as compared to SEQ ID NO: 2. Preferably, the polypeptide comprises the alterations N31C/G52C/A99C/K141C/T177C/V199C/N203L as compared to SEQ ID NO: 2. More typically, the polypeptide of the present invention comprises a substitution in one or more position(s) selected from the following: 30, 36, 43, 46, 57, 60, 64, 73, 79, 119, 121, 123, 130, 134, 138, 151, 155, 161, 162, 168, 176, 180, 184, 190, 207, 224, 230, 243, 273, 286, 336, 340, 358 and 375 using SEQ ID NO: 2 for numbering.

Position Numbering

The nomenclature used herein for defining amino acid positions is based on the amino acid sequence of the phytase derived from *Citrobacter braakii* ATCC 51113, the mature sequence of which is given in the sequence listing as SEQ ID NO: 2 (amino acids 1-411 of SEQ ID NO: 2). Accordingly, in the present context, the basis for numbering positions is SEQ ID NO: 2 starting with E1 and ending with E411.

When used herein the term "mature" part (or sequence) refers to that part of the polypeptide which is secreted by a cell which contains, as part of its genetic equipment, a polynucleotide encoding the polypeptide. In other words, the mature polypeptide part refers to that part of the polypeptide which remains after the signal peptide part, as well as a propeptide part, if any, has been cleaved off. The signal peptide part can be predicted by programs known in the art (e.g., SignalP). The expected signal peptide part of SEQ ID NO: 2 is included in the present sequence listing as SEQ ID NO: 8, which is encoded by SEQ ID NO: 7. SEQ ID NO: 2 is the expected mature part. Generally, the first amino acid of the mature part of an enzyme can be determined by N-terminal sequencing of the purified enzyme. Any difference between the signal peptide part and the mature part must then be due to the presence of a propeptide.

Modifications, such as Substitutions, Deletions, Insertions

A phytase variant can comprise various types of modifications relative to a template (i.e., a reference or comparative amino acid sequence such as SEQ ID NO: 2): An amino acid can be substituted with another amino acid; an amino acid can be deleted; an amino acid can be inserted; as well as any combination of any number of such modifications. In the present context the term insertion is intended to cover also N- and/or C-terminal extensions.

The general nomenclature used herein for a single modification is the following: XDcY, where "X" and "Y" independently designate a one-letter amino acid code, or a "*" (deletion of an amino acid), "D" designates a number, and "c" designates an alphabetical counter (a, b, c, and so forth), which is only present in insertions. Reference is made to the below Table which describes purely hypothetical examples of applying this nomenclature to various types of modifications.

Table

| Type | Description | Example |
|---|---|---|
| Substitution | X = Amino acid in template<br>D = Position in template<br>c empty<br>Y = Amino acid in variant | G80A<br>80<br>AALNNSIGVLGVAPSAELYAVKVLGASGSG<br>|||||||:|||||||||||||||||||||<br>AALNNSIAVLGVAPSAELYAVKVLGASGSG |

Table-continued

| Type | Description | Example |
|---|---|---|
| Insertion | X = "*"<br>D = Position in template before the insertion<br>c = "a" for first insertion at this position, "b" for next, etc. | *80aT *80bY *85aS<br>     80       85<br>AALNNSIG..VLGVA.PSAELYAVKVLGASG<br>\|\|\|\|\|\|\|\|  \|\|\|\|\|  \|\|\|\|\|\|\|\|\|\|\|\|\|\|\|<br>AALNNSIGTYVLGVASPSAELYAVKVLGASG |
| Deletion | X = Amino acid in template<br>D = Position in template<br>c empty<br>Y = "*" | V81*<br>  80<br>AALNNSIGVLGVAPSAELYAVKVLGASGSG<br>\|\|\|\|\|\|\|\| \|\|\|\|\|\|\|\|\|\|\|\|\|\|\|\|\|\|\|\|\|<br>AALNNSIG.LGVAPSAELYAVKVLGASGSG |
| N-terminal extension | Insertions at position "0". | *0aA *0bT *0cG<br>      1<br>...AQSVPWGISRVQ<br>   \|\|\|\|\|\|\|\|\|\|\|\|\|<br>ATGAQSVPWGISRVQ |
| C-terminal extension | Insertions after the N-terminal amino acid. | *275aS *275bT<br>                   270   275<br>ATSLGSTNLYGSGLVNAEAATR..<br>\|\|\|\|\|\|\|\|\|\|\|\|\|\|\|\|\|\|\|\|\|\|\|\|<br>ATSLGSTNLYGSGLVNAEAATRST |

As explained above, the position number ("D") is counted from the first amino acid residue of SEQ ID NO: 2.

Several modifications in the same sequence are separated by "/" (slash), e.g., the designation "1*/2*/3*" means that the amino acids in position number 1, 2, and 3 are all deleted, and the designation "104A/105F" means that the amino acid in position number 104 is substituted by A, and the amino acid in position number 105 is substituted by F.

Alternative modifications are separated by "," (comma), e.g., the designation "119R,K" means that the amino acid in position 119 is substituted with R or K.

The commas used herein in various other enumerations of possibilities mean what they usually do grammatically, viz. often and/or, e.g., the first comma in the listing "53V,Q, 121D, and/or 167Q" denotes an alternative (V or Q), whereas the two next commas should be interpreted as and/or options: 53 V or Q, and/or 121D, and/or 167Q.

In the present context, "at least one" (e.g., modification) means one or more, e.g., 1, 2, 3, 4, 5, 6, 7, 8, 9, or 10 modifications; or 12, 14, 15, 16, 18, 20, 22, 24, 25, 28, or 30 modifications; and so on, up to a maximum number of modifications of 125, 130, 140, 150, 160, 170, 180, 190, or of 200. The phytase variants of the invention, however, still have to be at least 74% identical to SEQ ID NO: 2, this percentage being determined as described above.

A substitution or extension without any indication of what to substitute or extend with refers to the insertion of any natural, or non-natural, amino acid, except the one that occupies this position in the template.

Identifying Corresponding Position Numbers

As explained above, the mature phytase of *Citrobacter braakii* ATCC 51113 (SEQ ID NO: 2) is used as the standard for position numbering and, thereby, also for the nomenclature.

For another phytase, in particular a phytase variant of the invention, the position corresponding to position D in SEQ ID NO: 2 is found by aligning the two sequences as specified above in the section entitled "Phytase polypeptides, percentage of identity". From the alignment, the position in the sequence of the invention corresponding to position D of SEQ ID NO: 2 can be clearly and unambiguously identified (the two positions on top of each other in the alignment).

FIG. 1 of the present invention is an example of an alignment of the phytase of SEQ ID NO: 2 and the phytase of SEQ ID NO: 9, and the example illustrates how corresponding positions in these two backbones are identified.

Below some additional, purely hypothetical, examples are included which are derived from the above Table which in the third column includes a number of alignments of two sequences.

Consider the third cell in the first row of the above Table: The upper sequence is the template, the lower the variant. Position number 80 refers to amino acid residue G in the template. Amino acid A occupies the corresponding position in the variant. Accordingly, this substitution is designated G80A.

Consider now the third cell in the second row of the above Table: The upper sequence is again the template and the lower the variant. Position number 80 again refers to amino acid residue G in the template. The variant has two insertions, viz. TY, after G80 and before V81 in the template. Whereas the T and Y of course would have their own "real" position number in the variant amino acid sequence, for the present purposes we always refer to the template position numbers, and accordingly the T and the Y are said to be in position number 80a and 80b, respectively.

Finally, consider the third cell in the last row of the above Table: Position number 275 refers to the last amino acid of the template. A C-terminal extension of ST are said to be in position number 275a and 275b, respectively, although, again, of course they have their own "real" position number in the variant amino acid sequence.

Modified Properties, Reference Phytase

In a particular embodiment, the method of the invention for producing phytase variants provides variants having modified, preferably improved, properties.

The terms "modified" and "improved" imply a comparison with another phytase. Examples of such other, reference, or comparative, phytases are: SEQ ID NO: 2 and/or SEQ ID NO: 6. Still further examples of reference phytases may be SEQ ID NO: 3, and/or SEQ ID NO: 4. A still further example of a reference phytase may be SEQ ID NO: 9, and variants thereof.

Non-limiting examples of properties that are modified, preferably improved, are the following: Thermostability, pH profile, specific activity, performance in animal feed, pelleting stability, protease-sensibility, and/or glycosylation pattern. The phytase variants produced by the method of the invention exhibits improved thermostability and may also have a modified, preferably improved, temperature profile, and/or it may incorporate a change of a potential protease cleavage site.

Thermal Performance
Temperature-Stability

Temperature stability may be determined as described in WO 2011/117396, Example 3 by determining the activity during 30 minutes incubation at temperatures from 60° C. or higher and comparing with a reference experiment performed at 37° C.

Thermostability

Thermostability may be determined as described in WO 2011/117396, Example 4, i.e., using DSC measurements to determine the denaturation temperature, Td, of the purified phytase protein. The Td is indicative of the thermostability of the protein: The higher the Td, the higher the thermostability. Accordingly, in a preferred embodiment, the phytase of the invention has a Td which is higher than the Td of a reference phytase, wherein Td is determined on purified phytase samples (preferably with a purity of at least 90% or 95%, determined by SDS-PAGE).

Heat-Stability

Heat stability may be determined as described in WO 2011/117396, Example 5 by determining the temperature/activity profile of the variant phytases.

Steam Stability

Steam stability may be determined as described in WO 2011/117396, Example 7 by determining the residual activity of phytase molecules after steam treatment at 85° C. or 90° C. for a short time.

Pelleting Stability

Pelleting stability may be determined as described in WO 2011/117396, Example 8 by using enzyme granulate pre-mixed with feed. This premix is mixed with feed. From the mixer the feed is conditioned with steam to 95° C. After conditioning the feed is pressed to pellets and the residual activity determined.

In preferred embodiments, the thermal properties such as heat-stability, temperature stability, thermostability, steam stability, and/or pelleting stability as provided by the residual activity, Td or other parameter of the phytase of the invention is higher than the corresponding value, such as the residual activity or Td, of the phytase of SEQ ID NO: 2, more preferably at least 101% thereof, or at least 102%, 103%, 104%, 105%, 106%, 107%, 108%, 109%, or at least 110% thereof. Even more preferably, the value of the parameter, such as residual activity or Td, of the phytase of the invention is at least 120%, 130%, 140%, 150%, 160%, 170%, 180%, or at least 190% of the value for the phytase of SEQ ID NO: 2.

In still further particular embodiments, the thermostable phytase of the invention has a melting temperature, Tm (or a denaturation temperature, Td), as determined using Differential Scanning Calorimetry (DSC) as described in the Examples (i.e., in 20 mM sodium acetate, pH 4.0), of at least 50° C. In still further particular embodiments, the Tm is at least 51, 52, 53, 54, 55, 56, 57, 58, 59, 60, 61, 62, 62.5. 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C. DSC measurements may also be performed as described in the Examples.

Temperature Profile/Temperature Stability

Whether or not a phytase of the invention has a modified temperature profile as compared to a reference phytase may be determined as described in WO 2011/117396, Example 5. Accordingly, in a particular embodiment the phytase of the invention has a modified temperature profile as compared to a reference phytase, wherein the temperature profile is determined as phytase activity as a function of temperature on sodium phytate at pH 5.5 in the temperature range of 20-90° C. (in 10° C. steps). A preferred buffer is in 0.25 M Na-acetate buffer pH 5.5. The activity at each temperature is preferably indicated as relative activity (in %) normalized to the value at optimum temperature. The optimum temperature is that temperature within the tested temperatures (i.e., those with 5-10° C. jumps) where the activity is highest.

Performance in Animal Feed

In a particular embodiment the phytase of the invention has an improved performance in animal feed as compared to a reference phytase. The performance in animal feed may be determined by the in vitro model. Accordingly, in a preferred embodiment the phytase of the invention has an improved performance in animal feed, wherein the performance is determined in an in vitro model, by preparing feed samples composed of 30% soybean meal and 70% maize meal with added $CaCl_2$ to a concentration of 5 g calcium per kg feed; pre-incubating them at 40° C. and pH 3.0 for 30 minutes followed by addition of pepsin (3000 U/g feed) and phytase; incubating the samples at 40° C. and pH 3.0 for 60 minutes followed by pH 4.0 for 30 minutes; stopping the reactions; extracting phytic acid and inositol-phosphates by addition of HCl to a final concentration of 0.5 M and incubation at 40° C. for 2 hours, followed by one freeze-thaw cycle and 1 hour incubation at 40° C.; separating phytic acid and inositol-phosphates by high performance ion chromatography; determining the amount of residual phytate phosphorus (IP6-P); calculating the difference in residual IP6-P between the phytase-treated and a non-phytase-treated blank sample (this difference is degraded IP6-P); and expressing the degraded IP6-P of the phytase of the invention relative to degraded IP6-P of the reference phytase.

The phytase of the invention and reference phytase are dosed in the same amount, preferably based on phytase activity units (FYT). A suitable dosage is 100-5000 FYT/kg feed, such as 125 to 4000 FTY/kg feed, such as 125 to 3000 FTY/kg. The phytases may be dosed in the form of purified phytases, or in the form of fermentation supernatants. Purified phytases preferably have a purity of at least 95%, as determined by SDS-PAGE.

In preferred embodiments, the degraded IP6-P value of the purified phytase of the invention, relative to the degraded IP6-P value of the reference phytase, is at least 101%, or at least 102%, 103%, 104%, 105%, 110%, 115%, or at least 120%. In still further preferred embodiments, the degraded IP6-P value of the purified phytase of the invention, relative to the degraded IP6-P value of the reference phytase, is at least 125%, 130%, 140%, 150%, 160%, 170%, 180%, 190%, or at least 200%. Preferably, the degraded IP6-P value of the phytase of the invention, relative to the degraded IP6-P value of the SEQ ID NO: 2 phytase, is at least 105%, 110%, 113%, 115%, 120%, 125%, or at least 130%.

The relative performance of a phytase of the invention may also be calculated as the percentage of the phosphorous released by the reference phytase.

In a still further particular embodiment, the relative performance of the phytase of the invention may be calculated as the percentage of the phosphorous released by the phytase of the invention, relative to the amount of phosphorous released by the reference phytase.

In still further particular embodiments, the relative performance of the phytase of the invention is at least 105%, preferably at least 110, 120, 130, 140, 150, 160, 170, 180, 190, or at least 200%.

Steam Stability

Thermostability is an important parameter, but associated with that also steam stability is important. In this respect reference is made to WO 2011/117396, Example 8.

Low-Allergenic Variants

In a specific embodiment, the phytase variants produced by the method of the present invention are (also) low-allergenic variants, designed to invoke a reduced immunological response when exposed to animals, including man. The term immunological response is to be understood as any reaction by the immune system of an animal exposed to the phytase variant. One type of immunological response is an allergic response leading to increased levels of IgE in the exposed animal. Low-allergenic variants may be prepared using techniques known in the art. For example the phytase variant may be conjugated with polymer moieties shielding portions or epitopes of the phytase variant involved in an immunological response. Conjugation with polymers may involve in vitro chemical coupling of polymer to the phytase variant, e.g., as described in WO 96/17929, WO 98/30682, WO 98/35026, and/or WO 99/00489. Conjugation may in addition or alternatively thereto involve in vivo coupling of polymers to the phytase variant. Such conjugation may be achieved by genetic engineering of the nucleotide sequence encoding the phytase variant, inserting consensus sequences encoding additional glycosylation sites in the phytase variant and expressing the phytase variant in a host capable of glycosylating the phytase variant, see, e.g., WO 00/26354. Another way of providing low-allergenic variants is genetic engineering of the nucleotide sequence encoding the phytase variant so as to cause the phytase variants to self-oligomerize, effecting that phytase variant monomers may shield the epitopes of other phytase variant monomers and thereby lowering the antigenicity of the oligomers. Such products and their preparation are described in, e.g., WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the phytase variant by known gene manipulation techniques such as site directed mutagenesis (see, e.g., WO 00/26230, WO 00/26354 and/or WO 00/22103) and/or conjugation of a polymer may be done in sufficient proximity to the epitope for the polymer to shield the epitope.

Daily BW Gain Per Bird (BW Gain) and Feed Conversion Ratio (FCR)

Daily Body weight gain per bird (BW gain) and feed conversion ratio (FCR) were calculated as follows:
  Body weight gain per bird: difference between BW per bird at the end and at the beginning of a study
  Daily BWgain: difference between BW per bird at the end and at the beginning of the study divided by the number of days
  FCR: total feed consumption of a pen divided by total BW gain of that pen (total BW gain=total BW at the end+weight of removals and losses−total BW at the beginning).
  FI=FCR*WG Nucleic Acid Sequences and Constructs The present invention also relates to nucleic acid sequences comprising a nucleic acid sequence which encodes a phytase variant of the invention.

An aspect of the invention is directed to a method of preparing a recombinant polypeptide having phytase activity comprising:
  (a) cultivating a recombinant host cell comprising an exogenous polynucleotide selected from the group consisting of
    a. a polynucleotide having at least 70%, at least 75%, at least 80%, at least 85%, at least 90%, at least 95%, at least 98%, at least 99% or 100% identity to SEQ ID NO: 13;
    b. a polynucleotide having at least 70%, at least 75%, at least 80%, at least 85%, at least 90%, at least 95%, at least 98%, at least 99% or 100% identity to SEQ ID NO: 15;
    c. a polynucleotide having at least 70%, at least 75%, at least 80%, at least 85%, at least 90%, at least 95%, at least 98%, at least 99% or 100% identity to SEQ ID NO: 17;
    d. a polynucleotide having at least 70%, at least 75%, at least 80%, at least 85%, at least 90%, at least 95%, at least 98%, at least 99% identity or 100% identity to SEQ ID NO: 19;
    e. a polynucleotide having at least 70%, at least 75%, at least 80%, at least 85%, at least 90%, at least 95%, at least 98%, at least 99% or 100% identity to SEQ ID NO: 21;
  wherein the polynucleotide is expressed and the polypeptide is produced;
  (b) optionally isolating the polypeptide; and
  (c) optionally recovering the polypeptide.

An alternate aspect is directed to method of producing a polypeptide of the present invention, said method comprising:
  (a) cultivating a recombinant host cell comprising an exogenous polynucleotide encoding the polypeptide having phytase activity selected from the group consisting of
    a. a polypeptide having at least 70%, at least 75%, at least 80%, at least 85%, at least 90% or at least 95%, at least 98%, at least 99% or 100% identity to SEQ ID NO: 12;
    b. a polypeptide having at least 70%, at least 75%, at least 80%, at least 85%, at least 90% or at least 95%, at least 98%, at least 99% or 100% identity to SEQ ID NO: 14;
    c. a polypeptide having at least 70%, at least 75%, at least 80%, at least 85%, at least 90% or at least 95%, at least 98%, at least 99% or 100% identity to SEQ ID NO: 16;
    d. a polypeptide having at least 70%, at least 75%, at least 80%, at least 85%, at least 90% or at least 95%, at least 98%, at least 99% or 100% identity to SEQ ID NO: 18; and
    e. a polypeptide having at least 70%, at least 75%, at least 80%, at least 85%, at least 90%, at least 95%, at least 98%, at least 99% or 100% identity to SEQ ID NO: 20;
  wherein the polynucleotide is expressed and the polypeptide is produced;
  (b) optionally isolating the polypeptide; and
  (c) optionally recovering the polypeptide.

Typically, in the methods of the invention, the polypeptide having phytase activity comprises the substitutions N31C/G52C/A99C/K141C/T177C/V199C as compared to SEQ ID NO: 2. Preferably, in the methods of the invention, the polypeptide having phytase activity comprises the substitutions N31C/G52C/A99C/K141C/T177C/V199C/N203L as compared to SEQ ID NO: 2. More typically, the polypeptide further comprises a substitution in one or more position(s) selected from the following: 30, 36, 43, 46, 57, 60, 64, 73, 79, 119, 121, 123, 130, 134, 138, 151, 155, 161, 162, 168, 176, 180, 184, 190, 207, 224, 230, 243, 273, 286, 336, 340, 358 and 375 using SEQ ID NO: 2 for numbering.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into a template phytase coding sequence or a subsequence thereof, wherein the mutant nucleic acid sequence encodes a variant phytase. The introduction of a mutation into the nucleic acid sequence to exchange one nucleotide for another nucleotide may be accomplished by any of the methods known in the art, e.g., by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the phytase enzyme by any technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent phytase in question. This may, e.g., be advantageous when certain regions of the enzyme have been identified to be of particular importance for a given property of the enzyme.

Alternative methods for providing variants of the invention include gene shuffling, e.g., as described in WO 95/22625 or in WO 96/00343, and the consensus derivation process as described in EP 897985.

Nucleic Acid Constructs

A nucleic acid construct comprises a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" denotes herein a configuration in which a control sequence is placed at an appropriate position relative to the coding sequence of the polynucleotide sequence such that the control sequence directs the expression of the coding sequence of a polypeptide.

When used herein the term "coding sequence" (CDS) means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression Vector

The term "expression" includes any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide of the invention, and which is operably linked to additional nucleotides that provide for its expression.

A nucleic acid sequence encoding a phytase variant of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a phytase variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

The phytase variant may also be co-expressed together with at least one other enzyme of animal feed interest, such as a phytase, phosphatase, xylanase, galactanase, alpha-galactosidase, protease, phospholipase, amylase, and/or beta-glucanase. The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The phytase variant may also be expressed as a fusion protein, i.e., that the gene encoding the phytase variant has been fused in frame to the gene encoding another protein. This protein may be another enzyme or a functional domain from another enzyme.

Host Cells

The term "host cell", as used herein, includes any cell type which is susceptible to transformation, transfection, transduction, and the like with a nucleic acid construct comprising a polynucleotide of the present invention.

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication.

The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus*, *Bacillus licheniformis*, *Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F.A., Passmore, S. M., and Davenport, R.R., eds, Soc. App. Bacteriol. Symposium Series No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Pichia pastoris*, *Pichia methanolica*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Coprinus*, *Coriolus*, *Cryptococcus*, *Filobasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarchochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceripo-*

*riopsis subrufa*, or *Ceriporiopsis subvermispora*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention relates to methods for producing a phytase variant comprising (a) cultivating a host cell under conditions conducive for production of the phytase; and (b) recovering the phytase.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Compositions and Uses

In still further aspects, the present invention relates to compositions comprising a polypeptide of the present invention, as well as methods of using these.

The polypeptide compositions may be prepared in accordance with methods known in the art and may be in the form of a liquid or a dry composition. The polypeptide to be included in the composition may be stabilized in accordance with methods known in the art.

For a liquid formulation, the formulating agent may comprise a polyol (such as, e.g., glycerol, ethylene glycol or propylene glycol), a salt (such as, e.g., sodium chloride, sodium benzoate, potassium sorbate) or a sugar or sugar derivative (such as, e.g., dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate. The formulating agent may comprise a salt (organic or inorganic zinc, sodium, potassium or calcium salts such as, e.g., calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as, e.g., sucrose, dextrin, glucose, lactose, sorbitol).

In an embodiment, the solid composition is in the form of granulates or microgranulates. The granule may have a matrix structure where the components are mixed homogeneously. However, the granule typically comprises a core particle and one or more coatings, which typically are salt and/or wax coatings. Examples of waxes are polyethylene glycols; polypropylenes; Carnauba wax; Candelilla wax; bees wax; hydrogenated plant oil or animal tallow such as hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; micro-crystalline wax; paraffin's; and fatty acids, such as hydrogenated linear long chained fatty acids and derivatives thereof. A preferred wax is palm oil or hydrogenated palm oil. The core particle can either be a homogeneous blend of phytase of the invention optionally combined with one or more additional enzymes and optionally together with one or more salts or an inert particle with the phytase of the invention optionally combined with one or more additional enzymes applied onto it.

In an embodiment, the material of the core particles are selected from the group consisting of inorganic salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as, e.g., sucrose, dextrin, glucose, lactose, sorbitol), sugar or sugar derivative (such as, e.g., sucrose, dextrin, glucose, lactose, sorbitol), small organic molecules, starch, flour, cellulose and minerals and clay minerals (also known as hydrous aluminium phyllosilicates). In a preferred embodiment, the core comprises a clay mineral such as kaolinite or kaolin.

The salt coating is typically at least 1 μm thick and can either be one particular salt or a mixture of salts, such as $Na_2SO_4$, $K_2SO_4$, $MgSO_4$ and/or sodium citrate. Other examples are those described in, e.g., WO 2008/017659, WO 2006/034710, WO 97/05245, WO 98/54980, WO 98/55599, WO 00/70034 or polymer coating such as described in WO 01/00042.

In another embodiment, the composition is a solid composition comprising the phytase of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate and calcium carbonate. In a preferred embodiment, the solid composition is in granulated form. In an embodiment, the solid composition is in granulated form and comprises a core particle, an enzyme layer comprising the phytase of the invention and a salt coating.

In a further embodiment, the formulating agent is selected from one or more of the following compounds: glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose. In a preferred embodiment, the formulating agent is selected from one or more of the following compounds: 1,2-propylene glycol, 1,3-propylene glycol, sodium sulfate, dextrin, cellulose, sodium thiosulfate, kaolin and calcium carbonate.

The phytase of the invention can be used for degradation, in any industrial context, of, for example, phytate, phytic acid, and/or the mono-, di-, tri-, tetra- and/or penta-phosphates of myo-inositol. It is well known that the phosphate moieties of these compounds chelates divalent and trivalent cations such as metal ions, i.e., the nutritionally essential ions of calcium, iron, zinc and magnesium as well as the trace minerals manganese, copper and molybdenum. Besides, the phytic acid also to a certain extent binds proteins by electrostatic interaction.

Accordingly, preferred uses of the polypeptides or polynucleotides of the invention are in animal feed preparations (including human food) or in additives for such preparations.

In a particular embodiment, the polypeptide or polynucleotide of the invention can be used for improving the nutritional value of an animal feed. Non-limiting examples of improving the nutritional value of animal feed (including human food), are: improving feed digestibility; promoting growth of the animal; improving feed utilization; improving bio-availability of proteins; increasing the level of digestible phosphate; improving the release and/or degradation of phytate; improving bio-availability of trace minerals; improving bio-availability of macro minerals; eliminating the need for adding supplemental phosphate, trace minerals, and/or macro minerals; and/or improving egg shell quality. The nutritional value of the feed is therefore increased, and the growth rate and/or weight gain and/or feed conversion (i.e., the weight of ingested feed relative to weight gain) of the animal is/are improved. In another particular embodiment, the polypeptide or polynucleotide of the invention can be used for improving nutrient retention, and/or nutrient digestibility in an animal.

Furthermore, the polypeptide or polynucleotide of the invention can be used for reducing phytate level of manure.

Animals, Animal Feed, and Animal Feed Additives

The term animal includes all animals, including human beings. Examples of animals are non-ruminants, and ruminants. Ruminant animals include, for example, animals such as sheep, goat, and cattle, e.g., cow such as beef cattle and dairy cows. In a particular embodiment, the animal is a non-ruminant animal. Non-ruminant animals include monogastric animals, e.g., pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

The term feed or feed composition means any compound, preparation, mixture, or composition suitable for, or intended for intake by an animal.

In the use according to the invention the polypeptide or polynucleotide can be fed to the animal before, after, or simultaneously with the diet. The latter is preferred.

The invention further relates to a method of enhancing one or more of the group selected from growth rate, phosphorus digestibility, whole-body phosphorus retention and/or reducing the FCR in an animal, said method comprising feeding the animal the phytase as defined herein. The method of the invention typically comprises phytase supplementation doses of 100-5000 FYT/kg feed, such as 125 to 4000 FTY/kg feed, such as 125 to 3000 FTY/kg feed.

The invention is further directed to a method of enhancing the growth rate or reducing the FCR in a mono-gastric animal, said method comprising feeding the animal the phytase as defined herein. The method of the invention typically comprises phytase supplementation doses of 100-5000 FYT/kg feed, such as 125 to 4000 FTY/kg feed, such as 125 to 3000 FTY/kg feed.

The invention is further directed to a method of enhancing the growth rate or reducing the FCR in an animal selected from the group consisting of poultry, swine, fish or crustacean, said method comprising feeding the animal the phytase as defined herein. The method of the invention typically comprises phytase supplementation doses of 100-5000 FYT/kg feed, such as 125 to 4000 FTY/kg feed, such as 125 to 3000 FTY/kg feed.

The invention is further directed to a method of enhancing the growth rate or reducing the FCR in poultry, said method comprising feeding the poultry the phytase as defined herein. The poultry may be typically selected from the group consisting of turkeys, ducks and chickens (including but not limited to broiler chicks, layers), typically chickens, particularly broiler chickens and layer chickens. The method of the invention typically comprises phytase supplementation doses of 100-5000 FYT/kg feed, such as 125 to 4000 FTY/kg feed, such as 125 to 3000 FTY/kg feed.

The invention is further directed to a method of enhancing the growth rate or reducing the FCR in swine, said method comprising feeding the swine the phytase as defined herein. The method of the invention typically comprises phytase supplementation doses of 100-5000 FYT/kg feed, such as 125 to 4000 FTY/kg feed, such as 125 to 3000 FTY/kg feed.

The invention is further directed to a method of enhancing the growth rate or reducing the FCR in fish or crustaceans said method comprising feeding the fish or crustaceans the phytase as defined herein. The fish may typically be selected from the group consisting of salmon, trout, tilapia, catfish, seabream such as gilthead seabream, bass, such as seabass, and carp. The crustaceans may typically be selected from the group consisting of lobster, crab, crayfish, krill, shrimp and prawn. The method of the invention typically comprises phytase supplementation doses of 100-5000 FYT/kg feed, such as 125 to 4000 FTY/kg feed, such as 125 to 3000 FTY/kg feed.

In a particular embodiment, the polypeptide, in the form in which it is added to the feed, or when being included in a feed additive, is substantially pure. In a particular embodiment it is well-defined. The term "well-defined" means that the phytase preparation is at least 50% pure as determined by Size-exclusion chromatography (see Example 12 of WO 01/58275). In other particular embodiments the phytase preparation is at least 60, 70, 80, 85, 88, 90, 92, 94, or at least 95% pure as determined by this method.

A substantially pure, and/or well-defined polypeptide preparation is advantageous. For instance, it is much easier to dose correctly to the feed a polypeptide that is essentially free from interfering or contaminating other polypeptides. The term dose correctly refers in particular to the objective of obtaining consistent and constant results, and the capability of optimising dosage based upon the desired effect.

For the use in animal feed, however, the phytase polypeptide of the invention need not be that pure; it may, e.g., include other polypeptides, in which case it could be termed a phytase preparation.

The phytase preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original polypeptide preparation, whether used according to (a) or (b) above.

Polypeptide preparations with purities of this order of magnitude are in particular obtainable using recombinant methods of production, whereas they are not so easily obtained and also subject to a much higher batch-to-batch variation when the polypeptide is produced by traditional fermentation methods.

Such polypeptide preparation may of course be mixed with other polypeptides.

The polypeptide can be added to the feed in any form, be it as a relatively pure polypeptide, or in admixture with other components intended for addition to animal feed, i.e., in the form of animal feed additives, such as the so-called premixes for animal feed.

In a further aspect the present invention relates to compositions for use in animal feed, such as animal feed, and animal feed additives, e.g., premixes.

A further aspect of the invention is directed to an animal feed additive comprising the phytase, as defined herein. The animal feed additive may be for use in a feed for a monogastric or ruminant, typically a monogastric animal. The animal feed additive is for use in a animal feed for an animal typically selected from the group consisting poultry, swine, fish or crustacean. The animal feed additive typically comprises the phytase in amount 100-5000 FYT/kg feed, such as 125 to 4000 FTY/kg feed, such as 125 to 3000 FTY/kg feed.

The invention is further directed to an animal feed additive comprising the phytase, as defined herein, for use in a feed for poultry. The feed additive for poultry is typically for feed for poultry selected from the group consisting of turkeys, ducks and chickens (including but not limited to broiler chicks, layers), typically chickens, particularly broiler chickens and layer chickens.

The invention is further directed to an animal feed additive comprising the phytase, as defined herein, for use in a feed for swine.

The invention is further directed to an animal feed additive comprising the phytase, as defined herein, for use in a feed for fish or crustaceans. The fish is typically be selected from the group consisting of salmon, trout, tilapia, catfish, seabream such as gilthead seabream, bass, such as seabass, and carp. The crustaceans may typically be selected from the group consisting of lobster, crab, crayfish, krill, shrimp and prawn.

Apart from the polypeptide of the invention, the animal feed additives of the invention contain at least one fat-soluble vitamin, and/or at least one water soluble vitamin, and/or at least one trace mineral. The feed additive may also contain at least one macro mineral.

Further, optional, feed-additive ingredients are colouring agents, e.g., carotenoids such as beta-carotene, astaxanthin, and lutein; aroma compounds; stabilisers; antimicrobial peptides; polyunsaturated fatty acids; reactive oxygen generating species; and/or at least one other polypeptide selected from amongst phytase (EC 3.1.3.8 or 3.1.3.26); phosphatase (EC 3.1.3.1; EC 3.1.3.2; EC 3.1.3.39); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

As demonstrated in Example 14 in feeding broilers, a combination of a protease and the phytase of the invention increased protein digestibility by 0.7 to 1.6%, protein retention by 0.9 to 4.4% and energy retention by 0.6 to 1.3%. This resulted in an improvement in body weight gain (BWG) by 2.3 or 3.7% and feed conversion ratio by 4.6 or 2.8%. Accordingly, an embodiment of the invention is directed to an animal feed or animal feed additive comprising the phytase of the invention and a protease. The protease may be selected from the proteases comprised in Ronozyme ProAct™, Ronozyme ProAct360™, Axtra® PRO, Avizyme 1502, Cibenza, Enolzyme, Poultrygrow-250 or Aquagrow-175, preferably selected from Ronozyme ProAct™, Ronozyme ProAct360™, Axtra® PRO and Cibenza, more preferably selected from Ronozyme ProAct™ Ronozyme ProAct360™, most preferably Ronozyme ProAct360™. The invention is further directed to an animal feed or animal feed additive comprising the phytase of the invention and a protease selected from the group consisting of a protease having at least 70% sequence identity, to SEQ ID NO:1 or SEQ ID NO: 2 of WO0158276 and of a protease having at least 75% sequence identity to SEQ ID NO:3 of WO 2019/043191. In one embodiment, the protease is selected from a protease having at least 75% sequence identity, such as at least 80% sequence identity, such as at least 85% sequence identity, such as at least 90% sequence identity, such as at least 95% sequence identity, such as at least 98% sequence identity, such as at least 99% sequence identity, such as 100% sequence identity to a protease comprising the sequence of SEQ ID NO: 22 of the present invention.

Typically, the animal feed comprising the protease and the phytase comprises 100 to 5,000 FYT/kg of the phytase in the feed, such as 500 to 2000 FYT/kg. Typically the the animal feed comprising the protease and the phytase comprises 10,000 to 50,000 U/kg of the protease in the feed, such as 15,000 to 35,000 U/kg typically 20,000 to 40,000 U/kg.

In a particular embodiment, these other polypeptides are well-defined (as defined above for phytase preparations).

The phytase of the invention may also be combined with other phytases, for example ascomycete phytases such as *Aspergillus* phytases, for example derived from *Aspergillus ficuum, Aspergillus niger*, or *Aspergillus awamori*; or basidiomycete phytases, for example derived from *Peniophora lycii, Agrocybe pediades, Trametes pubescens*, or *Paxillus involutus*; or derivatives, fragments or variants thereof which have phytase activity.

Thus, in preferred embodiments of the use in animal feed of the invention, and in preferred embodiments of the animal feed additive and the animal feed of the invention, the phytase of the invention is combined with such phytases.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and polypeptides such as an oxidase, an oxygenase or a syntethase.

Usually fat- and water-soluble vitamins, as well as trace minerals form part of a so-called premix intended for addition to the feed, whereas macro minerals are usually separately added to the feed. Either of these composition types, when enriched with a polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g., vitamin K3.

Examples of water-soluble vitamins are vitamin B12, biotin and choline, vitamin E1, vitamin B2, vitamin B6, niacin, folic acid and panthothenate, e.g., Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one polypeptide of the present invention.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington DC).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soybean meal, lupin meal and rapeseed meal.

In a particular embodiment, the vegetable protein source is material from one or more plants of the family Fabaceae, e.g., soybean, lupine, pea, or bean.

In another particular embodiment, the vegetable protein source is material from one or more plants of the family Chenopodiaceae, e.g., beet, sugar beet, spinach or *quinoa*.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can be, e.g., manufactured as mash feed (non pelleted) or pelleted feed. Typically, the milled feed-stuffs are mixed and sufficient amounts of essential vitamins and minerals are added according to the specifications for the species in question. Polypeptides can be added as solid or liquid polypeptide formulations. For example, a solid polypeptide formulation is typically added before or during the mixing step; and a liquid polypeptide preparation is typically added after the pelleting step. The polypeptide may also be incorporated in a feed additive or premix.

The final polypeptide concentration in the diet is within the range of 0.01-200 mg polypeptide protein per kg diet, for example in the range of 5-30 mg polypeptide protein per kg animal diet.

The phytase of the invention should of course be applied in an effective amount, i.e., in an amount adequate for improving solubilisation and/or improving nutritional value of feed. It is at present contemplated that the polypeptide is administered in one or more of the following amounts (dosage ranges): 0.01-200; 0.01-100; 0.5-100; 1-50; 5-100; 10-100; 0.05-50; or 0.10-10 —all these ranges being in mg phytase polypeptide protein per kg feed (ppm).

For determining mg phytase polypeptide protein per kg feed, the phytase is purified from the feed composition, and the specific activity of the purified phytase is determined using a relevant assay. The phytase activity of the feed composition as such is also determined using the same assay, and on the basis of these two determinations, the dosage in mg phytase protein per kg feed is calculated.

The same principles apply for determining mg phytase polypeptide protein in feed additives. Of course, if a sample is available of the phytase used for preparing the feed additive or the feed, the specific activity is determined from this sample (no need to purify the phytase from the feed composition or the additive).

Methods for Producing Fermentation Products

Yet another aspect of the present invention relates to the methods for producing a fermentation product, such as, e.g., ethanol, beer, wine, distillers dried grains (DDG), wherein the fermentation is carried out in the presence of a phytase produced by the present invention. Examples of fermentation processes include, for example, the processes described in WO 01/62947. Fermentation is carried out using a fermenting microorganism, such as, yeast.

In a particular embodiment, the present invention provides methods for producing fermentation product, comprising (a) fermenting (using a fermenting microorganism, such as yeast) a carbohydrate containing material (e.g., starch) in the presence of a phytase of the present invention and (b) producing the fermentation product from the fermented carbohydrate containing material.

In a particular embodiment, the present invention provides methods for producing ethanol, comprising fermenting (using a fermenting microorganism, such as yeast) a carbohydrate containing material (e.g., starch) in the presence of a phytase of the present invention and producing or recovering ethanol from the fermented carbohydrate containing material.

In another embodiment, the present invention provides methods for producing ethanol comprising a) hydrolyzing starch, e.g., by a liquefaction and/or saccharification process, a raw starch hydrolysis process, b) fermenting the resulting starch in the presence of a phytase of the present invention, and c) producing ethanol.

The phytase may be added to the fermentation process at any suitable stage and in any suitable composition, including alone or in combination with other enzymes, such as, one or more alpha-amylases, glucoamylases, proteases, and/or cellulases.

In another embodiment, the present invention provides methods for producing ethanol comprising hydrolyzing biomass, and fermenting (using a fermenting microorganism, such as yeast) the resulting biomass in the presence of a phytase of the present invention.

Plants

The present invention also relates to plants, e.g., a transgenic plant, plant part, or plant cell, comprising a polynucleotide of the present invention so as to express and produce the phytase in recoverable quantities. The phytase may be recovered from the plant or plant part. Alternatively, the plant or plant part containing the phytase may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a phytase may be constructed in accordance with methods known in the art. In short, the plant or plant cell is constructed by incorporating one or more expression constructs encoding a phytase into the plant host genome or chloroplast genome and propagating the resulting modified plant or plant cell into a transgenic plant or plant cell.

The expression construct is conveniently a nucleic acid construct that comprises a polynucleotide encoding a phytase operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the phytase is desired to be expressed. For instance, the expression of the gene encoding a phytase may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a phytase in the plant. For instance, the promoter enhancer element may be an intron that is placed between the promoter and the polynucleotide encoding a phytase. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a phytase can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a phytase of the present invention comprising: (a) cultivating a transgenic plant or a plant cell comprising a polynucleotide encoding the phytase under conditions conducive for production of the phytase; and (b) recovering the phytase.

The invention is further defined in the following paragraphs:

1. A phytase variant which has at least 70%, at least 75%, at least 80%, at least 85%, at least 90%, at least 95%, at least 97%, at least 98%, or at least 99% identity to SEQ ID NO: 2 and which comprises the alterations N31C/G52C/A99C/K141C/T177C/V199C/N203L as compared to SEQ ID NO: 2 and further comprises a substitution in one or more position(s) selected from the following: 30, 36, 43, 46, 57, 60, 64, 73, 79, 119, 121, 123, 130, 134, 138, 151, 155, 161, 162, 168, 176, 180, 184, 190, 207, 224, 230, 243, 273, 286, 336, 340, 358 and 375 using SEQ ID NO: 2 for numbering.

2. The variant of paragraph 1, comprising substitutions in the positions: 57, 73, 121, 134, 155, 207 and 273.

3. The variant of paragraph 2, further comprising substitutions in the positions: 36, 60, 64, 73, 119, 130, 138,161, 162, 168, 176, 180, 184, 190, 224, 230, 243, 336 and 340.

4. The variant of any of paragraphs 1-3, where the substitutions are selected among: 30Q, 36A, 43C, 46C, 57Y, 60H, 64Q, 73P, 79Q, 119P, 121P, 123C, 130T,C, 134Q, 138A, 151S, 155F, 161T, 162A, 168R 176P, 180N, 184Q, 190T, 207T, 224Q, 230E, 243N, 273L, 286S, 336R, 340L,P, 358Q and 375K.

5. The variant of any of paragraphs 1-4, comprising the substitutions 31C/52C/57Y/73P/99C/121P/134Q/141C/155F/177C/199C/203L/207T/273L.

6. The variant of paragraph 5, selected among variants comprising the substitutions selected from the group consisting of:

31C/52C/57Y/73P/99C/121P/134Q/141C/155F/177C/
  199C/203L/207T/273L;
31C/36A/52C/57Y/60H/64Q/73P/99C/119S/121P/130T/
  134Q/138A/141C/155F/161T/162A/176P/177C/180N/
  184Q/190T/199C/203L/207T/224Q/230E/243N/273L/
  336R/340L;
31C/36A/43C/46C/52C/57Y/60H/64Q/73P/99C/119S/
  121 P/130T/134Q/138A/141C/155F/161T/162A/176P/
  177C/180N/184Q/190T/199C/203L/207T/224Q/230E/
  243N/273L/286S/336R/340L;
31C/36A/52C/57Y/60H/64Q/73P/99C/119S/121P/123C/
  130C/134Q/138A/141C/151S/155F/161T/162A/176P/
  177C/180N/184Q/190T/199C/203L/207T/224Q/230E/
  243N/273L/336R/340L; and
31C/36A/43C/46C/52C/57Y/60H/64Q/73P/99C/119S/
  121 P/123C/130C/134Q/138A/141C/155F/161T/
  162A/176P/177C/180N/184Q/190T/199C/203L/207T/
  224Q/230E/243N/273L/286S/336R/340L.

7. The variant of paragraph 6, having the amino acid sequence of SEQ ID NO: 2 with the substitutions selected from the group consisting of:

N31C/G52C/E57Y/N73P/A99C/N121P/S134Q/K141C/
  Y155F/T177C/V199C/N203L/P207T/M273L;
N31C/Q36A/G52C/E57Y/Q60H/L64Q/N73P/A99C/
  E119S/N121P/M130T/S134Q/L138A/K141C/Y155F/
  S161T/S162A/E176P/T177C/T180N/S184Q/P190T/
  V199C/N203L/P207T/E224Q/Q230E/R243N/M273L/
  K336R/T340L;
N31C/Q36A/P43C/W46C/G52C/E57Y/Q60H/L64Q/
  N73P/A99C/E119S/N121P/M130T/S134Q/L138A/
  K141C/Y155F/S161T/S162A/E176P/T177C/T180N/
  S184Q/P190T/V199C/N203L/P207T/E224Q/Q230E/
  R243N/M273L/N286S/K336R/T340L;
N31C/Q36A/G52C/E57Y/Q60H/L64Q/N73P/A99C/
  E119S/N121P/P123C/M130C/S134Q/L138A/K141C/
  N151S/Y155F/S161T/S162A/E176P/T177C/T180N/
  S184Q/P190T/V199C/N203L/P207T/E224Q/Q230E/
  R243N/M273L/K336R/T340L; or
N31C/Q36A/P43C/W46C/G52C/E57Y/Q60H/L64Q/
  N73P/A99C/E119S/N121P/P123C/M130C/S134Q/
  L138A/K141C/Y155F/S161T/S162A/E176P/T177C/
  T180N/S184Q/P190T/V199C/N203L/P207T/E224Q/
  Q230E/R243N/M273L/N286S/K336R/T340L.

8. The variant of any of paragraphs 1-7, wherein the parent phytase has at least 75%, at least 80%, at least 85%, at least 90%, at least 95%, at least 96%, at least 97%, at least 98%, at least 99% or 100% sequence identity to the mature polypeptide of SEQ ID NO: 2.

9. The variant of any of paragraphs 1-8, wherein the parent phytase comprises or consists of the mature polypeptide of SEQ ID NO: 2.

10. The variant of any of paragraphs 1-9, which has an improved thermostability in comparison with the phytase having the amino acid sequence of SEQ ID NO: 2 and the substitutions N31C/G52C/A99C/K141C/T177C/V199C/N203L.

11. A polynucleotide encoding the variant of any of paragraphs 1-10.

12. A nucleic acid construct or an expression vector comprising the polynucleotide of paragraph 11.

13. A host cell comprising the polynucleotide of paragraph 11.

14. A method of producing a phytase variant of any of paragraphs 1-10, comprising:
   cultivating the host cell of paragraph 13 under conditions suitable for expression of the variant; and
   recovering the variant.

15. A plant comprising the phytase variant of any of paragraphs 1-10 and/or the polynucleotide of paragraph 11.

16. A composition comprising at least one phytase variant of any of paragraphs 1-10.

17. The composition of paragraph 16 further comprising at least one fat soluble vitamin;
at least one water soluble vitamin; and/or
at least one trace mineral.

18. The composition of paragraph 16 or 17, further comprising at least one enzyme selected from the following group of enzymes: amylase, phytase, phosphatase, xylanase, galactanase, alpha-galactosidase, protease, phospholipase and/or beta-glucanase.

19. The composition of any of paragraphs 16-18, which is an animal feed additive.

20. An animal feed composition having a crude protein content of 50 to 800 g/kg and comprising the phytase variant of any of paragraphs 1-10, the polynucleotide of paragraph 11, or the composition of any of paragraphs 16-19.

21. A method of improving the nutritional value of an animal feed, wherein the phytase variant of any of paragraphs 1-10, the polynucleotide of paragraph 11, or the composition of any of paragraphs 16-19 is added to the feed.

22. A process for reducing phytate levels in animal manure comprising feeding an animal with an effective amount of the feed composition of paragraph 20.

23. A method for the treatment of vegetable proteins, comprising adding the phytase variant of any of paragraphs 1-10, the polynucleotide of paragraph 11, or the composition of any of paragraphs 16-19 to at least one vegetable protein or protein source.

24. A method for increasing weight gain and/or improving Feed Conversion Ratio of an animal, the method comprising applying to the animal a feed with an efficient amount of the phytase variant of any of paragraphs 1-10, the polynucleotide of paragraph 11, or the composition of any of paragraphs 16-19.

25. Use of the phytase variant of any of paragraphs 1-10, the polynucleotide of paragraph 11, or the composition of any of paragraphs 16-19 in animal feed; in the preparation of animal feed; for improving the nutritional value of animal feed; for reducing phytate levels in animal manure; for the treatment of vegetable proteins; for liberating phosphorous from a phytate substrate; or for increasing weight gain, improving specific growth rate and/or improving Feed Conversion Ratio of an animal; or for improving nutrient retention, and/or nutrient digestibility in an animal.

26. A method for producing a fermentation product, comprising (a) fermenting using a fermenting microorganism, a carbohydrate containing material in the presence of a phytase variant of any of paragraphs 1-10 or the polynucleotide of paragraph 11, and (b) producing the fermentation product of fermentation coproduct from the fermented carbohydrate containing material.

27. The method of paragraph 26, wherein the fermentation product is ethanol, beer, wine or distillers dried grains (DDG).

28. An isolated polypeptide having phytase activity, selected from the group consisting of
   a) a polypeptide having at least 70%, at least 75%, at least 80%, at least 85%, at least 90%, at least 95%, at least 98%, at least 99% or 100% identity to SEQ ID NO: 12;
   b) a polypeptide having at least 70%, at least 75%, at least 80%, at least 85%, at least 90%, at least 95%, at least 98%, at least 99% or 100% identity to SEQ ID NO: 14;
   c) a polypeptide having at least 70%, at least 75%, at least 80%, at least 85%, at least 90%, at least 95%, at least 98%, at least 99% or 100% identity to SEQ ID NO: 16;
   d) a polypeptide having at least 70%, at least 75%, at least 80%, at least 85%, at least 90%, at least 95%, at least 98%, at least 99% or 100% identity to SEQ ID NO: 18; and
   e) a polypeptide having at least 70%, at least 75%, at least 80%, at least 85%, at least 90%, at least 95%, at least 98%, at least 99% or 100% identity to SEQ ID NO: 20.

29. The polypeptide of paragraph 28, obtained or obtainable from *Citrobacter* braakii.

30. The isolated polypeptide of paragraph 28 or 29, wherein said polypeptide is pH stable and thermostable such that it comprises one or more of the following properties
   i. an unfolding temperature at pH 4 of at least 75° C.;
   ii. an unfolding temperature at pH 3 of at least 70° C.; and
   iii. an unfolding temperature at pH 2 of at least 55° C.

31. The isolated polypeptide of any of paragraphs 28 to 30, wherein said polypeptide is acid stable such that it maintains a residual activity level above 90% after 24 hours at each of pH 2, 3, 4, 5, 6, 7 and 8.

32. The polypeptide of any of paragraphs 28 to 31 comprising the alterations N31C/G52C/A99C/K141C/T177C/V199C as compared to SEQ ID NO: 2.

33. The polypeptide of any of paragraphs 28 to 32 comprising a substitution in one or more position(s) selected from the following: 30, 36, 43, 46, 57, 60, 64, 73, 79, 119, 121, 123, 130, 134, 138, 151, 155, 161, 162, 168, 176, 180, 184, 190, 207, 224, 230, 243, 273, 286, 336, 340, 358 and 375 using SEQ ID NO: 2 for numbering.

34. A method of preparing a recombinant polypeptide having phytase activity comprising:
   (a) cultivating a recombinant host cell comprising an exogenous polynucleotide selected from the group consisting of
      a. a polynucleotide having at least 70%, at least 75%, at least 80%, at least 85%, at least 90%, at least 95%, at least 98%, at least 99% or 100% identity to SEQ ID NO: 13;
      b. a polynucleotide having at least 70%, at least 75%, at least 80%, at least 85%, at least 90%, at least 95%, at least 98%, at least 99% or 100% identity to SEQ ID NO: 15;
      c. a polynucleotide having at least 70%, at least 75%, at least 80%, at least 85%, at least 90%, at least 95%, at least 98%, at least 99% or 100% identity to SEQ ID NO: 17;
      d. a polynucleotide having at least 70%, at least 75%, at least 80%, at least 85%, at least 90%, at least 95%, at least 98%, at least 99% or 100% identity to SEQ ID NO: 19;
      e. a polynucleotide having at least 70%, at least 75%, at least 80%, at least 85%, at least 90%, at least 95%, at least 98%, at least 99% or 100% identity to SEQ ID NO: 21;
   wherein the polynucleotide is expressed and the polypeptide is produced;
   (b) optionally isolating the polypeptide; and
   (c) optionally recovering the polypeptide.

35. A method of producing a polypeptide having phytase activity, comprising:
   (a) cultivating a recombinant host cell comprising an exogenous polynucleotide encoding the polypeptide having phytase activity selected from the group consisting of
      a. a polypeptide having at least 70%, at least 75%, at least 80%, at least 85%, at least 90%, at least 95%, at least 98%, at least 99% or 100% identity to SEQ ID NO: 12;
      b. a polypeptide having at least 70%, at least 75%, at least 80%, at least 85%, at least 90%, at least 95%, at least 98%, at least 99% or 100% identity to SEQ ID NO: 14;
      c. a polypeptide having at least 70%, at least 75%, at least 80%, at least 85%, at least 90%, at least 95%, at least 98%, at least 99% or 100% identity SEQ ID NO: 16;
      d. a polypeptide having at least 70%, at least 75%, at least 80%, at least 85%, at least 90%, at least 95%, at least 98%, at least 99% or 100% identity SEQ ID NO: 18; and
      e. a polypeptide having at least 70%, at least 75%, at least 80%, at least 85%, at least 90%, at least 95%, at least 98%, at least 99% or 100% identity to SEQ ID NO: 20;
   wherein the polynucleotide is expressed and the polypeptide is produced;
   (b) optionally isolating the polypeptide; and
   (c) optionally recovering the polypeptide.

36. The method of paragraph 35, wherein the polypeptide having phytase activity comprises the substitutions N31C/G52C/A99C/K141C/T177C/V199C as compared to SEQ ID NO: 2.

37. The method of any of paragraphs 34 to 36 wherein the polypeptide further comprises a substitution in one or more position(s) selected from the following: 30, 36, 43, 46, 57, 60, 64, 73, 79, 119, 121, 123, 130, 134, 138, 151, 155, 161, 162, 168, 176, 180, 184, 190, 207, 224, 230, 243, 273, 286, 336, 340, 358 and 375 using SEQ ID NO: 2 for numbering.38. An animal feed additive comprising the phytase defined in any of paragraphs 1 to 10, for use in a animal feed for an animal selected from the group consisting poultry, swine, fish or crustacean.

39. The animal feed additive according to paragraph 38, for use in a feed for poultry wherein the poultry is selected from the group consisting of turkeys, ducks and chickens (including but not limited to broiler chicks, layers), typically chickens, particularly broiler chickens and layer chickens.

40. The animal feed additive of paragraph 38, for use in a feed for swine.

41. The animal feed additive of paragraph 38, for use in a feed for fish or crustaceans.

42. The animal feed additive of paragraph 41, wherein the fish is selected from the group consisting of salmon, trout, tilapia, catfish, seabream such as gilthead seabream, bass, such as seabass, and carp and wherein the crustaceans is selected from the group consisting of lobster, crab, crayfish, krill, shrimp and prawn.

43. The animal feed additive of any of paragraphs 38 to 42, comprising the phytase of paragraphs 1 to 10 in amount 100-5000 FYT/kg feed, such as 125 to 4000 FTY/kg feed, such as 125 to 3000 FTY/kg feed.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The present invention is further described by the following examples that should not be construed as limiting the scope of the invention.

EXAMPLES

Chemicals used were commercial products of at least reagent grade.

Example 1: Preparation of Variants, and Determination of Activity

Expression of phytase variants in Aspergillus oryzae

The constructs comprising the C. braakii phytase variant genes in the examples were used to construct expression vectors for Aspergillus. The Aspergillus expression vectors consist of an expression cassette based on the Aspergillus niger neutral amylase II promoter fused to the Aspergillus nidulans triose phosphate isomerase non translated leader sequence (Pna2/tpi) and the Aspergillus niger amyloglycosidase terminator (Tamg). Also present on the plasmid was the Aspergillus selective marker pyrG from Aspergillus nidulans enabling growth on miminal media for an aspergillus which is pyrG minus. The expression plasmids for phytase variants were transformed into Aspergillus as described in Lassen et al. (2001), Applied and Environmental Micorbiology, 67, 4701-4707. For each of the constructs 4-6 strains were isolated, purified and cultivated in microtiterplates. Expression was determined using a p-nitrophenyl phosphate substrate. The best producing strain was fermented in Shake flasks.

Purification of C. Braakii Phytase Variants

The fermentation supernatant with the phytase variant was filtered through a Fast PES Bottle top filter with a 0.22 µm cut-off. The resulting solution was diluted with water to the double volume and pH was adjusted to 4.5 with acetic acid. Occasionally, the solution became a little cloudy and this removed by filtration through a Fast PES Bottle top filter with a 0.22 µm cut-off.

After pretreatment the phytase variant was purified by chromatography on S Sepharose, approximately 30 ml in a XK26 column, using as buffer A 50 mM sodium acetate pH 4.5, and as buffer B 50 mM sodium acetate+1 M NaCl pH 4.5. The fractions from the column were analyzed for activity using the phosphatase assay (see below) and fractions with activity were pooled.

In some cases the solution containing the purified phytase variant was concentrated using an Amicon ultra-15 filtering device with a 30 kDa cut-off membrane.

The molecular weight, as estimated from SDS-PAGE, was approximately 45-50 kDa and the purity was >95%.

Determination of Phosphatase Activity 75 microliter phytase-containing enzyme solution is dispensed in a microtiter plate well, e.g., NUNC 269620 and 75 microliter substrate is added (for preparing the substrate, two 5 mg p-nitrophenyl phosphate tablets (Sigma, Cat.No. N-9389) are dissolved in 10 ml 0.1 M Na-acetate buffer, pH 5.5). The plate is sealed and incubated 15 min., shaken with 750 rpm at 37° C. After the incubation time 75 microliter stop reagent is added (the stop reagent is 0.1 M di-sodiumtetraborate in water) and the absorbance at 405 nm is measured in a microtiter plate spectrophotometer. One phosphatase unit is defined as the enzyme activity that releases 1 micromol phosphate/min under the given reaction conditions (buffer blind subtracted). The absorbance of 1 micromol p-nitrophenol is determined to be 56 AU (AU=absorbancy units) under assay conditions.

Determination of Phytase Activity 75 microliter phytase-containing enzyme solution, appropriately diluted in 0.25 M sodium acetate, 0.005% (w/v) Tween-20. pH 5.5, is dispensed in a microtiter plate well, e.g., NUNC 269620, and 75 microliter substrate is added (prepared by dissolving 100 mg sodium phytate from rice (Aldrich Cat.No. 274321) in 10 ml 0.25 M sodium acetate buffer, pH 5.5). The plate is sealed and incubated 15 min. shaken with 750 rpm at 37° C. After incubation, 75 microliter stop reagent is added (the stop reagent being prepared by mixing 10 ml molybdate solution (10% (w/v) ammonium hepta-molybdate in 0.25% (w/v) ammonia solution), 10 ml ammonium vanadate (0.24% commercial product from Bie&Berntsen, Cat.No. LAB17650), and 20 ml 21.7% (w/v) nitric acid), and the absorbance at 405 nm is measured in a microtiter plate spectrophotometer. The phytase activity is expressed in the unit of FYT, one FYT being the amount of enzyme that liberates 1 micromole inorganic ortho-phosphate per minute under the conditions above. An absolute value for the measured phytase activity may be obtained by reference to a standard curve prepared from appropriate dilutions of inorganic phosphate, or by reference to a standard curve made from dilutions of a phytase enzyme preparation with known activity (such standard enzyme preparation with a known activity is available on request from Novozymes A/S, Krogshoejvej 36, DK-2880 Bagsvaerd).

Example 2: Single Position Variants

The parent phytase for this example was a variant having the sequence of SEQ ID NO: 2 with the substitutions: (var300) N31C/G52C/A99C/K141C/T177C/V199C/N203L.

96 single position variants of the parent phytase was prepared as described in Example 1. The substitutions were selected based on alignment of known phytases and identification of consensus sequences as known in the art. The thermostability of the variants were tested using Protein Thermal Shift™ (Applied Biosystems, Carlsbad, CA, US) according to the manufacturer's instructions. Variants having improved thermostability compared with the parent are shown in Table 1.

TABLE 1

| Variant | T (° C.) |
|---|---|
| K30Q | 70 |
| Q60H | 70 |
| L64Q | 70 |
| E119S | 70 |
| N121P | 71 |
| L138A | 70 |
| S162A | 70 |
| T180N | 70 |
| P190T | 70 |
| R243N | 70 |
| M273L | 71 |
| K336R | 70 |
| T340L | 70 |
| D358Q | 72 |
| Q36A | 70 |
| E57Y | 71 |
| N73P | 71 |
| S79Q | 70 |
| M130T | 70 |
| S134Q | 71 |
| Y155F | 71 |

TABLE 1-continued

| Variant | T (° C.) |
|---|---|
| S161T | 70 |
| N168R | 70 |
| E176P | 70 |
| S184Q | 70 |
| P207T | 72 |
| E224Q | 70 |
| Q230E | 70 |
| T340P | 70 |
| D375K | 70 |

Example 3: Combining Beneficial Positions

Based on the results disclosed in Example 2, a variant combining several of the beneficial substitutions was generated having the sequence of SEQ ID NO: 2 with the substitutions:
(var400):
N31C/G52C/E57Y/N73P/A99C/N121 P/S134Q/K141C/Y155F/T177C/V199C/N203L/P207T/M273L A gene was designed and the variant produced as described in Example 1. Thermal shift assay was performed in triplicate on the variant showing 81° C.

Example 4: Further Combinatorial Variants

Based on the results disclosed in Example 2 a variant combining further beneficial substitutions using the variant generated in Example 3 as the parent phytase. Following variants having the sequence of SEQ ID NO: 2 with the substitutions were generated:

```
(var404)
N31C/Q36A/G52C/E57Y/Q60H/N73P/A99C/E119S/N121P/M130T/S134Q/L138A/K141C/
Y155F/S161T/S162A/E176P/T177C/T180N/S184Q/P190T/V199C/N203L/P207T/E224Q/
Q230E/R243N/M273L/K336R/T340L (var405)
N31C/Q36A/P43C/W46C/G52C/E57Y/Q60H/L64Q/N73P/A99C/E119S/N121P/M130T/S134Q/
L138A/K141C/Y155F/S161T/S162A/E176P/T177C/T180N/S184Q/P190T/V199C/N203L/
P207T/E224Q/Q230E/R243N/M273L/N286S/K336R/T340L (var406)
N31C/Q36A/G52C/E57Y/Q60H/L64Q/N73P/A99C/E119S/N121P/P123C/M130C/S134Q/L138A/
K141C/N151S/Y155F/S161T/S162A/E176P/T177C/T180N/S184Q/P190T/V199C/N203L/
P207T/E224Q/Q230E/R243N/M273L/K336R/T340L (var411)
N31C/Q36A/P43C/W46C/G52C/E57Y/Q60H/L64Q/N73P/A99C/E119S/N121P/P123C/M130C/
S134Q/L138A/K141C/Y155F/S161T/S162A/E176P/T177C/T180N/S184Q/P190T/V199C/
N203L/P207T/E224Q/Q230E/R243N/M273L/N286S/K336R/T340L
```

Example 5: Thermostability of Generated Variants

The following variants were constructed and tested for thermostability: IDC-25 DNA

TABLE 2

| Phytase | Substitutions |
|---|---|
| var400 | N31C/G52C/E57Y/N73P/A99C/N121P/S134Q/K141C/Y155F/T177C/V199C/N203L/P207T/M273L |
| var404 | N31C/Q36A/G52C/E57Y/Q60H/N73P/A99C/E119S/N121P/M130T/S134Q/L138A/K141C/Y155F/S161T/S162A/E176P/T177C/T180N/S184Q/P190T/V199C/N203L/P207T/E224Q/Q230E/R243N/M273L/K336R/T340L |
| var405 | N31C/Q36A/P43C/W46C/G52C/E57Y/Q60H/L64Q/N73P/A99C/E119S/N121P/M130T/S134Q/L138A/K141C/Y155F/S161T/S162A/E176P/T177C/T180N/S184Q/P190T/V199C/N203L/P207T/E224Q/Q230E/R243N/M273L/N286S/K336R/T340L |

TABLE 2-continued

Phytase  Substitutions var406   N31C/Q36A/G52C/E57Y/Q60H/L64Q/N73P/A99C/E119S/N121P/P123C/M130C/
         S134Q/L138A/K141C/N151S/Y155F/S161T/S162A/E176P/T177C/T180N/S184Q/
         P190T/V199C/N203L/P207T/E224Q/Q230E/R243N/M273L/K336R/T340L var411   N31C/Q36A/P43C/W46C/G52C/E57Y/Q60H/L64Q/N73P/A99C/E119S/N121P/P1
         23C/M130C/S134Q/L138A/K141C/Y155F/S161T/S162A/E176P/T177C/T180N/
         S184Q/P190T/V199C/N203L/P207T/E224Q/Q230E/R243N/M273L/N286S/K336R/
         T340L The variants were tested for thermostability by nano Differential Scanning Fluorescence (nanoDSF).

Nano-DSF monitors intrinsic tryptophan (Trp) fluorescence of the protein as a function of temperature at 330 and 350 nm. The temperature stability of a protein can be expressed by Tm (the temperature at which there is an equal population of folded and unfolded molecules) found at the inflection point of the fluorescence signal.

NanoDSF was performed with a nanoDSF Prometheus NT.48 instrument (NanoTemper Technologies GmbH, Munchen, Germany). Phytase variant samples (purified as described in Example 1, all of them in 50 mM Na-acetate, pH 4.5) were loaded into nanoDSF standard grade capillaries (NanoTemper Technologies GmbH; catalog number PR-C002) through capillary action. Three capillaries were filled for each sample. The capillaries were then placed into the instrument (up to 48 single capillaries can be loaded in a single run) and the laser intensity required for optimum signal generation was determined. The samples were run with the following experimental setting: temperature slope 2° C./minute, start temperature 20° C. and end temperature 95° C.

The data was analyzed using the software that is supplied with the instrument (PR. ThermControl v2.0.4, NanoTemper Technologies GmbH) and the Tm (for the ratio 350 nm/330 nm) was determined (results shown in Table 3 below).

Further the variants were tested using DSC using the assay disclosed in WO 2011/117396 Example 4. Results are shown in Table 3.

TABLE 3

| Designation | nDSF (broth) (° C.) | nDSF (purified) (° C.) | DSC (° C.) |
|---|---|---|---|
| var400 | 83.7 | 82.5 | 85.6 |
| var404 | 86.1 | 85.4 | 88.3 |
| var405 | 86.1 | 86.2 | 88.9 |
| var406 | 88.7 | 88.1 | 90.6 |
| var411 | 88.8 | 88.1 | |

The variants were also tested for thermostability in the pH range 1.0 to 8.5 using NanoDSF (described above). The variant samples were in 0.1 M glycine, 0.1 M acetic acid, 0.1 M Bis-Tris, adjusted to the desired pH with either 0.5 M HCl or 0.1 M NaOH. The temperature slope was 3.33° C./minute in this experiment. Results are shown in Tables 4a and 4b.

TABLE 4a

| | pH | | | | | | | |
|---|---|---|---|---|---|---|---|---|
| Phytase | 1.0 | 1.5 | 2.0 | 2.5 | 3.0 | 3.5 | 4.0 | 4.5 |
| C.b. wt SEQ ID 2 | ns | 44.2 | 46.0 | 49.3 | 53.6 | 58.6 | 61.5 | 63.4 |

TABLE 4a-continued

| | pH | | | | | | | |
|---|---|---|---|---|---|---|---|---|
| Phytase | 1.0 | 1.5 | 2.0 | 2.5 | 3.0 | 3.5 | 4.0 | 4.5 |
| var300 | 44.3 | 47.9 | 52.7 | 58.8 | 65.2 | 70.3 | 73.8 | 75.2 |
| var400 | 52.7 | 56.2 | 60.2 | 65.9 | 71.5 | 76.8 | 80.1 | 81.9 |
| var404 | 57.1 | 61.0 | 64.4 | 69.7 | 75.6 | 80.5 | 83.3 | 85.5 |
| var405 | 58.8 | 61.8 | 65.6 | 70.6 | 76.3 | 81.1 | 84.7 | 86.4 |
| var406 | 62.4 | 64.6 | 67.9 | 72.6 | 77.8 | 83.5 | 85.9 | 88.2 |
| var411 | 62.9 | 65.0 | 68.0 | 72.8 | 78.3 | 83.5 | 86.0 | 88.2 |

TABLE 4b

| | pH | | | | | | | |
|---|---|---|---|---|---|---|---|---|
| Phytase | 5.0 | 5.5 | 6.0 | 6.5 | 7.0 | 7.5 | 8.0 | 8.5 |
| C.b. wt SEQ ID 2 | 63.9 | 63.7 | 63.8 | 62.7 | 61.4 | 60.0 | 58.7 | 57.6 |
| var300 | 76.5 | 76.2 | 76.2 | 75.9 | 74.8 | 73.8 | 73.3 | 72.3 |
| var400 | 83.3 | 83.6 | 84.1 | 83.5 | 83.4 | 82.0 | 81.8 | 81.1 |
| var404 | 86.9 | 87.1 | 87.5 | 87.6 | 87.2 | 86.7 | 86.1 | 85.6 |
| var405 | 87.3 | 88.0 | 88.4 | 89.2 | 89.2 | 88.6 | 88.5 | 88.0 |
| var406 | 89.6 | 90.3 | 90.5 | 90.5 | 91.6 | 91.4 | 90.7 | 89.7 |
| var411 | 89.2 | 89.5 | 89.9 | 90.0 | 90.1 | 89.5 | 88.9 | 88.4 |

Conclusion: The variants have increased unfolding temperatures at all pH-values tested. The variants have improved thermostability compared to the wild type at all pHs.

Example 6: pH-stability

The pH stability of the purified phytases of C.b. Wt (SEQ ID NO: 2) and var400 (SEQ ID NO: 12) at 37° C. was determined by measuring residual phytase activity after incubation at 37° C. and at various pH values for 1.0 and 24 hours. The phytases were incubated in 0.1 M glycine, 0.1 M acetic acid, 0.1 M Bis-Tris, adjusted to the desired pH. Samples of the respective incubation mixtures were withdrawn after 0, 1.0 and 24 hours, the pH of the samples was adjusted to 5.5 by dilution in 0.25 M sodium acetate, 0.005% (w/v) Tween20, pH 5.5), and the residual activity at pH 5.5 was determined using the method described in Example 1. The results, normalized to the activity found at 0 hours, are shown for 24 hours in Table 5 below.

TABLE 5 pH stability at 37° C.

| pH | C.b. Wt (SEQ ID NO: 2) | var400 (SEQ ID NO: 12) |
|---|---|---|
| | 24 hours | |
| 1.0 | 1 | 64 |
| 2.0 | 12 | 96 |
| 3.0 | 61 | 101 |
| 4.0 | 99 | 102 |
| 5.0 | 97 | 105 |
| 6.0 | 101 | 94 |
| 7.0 | 105 | 97 |
| 8.0 | 90 | 103 |

Var400 has higher residual activity after incubation at very low pH (pH 1.0-3.0) after 24 hours incubation.

Example 7: pH-Stability in the Presence of Pepsin

The pH stability of the purified phytases of C.b. Wt (SEQ ID NO: 2) and variants (see tables below) at 37° C. and in the presence of pepsin was determined by measuring residual phytase activity after incubation at 37.C and at various pH values for 30 and 60 minutes, respectively. The phytases were incubated in 0.1 M glycine, 0.1 M acetic acid, 0.1 M Bis-Tris, adjusted to the desired pH and added 500 U/ml of pepsin (Sigma P7000). Samples of the respective incubation mixtures were withdrawn after 0, 30 minutes and 60 minutes, the pH of the samples was adjusted to 5.5 by dilution in 0.25 M sodium acetate, 0.005% (w/v) Tween20, pH 5.5), and the residual activity at pH 5.5 was determined using the method described in Example 1. The results, normalized to the activity found at 0 hours, are shown in Tables 6 and 7 below.

TABLE 6

Residual activity after 30 minutes incubation.

| Phytase | pH | | | | | | | |
| | 1.0 | 1.5 | 2.0 | 2.5 | 3.0 | 3.5 | 4.0 | 4.5 |
|---|---|---|---|---|---|---|---|---|
| var300 | 3 | 3 | 24 | 62 | 78 | 86 | 88 | 93 |
| var400 | 28 | 48 | 81 | 93 | 89 | 93 | 96 | 97 |
| var404 | 77 | 87 | 95 | 97 | 98 | 93 | 100 | 95 |
| var405 | 84 | 91 | 94 | 96 | 96 | 100 | 98 | 102 |
| var406 | 89 | 90 | 95 | 100 | 101 | 97 | 96 | 96 |
| var411 | 94 | 93 | 91 | 92 | 91 | 97 | 96 | 93 |

TABLE 7

Residual activity after 60 minutes incubation.

| Phytase | pH | | | | | | | |
| | 1.0 | 1.5 | 2.0 | 2.5 | 3.0 | 3.5 | 4.0 | 4.5 |
|---|---|---|---|---|---|---|---|---|
| var300 | 5 | 4 | 13 | 59 | 77 | 88 | 92 | 97 |
| var400 | 14 | 36 | 73 | 88 | 81 | 86 | 92 | 99 |
| var404 | 67 | 81 | 90 | 90 | 93 | 87 | 98 | 95 |
| var405 | 78 | 83 | 88 | 90 | 93 | 99 | 95 | 101 |
| var406 | 88 | 86 | 90 | 98 | 92 | 95 | 94 | 94 |
| var411 | 92 | 90 | 86 | 88 | 89 | 92 | 94 | 93 |

The variants have increased pH-stability in the presence of pepsin at pH-values below 3.0 compared to the var300 reference.

Example 8: Efficacy Study of a Phytase in Broiler Chickens and Weaned Piglets

In the broiler study, birds (Cobb 500, male, commercially available from Yukou Poultry Husbandary Co., Ltd., Beijing, China) were housed in wire-floored battery cages in an environmentally controlled room. At the start of trial (day 8 of age), birds were sorted by weight and divided into replicate groups, each comprising 8 birds. The birds with similar cage weight were randomly allocated to one of the different treatments, and each treatment was replicated with 12 cages. There were 8 dietary treatments consisting of a negative control and the negative control supplemented with 7 levels of the phytase variant (var400): 187.5, 375, 750, 1125, 1500, 1875 or 2250 FYT/kg. A basal diet was prepared with corn and soybean meal as the main ingredients, and was formulated to be deficient only in total P (0.46%). The phytase variant was pre-mixed with a small amount of the basal diet before the complete mixing of the experimental diets to ensure uniformity of mixing. The feed was pelleted at 75° C. The analyzed phytase variant activities of the dietary treatments were 182, 328, 640, 1060, 1347, 1560 and 1931 FYT/kg.

The experimental diets were supplied to birds from days 8 to 18 of age, feed and water were supplied ad libitum through the whole trial. At days 8 and 17 of age, feed consumption and body weight (BW) by cage were recorded to calculate the body weight gain (WG), feed intake (FI) and the feed conversion ratio (FCR). Excreta were collected on day 14 through day 17. During this period, the excreta from 12 cages of each treatment were quantitatively collected once per day, and the excreta per cage from the 4 days were pooled together, frozen immediately at −20° C. after collection. After thawing, the total excreta of each cage were homogenized, and the representative sub-samples were taken and freeze-dried for the determination of dry matter (DM), P, Ca and phytate-P. The total amount of feed consumption during the excreta collection period was recorded as well. At day 18 of age, the right tibia was taken from 2 birds randomly chosen from each of the 12 replicate cages. Tibias were defleshed, and cartilaginous caps were removed after collection. They were kept frozen in plastic bags at −20° C. to maintain wetness until analysis of ash, Ca and total P content.

In the piglet study, 140 castrated male piglets (Redon x Large White) were used. The piglets were weaned at 28 days of age and had an average body weight of 7.5±1.1 kg (mean±standard deviation) at the start of trial. The piglets were housed in 35 flat-deck cages with 4 animals per cage in an environmentally controlled room. Each cage had a plastic-coated welded wire floor and was equipped with two water nipples and two stainless-steel feeders. The experimental diets were fed for 42 days which were divided into a starter phase of 14 days and a grower phase of 28 days. Water and feed were supplied ad libitum. The feed was offered in mash form.

There were 7 dietary treatments consisting of a positive control (PC), a negative control (NC) and the NC supplemented with 187.5, 375, 750, 1500 or 3000 FYT test phytase/kg feed (on analysis: 266, 383, 771, 1445, and 2914 FYT/kg in starter diets; 219, 395, 884, 1408, and 2730 FYT/kg in growerdiets). The PC diets for the starter and grower phases met the pig's requirement for energy and nutrients prescribed by NRC (2012) for the body weight range of 7 to 11 kg and 11 to 25 kg, respectively, and were formulated with corn, soybean meal and rapeseed meal as the main ingredients. The NC diets were established by withdrawing the dicalcium phosphate from the PC diets resulting in P deficient diets (0.43% and 0.41% total P for starter and grower, respectively) with adequate Ca. The ingredient and nutrition compositions of diets are shown in Table 8.

TABLE 8 ingredient and nutrition composition of experimental diets in broiler and piglet trials, %

| Ingredient | Broiler trial 8-18 day of age NC | Piglet trial Starter NC | Piglet trial Starter PC | Piglet trial Grower NC | Piglet trial Grower PC |
|---|---|---|---|---|---|
| Corn | 60.14 | 54.35 | 53.60 | 59.45 | 58.75 |
| Soybean meal | 33.50 | 24.00 | 24.00 | 20.00 | 20.00 |
| Rapeseed meal | — | 12.00 | 12.00 | 12.00 | 12.00 |
| Soybean oil | 2.50 | 4.50 | 4.70 | 3.70 | 3.90 |
| NaCl | 0.41 | 0.20 | 0.20 | 0.05 | 0.05 |
| NaHCO$_3$ | 0.14 | 0.35 | 0.35 | 0.35 | 0.35 |
| DL-Met | 0.58 | 0.10 | 0.10 | 0.05 | 0.05 |
| L-Lys HCl | 0.37 | 0.25 | 0.25 | 0.25 | 0.25 |
| L-Thr | 0.15 | 0.10 | 0.10 | 0.05 | 0.05 |
| L-Val | — | 0.15 | 0.15 | 0.10 | 0.10 |
| Limestone | 1.06 | 1.00 | 0.00 | 0.70 | 0.00 |
| Dicalcium phosphate | 0.55 | 0.00 | 1.55 | 0.00 | 1.20 |
| Vit-Min Premix[1] | 0.50 | 3.00 | 3.00 | 3.00 | 3.00 |
| TiO$_2$ | 0.10 | 0.00 | 0.00 | 0.30 | 0.30 |
| Total | 100.00 | 100.00 | 100.00 | 100.00 | 100.00 |
| CP, % | 21.5 | 20.0 | 19.9 | 18.6 | 18.5 |
| ME, kcal/kg | 3066 | 3404 | 3396 | 3374 | 3367 |
| Dig Lys, % | 1.25 | 1.35 | 1.35 | 1.26 | 1.26 |
| Dig Met, % | 0.85 | 0.43 | 0.43 | 0.37 | 0.37 |
| Dig Thr, % | 0.83 | 0.83 | 0.83 | 0.74 | 0.74 |
| Digestible P, % | — | 0.17 | 0.40 | 0.16 | 0.34 |
| Total P, % | 0.46 | 0.43 | 0.72 | 0.41 | 0.64 |
| Phytate P, % | 0.24 | 0.28 | 0.28 | 0.27 | 0.27 |
| Calcium, % | 0.70 | 0.83 | 0.84 | 0.71 | 0.74 |

[1]Broiler premix supplied per kg of diet: vitamin A, 10,000 IU; vitamin D$_3$, 2,240 IU; 25-OH—D$_3$, 69 µg; vitamin E, 50 IU; vitamin K$_3$, 3 mg; vitamin B$_1$, 2 mg; vitamin B$_2$, 7 mg; vitamin B$_6$, 4 mg; vitamin B$_{12}$, 20 µg; biotin, 250 µg; folic acid, 2 mg; niacin, 60 mg; D-pantothenic acid, 12 mg; Fe, 40 mg; Cu, 15 mg; Mn, 110 mg; Zn, 90 mg; I, 0.5 mg; Se, 0.25 mg; and choline, 400 mg.

Piglet premix supplied per kg of diet: vitamin A, 15,000 IU; vitamin D$_3$, 1,998 IU; vitamin E, 100 IU; vitamin K$_3$, 20 mg; vitamin B$_1$, 3.0 mg; vitamin B$_2$, 10 mg; vitamin B$_6$, 6 mg; vitamin B$_{12}$, 40 µg; biotin, 200 µg; D-pantothenic acid, 25 mg; folic acid, 1.5 mg; niacin, 35 mg; vitamin C, 100 mg; Cu, 160 mg; I, 2.0 mg; Fe, 200 mg; Mn, 60 mg; Zn, 100 mg; Se, 400 µg; choline, 375 mg; sodium, 1.5 g; chlorine, 3.2 g; Ca, 2.8 g; lysine, 2.9 g; methionine, 0.5 g; threonine, 1.4 g; tryptophan, 0.3 g; and valine, 0.2 g.

The pigs were weighed individually and feed consumption was recorded for each pen to calculate average daily gain (ADG), average daily feed intake (ADFI) and FCR. At the end of the trial, 2 pigs of each pen with body weight closest to the average body weight of their pen were slaughtered for collection of femurs. The right femurs were separated and removed of the soft tissue. A diaphysis section (~3.5 cm in length) of each femur was obtained by sawing and then subjected to compression to determine the force in Newton to break the bone. The broken bones were used for the determination of ash, Ca and P content.

The samples of diets and excreta collected from broiler and pig trials were ground to pass through a 0.5-mm screen before analysis. All samples were analyzed in duplicate. The samples were dried at 105° C. in an oven for 4 hours for dry matter determination (method 934.01; AOAC International, 2006). Ca and P were determined by Inductively Coupled Plasma-Optical Emission Spectrometry (ICP-OES; 5100 Dual View, Agilent, Santa Clara, CA, USA; method 985.01; AOAC International, 2006) after sulfuric acid mineralization. Dietary phytate P was calculated as the difference between total P and free P. Total P was determined after treating the dietary samples with megadose of phytase to release the P bound by phytate. The free P, not bound by phytate, was determined after overnight extraction in 0.66 M HCl. Phytase activity was measured by a colorimetric method. One phytase unit was defined as the amount of enzyme that releases 1 pmol of inorganic phosphate from 5.0 mM phytate per minute at 37° C. and pH 5.5.

In both broiler and pig trials, the data were analyzed by one-way ANOVA using GLM procedure of SAS (SAS Inc., Gary, NC, USA, version 9.0). Orthogonal contrasts were constructed to test the linear and quadratic effects of phytase variant supplementation to the NC diet. Tukey's multiple comparison test was also applied in broiler trial. The least square means are presented.

Result

In the broiler study, the body weight gain and feed consumption of birds in NC was 10~15% lower than Cobb 500 performance targets during days 8 to 17 of age, which was attributed to the P deficiency in NC diet. The increasing addition of the phytase variant to the NC diet improved the 8-17 d body weight gain and feed intake of birds both linearly and quadratically (p<0.01). The achievement of performance targets was observed in treatments with high doses of phytase variant while no adverse effect was noted. Additionally, the data from excreta demonstrated that the P release from phytate-P degradation, and the corresponding retention of P and Ca were improved both linearly and quadratically (p<0.01) with the increase of phytase variant supplementation. Consistent with the performance and excreta results, Ca and P were increasingly deposited in the bone ash in a dose-dependent manner with the increase of phytase variant addition.

In the piglet study, the growth performance of piglets was depressed by deficiency of P in feed as demonstrated by the significant reduction in ADG and ADFI of the NC piglets in comparison to PC during day 14 to 42 and the overall trial duration, which was gradually corrected by the increasing addition of the phytase variant. The test phytase improved ADG and ADFI during day 14 to 42 and the overall trial duration both linearly and quadratically (p<0.01) with the increasing dose of phytase variant. This pattern was also observed with the average body weight of the piglets at the end of the trial. In keeping with the growth performance results, the significant improvement (p<0.01) in bone strength and bone content of ash, Ca and P in association with added phytase variant also showed a dose-response relationship. Moreover, the growth performance and bone measurements achieved at 3,000 FYT/kg feed, the highest dose of phytase variant tested in the current study, exceeded the levels of the PC without causing any noticeable adverse effect during the trial. This showed that both the Ca and P supplied in the form of dicalcium phosphate in the PC diets could be completely replaced by phytase variant when included at 3,000 FYT/kg feed.

TABLE 9 growth performance, retention of Ca (%) and P (%), phytate-P degradation (%) in excreta and bone parameters of broilers.

| Items | Phytase variant treatments, FYT/kg feed | | | | | | | | SEM | P-value | Linear | Quadratic |
|---|---|---|---|---|---|---|---|---|---|---|---|---|
| | NC | 187.5 | 375 | 750 | 1125 | 1500 | 1875 | 2250 | | | | |
| Body weight, g | | | | | | | | | | | | |
| D 8 | 193 | 192 | 192 | 192 | 192 | 192 | 192 | 193 | 0.3 | 0.08 | 0.68 | 0.11 |
| D 17 | 652$^a$ | 687$^b$ | 691$^b$ | 710$^{bc}$ | 716$^{bc}$ | 710$^{bc}$ | 724$^c$ | 716$^{bc}$ | 7.3 | <0.01 | <0.01 | <0.01 |
| D8 to 17 | | | | | | | | | | | | |
| WG, g | 460$^a$ | 495$^b$ | 499$^b$ | 518$^{bc}$ | 524$^{bc}$ | 518$^{bc}$ | 532$^c$ | 523$^{bc}$ | 7.3 | <0.01 | <0.01 | <0.01 |
| FI, g | 572$^a$ | 600$^{ab}$ | 609$^{ab}$ | 618$^b$ | 621$^b$ | 608$^{ab}$ | 640$^b$ | 622$^b$ | 10.0 | <0.01 | <0.01 | 0.05 |
| FCR, g/g | 1.244 | 1.215 | 1.220 | 1.195 | 1.187 | 1.174 | 1.205 | 1.190 | 0.017 | 0.10 | 0.01 | 0.06 |
| Excreta | | | | | | | | | | | | |
| Ca retention | 55.08$^a$ | 63.00$^b$ | 66.03$^b$ | 73.14$^c$ | 74.64$^c$ | 75.70$^c$ | 73.43$^c$ | 73.19$^c$ | 0.84 | <0.01 | <0.01 | <0.01 |
| P retention | 64.41$^a$ | 71.46$^b$ | 75.63$^c$ | 80.52$^d$ | 82.48$^d$ | 83.31$^d$ | 81.95$^d$ | 81.87$^d$ | 0.65 | <0.01 | <0.01 | <0.01 |
| Phytate-P degradation | 64.01$^a$ | 77.03$^b$ | 82.99$^c$ | 89.17$^d$ | 92.88$^{de}$ | 94.38$^e$ | 91.86$^{de}$ | 94.56$^e$ | 0.97 | <0.01 | <0.01 | <0.01 |
| Bone | | | | | | | | | | | | |
| Ash, % | 46.80$^a$ | 50.14$^b$ | 51.22$^{bc}$ | 52.36$^{cd}$ | 52.93$^{cde}$ | 53.56$^{de}$ | 54.67$^e$ | 53.74$^{de}$ | 0.46 | <0.01 | <0.01 | <0.01 |
| Ca, % | 17.10$^a$ | 18.26$^b$ | 18.57$^{bc}$ | 19.07$^{bcd}$ | 19.22$^{cd}$ | 19.38$^{cd}$ | 19.96$^d$ | 19.38$^{cd}$ | 0.20 | <0.01 | <0.01 | <0.01 |
| P, % | 8.05$^a$ | 8.61$^b$ | 8.91$^{bc}$ | 9.22$^{cd}$ | 9.38$^{de}$ | 9.44$^{de}$ | 19.67$^e$ | 9.39$^{de}$ | 0.09 | <0.01 | <0.01 | <0.01 |

Means with different superscript within the same row differ significantly (P < 0.05).

TABLE 10 growth performance and bone parameters of the piglets

| Items | Phytase variant treatments, FYT/kg feed | | | | | | | PC VS. NC | P-value | |
|---|---|---|---|---|---|---|---|---|---|---|
| | PC | NC | 187.5 | 375 | 750 | 1500 | 3000 | SEM | | Linear | Quadratic |
| Body weight, kg | | | | | | | | | | | |
| D 0 | 7.4 | 7.5 | 7.5 | 7.4 | 7.4 | 7.4 | 7.5 | 0.05 | 0.23 | 0.81 | 0.34 |
| D 14 | 10.9 | 10.1 | 10.6 | 10.0 | 10.8 | 10.5 | 11.1 | 0.33 | 0.13 | 0.05 | 0.94 |
| D 42 | 25.9 | 19.6 | 22.5 | 22.6 | 25.3 | 25.7 | 27.0 | 0.70 | <0.01 | <0.01 | <0.01 |
| D 0 to 14 | | | | | | | | | | | |
| ADG, g/d/pig | 247 | 181 | 221 | 184 | 238 | 221 | 258 | 24 | 0.06 | 0.04 | 0.74 |
| ADFI, g/d/pig | 369 | 324 | 351 | 294 | 384 | 337 | 373 | 26 | 0.24 | 0.19 | 0.86 |
| FCR, g/g | 1.52 | 1.82 | 1.61 | 1.64 | 1.65 | 1.53 | 1.44 | 0.08 | 0.02 | 0.01 | 0.44 |
| D 14 to 42 | | | | | | | | | | | |
| ADG, g/d/pig | 537 | 338 | 425 | 448 | 521 | 541 | 570 | 19 | <0.01 | <0.01 | <0.01 |
| ADFI, g/d/pig | 721 | 432 | 564 | 578 | 707 | 627 | 717 | 25 | <0.01 | <0.01 | <0.01 |
| FCR, g/g | 1.34 | 1.27 | 1.32 | 1.28 | 1.36 | 1.16 | 1.27 | 0.06 | 0.41 | 0.41 | 0.43 |
| D 0 to 42 | | | | | | | | | | | |
| ADG, g/d/pig | 440 | 286 | 357 | 360 | 426 | 434 | 466 | 17 | <0.01 | <0.01 | <0.01 |
| ADFI, g/d/pig | 603 | 396 | 493 | 483 | 599 | 530 | 602 | 21 | <0.01 | <0.01 | <0.01 |
| FCR, g/g | 1.40 | 1.45 | 1.42 | 1.40 | 1.46 | 1.28 | 1.33 | 0.05 | 0.48 | 0.05 | 0.33 |
| Bone, % | | | | | | | | | | | |
| Strength, N | 366 | 95 | 171 | 229 | 275 | 344 | 417 | 28 | <0.01 | <0.01 | <0.01 |
| Ash | 63.1 | 56.8 | 59.9 | 60.9 | 60.4 | 61.8 | 63.6 | 0.77 | <0.01 | <0.01 | 0.09 |
| Ca | 23.6 | 21.4 | 22.7 | 23.0 | 22.6 | 23.3 | 24.0 | 0.31 | <0.01 | <0.01 | 0.12 |
| P | 11.0 | 9.6 | 10.2 | 10.4 | 10.4 | 10.9 | 11.3 | 0.15 | <0.01 | <0.01 | 0.02 |

8 replicates for each treatment.

Example 9: Apparent Total Tract Digestibility of Calcium and Phosphorus in Late-Gestation and Lactating Sows Supplemented with a Phytase Variant The objective of this study was to evaluate a phytase variant (var400) in late-gestation and lactating sows with a genetic background of Large white, Landrace and Duroc and fed diets formulated using the National Research Council (NRC) (2012) suggested digestible P for feed ingredients. Forty-five late-gestation sows and 45 lactating sows were used in Examples 1 and 2, respectively, in a completely randomized design. The sows were provided with a control diet (Table 11) and the control diet added with 187.5 or 375

FYT phytase/kg feed. The diets were devoid of any inorganic P supplement and included 3 g/kg TiO$_2$ as an indigestible marker. Each dietary treatment was replicated with 15 sows individually-housed in farrowing stalls. The sows were allowed to adapt to the experimental diets for 5 days before a 5-d fecal collection by grab sampling. Digestibility of dry matter, Ca and P were calculated using the following equations:

$$D_d = [1-(Ti_i/Ti_o)] \times 100;$$

$$D_m = [1-(T_i/T_o) \times (M_o/M_i)] \times 100;$$

where $D_d$ and $D_m$ are the digestibility of DM and minerals (%), respectively; $T_i$ and $T_o$ are the titanium concentration in diet and feces, respectively (% of DM); $M_i$ and $M_o$ are the concentrations of minerals in diet and feces (% of DM), respectively. The digested Ca and P were calculated by multiplying the concentration of Ca and P in feed (%) by their corresponding $D_m$.

The digestibility and performance data were analyzed by a GLM procedure of SAS (SAS Inst. Inc., Cary, NC) with the model including the dietary treatment as the only fixed effect and error term. Orthogonal contrasts were constructed to test the linear and quadratic effects of supplementation of phytase and to compare control with the treatments with added phytase.

The results are shown in Table 12. The phytase released 0.07-0.12% digestible P for saws depending on the phytase dose and physiological stage of sows (more P release for lactating sows).

TABLE 11

Ingredient and nutrient composition of the basal diets (g/kg of feed, as-is basis)

| Items | Gestation | Lactation |
|---|---|---|
| Ingredients | | |
| Corn | 680.0 | 620.0 |
| Soybean meal | 80.0 | 140.0 |

TABLE 11-continued

Ingredient and nutrient composition of the basal diets (g/kg of feed, as-is basis)

| Items | Gestation | Lactation |
|---|---|---|
| Wheat bran[a] | 200.0 | 120.0 |
| Full-fat soybean | 0.0 | 50.0 |
| Soybean oil | 0.0 | 32.0 |
| NaCl | 2.0 | 3.0 |
| NaHCO$_3$ | 3.5 | 3.5 |
| L-Lys•HCl | 4.0 | 3.5 |
| DL-Met | 1.0 | 0.5 |
| L-Thr | 1.5 | 1.5 |
| L-Val | 0.5 | 1.5 |
| L-Trp | 0.5 | 0.5 |
| Limestone | 19.0 | 15.5 |
| Vitamin-mineral premix[b] | 5.0 | 5.0 |
| Stay C, 35% vitamin C | 0.0 | 0.5 |
| TiO$_2$ | 3.0 | 3.0 |
| Total | 1000.0 | 1000.0 |
| Calculated nutrients and energy | | |
| ME, MJ/kg | 12.7 | 13.9 |
| Crude protein | 12.8 | 15.6 |
| Total Ca | 8.4 | 7.3 |
| Total P | 4.3 | 4.0 |
| Phytate P | 3.5 | 3.0 |
| Apparent total tract digestible P | 1.6 | 1.4 |
| Standardized total tract digestible P | 2.0 | 1.8 |
| Standardized ileal digestible | | |
| Lysine | 7.1 | 8.6 |
| Methionine | 2.8 | 2.6 |
| Threonine | 4.9 | 5.9 |
| Tryptophan | 1.6 | 1.9 |
| Valine | 4.9 | 7.0 |

[a]Wheat bran was pelleted at 95° C. before the mixing of diet.
[b]Premix supplied per kilogram of diet: vitamin A, 12,000 IU; vitamin D$_3$, 2,000 IU; vitamin E, 115 mg; vitamin K$_3$, 5.0 mg; vitamin B$_1$, 2.0 mg; vitamin B$_2$, 6 mg; vitamin B$_6$, 3.0 mg; vitamin B$_{12}$, 28 µg; D-biotin, 700 µg; pantothenic acid, 20 mg; folic acid, 5 mg; niacin, 30 mg; Cu (tribasic copper chloride), 20 mg; I (potassium iodate), 0.45 mg; Fe (ferrous sulfate), 120 mg; Mn (manganese sulfate), 60 mg; Zn (zinc sulfate), 100 mg; Se (sodium selenite), 400 µg; choline (choline chloride), 600 mg; and Ca (calcium carbonate) 0.5 g.

TABLE 12

Apparent total-tract digestibility of calcium (Ca) and phosphorus (P) and digested Ca and P in feed for gestating and lactating sows, %[a]

| Items | Treatments, FYT/kg feed | | | SEM[b] | Significance level | | |
|---|---|---|---|---|---|---|---|
| | Control | 187.5 | 375.0 | | Phytase | Linear | Quadratic |
| Gestation | | | | | | | |
| Dry matter | 82.7 | 81.9 | 82.1 | 0.336 | 0.121 | 0.254 | 0.253 |
| Calcium | 28.7 | 32.2 | 33.9 | 1.255 | 0.007 | 0.006 | 0.548 |
| Phosphorus | 15.3 | 28.1 | 33.8 | 1.071 | <0.001 | <0.001 | 0.011 |
| Digested Ca | 0.23 | 0.28 | 0.29 | 0.011 | <0.001 | <0.001 | 0.293 |
| Digested P | 0.07 | 0.14 | 0.17 | 0.005 | <0.001 | <0.001 | 0.006 |
| Digested Ca/digested P | 3.22 | 2.02 | 1.78 | 0.112 | <0.001 | <0.001 | 0.001 |
| Lactation | | | | | | | |
| Dry matter | 86.7 | 86.4 | 86.3 | 0.294 | 0.404 | 0.384 | 0.870 |
| Calcium | 33.9 | 36.4 | 40.7 | 1.486 | 0.016 | 0.003 | 0.603 |
| Phosphorus | 23.6 | 43.9 | 50.2 | 0.903 | <0.001 | <0.001 | <0.001 |
| Digested Ca | 0.24 | 0.25 | 0.29 | 0.010 | 0.046 | 0.007 | 0.414 |
| Digested P | 0.10 | 0.19 | 0.22 | 0.004 | <0.001 | <0.001 | <0.001 |
| Digested Ca/P | 2.43 | 1.32 | 1.28 | 0.045 | <0.001 | <0.001 | <0.001 |
| Reproductive stage Treatment Interaction | | | | | | | |
| Dry matter | <0.001 | 0.222 | 0.716h | | | | |
| Calcium | <0.001 | <0.001 | 0.622 | | | | |

TABLE 12-continued

Apparent total-tract digestibility of calcium (Ca) and phosphorus (P) and digested Ca and P in feed for gestating and lactating sows, %[a]

| | Treatments, FYT/kg feed | | | | Significance level | |
|---|---|---|---|---|---|---|
| Items | Control | 187.5 | 375.0 | SEM[b] | Phytase | Linear | Quadratic |
| Phosphorus | <0.001 | <0.001 | <0.001 | | | | |
| Digested Ca/digested P | 0.514 | <0.001 | 0.313 | | | | |
| Digested P | <0.001 | <0.001 | <0.001 | | | | |
| Digested Ca/P | <0.001 | <0.001 | 0.222 | | | | |

[a]Each least square mean represents 15 observations
[b]SEM: sandard error of mean.

Example 10: Phytase Efficacy in Rainbow Trout (Oncorhynchus Mykiss)

Experimental Diets

Experimental diets were prepared in the experimental feed mill of the Research Centre for Animal Nutrition & Health, DSM Nutritional Products in Village-Neuf (France) according to the formulation detailed in Table 13. Diets were prepared in mash and produced as extruded pellets using a Bühler twin screw extruder. After extrusion, pellets were coated with a mixture of oils heated at 40° C. and phytase (var400). Experimental diets were kept at 4° C. during the feeding trial.

Theoretical calculations were 0.821% for total phosphorus, 0.326% for phytate phosphorus and 11.5 g/Kg phytic acid (according to Allix 3 software, A-systems, France).

Fish and Rearing Facilities

Two hundred and forty monosex (all female) Rainbow trout (IBW=46.3±1.2g) were randomly distributed in twelve tanks (250L; twenty fish per tank).

TABLE 13

Detailed composition (%) of the basal diet and calculated crude protein/lipid in the diet

| Ingredient | Experimental diet |
|---|---|
| Fish meal | 13.20 |
| Soybean meal | 8.00 |
| SPC | 17.00 |
| Rapeseed meal | 7.00 |
| Sunflower meal | 8.00 |
| Wheat | 11.00 |
| Wheat gluten | 12.00 |
| Fish oil | 11.00 |
| Rapeseed oil | 9.90 |
| Choline chloride 60% | 0.4 |
| DSM OVM VMF | 0.5 |
| L-Lysine | 0.5 |
| L-Methionine | 0.2 |
| Yttrium oxide | 200 ppm |
| Guar gum | 0.3 |
| Calc. crude protein | 40.0 |
| Calc. crude lipid | 24.0 |

Feeding

Animals were fed for 91 days. Trout were fed by hand twice a day (morning and afternoon) during the week and by automatic feeders during weekends. All fish were fed according to feeding ration table for a similar commercial diet fed to fish maintained at the same water temperature. Feed consumption and body weight thorough the experiment are represented in FIG. 2. Feed consumption is calculated as percentage, based on the actual intake per week and the growth of the fish (specific growth rate) during the 2-week period. Feed consumption ranged from 2.31% to 1.65% throughout the experimental feeding (FIG. 2).

Zootechnical Parameters

Fish were individually weighed at the beginning of the trial and the mean body weight of the fish per triplicate tanks was determined after bulk weighing of the fish at each time point considered. Bulk weight was recorded every two weeks. Before handling, fish were anesthetized (0.08 g/L tricaine methane sulfonate; MS222; PharmaQ Ltd., Overhalla, Norway).

The following zootechnical parameters were measured/calculated:
Survival (%)
Performance
Initial body weight, IBW (g)
Final body weight, FBW (g)
Weight gain, WG as FBW− IBW (g)
Specific growth rate, SGR as $\{100*(\ln(FBW/IBW))\}*d^{-1}$ (% BW $d^{-1}$)
Feed utilization
Feed conversion ratio, FCR as Feed Intake*biomass gain$^{-1}$ (as-fed basis)

Phosphorus Whole Body Retention

At the beginning and at the end of the trial, whole fish were sampled and frozen at −80° C. to analyze phosphorus whole body retention.

Plasma

At the end of the experimental feeding trial, five fish per tank (15 fish per treatment) were individually anaesthetized using 80 mg MS222-L$^{-1}$.

Four mL of blood were sampled using a lithium-heparin 4.5 mL syringe and kept in ice until further processing. Blood samples were centrifuged (10 min, 2000g, 4° C.) and 1.5 mL plasma aliquots were frozen (−20° C.) until analysis. Samples were analyzed individually.

Samples were analyzed individually but each tank was considered as a replicate for statistical purposes.

Apparent Digestibility Coefficient (ADC)

Two different faeces collection were done 77 and 91 days after the start of the experimental feeding for the determination of phosphorus ADC. Animals were slightly anaesthetized (80 mg MS222-L$^{-1}$) and fecal material from all fish in each tank was collected by manually stripping faeces from the distal portion of the intestine by applying pressure to the abdominal cavity using three passes for each fish. Samples from both collection days were pooled and one sample per tank was lyophilized prior to storage and analysis.

The apparent digestibility coefficient (ADC) was calculated as outlined by the NRC (2001) on a dry matter basis:

$$ADC(\%)=100-[(CMf/CMe) \times (CNe/CNf)] \times 100$$

CMf=concentration of marker in feed;
CMe=concentration of marker in faeces;
CNf=concentration of nutrient in feed;
CNe=concentration of nutrient in faeces Phosphorus release represents the % of phosphorus released due to phytase supplementation. It is calculated as follows:

(% total $P$ of the feed×Phosphorus ADCPHY $X$)−(% total $P$ of the feed*Phosphorus ADCtest)

Where % total P is the total percentage of phosphorus in the diet; ADCPHY X is the digestibility of the phosphorus at a given phytase dose; and Phosphorus ADCtest is the phosphorus digestibility of the test diet without phytase supplementation.

Bone Phosphorus Retention

Figure 3:
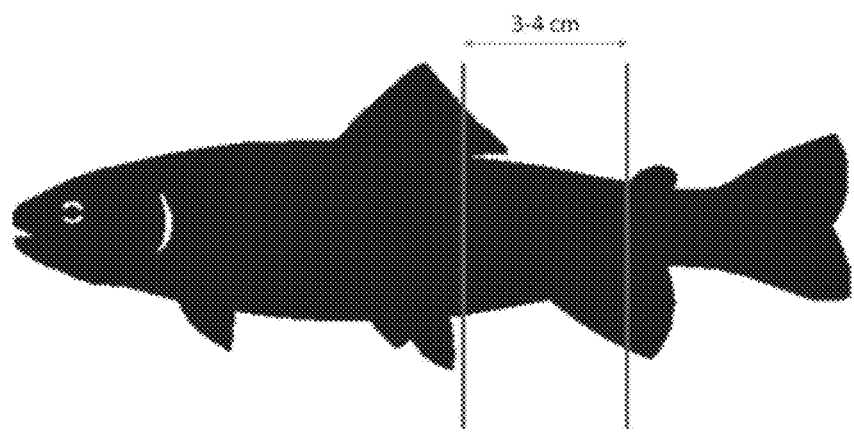
FIG. 3 shows schema for bone P retention sampling.
Figure 4:
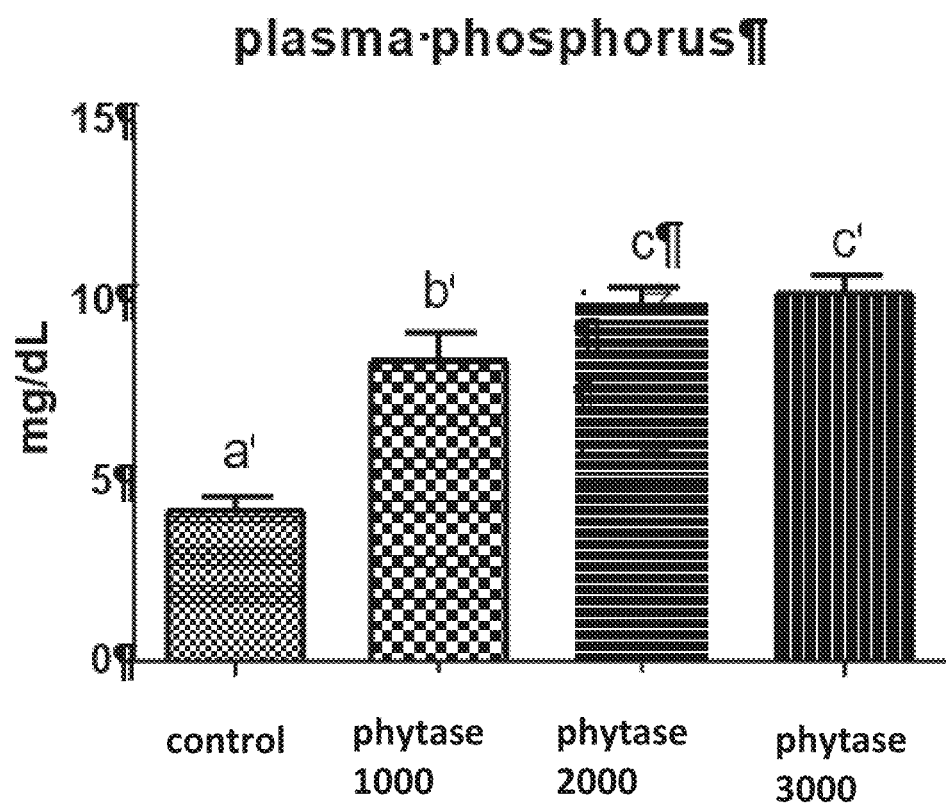
FIG. 4 shows phosphorus in the plasma of fish from different experimental treatments after 91 days of feeding. Data are presented as mean±SD (Standard Deviation). Significant treatments (p<0.05) are shown by different letters.

At the beginning and at the end of the trial, a 3-4 cm slide (see FIG. 3) was sampled in five fish per tank(15 fish per treatment) and frozen at −80° C. Skin and flesh will be removed to further process only the bones for analysis.

Analyses and Calculations

The analyses of the nutrient content in the feed, excreta, plasma, whole fish and vertebra samples were performed according to standard methods (VDLUFA 1976; AOAC, 2006).

Phytate-P in feed were measured by enzyme laboratory DNP R&D Solution Center (Kaiseraugst) with an enzymatic method using ammonium molybdate by calculation of the difference between the total P and free P, according to Zhai et al., 2001.

The crude protein was determined by a nitrogen analyzer (FP 528, LECO, St. Joseph, USA) using the Dumasmethod (CP=N*6.25).

Gross energy measurements were performed using an adiabatic bomb calorimeter (C 2000 basic, IKA, Staufen, Germany).

Calcium, Phosphorus, Zinc and Yttrium oxide concentrations in feed, whole fish, vertebra and excreta were determined by Inductively Coupled Plasma-Optical Emission Spectrometry (ICP-OES, 5100 Dual View, Agilent) according to DIN EN ISO 11885:1997 (DIN EN ISO 1998; AOAC, 2006) after sulfuric acid mineralization. Water analysis of phosphorus were performed on the same instrument on frozen water samples by direct injection.

The plasma concentrations of P concentration were determined by the mean of a Biomedical automate COBAS 6000 (Roche Diagnostics, CH-4202 Basel) using the respective Roche Diagnostic kits.

The lipid analyses of feed were performed at the external company Larebron by hot acidic etching with hydrochloric acid, followed by continuous extraction with petroleum ether and determination with a gravimetric method.

Phytase analysis in the diets was done at BioPract GmbH, Germany, according to ISO 30024:2009 (Animal feeding stuffs—Determination of phytase activity, www.iso.org/standard/45787.html).

Result

Table 14 shows the analytical results obtained at BioPract GmbH.

TABLE 14

Phytase content in the eight experimental treatments.

| Treatment ID | Dose U/Kg (theoretical) | Pellet Ø (mm) | Dose U/Kg (analytical) |
|---|---|---|---|
| P | Control-0 | 3 | LOD |
| Q | phytase 1000 FYT/kg | 3 | 955 |
| R | phytase 2000 FYT/kg | 3 | 1740 |
| S | phytase 3000 FYT/kg | 3 | 2477 |
| P | Control-0 | 4 | LOD |
| Q | phytase 1000 FYT/kg | 4 | 977 |
| R | phytase 2000 FYT/kg | 4 | 1719 |
| S | phytase 3000 FYT/kg | 4 | 2895 |

LOD = below level of detection.

Fish Behavior and Water Quality

No mortality was recorded through the whole experiment and fish accepted well all the experimental diets.

Performance

Table 15 shows the zootechnical parameters at the end of the 91-day experimental feeding period. Control diet showed the poorest growth rate. Supplementation with phytase had a positive impact in growth. This trend was dose-related and supplementation in 1000 FYT/Kg group growth was significantly higher than the control group; similarly, animals with 2000 and 3000 FYT/Kg enzyme supplementation perform significantly better than the 1000 FYT/Kg.

Specific growth rate and feed conversion ratio were also significantly improved with any inclusion level of phytase but independently from the inclusion level.

TABLE 15

Survival and growth performance of fish (day 0 to day 91).

| ID | Dose | Survival | IBW | FBW | SGR | FCR |
|---|---|---|---|---|---|---|
| P | Control -0 | 100 ± 0 | 46.3 ± 0.0 | 334.7 ± 7.0 c | 2.17 ± 0.02 b | 0.87 ± 0.0 a |
| Q | phytase 1000 FYT/kg | 100 ± 0 | 46.3 ± 0.0 | 357.2 ± 10.1 b | 2.25 ± 0.03 a | 0.83 ± 0.01 b |
| R | phytase 2000 FYT/kg | 100 ± 0 | 46.3 ± 0.0 | 374.4 ± 3.0 a | 2.30 ± 0.01 a | 0.82 ± 0.01 b |
| S | phytase 3000 FYT/kg | 98.3 ± 2.9 | 46.3 ± 0.0 | 376.0 ± 9.7 a | 2.30 ± 0.03 a | 0.81 ± 0.01 b |
| | Sign | ns | ns | p = 0.0006 | p = 0.0006 | P = 0.0004 |

Survival percentages referred to the whole duration of the trial;

IBW: Initial Body Weight (g);

FBW: Final Body Weigh (g)t;

SGR: specific growth rate (% BW/day);

FCR: feed conversion ratio (as-fed basis).

Data arepresented as mean ± SD (Standard Deviation).

Sign. = significance;

Ns: no significant differences were observed between treatments.

Whole Body Phosphorus Retention

Table 16 shows the whole body retention (% of intake) for minerals and protein. Significant improvement in whole body zinc and protein retention at any supplementation dose. Phosphorus was significantly improved when phytase was supplemented at 1000 and 3000 FYT/Kg. Surprisingly, phytase inclusion at 2000 FYT/Kg showed an intermediate response.

TABLE 16

Phosphorus, zinc, calcium and protein whole body retention (% of intake; day 0 to day 91).

| ID | Dose | Phosphorus | Zinc | Calcium | Protein |
|----|------|------------|------|---------|---------|
| P | Control-0 | 1.64 ± 0.29 b | 0.60 ± 0.04 b | 0.52 ± 0.12 | 2.22 ± 0.08 b |
| Q | phytase 1000 FYT/kg | 2.63 ± 0.56 a | 1.25 ± 0.25 a | 1.68 ± 0.78 | 2.65 ± 0.32 a |
| R | phytase 2000 FYT/kg | 2.27 ± 0.37 ab | 1.15 ± 0.24 a | 1.34 ± 0.38 | 2.48 ± 0.02 ab |
| S | phytase 3000 FYT/kg | 2.60 ± 0.17 a | 1.28 ± 0.10 a | 1.48 ± 0.30 | 2.57 ± 0.03 ab |
|   | Sign | p = 0.0398 | p = 0.0055 | Ns p = 0.0640 | Ns p = 0.0526 |

Data are presented as mean ± SD (Standard Deviation; n = 3).
Sign. = significance;
Ns: no significant differences were observed between treatments.

Phosphorus Content in Plasma

Plasma phosphorus concentration was significantly increased with the supplementation of phytase. The supplementation of the exogenous enzyme increased the circulating phosphorus 1.99, 2.3 and 2.44 fold when compared to control diet.

Apparent Digestibility Coefficient (ADC)

The faecal digestibility for dry matter, protein, energy and minerals (phosphorus, calcium and zinc) is summarized in the Table 17.

Data show that the supplementation of phytase from 1000 FYT/kg significantly improved the faecal dry matter, energy digestibility as well as the faecal calcium, phosphorus and zinc digestibility. Phosphorus digestibility was increased by 60.1, 82.9 and 89.7% for phytase 1000 FYT/kg, phytase 2000 FYT/kg and phytase 3000 FYT/kg, respectively, when compared to the non-supplemented control group. Accordingly, based on the above results, an aspect of the invention is directed to method of feeding fish comprising adding the phytase, as defined herein, such as in an amount of 500 to 5000 FYT/kg. In typical embodiments, the amount of phytase is from 500 to 3000 FYT/kg, such as 750 to 3000 FYT/kg, such as 1000 to 3000 FYT/kg.

Bone Phosphorus Retention

Retention of phosphorus is summarized in Table 18. In the vertebrae, percentage of ash and the concentration of phosphorus increased significantly with phytase incorporation when compared to the negative control.

TABLE 18

Retention of ash and phosphorus in vertebrae of fish (% of DM) after 91 days of experimental feeding.

| ID | Dose | Ash | Phosphorus |
|----|------|-----|------------|
| P | Control-0 | 21.2 ± 3.4b | 3.77 ± 0.66b |
| Q | phytase 1000 FYT/kg | 28.6 ± 1.4a | 5.16 ± 0.26a |
| R | phytase 2000 FYT/kg | 28.6 ± 3.0a | 5.17 ± 0.58a |
| S | phytase 3000 FYT/kg | 28.9 ± 1.0a | 5.26 ± 0.19a |
|   | sign | p = 0.0116 | p = 0.013 |

Newman-Keuls test: Means within a row, not sharing a common superscript, are significantly different (p < 0.05). Digestibility were calculated with n = 3 tanks per treatment.

Conclusion

The supplementation of the reference diet (0.74 total phosphorus) with the phytase at 1000, 2000 and 3000 FYT/kg showed a dose-dependent and significant increase in growth, plasma phosphorus and plasma apparent digestibility after 91 days of experimental feeding. The inclusion of phytase at any level increased the retention of phosphorus in whole body and vertebrae of the animals.

The phytase of the invention is efficient in releasing phosphorus from phytate and the invention is directed in part

TABLE 17

Apparent digestibility coefficient (%) and phosphorus release (Phos. Rel .; % phosphorus/kg feed).

| ID | Dose | Dry matter | Protein | Energy | Phosphorus | Calcium | Zinc | Phos. Rel. |
|----|------|------------|---------|--------|------------|---------|------|------------|
| P | Control -0 | 69.8 ± 0.18$^c$ | 89.6 ± 0.08$^b$ | 78.9 ± 0.13$^c$ | 32.1 ± 1.06$^d$ | −0.6 ± 2.03$^c$ | 20.0 ± 0.97$^c$ | |
| Q | phytase 1000 FYT/kg | 71.3 ± 0.55$^b$ | 90.0 ± 0.19$^b$ | 79.6 ± 0.31$^b$ | 51.4 ± 0.62$^c$ | 5.2 ± 1.46$^b$ | 28.6 ± 0.65$^b$ | 0.14 |
| R | phytase 2000 FYT/kg | 71.4 ± 0.16$^b$ | 90.0 ± 0.21$^b$ | 79.5 ± 0.07$^b$ | 58.7 ± 0.31$^b$ | 7.3 ± 1.26$^{ba}$ | 32.0 ± 1.90$^a$ | 0.20 |
| S | phytase 3000 FYT/kg | 72.6 ± 0.30$^a$ | 90.6 ± 0.20$^a$ | 80.2 ± 0.30$^a$ | 60.9 ± 1.89$^a$ | 10.2 ± 1.89$^a$ | 34.0 ± 2.09$^a$ | 0.21 |
|   | Sign | p = 0.0001 | p = 0.0013 | p = 0.0006 | p < 0.0001 | p = 0.0003 | p <0.0001 | |

Newman-Keuls test: Means within a row, not sharing a common superscript, are significantly different (p < 0.05). Digestibility were calculated with n = 3 tanks per treatment.

to the use of the phytase when fish meal in the diets of salmonid fish is replaced by vegetable raw materials rich in this antinutritional factor.

Example 11: Effect of Graded Supplemental Levels of Phytase on the Growth Performance, Whole-Body Nutrient Retention and Nutrient Digestibility in European Seabass (*Dicentrarchus labrax*) Fed a Plant-Protein Rich Diet The trial comprised five dietary treatments: a control diet (CTRL) with a total dietary phosphorus (P) level of 0.7%, in which a significant fraction of P was present in the form of phytate-bound P (0.3%). Three other diets, based on the CTRL formulation, were supplemented with phytase (var400) at graded doses (500, 1000 and 2000 FTY/kg feed) (diets PHY500, PHY1000, PHY2000). Phytase was applied post-extrusion by coating. A fifth diet (MCP), also based on the CTRL formulation, was supplemented with monocalcium phosphate, to a total P level of 0.9% and an available P level higher than the known requirements of the species. All diets were isonitrogenous, isolipidic and isoenergetic. Quadruplicate groups of 38 European seabass, with a mean initial body weight of 57.6±3.8 g were fed one of the five experimental diets during 94 days, with a water temperature profile of 22.1±0.4° C.

TABLE 19

Formulation of experimental diets and measured phytase activity

| Ingredients, % | CTRL | PHY500 | PHY1000 | PHY2000 | MCP |
|---|---|---|---|---|---|
| Fishmeal Super Prime | 7.50 | 7.50 | 7.50 | 7.50 | 7.50 |
| Fish protein hydrolysate | 2.50 | 2.50 | 2.50 | 2.50 | 2.50 |
| Wheat gluten | 10.10 | 10.10 | 10.10 | 10.10 | 10.50 |
| Corn gluten meal | 20.00 | 20.00 | 20.00 | 20.00 | 20.00 |
| Soybean meal | 24.00 | 24.00 | 24.00 | 24.00 | 24.00 |
| Rapeseed meal | 12.00 | 12.00 | 12.00 | 12.00 | 12.00 |
| Sunflower meal | 5.00 | 5.00 | 5.00 | 5.00 | 5.00 |
| Wheat bran | 3.03 | 3.03 | 3.03 | 3.03 | 1.43 |
| Fish oil | 5.00 | 5.00 | 5.00 | 5.00 | 5.00 |
| Rapeseed oil | 9.60 | 9.60 | 9.60 | 9.60 | 9.60 |
| Vitamin and mineral premix | 1.00 | 1.00 | 1.00 | 1.00 | 1.00 |
| Antioxidant | 0.20 | 0.20 | 0.20 | 0.20 | 0.20 |

TABLE 19-continued

Formulation of experimental diets and measured phytase activity

| Ingredients, % | CTRL | PHY500 | PHY1000 | PHY2000 | MCP |
|---|---|---|---|---|---|
| Monocalcium phosphate | | | | | 1.20 |
| L-Tryptophan | 0.02 | 0.02 | 0.02 | 0.02 | 0.02 |
| DL-Methionine | 0.03 | 0.03 | 0.03 | 0.03 | 0.03 |
| Yttrium oxide | 0.02 | 0.02 | 0.02 | 0.02 | 0.02 |
| phytase (FTY/kg) | | 500 | 1000 | 2000 | |

Result

At the end of the trial, the final body weight (FBW) ranged between 142.0 and 156.5 grams. Fish from the best performing treatment (PHY2000) showed a 2.7-fold increase of initial body weight (IBW). At day 94, all supplemented diets resulted on a significantly higher FBW and SGR than those fed the CTRL diet (P<0.05). Fish fed the PHY500, PHY1000, PHY2000 and MCPdiets showed a significantly lower FCR than those fed the CTRL diet (P<0.05). The CTRL treatment was consistently associated to significantly lowest values among the various treatments for whole-body phosphorus retention and apparent digestibility of phosphorus. The higher phytase supplementation doses (1000 and 2000 FTY/kg) led to a significant increase of whole-body P content (P<0.05). Fish fed the MCP diet showed a significantly higher whole-body P retention than those fed the CTRL diet, although significantly lower than those fed the PHY1000 and PHY2000 diets. Significant enhancements of total P and phytate-P digestibility were associated to increasing dietary doses of phytase, with dietary treatment PHY2000 having a significantly higher P digestibility than PHY1000, and the later having a significantly higher P digestibility than PHY500. Additionally, the increase of phytase supplementation doses (0, 500, 1000 and 2000 FTY/kg) was also positively associated to a stepwise increase of whole-body phosphorus retention. Accordingly, based on the above results, an aspect of the invention is directed to method of feeding fish comprising adding the phytase, as defined herein, such as in an amount of 250 to 5000 FYT/kg. In typical embodiments, the amount of phytase is from 300 to 4000 FYT/kg, such as 500 to 3000 FYT/kg.

TABLE 20

Growth performance after 94 days of feeding (end of the trial).

| | CTRL | PHY500 | PHY1000 | PHY2000 | MCP | P-value |
|---|---|---|---|---|---|---|
| Survival, % | 99.3 ± 1.3 | 100.0 ± 0.0 | 100.0 ± 0.0 | 100.0 ± 0.0 | 100.0 ± 0.0 | 0.438 |
| IBW, g | 57.6 ± 0.1 | 57.5 ± 0.1$^b$ | 57.5 ± 0.1$^b$ | 57.6 ± 0.1$^c$ | 57.5 ± 0.1$^c$ | 0.572 |
| FBW, g | 42.0 ± 2.4$^a$ | 148.6 ± 1.6 | 153.0 ± 1.6 | 156.5 ± 2.6 | 152.5 ± 2.9 | <0.001 |
| SGR, %/d | 0.96 ± 0.02$^a$ | 1.01 ± 0.01$^b$ | 1.04 ± 0.01$^c$ | 1.06 ± 0.02$^c$ | 1.04 ± 0.02$^c$ | <0.001 |
| FCR | 1.35 ± 0.07$^b$ | 1.25 ± 0.03$^a$ | 1.24 ± 0.02$^a$ | 1.19 ± 0.01$^a$ | 1.24 ± 0.02$^a$ | <0.001 |
| FI, % ABW/d | 1.21 ± 0.05 | 1.18 ± 0.03 | 1.19 ± 0.02 | 1.17 ± 0.02 | 1.19 ± 0.03 | 0.412 |
| PER | 1.62 ± 0.08$^a$ | 1.75 ± 0.05$^b$ | 1.77 ± 0.03$^{bc}$ | 1.83 ± 0.02$^c$ | 1.74 ± 0.03$^b$ | <0.001 |

Values are means ± standard deviation (n = 4).

Values within a row with different superscripts, denote a statistical difference (P < 0.05).

TABLE 21

Whole-body nutrient retention (% of intake).

| | CTRL | PHY500 | PHY1000 | PHY2000 | MCP | P-value |
|---|---|---|---|---|---|---|
| Protein, % | 21.2 ± 2.1$^a$ | 23.3 ± 0.5$^{ab}$ | 23.6 ± 2.0$^{ab}$ | 24.6 ± 0.7$^b$ | 22.2 ± 0.4$^{ab}$ | 0.027 |
| Fat, % | 61.5 ± 2.1 | 67.7 ± 1.3 | 67.9 ± 3.7 | 66.4 ± 2.8 | 65.6 ± 5.7 | 0.118 |
| Energy, % | 31.5 ± 1.9$^{ab}$ | 34.3 ± 1.6$^b$ | 32.0 ± 1.8$^{ab}$ | 31.4 ± 0.7$^{ab}$ | 29.9 ± 1.0$^a$ | 0.013 |
| Phosphorus, % | 40.3 ± 1.3$^a$ | 44.9 ± 1.6$^b$ | 51.8 ± 1.5$^c$ | 62.0 ± 2.9$^d$ | 46.3 ± 3.3$^b$ | <0.001 |
| Calcium, % | 36.9 ± 1.8$^b$ | 40.7 ± 4.4$^b$ | 47.0 ± 2.8$^c$ | 48.5 ± 3.6$^c$ | 30.1 ± 3.6$^a$ | <0.001 |

Values are average ± standard deviation (n = 4).
Values within a row with different superscripts, denote a statistical difference (P < 0.05).

TABLE 22

Apparent digestibility coefficients (ADC, %) of nutrients.

| | CTRL | PHY500 | PHY1000 | PHY2000 | MCP | P-value |
|---|---|---|---|---|---|---|
| Dry matter, % | 66.9 ± 0.3$^b$ | 70.4 ± 0.7$^d$ | 69.0 ± 1.2$^{cd}$ | 68.2 ± 1.1$^{bc}$ | 64.1 ± 1.4$^a$ | <0.001 |
| Protein, % | 89.4 ± 0.1$^a$ | 91.2 ± 0.6$^c$ | 90.6 ± 0.3$^b$ | 90.2 ± 0.5$^b$ | 88.9 ± 0.3$^a$ | <0.001 |
| Phosphorus, % | 33.5 ± 1.3$^a$ | 41.4 ± 3.0$^b$ | 50.1 ± 2.3$^c$ | 62.8 ± 0.7$^d$ | 52.8 ± 2.3$^c$ | <0.001 |
| Phytate-P, % | 23.9 ± 0.8$^b$ | 33.5 ± 1.7$^c$ | 37.2 ± 3.0$^c$ | 42.4 ± 1.8$^d$ | 18.1 ± 4.4$^a$ | <0.001 |
| Calcium, % | 37.8 ± 1.1$^b$ | 40.5 ± 0.7$^b$ | 38.5 ± 2.4$^b$ | 38.2 ± 3.6$^b$ | 29.8 ± 2.7$^a$ | <0.001 |

Values are average ± standard deviation (n = 4).
Values within a row with different superscripts, denote a statistical difference (P < 0.05).

Conclusion

The phytase at supplementation doses of 500 to 5000 FTY/kg feed, such as 500 to 3000 FTY/kg, such as 500 to 2500 FTY/kg, such as 500 to 2000 FTY/kg such as 1000 to 2000 FTY/kg feed is an effective strategy to enhance the growth rate, phosphorus digestibility, whole-body phosphorus retention and reduce FCR in European seabass fed plant protein-rich diets.

Example 12: Efficacy of a Phytase on the Growth Performance, Whole-Body Nutrient Retention and Nutrient Digestibility in Nile Tilapia (Oreochromis niloticus)Fed Plant-Protein Rich Diets The trial comprised five dietary treatments: a control diet (CTRL) with a total dietary phosphorus (P) level of 0.96%, in which a significant fraction of P was present in the form of phytate-bound P (0.6%). Three other diets, based on the CTRL formulation, were supplemented with phytase (var400) at graded doses (500, 1000 and 2000 FTY/kg feed) (diets PHY500, PHY1000, PHY2000). Phytase was applied post-extrusion by coating. A fifth diet (DCP), also based on the CTRL formulation, was supplemented with dicalcium phosphate, to a total P level of 1.2% and an available P level higher than the known requirements of the species. All diets were isonitrogenous, isolipidic and isoenergetic. Quadruplicate groups of 30 tilapia, with a mean initial body weight of 39.5±1.4 g were fed one of the five experimental diets during 93 days, with a water temperature profile of 25.5±0.4° C.

TABLE 23

Formulation of experimental diets

| Ingredients, % | CTRL | PHY500 | PHY1000 | PHY2000 | DCP |
|---|---|---|---|---|---|
| Fishmeal 60[1] | 2.50 | 2.50 | 2.50 | 2.50 | 2.50 |
| Guar korma meal[2] | 4.50 | 4.50 | 4.50 | 4.50 | 4.80 |
| Soybean meal | 32.50 | 32.50 | 32.50 | 32.50 | 32.50 |
| Rapeseed meal | 20.00 | 20.00 | 20.00 | 20.00 | 20.00 |
| Wheat bran | 14.00 | 14.00 | 14.00 | 14.00 | 14.00 |
| Rice bran | 14.00 | 14.00 | 14.00 | 14.00 | 14.00 |
| Corn meal | 8.20 | 8.20 | 8.20 | 8.20 | 6.53 |
| Fish oil | 0.50 | 0.50 | 0.50 | 0.50 | 0.50 |
| Rapeseed oil | 1.90 | 1.90 | 1.90 | 1.90 | 2.00 |
| Vit & Min premix | 1.00 | 1.00 | 1.00 | 1.00 | 1.00 |
| Antioxidant | 0.20 | 0.20 | 0.20 | 0.20 | 0.20 |
| Dicalcium phosphate | | | | | 1.60 |
| Calcium carbonate | 0.33 | 0.33 | 0.33 | 0.33 | |
| L-Lysine HCl | 0.10 | 0.10 | 0.10 | 0.10 | 0.10 |
| L-Tryptophan | 0.05 | 0.05 | 0.05 | 0.05 | 0.05 |
| DL-Methionine | 0.20 | 0.20 | 0.20 | 0.20 | 0.20 |
| Yttrium oxide | 0.02 | 0.02 | 0.02 | 0.02 | 0.02 |
| phytase (FTY/kg) | | 500 | 1000 | 2000 | |

[1]COFACO 60: 62.3% crude protein (CP), 8.4% crude fat (CF), COFACO, Portugal;
[2]Guar Korma: 55.3% CP, 7.8% CF, KFEED Ltd, Bulgaria.

Result

At the end of the trial, fish from the best performing treatment (PHY2000) showed a 4.7-fold increase of initial body weight. Fish fed the CTRL diet showed a significantly lower FBW, SGR, PER, and a higher FCR than those fed all other diets (P<0.05). Moreover, fish fed the PHY1000, PHY2000 and DCP diets showed a significantly higher FBW and SGR than those fed the PHY500 and CTRL diets (P<0.05). Fish fed the PHY2000 diet showed a significantly lower FCR than those fed the PHY500 diet (P<0.05). Feed intake (FI) varied between 1.75 and 1.82% ABW per day and was not significantly affected by dietary treatments (P>0.05). Fish fed the CTRL diet showed a significantly lower whole-body phosphorus (P) content than those fedall other diets (P<0.05). The graded increase of phytase supplementation doses resulted on significant increases of whole-body P content (P<0.05). The graded increase of dietary phytase resulted on significant increases of whole-body P retention (P<0.05). Fish fed the DCP diet showed a significantly higher whole-body P retention than those fed the CTRL and PHY500 diets (P<0.05), although significantly lower than those fed the PHY1000 and PHY2000 diets (P<0.05). Fish fed the CTRL diet showed a significantly lower P digestibility than those fed all other diets (P<0.05). Significant enhancements (P<0.05) of P digestibility were associated to increasing dietary doses of the phytase, with dietary treatment PHY2000 having a significantly higher P digestibility than PHY1000 (P<0.05), and the later having a significantly higher P digestibility than PHY500 (P<0.05). Phosphorus digestibility of the DCP diet was significantly lower than that of diet PHY2000 (P<0.05) and significantly higher than that of PHY500 and CTRL diets (P<0.05).

in which a significant fraction of P was present in the form of phytate-bound P (0.4%). Three other diets, based on the CTRL formulation, were supplemented with phytase (var400) at graded doses (500, 1000 and 2000 FTY/kg feed) (diets PHY500, PHY1000, PHY2000). Phytase was applied post-extrusion by coating. A fifth diet (MCP), also based on the CTRL formulation, was supplemented with monocalcium phosphate, to a total P level of 1.1% and an available P level higher than the known requirements of the species. All diets were isonitrogenous, isolipidic and isoenergetic. Quadruplicate groups of 37 gilthead seabream, with a mean

TABLE 24

Growth performance after 93 days of feeding (end of the trial).

|  | CTRL | PHY500 | PHY1000 | PHY2000 | DCP | P-value |
|---|---|---|---|---|---|---|
| Survival, % | 99.2 ± 1.7 | 99.2 ± 1.7 | 99.2 ± 1.7 | 100.0 ± 0.0 | 100.0 ± 0.0 | 0.736 |
| IBW, g | 39.7 ± 0.1 | 39.5 ± 0.3 | 39.7 ± 0.2 | 39.2 ± 0.3 | 39.6 ± 0.4 | 0.187 |
| FBW, g | 144.1 ± 8.0$^a$ | 162.6 ± 3.3$^b$ | 175.3 ± 3.1$^c$ | 183.7 ± 6.4$^c$ | 174.6 ± 4.6$^c$ | <0.001 |
| SGR, %/d | 1.39 ± 0.06$^a$ | 1.52 ± 0.03$^b$ | 1.60 ± 0.02$^c$ | 1.66 ± 0.03$^c$ | 1.60 ± 0.03$^c$ | <0.001 |
| FCR | 1.45 ± 0.06$^c$ | 1.36 ± 0.05$^b$ | 1.31 ± 0.04$^{ab}$ | 1.26 ± 0.05$^a$ | 1.34 ± 0.02$^{ab}$ | <0.001 |
| FI, %ABW/d | 1.79 ± 0.06 | 1.78 ± 0.08 | 1.78 ± 0.04 | 1.75 ± 0.07 | 1.82 ± 0.02 | 0.672 |
| PER | 2.28 ± 0.10$^a$ | 2.43 ± 0.10$^b$ | 2.54 ± 0.08$^{bc}$ | 2.63 ± 0.10$^c$ | 2.47 ± 0.03$^b$ | <0.001 |

Values are means ± standard deviation (n = 4).
Values within a row with different superscripts, denote a statistical difference (P < 0.05).

TABLE 25

Whole-body nutrient retention (% of intake)

|  | CTRL | PHY500 | PHY1000 | PHY2000 | DCP | P-value |
|---|---|---|---|---|---|---|
| Protein, % | 36.7 ± 3.6$^a$ | 40.6 ± 1.8$^b$ | 42.7 ± 2.5$^b$ | 44.0 ± 1.7$^b$ | 41.6 ± 1.7$^b$ | 0.007 |
| Fat, % | 77.2 ± 10.4 | 83.5 ± 6.1 | 87.1 ± 7.1 | 81.5 ± 2.0 | 80.1 ± 5.0 | 0.324 |
| Energy, % | 28.1 ± 2.2$^a$ | 30.4 ± 1.7$^{ab}$ | 32.2 ± 2.0$^b$ | 31.6 ± 1.0$^b$ | 30.5 ± 0.6$^{ab}$ | 0.025 |
| Phosphorus, % | 26.2 ± 1.5$^a$ | 35.5 ± 0.7$^b$ | 45.2 ± 0.3$^d$ | 50.7 ± 1.3$^e$ | 38.7 ± 1.1$^c$ | <0.001 |
| Calcium, % | 40.9 ± 2.7$^b$ | 43.5 ± 1.9$^b$ | 48.1 ± 2.5$^c$ | 48.8 ± 3.0$^c$ | 33.8 ± 1.3$^a$ | <0.000 |

Values are average ± standard deviation (n = 4).
Values within a row with different superscripts, denote a statistical difference (P < 0.05).

TABLE 26

Apparent digestibility coefficients (ADC, %) of nutrients.

|  | CTRL | PHY500 | PHY1000 | PHY2000 | DCP | P-value |
|---|---|---|---|---|---|---|
| Dry matter, % | 68.3 ± 1.7$^a$ | 71.5 ± 0.5$^b$ | 71.3 ± 0.1$^b$ | 72.9 ± 0.1$^c$ | 71.4 ± 0.5$^b$ | <0.001 |
| Protein, % | 83.6 ± 0.9$^a$ | 84.4 ± 0.4$^{ab}$ | 84.2 ± 0.3$^{ab}$ | 84.9 ± 0.3$^b$ | 84.0 ± 0.3$^{ab}$ | 0.020 |
| Phosphorus, % | 27.7 ± 2.2$^a$ | 37.4 ± 1.6$^b$ | 46.8 ± 1.5$^c$ | 64.3 ± 1.2$^d$ | 47.5 ± 3.0$^c$ | <0.001 |
| Phytate-P, % | 21.2 ± 3.8$^a$ | 36.5 ± 3.6$^b$ | 46.6 ± 1.8$^c$ | 51.3 ± 1.5$^d$ | 21.5 ± 1.5$^a$ | <0.001 |
| Calcium, % | 50.8 ± 3.7$^{ab}$ | 52.4 ± 1.8$^{ab}$ | 53.1 ± 2.0$^{ab}$ | 54.9 ± 1.7$^b$ | 48.0 ± 3.0$^a$ | 0.019 |

Values are average ± standard deviation (n = 4).
Values within a row with different superscripts, denote a statistical difference (P < 0.05).

Conclusion

The phytase at supplementation doses of 500, 1000 and 2000 FTY/kg feed, s u c as 5 0 0 t o 2 0 0 F Y T/k g is an effective strategy to enhance the growth rate, phosphorus digestibility, whole-body phosphorus retention and reduce FCR in Nile tilapia fed plant protein-rich diets.

Example 13: Effect of Graded Supplemental Levels of Phytase on the Growth Performance, Whole-Body Nutrient Retention and Nutrient Digestibility in Gilthead Seabream (*Sparus aurata*) Fed a Plant-Protein Rich Diet The trial comprised five dietary treatments: a control diet (CTRL) with a total dietary phosphorus (P) level of 0.78%, initial body weight of 55.3±4.1 g were fed one of the five experimental diets during 94 days, with a water temperature profile of 22.4±0.2° C.

TABLE 27

Formulation of experimental diets.

| Ingredients, % | CTRL | PHY500 | PHY1000 | PHY2000 | MCP |
|---|---|---|---|---|---|
| Fishmeal Supre Prime | 7.50 | 7.50 | 7.50 | 7.50 | 7.50 |
| Fish protein hydrolysate | 2.50 | 2.50 | 2.50 | 2.50 | 2.50 |
| Wheat gluten | 7.40 | 7.40 | 7.40 | 7.40 | 7.70 |
| Corn gluten meal | 19.00 | 19.00 | 19.00 | 19.00 | 19.00 |

TABLE 27-continued

Formulation of experimental diets.

| Ingredients, % | CTRL | PHY500 | PHY1000 | PHY2000 | MCP |
|---|---|---|---|---|---|
| Soybean meal | 24.00 | 24.00 | 24.00 | 24.00 | 24.00 |
| Rapeseed meal | 8.50 | 8.50 | 8.50 | 8.50 | 8.50 |
| Sunflower meal | 14.00 | 14.00 | 14.00 | 14.00 | 14.00 |
| Wheat bran | 3.33 | 3.33 | 3.33 | 3.33 | 1.83 |
| Fish oil | 5.00 | 5.00 | 5.00 | 5.00 | 5.00 |
| Rapeseed oil | 7.50 | 7.50 | 7.50 | 7.50 | 7.50 |
| Vitamin and mineral premix | 1.00 | 1.00 | 1.00 | 1.00 | 1.00 |
| Antioxidant | 0.20 | 0.20 | 0.20 | 0.20 | 0.20 |
| Monocalcium phosphate | | | | | 1.20 |
| L-Tryptophan | 0.02 | 0.02 | 0.02 | 0.02 | 0.02 |
| DL-Methionine | 0.03 | 0.03 | 0.03 | 0.03 | 0.03 |
| Yttrium oxide | 0.02 | 0.02 | 0.02 | 0.02 | 0.02 |
| Phytase (FTY/kg) | | 500 | 1000 | 2000 | |

Result

At the end of the trial, the final body weight (FBW) ranged between 142.8 and 157.5 grams. Fish with the highest weight gain showed a 2.8-fold increase of their initial body weight (IBW). The specific growth rate (SGR) varied between 1.01 and 1.11%/day. At day 94, all supplemented diets resulted on a significantly higher FBW and SGR than those fed the CTRL diet (P<0.05). Fish fed the PHY500, PHY1000, PHY2000 and MCP diets showed a significantly lower FCR than those fed the CTRL diet (P<0.05). The CTRL treatment was consistently associated to significantly lowest values among the various treatments for whole-body phosphorus retention and apparent digestibility of phosphorus. The higher phytase supplementation doses (1000 and 2000 FTY/kg) led to a significant whole-body P retention in comparison to both CTRL and MCP treatments (P<0.05). Significant enhancements of total P and phytate-P digestibility were associated to increasing dietary doses of phytase, with dietary treatment PHY2000 having a significantly higher P digestibility than PHY500 (P<0.05). Additionally, the increase of phytase supplementation doses (0, 500, 1000 and 2000 FTY/kg) was also positively associated to an increase of whole-body phosphorus retention.

TABLE 28

Growth performance after 94 days of feeding.

| | CTRL | PHY500 | PHY1000 | PHY2000 | MCP | P-value |
|---|---|---|---|---|---|---|
| Survival, % | 100.0 ± 0.0 | 100.0 ± 0.0 | 100.0 ± 0.0 | 100.0 ± 0.0 | 100.0 ± 0.0 | — |
| IBW, g | 55.4 ± 0.6 | 55.3 ± 0.3 | 55.2 ± 0.5 | 55.6 ± 0.2 | 55.4 ± 0.4 | 0.791 |
| FBW, g | 142.8 ± 2.4$^a$ | 148.4 ± 0.7$^b$ | 156.2 ± 1.8$^c$ | 156.7 ± 1.2$^c$ | 157.5 ± 1.5$^c$ | <0.001 |
| SGR, %/d | 1.01 ± 0.01$^a$ | 1.05 ± 0.01$^b$ | 1.11 ± 0.01$^c$ | 1.10 ± 0.01$^c$ | 1.11 ± 0.01$^c$ | <0.001 |
| FCR | 1.29 ± 0.04$^c$ | 1.21 ± 0.03$^b$ | 1.12 ± 0.03$^a$ | 1.14 ± 0.03$^{ab}$ | 1.16 ± 0.05$^{ab}$ | <0.001 |
| FI, %ABW/d | 1.21 ± 0.03$^b$ | 1.17 ± 0.03$^{ab}$ | 1.14 ± 0.02$^a$ | 1.15 ± 0.02$^{ab}$ | 1.18 ± 0.04$^{ab}$ | 0.048 |
| PER | 1.74 ± 0.05$^a$ | 1.86 ± 0.05$^b$ | 2.01 ± 0.06$^c$ | 1.97 ± 0.05$^{bc}$ | 1.95 ± 0.09$^{bc}$ | <0.001 |

Values are means ± standard deviation (n = 4).
Values within a row with different superscripts, denote a statistical difference (P < 0.05).

TABLE 29

Whole-body nutrient and energy retention (% of intake).

| | CTRL | PHY500 | PHY1000 | PHY2000 | MCP | P-value |
|---|---|---|---|---|---|---|
| Protein, % | 26.5 ± 1.9$^a$ | 28.2 ± 1.5$^{ab}$ | 30.7 ± 0.8$^b$ | 30.6 ± 2.3$^b$ | 28.7 ± 1.9$^{ab}$ | 0.021 |
| Fat, % | 60.4 ± 4.5 | 63.1 ± 7.5 | 63.7 ± 3.4 | 69.5 ± 6.2 | 63.6 ± 3.3 | 0.210 |
| Energy, % | 29.9 ± 2.5$^a$ | 33.3 ± 2.6$^{abc}$ | 35.2 ± 1.2$^{bc}$ | 35.9 ± 2.4$^c$ | 31.2 ± 1.9$^{ab}$ | 0.006 |
| Phosphorus, % | 45.9 ± 2.6$^a$ | 53.5 ± 2.9$^a$ | 62.6 ± 5.3$^b$ | 59.9 ± 3.6$^b$ | 48.0 ± 5.7$^a$ | <0.001 |
| Calcium, % | 44.7 ± 2.0$^b$ | 52.9 ± 4.4$^c$ | 59.9 ± 3.4$^d$ | 60.7 ± 5.0$^d$ | 37.2 ± 1.1$^a$ | <0.001 |

Values are average ± standard deviation (n = 4).
Values within a row with different superscripts, denote a statistical difference (P < 0.05).

TABLE 30

Apparent digestibility coefficients (ADC, %) of nutrients.

| | CTRL | PHY500 | PHY1000 | PHY2000 | MCP | P-value |
|---|---|---|---|---|---|---|
| Dry matter, % | 63.4 ± 1.0$^a$ | 66.3 ± 0.8$^b$ | 66.5 ± 2.2$^b$ | 65.1 ± 1.7$^{ab}$ | 62.5 ± 0.8$^a$ | 0.004 |
| Protein, % | 86.3 ± 0.9 | 87.5 ± 0.7 | 88.0 ± 1.3 | 87.0 ± 1.1 | 86.3 ± 0.8 | 0.117 |
| Phosphorus, % | 34.5 ± 1.1$^a$ | 49.4 ± 1.5$^b$ | 57.2 ± 4.3$^c$ | 60.4 ± 3.4$^{cd}$ | 62.6 ± 1.2$^d$ | <0.001 |
| Phytate-P, % | 32.4 ± 1.0$^a$ | 39.1 ± 3.2$^b$ | 39.8 ± 3.8$^b$ | 45.7 ± 4.4$^c$ | 30.8 ± 2.3 | <0.001 |
| Calcium, % | 35.0 ± 1.7$^b$ | 36.1 ± 4.7$^b$ | 42.7 ± 5.0$^c$ | 43.1 ± 2.0$^c$ | 29.9 ± 2.3 | <0.001 |

Values are average ± standard deviation (n = 4).
Values within a row with different superscripts, denote a statistical difference (P < 0.05).

Conclusion

The phytase at supplementation doses of 500, 1000 and 2000 FTY/kg feed is an effective strategy to enhance the growth rate and phosphorus digestibility. Phytase at supplementation doses of 1000 and 2000 FTY/kg feed significantly increase whole-body phosphorus retention in gilthead seabream fed plant protein-rich diets.

Example 14: Efficacy of a Phytase with a Protease in Broilers

The effect on the growth performance of broilers using feed with 1,500 FYT/kg of phytase (var400) and 30,000 U/kg of protease (Ronozyme®ProAct 360) was investigated. Male broilers (Ross 308) were fed one of the four diets as described in Table 31 from hatch to day 28 post-hatch. Each treatment had 8 replicate cages of 6 birds per cage. The basal diets used in the trial were diet with standard Ca, standard crude protein diet or a low Ca, high crude protein diet (Table 32).

TABLE 31

Treatment designation

| Treatment | Basal Diet | Protease, U/kg[1] | Phytase, U/kg[2] |
|---|---|---|---|
| 1 | Standard Ca and CP | 0 | 500 |
| 2 |  | 30,000 | 1,500 |
| 3 | Low Ca and high CP | 0 | 500 |
| 4 |  | 30,000 | 1,500 |

[1]Protease was included in the diets over the top (e.g., no further amino acid or protein matrix was applied).
[2]500 U/kg of phytase was included in the diets to provide 0.15% avP, 0.17% Ca and 0.018% Na. No extra nutrients were removed when the additional 1,000 U/kg was included.

TABLE 32

Starter and grower experimental diets

| Ingredient | Treatment 1, 2 (fed from days 0-14) | Treatment 3, 4 (fed from days 0-14) | Treatment 1, 2 (fed from days 15-28) | Treatment 3, 4 (fed from days 15-28) |
|---|---|---|---|---|
| Corn | 59.10% | 56.19% | 61.52% | 58.61% |
| Soybean meal | 34.98% | 38.43% | 31.79% | 35.26% |
| Soy oil | 1.86% | 1.93% | 3.03% | 3.10% |
| Salt | 0.13% | 0.12% | 0.13% | 0.12% |
| Limestone | 0.77% | 0.12% | 0.66% |  |
| Dicalcium phosphate | 1.53% | 1.48% | 1.33% | 1.28% |
| Lysine HCl | 0.23% | 0.24% | 0.17% | 0.18% |
| DL-Methionine | 0.32% | 0.36% | 0.26% | 0.30% |
| Threonine | 0.09% | 0.10% | 0.05% | 0.060% |
| Valine | 0.038% | 0.059% |  | 0.013% |
| Vitamin and mineral premix | 1.00% | 1.00% | 1.00% | 1.00% |
| TiO Marker |  |  | 0.10% | 0.10% |
| TOTAL | 100.0% | 100.0% | 100.0% | 100.0% |
| Nutrients |  |  |  |  |
| Crude protein % | 22.50 | 24.00 | 21.00 | 22.50 |
| Poult ME kcal/kg | 3000.00 | 3000.00 | 3100.00 | 3100.00 |
| DM, % | 87.07 | 87.04 | 87.04 | 87.00 |
| Calcium % | 1.00 | 0.75 | 0.90 | 0.65 |
| Phosphorus % | 0.68 | 0.69 | 0.63 | 0.64 |
| Available P % | 0.35 | 0.35 | 0.31 | 0.31 |
| Phytate P % | 0.26 | 0.27 | 0.26 | 0.26 |
| Crude Fibre % | 2.23 | 2.28 | 2.18 | 2.23 |
| D Met + Cys % | 0.95 | 1.02 | 0.85 | 0.93 |
| D Lys % | 1.28 | 1.38 | 1.15 | 1.25 |
| D Thr % | 0.83 | 0.90 | 0.75 | 0.81 |
| Available P % | 0.35 | 0.35 | 0.31 | 0.31 |
| Na % | 0.18 | 0.18 | 0.18 | 0.18 |
| Cl % | 0.36 | 0.36 | 0.35 | 0.35 |

Results

TABLE 33

Growth performance of broilers fed standard Ca and crude protein or low Ca and high crude protein diets without or with protease and an extra 1,000 U/kg of phytase from hatch to day 28 post-hatch

| Dietary Ca | Dietary crude protein | Protease, U/kg | Phytase, U/kg | Feed intake, g/bird | BW gain, g/bird | FCR, g:g |
|---|---|---|---|---|---|---|
| Standard Ca | Standard CP | 0 | 500 | 2,376 | 1,683 | 1.427 |
|  |  | 30,000 | 1,500 | 2,341 | 1,722 | 1.362 |
|  | Percent delta |  |  | −1.5% | +2.3% | −4.6% |
| Low Ca | High CP | 0 | 500 | 2,349 | 1,795 | 1.318 |
|  |  | 30,000 | 1,500 | 2,370 | 1,861 | 1.281 |
|  | Percent delta |  |  | +0.9% | +3.7% | −2.8% |

TABLE 34

Apparent nutrient digestibility of broilers fed standard Ca and crude protein or low Ca and high crude protein diets without or with protease and an extra 1,000 U/kg of phytase from hatch to day 28 post-hatch

| Dietary Ca | Dietary crude protein | Protease, U/kg | Phytase, U/kg | Ileal protein digestibility, % | Fecal protein retention, % | Fecal energy retention, % |
|---|---|---|---|---|---|---|
| Standard Ca | Standard CP | 0 | 500 | 82.5 | 63.4 | 77.0 |
|  |  | 30,000 | 1,500 | 83.8 | 66.2 | 78.0 |
|  | Percent delta |  |  | +1.6% | +4.4% | +1.3% |
| Low Ca | High CP | 0 | 500 | 84.8 | 66.5 | 77.8 |
|  |  | 30,000 | 1,500 | 85.4 | 67.1 | 78.3 |
|  | Percent delta |  |  | +0.7% | +0.9% | +0.6% |

Conclusion

Feeding broilers protease in combination with an extra 1,000 FYT/kg of phytase increased protein digestibility by 0.7 to 1.6%, protein retention by 0.9 to 4.4% and energy retention by 0.6 to 1.3%. This resulted in an improvement in body weight gain (BWG) by 2.3 or 3.7% and feed conversion ratio by 4.6 or 2.8%.

The invention claimed is:

1. A phytase variant which has phytase activity and an amino acid sequence having at least 70% identity to SEQ ID NO: 2, which comprises alterations N31C/G52C/A99C/K141C/T177C/V199C/N203L as compared to SEQ ID NO: 2, and which further comprises a substitution in one or more position selected from the following: 30, 36, 43, 46, 57, 60, 64, 73, 79, 119, 121, 123, 130, 134, 138, 151, 155, 161, 162, 168, 176, 180, 184, 190, 207, 224, 230, 243, 273, 286, 336, 340, 358 and 375, using SEQ ID NO: 2 for numbering.

2. The variant of claim 1, comprising substitutions in the positions: 57, 73, 121, 134, 155, 207 and 273.

3. The variant of claim 2, further comprising substitutions in the positions: 36, 60, 64, 73, 119, 130, 138,161, 162, 168, 176, 180, 184, 190, 224, 230, 243, 336 and 340.

4. The variant of claim 1, where the substitutions are selected among: 30Q, 36A, 43C, 46C, 57Y, 60H, 64Q, 73P, 79Q, 119P, 121P, 123C, 130T, 130C, 134Q, 138A, 151S, 155F, 161T, 162A, 168R 176P, 180N, 184Q, 190T, 207T, 224Q, 230E, 243N, 273L, 286S, 336R, 340L, 340P, 358Q and 375K.

5. The variant of claim 1, comprising the substitutions 57Y/73P/121P/134Q/155F/207T/273L.

6. A phytase variant which has phytase activity and an amino acid sequence having at least 70% identity to SEO ID NO: 2, and which comprises alterations and substitutions, as compared to SEO ID NO: 2, selected from the group consisting of:

31C/52C/57Y/73P/99C/121P/134Q/141C/155F/177C/199C/203L/207T/273L;

31C/36A/52C/57Y/60H/64Q/73P/99C/119S/121P/130T/134Q/138A/141C/155F/161T/162A/176P/177C/180N/184Q/190T/199C/203L/207T/224Q/230E/243N/273L/336R/340L;

31C/36A/43C/46C/52C/57Y/60H/64Q/73P/99C/119S/121P/130T/134Q/138A/141C/155F/161T/162A/176P/177C/180N/184Q/190T/199C/203L/207T/224Q/230E/243N/273L/2865/336R/340L;

31C/36A/52C/57Y/60H/64Q/73P/99C/119S/121P/123C/130C/134Q/138A/141C/151S/155F/161T/162A/176P/177C/180N/184Q/190T/199C/203L 207T/224Q/230E/243N/273L/336R/340L; and 31C/36A/43C/46C/52C/57Y/60H/64Q/73P/99C/119S/121P/123C/130C/134Q/138A/141C/155F/161T/162A/176P/177C/180N/184Q/190T/199C/203L/207T/224Q/230E/243N/273L/286S/336R/340L.

7. The variant of claim 6, having an amino acid sequence which has at least 75% sequence identity to the amino acid sequence of SEQ ID NO: 2 comprising alterations and substitutions, as compared to SEO ID NO: 2, selected from the group consisting of:

N31C/G52C/E57Y/N73P/A99C/N121P/S134Q/K141C/Y155F/T177C/V199C/N203L/P207T/M273L;

N31C/Q36A/G52C/E57Y/Q60H/L64Q/N73P/A99C/E119S/N121P/M13OT/S134Q/L138A/K141C/Y155F/S161T/S162A/E176P/T177C/T180N/S184Q/P190T/V199C/N203L/P207T/E224Q/Q230E/R243N/M273L/K336R/T340L;

N31C/Q36A/P43C/W46C/G52C/E57Y/Q60H/L64Q/N73P/A99C/E119S/N121P/M130T/S134Q/L138A/K141C/Y155F/S161T/S162A/E176P/T177C/T180N/S184Q/P190T/V199C/N203L/P207T/E224Q/Q230E/R243N/M273L/N286S/K336R/T340L;

N31C/Q36A/G52C/E57Y/Q60H/L64Q/N73P/A99C/E119S/N121P/P123C/M130C/S134Q/L138A/K141C/N151S/Y155F/S161T/S162A/E176P/T177C/T180N/S184Q/P190T/V199C/N203L/P207T/E224Q/Q230E/R243N/M273L/K336R/T340L; and N31C/Q36A/P43C/W46C/G52C/E57Y/Q60H/L64Q/N73P/A99C/E119S/N121P/P123C/M130C/S134Q/L138A/K141C/Y155F/S161T/S162A/E176P/T177C/T180N/S184Q/P190T/V199C/N203L/P207T/E224Q/Q230E/R243N/M273L/N286S/K336R/T340L.

8. A composition comprising at least one phytase variant according to claim 1.

9. The composition of claim 8 further comprising
at least one fat soluble vitamin;
at least one water soluble vitamin; and/or
at least one trace mineral.

10. The composition of claim 8, further comprising at least one additional enzyme selected from amylases, phytases other than said phytase variant, phosphatases, xylanases, galactanases, alpha-galactosidases, proteases, phospholipases and beta-glucanases.

11. An animal feed composition having a crude protein content of 50 to 800 g/kg and comprising the phytase variant of claim 1.

12. The phytase variant of claim 1, having at least 75% identity to SEQ ID NO: 2.

13. The phytase variant of claim 1, having at least 80% identity to SEQ ID NO: 2.

14. The phytase variant of claim 1, having at least 85% identity to SEQ ID NO: 2.

15. The phytase variant of claim 1, having at least 90% identity to SEQ ID NO: 2.

16. The phytase variant of claim 6, having at least 80% identity to SEQ ID NO: 2.

17. A phytase variant comprising an amino acid sequence selected from SEQ ID NO: 12, SEQ ID NO: 14, SEQ ID NO: 16, SEQ ID NO: 18 and SEQ ID NO: 20.

18. The phytase variant of claim 17, comprising SEQ ID NO: 12.

19. The phytase variant of claim 17, comprising SEQ ID NO: 14.

20. The phytase variant of claim 17, comprising SEQ ID NO: 18.

* * * * *